(12) United States Patent
Lieber et al.

(10) Patent No.: US 8,753,639 B2
(45) Date of Patent: Jun. 17, 2014

(54) COMPOSITIONS AND METHODS FOR MODULATING THE ACTIVITY OF COMPLEMENT REGULATORY PROTEINS ON TARGET CELLS

(75) Inventors: André Lieber, Seattle, WA (US); Hongjie Wang, Seattle, WA (US); Ronald Jay Berenson, Mercer Island, WA (US); Darrick Carter, Seattle, WA (US)

(73) Assignees: University of Washington through its Center for Commercialization, Seattle, WA (US); Compliment Corporation, Mercer Island, WA (US)

( * ) Notice: Subject to any disclaimer, the term of this patent is extended or adjusted under 35 U.S.C. 154(b) by 608 days.

(21) Appl. No.: 12/751,943

(22) Filed: Mar. 31, 2010

(65) Prior Publication Data
US 2010/0255011 A1   Oct. 7, 2010

Related U.S. Application Data

(60) Provisional application No. 61/165,434, filed on Mar. 31, 2009, provisional application No. 61/255,450, filed on Oct. 27, 2009.

(51) Int. Cl.
*C07K 14/075* (2006.01)

(52) U.S. Cl.
USPC ................ 424/174.1; 530/389.7; 530/324

(58) Field of Classification Search
None
See application file for complete search history.

(56) References Cited

U.S. PATENT DOCUMENTS

| 6,348,568 B1 * | 2/2002 | Barney et al. ............... 530/300 |
| 7,390,795 B2 | 6/2008 | Pepys |
| 2004/0002060 A1 * | 1/2004 | Kaleko et al. ................. 435/5 |

FOREIGN PATENT DOCUMENTS

| CN | 101068933 A | 11/2007 |
| WO | 2006/026331 A2 | 3/2006 |

OTHER PUBLICATIONS

Grote et al., "Live attenuated measles virus induces regression of human lymphoma xenografts in immunodeficient mice", Blood, 2001, pp. 3746-3754.*
Adams, G.P., and L.M. Weiner, "Monoclonal Antibody Therapy of Cancer," Nature Biotechnology 23(9):1147-1157, Sep. 2005.
Binz, H.K., and A. Plückthun, "Engineered Proteins as Specific Binding Reagents," Current Opinion in Biotechnology 16(4):459-469, Aug. 2005.
Campoli, M., and S. Ferrone, "Immunotherapy of Malignant Disease: The Coming Age of Therapeutic Monoclonal Antibodies," Cancer: Principles & Practice of Oncology 23(1 & 2):1-19, 2009.
Castillo, J., et al., "Newer Monoclonal Antibodies for Hematological Malignancies," Experimental Hematology 36(7):755-768, Jul. 2008.
Clackson, T., and J.A. Wells, "In Vitro Selection From Protein and Peptide Libraries," Trends in Biotechnology 12(4):173-184, May 1994.
Dall'Acqua, W.F., et al., "Modulation of the Effector Functions of a Human IgG1 Through Engineering of Its Hinge Region," Journal of Immunology 177(2):1129-1138, Jul. 2006.
Donev, R.M., et al., Modulation of CD59 Expression by Restrictive Silencer Factor-Derived Peptides in Cancer Immunotherapy for Neuroblastoma, Cancer Research 68(14):5979-5987, Jul. 2008.
Dipaolo, N., et al., "Evaluation of Adenovirus Vectors Containing Serotype 35 Fibers for Vaccination," Molecular Therapy 13(4):756-765, Apr. 2006.
Fishelson, Z., et al., "Obstacles to Cancer Immunotherapy: Expression of Membrane Complement Regulatory Proteins (mCRPs) in Tumors," Molecular Immunology 40(2-4):109-123, Sep. 2003.
Gancz, D., and Z. Fishelson, "Cancer Resistance to Complement-Dependent Cytotoxicity (CDC): Problem-Oriented Research and Development," Molecular Immunology 46(14):2794-2800, Jun. 2009.
Gelderman, K.A., et al., "The Inhibitory Effect of CD46, CD55, and CD59 on Complement Activation After Immunotherapeutic Treatment of Cervical Carcinoma Cells With Monoclonal Antibodies or Bispecific Monoclonal Antibodies," Laboratory Investigation 82(4):483-493, Apr. 2002.
Idusogie, E.E., et al., "Engineered Antibodies With Increased Activity to Recruit Complement," Journal of Immunology 166(4):2571-2575, Feb. 2001.
Kolev, M.V., et al., "Upregulating CD59: A New Strategy for Protection of Neurons From Complement-Mediated Degeneration," Pharmacogenomics Journal 10(1):12-19, Feb. 2009.
Leen, A.M., et al., "Cytotoxic T Lymphocyte Therapy With Donor T Cells Prevents and Treats Adenovirus and Epstein-Barr Virus Infections After Haploidentical and Matched Unrelated Stem Cell Transplantation," Blood 114(19):4283-4292, Nov. 2009.
Marie, J.C., et al., "Linking Innate and Acquired Immunity: Divergent Role of CD46 Cytoplasmic Domains in T Cell-Induced Inflammation," Nature Immunology 3(7):659-666, Jul. 2002.
Ni, S., et al., "Evaluation of Adenovirus Vectors Containing Serotype 35 Fibers for Tumor Targeting," Cancer Gene Therapy 13(12):1072-1081, Dec. 2006.
Perez, E.E., et al., "Establishment of HIV-1 Resistance in CD4+ T Cells by Genome Editing Using Zinc-Finger Nucleases," Nature Biotechnology 26(7):808-816, Jul. 2008.
"Sangamo BioSciences Announces Presentation of Preliminary Data From Phase 1 Safety Trial of SB-728-T for HIV/AIDS," Sangamo BioSciences, Inc., Jan. 19, 2010, <http://investor.sangamo.com/releasedetail.cfm?ReleaseID=438350> [retrieved Jan. 20, 2010], 2 pages.
Tuve, S., et al., "A New Group B Adenovirus Receptor Is Expressed at High Levels on Human Stem and Tumor Cells," Journal of Virology 80(24):12109-12120, Dec. 2006.

(Continued)

*Primary Examiner* — Karlheinz R Skowronek
*Assistant Examiner* — Lianko Garyu
(74) *Attorney, Agent, or Firm* — Christensen O'Connor Johnson Kindness PLLC

(57) ABSTRACT

This invention relates to agents capable of reducing the activity, amount or density of complement regulatory proteins (CRPs) on target cells. The invention also provides methods of identification of such agents, methods of making, and uses thereof.

30 Claims, 31 Drawing Sheets

(56) References Cited

OTHER PUBLICATIONS

Veronese, F.M., and G. Pasut, "PEGylation, Successful Approach to Drug Delivery," Drug Discovery Today 10(21):1451-1458, Nov. 2005.
Wang, H. et al., "Identification of CD46 Binding Sites Within the Adenovirus Serotype 35 Fiber Knob," Journal of Virology 81(23):12785-12792, Dec. 2007.
Wang, H. et al., "In Vitro and In Vivo Properties of Adenovirus Vectors With Increased Affinity to CD46," Journal of Virology 82(21):10567-10579, Nov. 2008.
Wang, H., et al., "A Recombinant Adenovirus Type 35 Fiber Knob Protein Sensitizes Lymphoma Cells to Rituximab Therapy," Blood 115(3):592-600, Jan. 2010.
Yan, J., et al., "The Role of Membrane Complement Regulatory Proteins in Cancer Immunotherapy," in J.D. Lambris (ed.), "Advances in Experimental Medicine and Biology," vol. 632, "Current Topics in Complement II," Springer, New York, 2009, pp. 159-174.
Yang, X., et al., "Highly Stable Trimers Formed by Human Immunodeficiency Virus Type 1 Envelope Glycoproteins Fused With the Trimeric Motif of T4 Bacteriophage Fibritin," Journal of Virology 76(9):4634-4642, May 2002.
Zell, S., et al., "Down-Regulation of CD55 and CD46 Expression by Anti-Sense Phosphorothioate Oligonucleotides (S-ODNs) Sensitizes Tumour Cells to Complement Attack," Clinical and Experimental Immunology 150(3):576-584, Dec. 2007.
Bannerji, R., et al., "Apoptotic-Regulatory and Complement-Protecting Protein Expression in Chronic Lymphocytic Leukemia: Relationship to In Vivo Rituximab Resistance," Journal of Clinical Oncology 21(8):1466-1471, Apr. 2003.
Gustafsson, D.J., et al., "The Arg279Glu Substitution in the Adenovirus Type 11p (Ad11p) Fiber Knob Abolishes EDTA-Resistant Binding to A549 and CHO-CD46 Cells, Converting the Phenotype to That of Ad7p," Journal of Virology 80(4):1897-1905, Feb. 2006.
Weyand, N.J., et al., "Monoclonal Antibody Detection of CD46 Clustering Beneath *Neisseria gonorrhoeae* Microcolonies," Infection and Immunity 74(4):2428-2435, Apr. 2006.
International Search Report mailed Mar. 29,2011, issued in corresponding PCT/US2010/029471, filed Mar. 31, 2010, 8 pages.
Extended European Search Report mailed Oct. 26, 2012, issued in corresponding European Application No. 10 764 877.6, filed Mar. 31, 2010, 6 pages.
Schmitt, C.A., et al., "Expression and Regulation by Interferon-γ of the Membrane-Bound Complement Regulators CD46 (MCP), CD55 (DAF) and CD59 in Gastrointestinal Tumours," European Journal of Cancer 35(1):117-124, Jan. 1999.
Acosta, J., et al., "Molecular Basis for a Link Between Complement and the Vascular Complications of Diabetes," PNAS (Proceedings of the National Academy of Sciences of the United States of America) 97(10):5450-5455, May 2000.
Annicchiarico, B.E., et al., "Orthotopic Liver Transplantation After Successful Treatment With Anti-CD20 Monoclonal Antibody (Rituximab) for Severe Steroid-Resistant Autoimmune Hemolytic Anemia: A Case Report," Transplantation Proceedings 41(4):1380-1382, May 2009.
Argyriou, A.A., "Molecularly Targeted Therapies for Dysimmune Neuropathies," Molecular Medicine 15(7-8):283-287, Jul./Aug. 2009.
Castillo, J., et al., "Ofatumumab, a Second-Generation Anti-CD20 Monoclonal Antibody, for the Treatment of Lymphoproliferative and Autoimmune Disorders," Expert Opinion on Investigational Drugs 18(4):491-500, Apr. 2009.
Coral, S., et al., "Overexpression of Protectin (CD59) Down-Modulates the Susceptibility of Human Melanoma Cells to Homologous Complement," Journal of Cellular Physiology 185(3):317-323, Dec. 2000.
Crimeen-Irwin, B., et al., "Ligand Binding Determines Whether CD46 Is Internalized by Clathrin-Coated Pits or Macropinocytosis," Journal of Biological Chemistry 278(47):46927-46937, Nov. 2003.

"Daratumumab (HuMax CD38): Multiple Myeloma," ©2010 Genmab A/S, Genmab.com, <http://www.genmab.com/Science%20And%20Research/Products%20in%20Development.aspx> [retrieved Jul. 1, 2010], 2 pages.
Dechant, M., et al., "Complement-Dependent Tumor Cell Lysis Triggered by Combinations of Epidermal Growth Factor Receptor Antibodies," Cancer Research 68(13):4998-5003, Jul. 2008.
Di Gaetano, N., et al., "Complement Activation Determines the Therapeutic Activity of Rituximab in Vivo," Journal of Immunology 171(3):1581-1587, Aug. 2003.
Di Paolo, N.C., et al., "Effect of Adenovirus-Mediated Heat Shock Protein Expression and Oncolysis in Combination With Low-Dose Cyclophosphamide Treatment on Antitumor Immune Responses," Cancer Research 66(2):960-969, Jan. 2006.
"FDA Approves Ofatumumab (Arzerra) for Patients With CLL Refractory to Fludarabine and Alemtuzumab," ©2009 American Society of Hematology, <http://www.hematology.org/News/2009/4384> [retrieved Jul. 1, 2010], 2 pages.
Fujita, T., et al., "The Mechanism of Action of Decay-Accelerating Factor (DAF): DAF Inhibits the Assembly of C3 Convertases by Dissociating C2a and Bb," Journal of Experimental Medicine 166(5):1221-1228, Nov. 1987.
Gaggar, A., et al., "Localization of Regions in CD46 That Interact With Adenovirus," Journal of Virology 79(12):7503-7513, Jun. 2005.
Golay, J., et al., "The Role of Complement in the Therapeutic Activity of Rituximab in a Murine B Lymphoma Model Homing in Lymph Nodes," Haematologica/The Hematology Journal 91(2):176-183, Feb. 2006.
Goodfellow, I.G., et al., "Echovirus Infection of Rhabdomyosarcoma Cells Is Inhibited by Antiserum to the Complement Control Protein CD59," Journal of General Virology 81(5):1393-1401, May 2000.
Guo, B., et al., "Mapping of Binding Epitopes of a Human Decay-Accelerating Factor Monoclonal Antibody Capable of Enhancing Rituximab-Mediated Complement-Dependent Cytotoxicity," Clinical Immunology 128(2):155-163, Aug. 2008.
Hara, T., et al., "Levels of Complement Regulatory Proteins, CD35 (CR1), CD46 (MCP) and CD55 (DAF) in Human Haematological Malignancies," British Journal of Haematology 82(2):368-373, Oct. 1992.
Hong, J.S., and J.A. Engler, "Domains Required for Assembly of Adenovirus Type 2 Fiber Trimers," Journal of Virology 70(10):7071-7078, Oct. 1996.
Illidge, T.M., et al., "Phase 1/2 Study of Fractioned (131)I-Rituximab in Low-Grade B-Cell Lymphoma: The Effect of Prior Rituximab Dosing and Tumor Burden on Subsequent Radioimmunotherapy," Blood 113(7)1412-1421, Feb. 2009.
Kuppachi, S. et al., "Membranous Nephropathy and Thrombotic Thrombocytopenic Purpura Treated With Rituximab," Journal of Nephrology 22(4):561-564, Jul./Aug. 2009.
Lapalombella, R., et al., "A Novel Raji-Burkitt's Lymphoma Model for Preclinical and Mechanistic Evaluation of CD52-Targeted Immunotherapeutic Agents," Clinical Cancer Research 14(2):569-578, Jan. 2008.
Maloney, D.G., "Follicular NHL: From Antibodies and Vaccines to Graft-Versus-Lymphoma Effects," Hematology, American Society of Hematology Education Program 2007:226-232, Jan. 2007.
Naderi, S., et al., "CD2-Mediated CD59 Stimulation in Keratinocytes Results in Secretion of IL-1α, IL-6, and GM-CSF: Implications for the Interaction of Keratinocytes With Intraepidermal T Lymphocytes," International Journal of Molecular Medicine 3(6):609-614, Jun. 1999.
Nelson, R.P., Jr, MD, et al., "Rituximab for the Treatment of Thymoma-Associated and De Novo Myasthenia Gravis: 3 Cases and Review," Journal of Clinical Neuromuscular Disease 10(4):170-177, Jun. 2009.
O'Brien, S.M., et al., "Rituximab Dose-Escalation Trial in Chronic Lymphocytic Leukemia," Journal of Clinical Oncology 19(8):2165-2170, Apr. 2001.
Osuka, F., et al., "Molecular Cloning and Characterization of Novel Splicing Variants of Human Decay-Accelerating Factor," Genomics 88(3):316-322, Sep. 2006.
Owczarczyk, K, et al., "Clinical Outcome and B Cell Depletion in Patients With Rheumatoid Arthritis Receiving Rituximab

(56) References Cited

OTHER PUBLICATIONS

Monotherapy in Comparison With Patients Receiving Concomitant Methotrexate," Annals of the Rheumatic Diseases 67(11):1648-1649, Nov. 2008.
Pache, L. et al., Variations in Species B Adenovirus Fibers Impact CD46 Association," Journal of Virology 82(16):7923-7931, Aug. 2008.
Persson, B.D., et al., "Adenovirus Type 11 Binding Alters the Conformation of Its Receptor CD46," Nature Structural & Molecular Biology 14(2):164-166, Feb. 2007.
Petereit, H.F., and A. Rubbert Roth, "Rituximab Levels in Cerebrospinal Fluid of Patients With Neurological Autoimmune Disorders," Multiple Sclerosis 15(2):189-192, Feb. 2009.
Sakurai, F., et al., "Downregulation of Human CD46 by Adenovirus Serotype 35 Vectors," Gene Therapy 14(11):912-919, Jun. 2007.
Schmid, L., et al., "Induction of Complete and Sustained Remission of Rheumatoid Pachymeningitis by Rituximab," Arthritis & Rheumatism 60(6):1632-1634, Jun. 2009.
Thomas, M.A., et al., "Immunosuppression Enhances Oncolytic Adenovirus Replication and Antitumor Efficacy in the Syrian Hamster Model," Molecular Therapy 16(10):1665-1673, Oct. 2008.
Tuve, S., et al., "Combination of Tumor Site-Located CTL-Associated Antigen-4 Blockade and Systemic Regulatory T-Cell Depletion Induces Tumor-Destructive Immune Responses," Cancer Research 67(12):5929-5939, Jun. 2007.
Varela, J.C., et al., "Upregulated Expression of Complement Inhibitory Proteins on Bladder Cancer Cells and Anti-MUC1 Antibody Immune Selection," International Journal of Cancer 123(6):1357-1363, Sep. 2008.
Wang, M., et al., "Phase 2 Trial of Rituximab Plus Hyper-CVAD Alternating With Rituximab Plus Methotrexate-Cytarabine for Relapsed or Refractory Aggressive Mantle Cell Lymphoma," Cancer 113(10):2734-2741, Nov. 2008.
Wang, S.-Y., and G. Weiner, "Complement and Cellular Cytotoxicity in Antibody Therapy of Cancer," Expert Opinion on Biological Therapy 8(6):759-768, Jun. 2008.
Yanagawa, B., et al., "Coxsackievirus B3-Associated Myocardial Pathology and Viral Load Reduced by Recombinant Soluble Human Decay-Accelerating Factor in Mice," Laboratory Investigation 83(1):75-85, Jan. 2003.
Yang, Y.-W., et al., "Early Diagnosis and Successful Treatment of Acute Antibody-Mediated Rejection of a Renal Transplant," Experimental and Clinical Transplantation 6(3):211-214, Sep. 2008.
Zent, C.S., et al., "Direct and Complement Dependent Cytotoxicity in CLL Cells From Patients With High Risk Early Stage Chronic Lymphocytic Leukemia (CLL) Treated With Alemtuzumab and Rituximab," Leukemia Research 32(12):1849-1856, Dec. 2008.
Ziller, F., et al., "Controlling Complement Resistance in Cancer by Using Human Monoclonal Antibodies That Neutralize Complement-Regulatory Proteins CD55 and CD59," European Journal of Immunology 35(7):2175-2183, Jul. 2005.
Notification of the First Office Action and Search Report mailed Jul. 10, 2013, issued in corresponding Chinese Application No. 201080022959.5, filed Mar. 31, 2010, with English translation, 11 pages.
Communication Pursuant to Article 93(3) EPC, mailed Feb. 27, 2014, issued in corresponding European Patent Application No. 10764877.6, filed Mar. 31, 2010, 5 pages.

\* cited by examiner

FIG. 1C

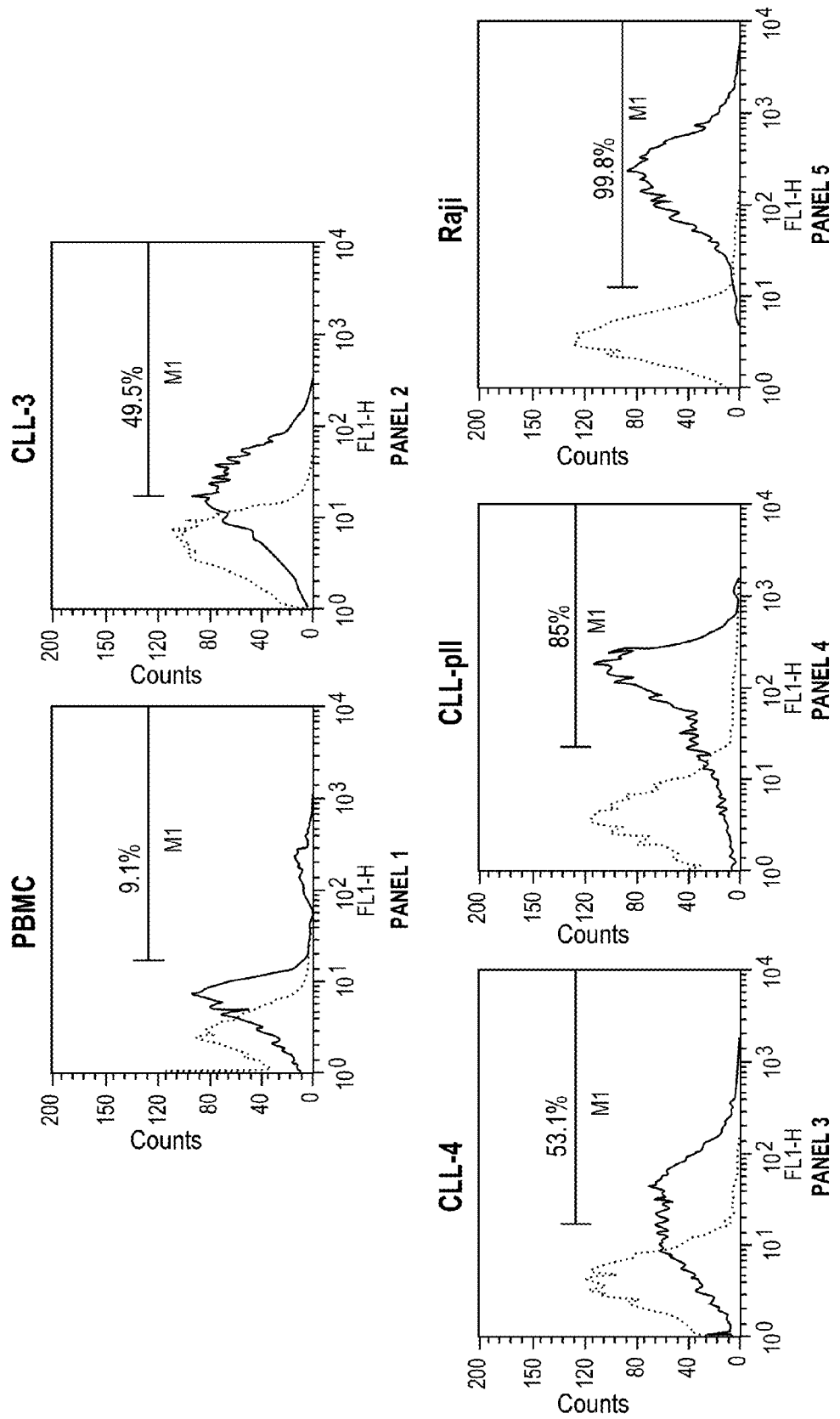

CD46 Levels as assessed by Flow Cytometry

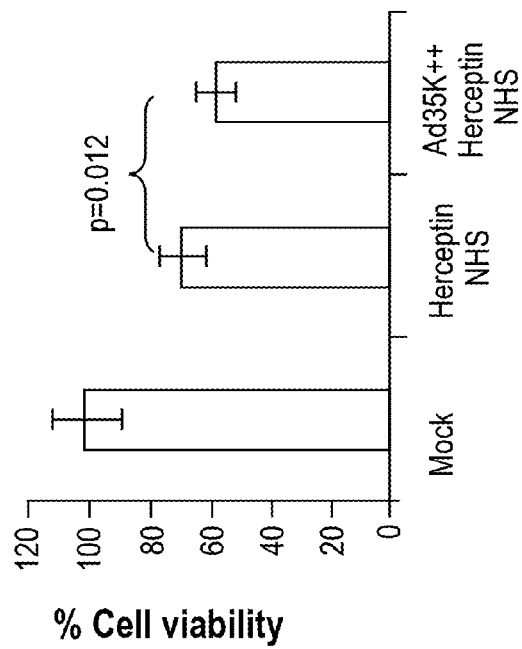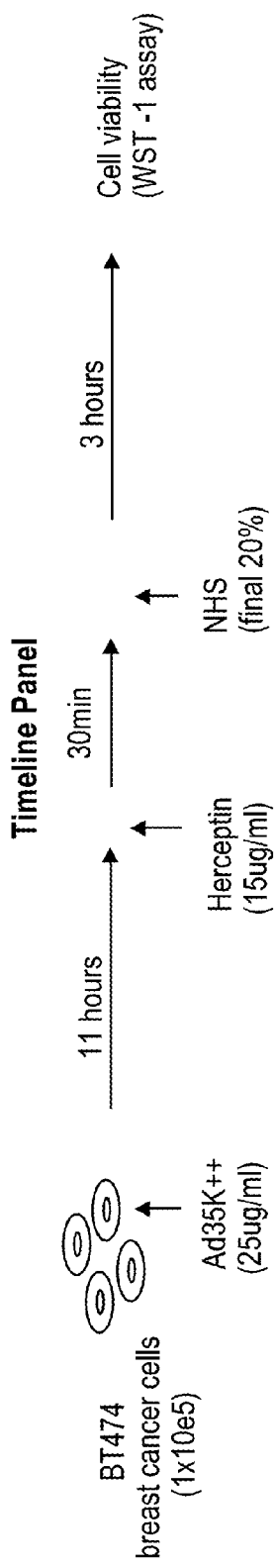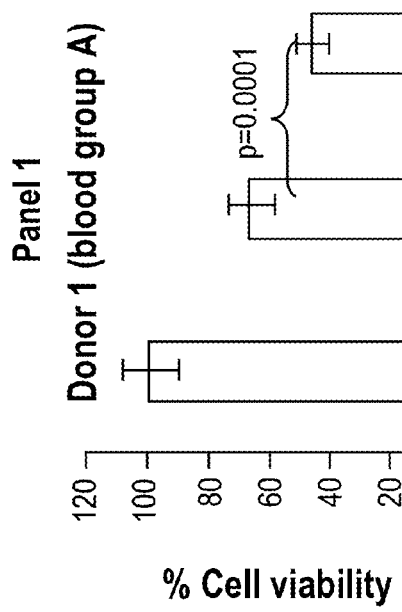
FIG. 14A
FIG. 14B

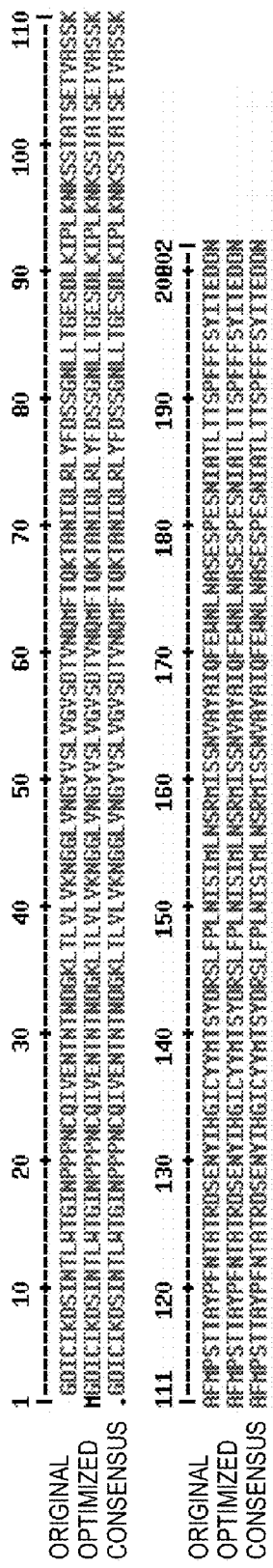
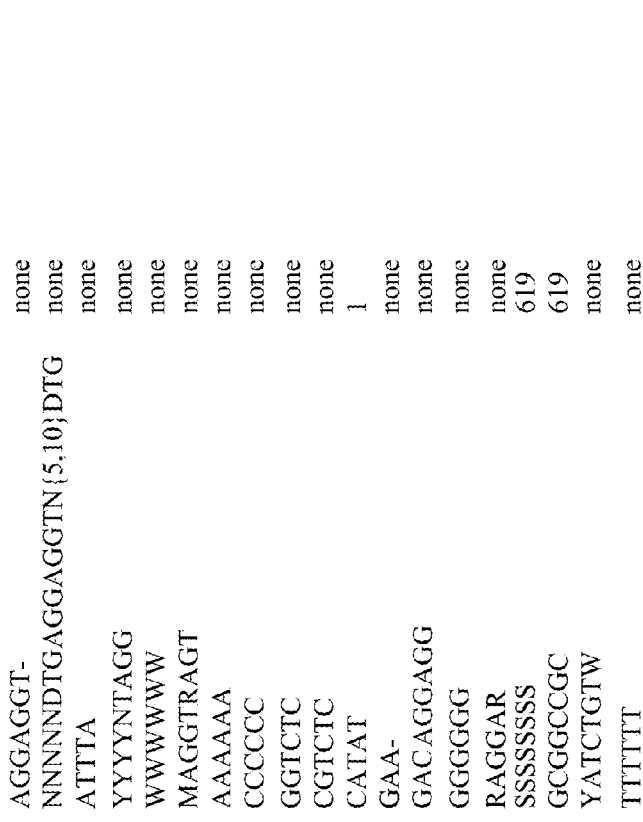
FIG. 15B
FIG. 15C

Lanes 1, 2: pET29a-Ad35K++ uninduced
Lanes 3, 4, 5, 6: pET29a-Ad35K++ induced with 1mM IPTG (different colonies)
Lane 7: pQE30-Ad35K++ uninduced (His tagged)
Lane 8: pQE30-Ad35K++ induced with 1mM IPTG
Lane 9: purified Ad35K++ (~2 ug/lane) (His tagged)

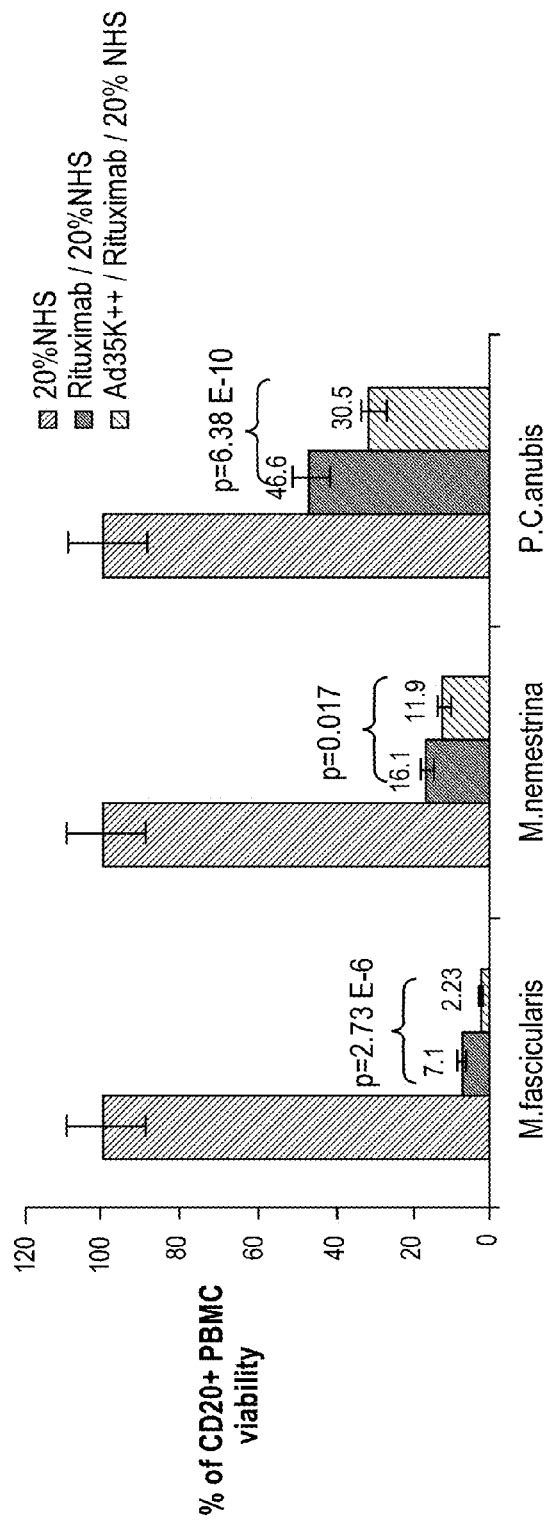
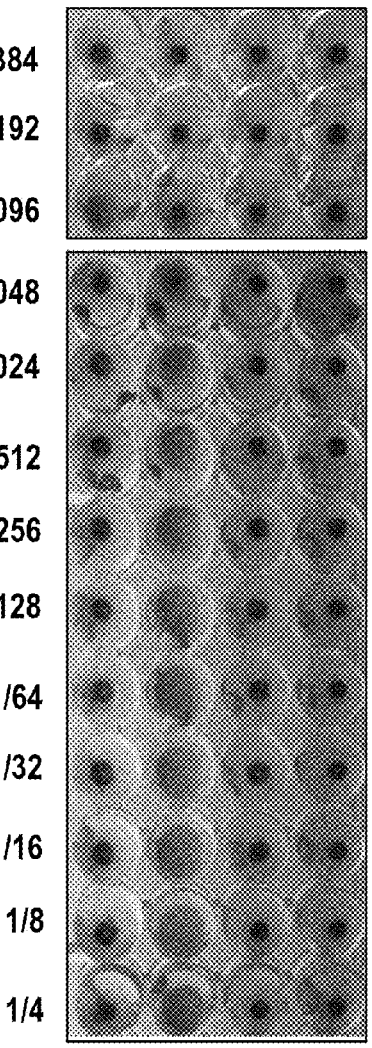
FIG. 16A
FIG. 16B

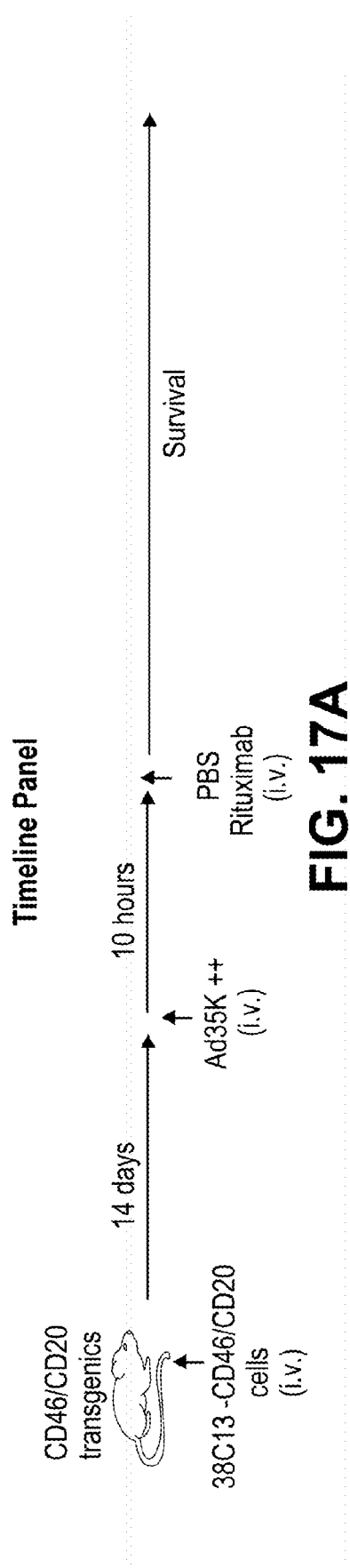
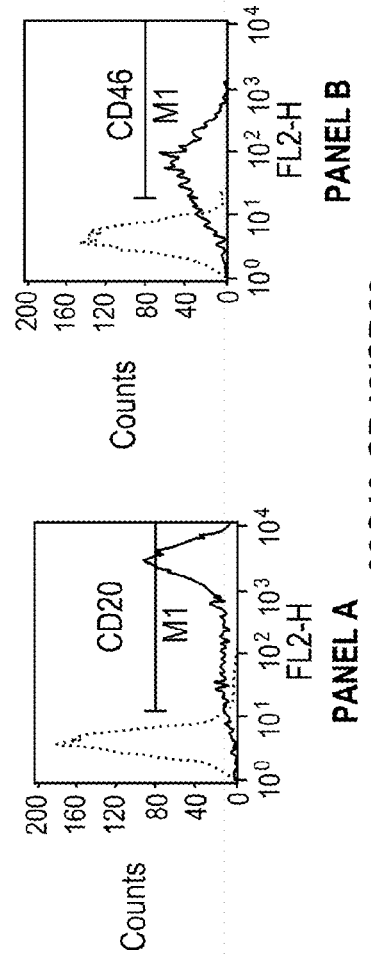
FIG. 17A
FIG. 17B
FIG. 17C

US 8,753,639 B2

SEQUENCE LISTING

```
<160> NUMBER OF SEQ ID NOS: 39

<210> SEQ ID NO 1
<211> LENGTH: 972
<212> TYPE: DNA
<213> ORGANISM: Adenovirus type 35
<220> FEATURE:
<221> NAME/KEY: CDS
<222> LOCATION: (1)..(972)

<400> SEQUENCE: 1 atg acc aag aga gtc cgg ctc agt gac tcc ttc aac cct gtc tac ccc        48
Met Thr Lys Arg Val Arg Leu Ser Asp Ser Phe Asn Pro Val Tyr Pro
1               5                   10                  15 tat gaa gat gaa agc acc tcc caa cac ccc ttt ata aac cca ggg ttt        96
Tyr Glu Asp Glu Ser Thr Ser Gln His Pro Phe Ile Asn Pro Gly Phe
                20                  25                  30 att tcc cca aat ggc ttc aca caa agc cca gac gga gtt ctt act tta       144
Ile Ser Pro Asn Gly Phe Thr Gln Ser Pro Asp Gly Val Leu Thr Leu
            35                  40                  45 aaa tgt tta acc cca cta aca acc aca ggc gga tct cta cag cta aaa       192
Lys Cys Leu Thr Pro Leu Thr Thr Thr Gly Gly Ser Leu Gln Leu Lys
        50                  55                  60 gtg gga ggg gga ctt aca gtg gat gac act gat ggt acc tta caa gaa       240
Val Gly Gly Gly Leu Thr Val Asp Asp Thr Asp Gly Thr Leu Gln Glu
65                  70                  75                  80 aac ata cgt gct aca gca ccc att act aaa aat aat cac tct gta gaa       288
Asn Ile Arg Ala Thr Ala Pro Ile Thr Lys Asn Asn His Ser Val Glu
                85                  90                  95 cta tcc att gga aat gga tta gaa act caa aac aat aaa cta tgt gcc       336
Leu Ser Ile Gly Asn Gly Leu Glu Thr Gln Asn Asn Lys Leu Cys Ala
            100                 105                 110
```

```
aaa ttg gga aat ggg tta aaa ttt aac aac ggt gac att tgt ata aag      384
Lys Leu Gly Asn Gly Leu Lys Phe Asn Asn Gly Asp Ile Cys Ile Lys
        115                 120                 125 gat agt att aac acc tta tgg act gga ata aac cct cca cct aac tgt      432
Asp Ser Ile Asn Thr Leu Trp Thr Gly Ile Asn Pro Pro Pro Asn Cys
130                 135                 140 caa att gtg gaa aac act aat aca aat gat ggc aaa ctt act tta gta      480
Gln Ile Val Glu Asn Thr Asn Thr Asn Asp Gly Lys Leu Thr Leu Val
145                 150                 155                 160 tta gta aaa aat gga ggg ctt gtt aat ggc tac gtg tct cta gtt ggt      528
Leu Val Lys Asn Gly Gly Leu Val Asn Gly Tyr Val Ser Leu Val Gly
                165                 170                 175 gta tca gac act gtg aac caa atg ttc aca caa aag aca gca aac atc      576
Val Ser Asp Thr Val Asn Gln Met Phe Thr Gln Lys Thr Ala Asn Ile
            180                 185                 190 caa tta aga tta tat ttt gac tct tct gga aat cta tta act gag gaa      624
Gln Leu Arg Leu Tyr Phe Asp Ser Ser Gly Asn Leu Leu Thr Glu Glu
        195                 200                 205 tca gac tta aaa att cca ctt aaa aat aaa tct tct aca gcg acc agt      672
Ser Asp Leu Lys Ile Pro Leu Lys Asn Lys Ser Ser Thr Ala Thr Ser
210                 215                 220 gaa act gta gcc agc agc aaa gcc ttt atg cca agt act aca gct tat      720
Glu Thr Val Ala Ser Ser Lys Ala Phe Met Pro Ser Thr Thr Ala Tyr
225                 230                 235                 240 ccc ttc aac acc act act agg gat agt gaa aac tac att cat gga ata      768
Pro Phe Asn Thr Thr Thr Arg Asp Ser Glu Asn Tyr Ile His Gly Ile
                245                 250                 255 tgt tac tac atg act agt tat gat aga agt cta ttt ccc ttg aac att      816
Cys Tyr Tyr Met Thr Ser Tyr Asp Arg Ser Leu Phe Pro Leu Asn Ile
            260                 265                 270 tct ata atg cta aac agc cgt atg att tct tcc aat gtt gcc tat gcc      864
Ser Ile Met Leu Asn Ser Arg Met Ile Ser Ser Asn Val Ala Tyr Ala
        275                 280                 285 ata caa ttt gaa tgg aat cta aat gca agt gaa tct cca gaa agc aac      912
Ile Gln Phe Glu Trp Asn Leu Asn Ala Ser Glu Ser Pro Glu Ser Asn
290                 295                 300 ata gct acg ctg acc aca tcc ccc ttt ttc ttt tct tac att aca gaa      960
Ile Ala Thr Leu Thr Thr Ser Pro Phe Phe Phe Ser Tyr Ile Thr Glu
305                 310                 315                 320 gac gac aac taa                                                      972
Asp Asp Asn <210> SEQ ID NO 2
<211> LENGTH: 323
<212> TYPE: PRT
<213> ORGANISM: Adenovirus type 35

<400> SEQUENCE: 2

Met Thr Lys Arg Val Arg Leu Ser Asp Ser Phe Asn Pro Val Tyr Pro
1               5                   10                  15

Tyr Glu Asp Glu Ser Thr Ser Gln His Pro Phe Ile Asn Pro Gly Phe
            20                  25                  30

Ile Ser Pro Asn Gly Phe Thr Gln Ser Pro Asp Gly Val Leu Thr Leu
        35                  40                  45

Lys Cys Leu Thr Pro Leu Thr Thr Thr Gly Gly Ser Leu Gln Leu Lys
    50                  55                  60

Val Gly Gly Gly Leu Thr Val Asp Asp Thr Asp Gly Thr Leu Gln Glu
65                  70                  75                  80

Asn Ile Arg Ala Thr Ala Pro Ile Thr Lys Asn Asn His Ser Val Glu
                85                  90                  95
```

```
Leu Ser Ile Gly Asn Gly Leu Glu Thr Gln Asn Asn Lys Leu Cys Ala
            100                 105                 110

Lys Leu Gly Asn Gly Leu Lys Phe Asn Asn Gly Asp Ile Cys Ile Lys
        115                 120                 125

Asp Ser Ile Asn Thr Leu Trp Thr Gly Ile Asn Pro Pro Asn Cys
130                 135                 140

Gln Ile Val Glu Asn Thr Asn Thr Asn Asp Gly Lys Leu Thr Leu Val
145                 150                 155                 160

Leu Val Lys Asn Gly Gly Leu Val Asn Gly Tyr Val Ser Leu Val Gly
                165                 170                 175

Val Ser Asp Thr Val Asn Gln Met Phe Thr Gln Lys Thr Ala Asn Ile
            180                 185                 190

Gln Leu Arg Leu Tyr Phe Asp Ser Ser Gly Asn Leu Leu Thr Glu Glu
        195                 200                 205

Ser Asp Leu Lys Ile Pro Leu Lys Asn Lys Ser Ser Thr Ala Thr Ser
210                 215                 220

Glu Thr Val Ala Ser Ser Lys Ala Phe Met Pro Ser Thr Thr Ala Tyr
225                 230                 235                 240

Pro Phe Asn Thr Thr Thr Arg Asp Ser Glu Asn Tyr Ile His Gly Ile
                245                 250                 255

Cys Tyr Tyr Met Thr Ser Tyr Asp Arg Ser Leu Phe Pro Leu Asn Ile
            260                 265                 270

Ser Ile Met Leu Asn Ser Arg Met Ile Ser Ser Asn Val Ala Tyr Ala
        275                 280                 285

Ile Gln Phe Glu Trp Asn Leu Asn Ala Ser Glu Ser Pro Glu Ser Asn
290                 295                 300

Ile Ala Thr Leu Thr Thr Ser Pro Phe Phe Ser Tyr Ile Thr Glu
305                 310                 315                 320

Asp Asp Asn

<210> SEQ ID NO 3
<211> LENGTH: 201
<212> TYPE: PRT
<213> ORGANISM: Adenovirus type 35

<400> SEQUENCE: 3

Gly Asp Ile Cys Ile Lys Asp Ser Ile Asn Thr Leu Trp Thr Gly Ile
1               5                   10                  15

Asn Pro Pro Asn Cys Gln Ile Val Glu Asn Thr Asn Thr Asn Asp
            20                  25                  30

Gly Lys Leu Thr Leu Val Leu Val Lys Asn Gly Gly Leu Val Asn Gly
        35                  40                  45

Tyr Val Ser Leu Val Gly Val Ser Asp Thr Val Asn Gln Met Phe Thr
50                  55                  60

Gln Lys Thr Ala Asn Ile Gln Leu Arg Leu Tyr Phe Asp Ser Ser Gly
65                  70                  75                  80

Asn Leu Leu Thr Asp Glu Ser Asp Leu Lys Ile Pro Leu Lys Asn Lys
                85                  90                  95

Ser Ser Thr Ala Thr Ser Glu Thr Val Ala Ser Ser Lys Ala Phe Met
            100                 105                 110

Pro Ser Thr Thr Ala Tyr Pro Phe Asn Thr Thr Thr Arg Asp Ser Glu
        115                 120                 125

Asn Tyr Ile His Gly Ile Cys Tyr Tyr Met Thr Ser Tyr Asp Arg Ser
130                 135                 140
```

```
Leu Phe Pro Leu Asn Ile Ser Ile Met Leu Asn Ser Arg Met Ile Ser
145                 150                 155                 160

Ser Asn Val Ala Tyr Ala Ile Gln Phe Glu Trp Asn Leu Asn Ala Ser
                165                 170                 175

Glu Ser Pro Glu Ser Asn Ile Ala Thr Leu Thr Thr Ser Pro Phe Phe
            180                 185                 190

Phe Ser Tyr Ile Thr Glu Asp Asp Asn
        195                 200

<210> SEQ ID NO 4
<211> LENGTH: 611
<212> TYPE: DNA
<213> ORGANISM: Artificial Sequence
<220> FEATURE:
<223> OTHER INFORMATION: Synthetic derived from adenovirus serotype 35
<220> FEATURE:
<221> NAME/KEY: CDS
<222> LOCATION: (1)..(606)

<400> SEQUENCE: 4 ggt gac att tgt ata aag gat agt att aac acc tta tgg act gga ata        48
Gly Asp Ile Cys Ile Lys Asp Ser Ile Asn Thr Leu Trp Thr Gly Ile
1               5                   10                  15 aac cct cca cct aac tgt caa att gtg gaa aac act aat aca aat gat        96
Asn Pro Pro Pro Asn Cys Gln Ile Val Glu Asn Thr Asn Thr Asn Asp
            20                  25                  30 ggc aaa ctt act tta gta tta gta aaa aac gga ggg ctt gtt aat ggc       144
Gly Lys Leu Thr Leu Val Leu Val Lys Asn Gly Gly Leu Val Asn Gly
        35                  40                  45 tac gtg tct cta gtt ggt gta tca gac act gtg aac caa atg ttc aca       192
Tyr Val Ser Leu Val Gly Val Ser Asp Thr Val Asn Gln Met Phe Thr
    50                  55                  60 caa aag aca gca aac atc caa tta aga tta tat ttt gac tct tct gga       240
Gln Lys Thr Ala Asn Ile Gln Leu Arg Leu Tyr Phe Asp Ser Ser Gly
65                  70                  75                  80 aat cta tta act ggt gaa tca gac tta aaa att cca ctt aaa aat aaa       288
Asn Leu Leu Thr Gly Glu Ser Asp Leu Lys Ile Pro Leu Lys Asn Lys
                85                  90                  95 tct tct aca gcg acc agt gaa act gta gcc agc agc aaa gcc ttt atg       336
Ser Ser Thr Ala Thr Ser Glu Thr Val Ala Ser Ser Lys Ala Phe Met
            100                 105                 110 cca agt act aca gct tat ccc ttc aac acc gct act agg gat agt gaa       384
Pro Ser Thr Thr Ala Tyr Pro Phe Asn Thr Ala Thr Arg Asp Ser Glu
        115                 120                 125 aac tac att cat gga ata tgt tac tac atg act agt tat gat aga agt       432
Asn Tyr Ile His Gly Ile Cys Tyr Tyr Met Thr Ser Tyr Asp Arg Ser
    130                 135                 140 cta ttt ccc ttg aac att tct ata atg ctg aac agc cgt atg att tct       480
Leu Phe Pro Leu Asn Ile Ser Ile Met Leu Asn Ser Arg Met Ile Ser
145                 150                 155                 160 tcc aat gtt gcc tat gcc ata caa ttt gaa tgg aat cta aat gca agt       528
Ser Asn Val Ala Tyr Ala Ile Gln Phe Glu Trp Asn Leu Asn Ala Ser
                165                 170                 175 gaa tct cca gaa agc aac ata gct acg ctg acc aca tcc ccc ttt ttc       576
Glu Ser Pro Glu Ser Asn Ile Ala Thr Leu Thr Thr Ser Pro Phe Phe
            180                 185                 190 ttt tct tac att aca gaa gac gac aac taa gctta                         611
Phe Ser Tyr Ile Thr Glu Asp Asp Asn
        195                 200

<210> SEQ ID NO 5
<211> LENGTH: 201
```

```
<212> TYPE: PRT
<213> ORGANISM: Artificial Sequence
<220> FEATURE:
<223> OTHER INFORMATION: Synthetic Construct

<400> SEQUENCE: 5

Gly Asp Ile Cys Ile Lys Asp Ser Ile Asn Thr Leu Trp Thr Gly Ile
1               5                   10                  15

Asn Pro Pro Asn Cys Gln Ile Val Glu Asn Thr Asn Thr Asn Asp
            20                  25                  30

Gly Lys Leu Thr Leu Val Leu Val Lys Asn Gly Gly Leu Val Asn Gly
            35                  40                  45

Tyr Val Ser Leu Val Gly Val Ser Asp Thr Val Asn Gln Met Phe Thr
        50                  55                  60

Gln Lys Thr Ala Asn Ile Gln Leu Arg Leu Tyr Phe Asp Ser Ser Gly
65                  70                  75                  80

Asn Leu Leu Thr Gly Glu Ser Asp Leu Lys Ile Pro Leu Lys Asn Lys
                85                  90                  95

Ser Ser Thr Ala Thr Ser Glu Thr Val Ala Ser Ser Lys Ala Phe Met
            100                 105                 110

Pro Ser Thr Thr Ala Tyr Pro Phe Asn Thr Ala Thr Arg Asp Ser Glu
            115                 120                 125

Asn Tyr Ile His Gly Ile Cys Tyr Tyr Met Thr Ser Tyr Asp Arg Ser
130                 135                 140

Leu Phe Pro Leu Asn Ile Ser Ile Met Leu Asn Ser Arg Met Ile Ser
145                 150                 155                 160

Ser Asn Val Ala Tyr Ala Ile Gln Phe Glu Trp Asn Leu Asn Ala Ser
                165                 170                 175

Glu Ser Pro Glu Ser Asn Ile Ala Thr Leu Thr Thr Ser Pro Phe Phe
            180                 185                 190

Phe Ser Tyr Ile Thr Glu Asp Asp Asn
            195                 200

<210> SEQ ID NO 6
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Wherein Xaa at position 9 is either "D"
      (wild-type) or "G" (mutant)

<400> SEQUENCE: 6

Asp Ser Ser Gly Asn Leu Leu Thr Xaa Glu Ser Asp Leu Lys Ile Pro
1               5                   10                  15

Leu

<210> SEQ ID NO 7
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(23)
<223> OTHER INFORMATION: Wherein Xaa at position 23 is either "T"
      (wild-type) or "A" (mutant)
<220> FEATURE:
<221> NAME/KEY: MISC_FEATURE
```

```
<222> LOCATION: (34)..(34)
<223> OTHER INFORMATION: Wherein Xaa at position 34 is either "I"
      (wild-type) or "L" (mutant)

<400> SEQUENCE: 7

Thr Ser Glu Thr Val Ala Ser Ser Lys Ala Phe Met Pro Ser Thr Thr
1               5                   10                  15

Ala Tyr Pro Phe Asn Thr Xaa Thr Arg Asp Ser Glu Asn Tyr Ile His
            20                  25                  30

Gly Xaa

<210> SEQ ID NO 8
<211> LENGTH: 12
<212> TYPE: PRT
<213> ORGANISM: Artificial Sequence
<220> FEATURE:
<223> OTHER INFORMATION: Synthetic

<400> SEQUENCE: 8

Leu Asn Ser Arg Met Ile Ser Ser Asn Val Ala Tyr
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Synthetic

<400> SEQUENCE: 9

Ala Ser Glu Ser Pro Glu Ser Asn Ile Ala Thr Leu Thr Thr Ser Pro
1               5                   10                  15

Phe

<210> SEQ ID NO 10
<211> LENGTH: 34
<212> TYPE: DNA
<213> ORGANISM: Artificial Sequence
<220> FEATURE:
<223> OTHER INFORMATION: Synthetic derived from adenovirus serotype 35

<400> SEQUENCE: 10
tttaaggatc cggtgacatt tgtataaagg atag                              34

<210> SEQ ID NO 11
<211> LENGTH: 30
<212> TYPE: DNA
<213> ORGANISM: Artificial Sequence
<220> FEATURE:
<223> OTHER INFORMATION: Synthetic derived from adenovirus serotype 35

<400> SEQUENCE: 11
tatataagct tagttgtcgt cttctgtaat                                   30

<210> SEQ ID NO 12
<211> LENGTH: 60
<212> TYPE: DNA
<213> ORGANISM: Artificial Sequence
<220> FEATURE:
<223> OTHER INFORMATION: Synthetic derived from adenovirus serotype 35

<400> SEQUENCE: 12
cgtcagcacg gatccggtga catttgtata aaggatagta ttaacacctt atggactgga  60

<210> SEQ ID NO 13
```

```
<211> LENGTH: 32
<212> TYPE: DNA
<213> ORGANISM: Artificial Sequence
<220> FEATURE:
<223> OTHER INFORMATION: Synthetic derived from adenovirus serotype 35

<400> SEQUENCE: 13
ccaagctcag ctaattaagc ttagttgtcg tc                                  32

<210> SEQ ID NO 14
<211> LENGTH: 369
<212> TYPE: PRT
<213> ORGANISM: Homo sapiens

<400> SEQUENCE: 14
```

| Met | Glu | Pro | Pro | Gly | Arg | Arg | Glu | Cys | Pro | Phe | Pro | Ser | Trp | Arg | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Pro | Gly | Leu | Leu | Leu | Ala | Ala | Met | Val | Leu | Leu | Tyr | Ser | Phe | Ser |
|-----|-----|-----|-----|-----|-----|-----|-----|-----|-----|-----|-----|-----|-----|-----|
|     |     |     | 20  |     |     |     |     | 25  |     |     |     |     | 30  |     |

| Asp | Ala | Cys | Glu | Glu | Pro | Pro | Thr | Phe | Glu | Ala | Met | Glu | Leu | Ile | Gly |
|-----|-----|-----|-----|-----|-----|-----|-----|-----|-----|-----|-----|-----|-----|-----|-----|
|     |     |     | 35  |     |     |     |     | 40  |     |     |     |     | 45  |     |     |

| Lys | Pro | Lys | Pro | Tyr | Tyr | Glu | Ile | Gly | Glu | Arg | Val | Asp | Tyr | Lys | Cys |
|-----|-----|-----|-----|-----|-----|-----|-----|-----|-----|-----|-----|-----|-----|-----|-----|
| 50  |     |     |     |     | 55  |     |     |     |     | 60  |     |     |     |     |     |

| Lys | Lys | Gly | Tyr | Phe | Tyr | Ile | Pro | Pro | Leu | Ala | Thr | His | Thr | Ile | Cys |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Asp | Arg | Asn | His | Thr | Trp | Leu | Pro | Val | Ser | Asp | Asp | Ala | Cys | Tyr | Arg |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Glu | Thr | Cys | Pro | Tyr | Ile | Arg | Asp | Pro | Leu | Asn | Gly | Gln | Ala | Val | Pro |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Ala | Asn | Gly | Thr | Tyr | Glu | Phe | Gly | Tyr | Gln | Met | His | Phe | Ile | Cys | Asn |
|-----|-----|-----|-----|-----|-----|-----|-----|-----|-----|-----|-----|-----|-----|-----|-----|
|     |     |     | 115 |     |     |     |     | 120 |     |     |     |     | 125 |     |     |

| Glu | Gly | Tyr | Tyr | Leu | Ile | Gly | Glu | Glu | Ile | Leu | Tyr | Cys | Glu | Leu | Lys |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Gly | Ser | Val | Ala | Ile | Trp | Ser | Gly | Lys | Pro | Pro | Ile | Cys | Glu | Lys | Val |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Leu | Cys | Thr | Pro | Pro | Lys | Ile | Lys | Asn | Gly | Lys | His | Thr | Phe | Ser |
|-----|-----|-----|-----|-----|-----|-----|-----|-----|-----|-----|-----|-----|-----|-----|
|     |     |     | 165 |     |     |     |     | 170 |     |     |     |     | 175 |     |

| Glu | Val | Glu | Val | Phe | Glu | Tyr | Leu | Asp | Ala | Val | Thr | Tyr | Ser | Cys | Asp |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Pro | Ala | Pro | Gly | Pro | Asp | Pro | Phe | Ser | Leu | Ile | Gly | Glu | Ser | Thr | Ile |
|-----|-----|-----|-----|-----|-----|-----|-----|-----|-----|-----|-----|-----|-----|-----|-----|
|     |     |     | 195 |     |     |     |     | 200 |     |     |     |     | 205 |     |     |

| Tyr | Cys | Gly | Asp | Asn | Ser | Val | Trp | Ser | Arg | Ala | Ala | Pro | Glu | Cys | Lys |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Val | Val | Lys | Cys | Arg | Phe | Pro | Val | Val | Glu | Asn | Gly | Lys | Gln | Ile | Ser |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Gly | Phe | Gly | Lys | Lys | Phe | Tyr | Tyr | Lys | Ala | Thr | Val | Met | Phe | Glu | Cys |
|-----|-----|-----|-----|-----|-----|-----|-----|-----|-----|-----|-----|-----|-----|-----|-----|
|     |     |     | 245 |     |     |     |     | 250 |     |     |     |     | 255 |     |     |

| Asp | Lys | Gly | Phe | Tyr | Leu | Asp | Gly | Ser | Asp | Thr | Ile | Val | Cys | Asp | Ser |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Asn | Ser | Thr | Trp | Asp | Pro | Pro | Val | Pro | Lys | Cys | Leu | Lys | Gly | Pro | Arg |
|-----|-----|-----|-----|-----|-----|-----|-----|-----|-----|-----|-----|-----|-----|-----|-----|
|     |     |     | 275 |     |     |     |     | 280 |     |     |     |     | 285 |     |     |

| Pro | Thr | Tyr | Lys | Pro | Pro | Val | Ser | Asn | Tyr | Pro | Gly | Tyr | Pro | Lys | Pro |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Glu | Glu | Gly | Ile | Leu | Asp | Ser | Leu | Asp | Val | Trp | Val | Ile | Ala | Val | Ile |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Val | Ile | Ala | Ile | Val | Val | Gly | Val | Ala | Val | Ile | Cys | Val | Val | Pro | Tyr |
|-----|-----|-----|-----|-----|-----|-----|-----|-----|-----|-----|-----|-----|-----|-----|-----|
|     |     |     | 325 |     |     |     |     | 330 |     |     |     |     | 335 |     |     |

```
Arg Tyr Leu Gln Arg Arg Lys Lys Gly Lys Ala Asp Gly Gly Ala
                340                 345                 350

Glu Tyr Ala Thr Tyr Gln Thr Lys Ser Thr Thr Pro Ala Glu Gln Arg
            355                 360                 365

Gly

<210> SEQ ID NO 15
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (9)..(9)
<223> OTHER INFORMATION: Wherein Xaa at position 9 is any amino acid;
      or D (wild type); or G (mutant); or E (conservative substitution)

<400> SEQUENCE: 15

Asp Ser Ser Gly Asn Leu Leu Thr Xaa Glu Ser Asp Leu Lys Ile Pro
1               5                   10                  15

<210> SEQ ID NO 16
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Wherein Xaa at position 6 is any amino acid;
      or D (wild type); or G (mutant); or E (conservative substitution)

<400> SEQUENCE: 16

Gly Asn Leu Leu Thr Xaa Glu Ser Asp Leu Lys
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Wherein Xaa at position 5 is any amino acid;
      or D (wild type); or G (mutant); or E (conservative substitution)

<400> SEQUENCE: 17

Asn Leu Leu Thr Xaa Glu Ser Asp Leu
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Wherein Xaa at position 4 is any amino acid;
      or D (wild type); or G (mutant); or E (conservative substitution)

<400> SEQUENCE: 18

Leu Leu Thr Xaa Glu Ser Asp
1               5
```

```
<210> SEQ ID NO 19
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Wherein Xaa at position 3 is any amino acid;
      or D (wild type); or G (mutant); or E (conservative substitution)

<400> SEQUENCE: 19

Leu Thr Xaa Glu Ser
1               5

<210> SEQ ID NO 20
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Wherein Xaa at position 2 is any amino acid;
      or D (wild type); or G (mutant); or E (conservative substitution)

<400> SEQUENCE: 20

Thr Xaa Glu
1

<210> SEQ ID NO 21
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Wherein Xaa at position 6 is any amino acid;
      or D (wild type); or G (mutant); or E (conservative substitution)

<400> SEQUENCE: 21

Gly Asn Leu Leu Thr Xaa Glu Ser
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Wherein Xaa at position 6 is any amino acid; or
<220> FEATURE:
<221> NAME/KEY: MISC_FEATURE
<222> LOCATION: (6)..(6)
<223> OTHER INFORMATION: Wherein Xaa at position 6 is any amino acid; or
<220> FEATURE:
<221> NAME/KEY: MISC_FEATURE
<222> LOCATION: (6)..(6)
<223> OTHER INFORMATION: Wherein Xaa at position 6 is G (mutant); or
<220> FEATURE:
<221> NAME/KEY: MISC_FEATURE
<222> LOCATION: (6)..(6)
<223> OTHER INFORMATION: Wherein Xaa at position 6 is E (conservative
      substitution)
```

```
<400> SEQUENCE: 22

Gly Asn Leu Leu Thr Xaa
1               5

<210> SEQ ID NO 23
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (23)..(23)
<223> OTHER INFORMATION: Wherein Xaa at position 23 is any amino acid;
      or T (wild type); or A (mutant); or is C, G, N, Q, S, or Y; or is
      F, I, L, M, P, V, or W
<220> FEATURE:
<221> NAME/KEY: MISC_FEATURE
<222> LOCATION: (23)..(23)
<223> OTHER INFORMATION: Wherein Xaa at position 34 is any amino acid;
      or I (wild type); or L (mutant); or is A, F, M. P, V, or W
<220> FEATURE:
<221> NAME/KEY: misc_feature
<222> LOCATION: (34)..(34)
<223> OTHER INFORMATION: Xaa can be any naturally occurring amino acid

<400> SEQUENCE: 23

Thr Ser Glu Thr Val Ala Ser Ser Lys Ala Phe Met Pro Ser Thr Thr
1               5                   10                  15

Ala Tyr Pro Phe Asn Thr Xaa Thr Arg Asp Ser Glu Asn Tyr Ile His
            20                  25                  30

Gly Xaa

<210> SEQ ID NO 24
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Wherein Xaa at position 4 is any amino acid;
      or T (wild type); or A (mutant); or is C, G, N, Q, S, or Y; or is
      F, I, L, M, P, V, or W
<220> FEATURE:
<221> NAME/KEY: MISC_FEATURE
<222> LOCATION: (15)..(15)
<223> OTHER INFORMATION: Wherein Xaa at position 15 is any amino acid;
      or I (wild type); or L (mutant); or is A, F, M. P, V, or W

<400> SEQUENCE: 24

Phe Asn Thr Xaa Thr Arg Asp Ser Glu Asn Tyr Ile His Gly Xaa
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Wherein Xaa at position 4 is any amino acid; or
      T (wild type); or A (mutant); or is C, G, N, Q, S, or Y; or is F,
      I, L, M, P, V, or W

<400> SEQUENCE: 25

Phe Asn Thr Xaa Thr Arg Asp
1               5
```

```
<210> SEQ ID NO 26
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Wherein Xaa at position 3 is any amino acid; or
      T (wild type); or A (mutant); or is C, G, N, Q, S, or Y; or is F,
      I, L, M, P, V, or W

<400> SEQUENCE: 26

Asn Thr Xaa Thr Arg
1               5

<210> SEQ ID NO 27
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Wherein Xaa at position 2 is any amino acid; or
      T (wild type); or A (mutant); or is C, G, N, Q, S, or Y; or is F,
      I, L, M, P, V, or W

<400> SEQUENCE: 27

Thr Xaa Thr
1

<210> SEQ ID NO 28
<211> LENGTH: 12
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein Xaa at position 1 is any amino acid; or
      T (wild type); or A (mutant); or is C, G, N, Q, S, or Y; or is F,
      I, L, M, P, V, or W
<220> FEATURE:
<221> NAME/KEY: MISC_FEATURE
<222> LOCATION: (12)..(12)
<223> OTHER INFORMATION: Wherein Xaa at position 12 is any amino acid;
      or I (wild type); or L (mutant); or is A, F, M. P, V, or W

<400> SEQUENCE: 28

Xaa Thr Arg Asp Ser Glu Asn Tyr Ile His Gly Xaa
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (11)..(11)
<223> OTHER INFORMATION: Wherein Xaa at position 11 is any amino acid;
      or I (wild type); or L (mutant); or is A, F, M. P, V, or W

<400> SEQUENCE: 29

Thr Arg Asp Ser Glu Asn Tyr Ile His Gly Xaa
1               5                   10
```

```
<210> SEQ ID NO 30
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Wherein Xaa at position 5 is any amino acid; or
      I (wild type); or L (mutant); or is A, F, M. P, V, or W

<400> SEQUENCE: 30

Tyr Ile His Gly Xaa
1               5

<210> SEQ ID NO 31
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Wherein Xaa at position 3 is any amino acid; or
      I (wild type); or L (mutant); or is A, F, M. P, V, or W

<400> SEQUENCE: 31

His Gly Xaa
1

<210> SEQ ID NO 32
<211> LENGTH: 27
<212> TYPE: PRT
<213> ORGANISM: Artificial Sequence
<220> FEATURE:
<223> OTHER INFORMATION: Synthetic

<400> SEQUENCE: 32

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 33
<211> LENGTH: 201
<212> TYPE: PRT
<213> ORGANISM: Adenovirus serotype 21

<400> SEQUENCE: 33

Gly Asp Ile Cys Ile Lys Asp Ser Ile Asn Thr Leu Trp Thr Gly Ile
1               5                   10                  15

Lys Pro Pro Pro Asn Cys Gln Ile Val Glu Asn Thr Asp Thr Asn Asp
            20                  25                  30

Gly Lys Leu Thr Leu Val Leu Val Lys Asn Gly Gly Leu Val Asn Gly
                35                  40                  45

Tyr Val Ser Leu Val Gly Val Ser Asp Thr Val Asn Gln Met Phe Thr
50                  55                  60

Gln Lys Ser Ala Thr Ile Gln Leu Arg Leu Tyr Phe Asp Ser Ser Gly
65                  70                  75                  80

Asn Leu Leu Thr Asp Glu Ser Asn Leu Lys Ile Pro Leu Lys Asn Lys
                85                  90                  95

Ser Ser Thr Ala Thr Ser Glu Ala Ala Thr Ser Ser Lys Ala Phe Met
```

```
                100                 105                 110
Pro Ser Thr Thr Ala Tyr Pro Phe Asn Thr Thr Thr Arg Asp Ser Glu
        115                 120                 125

Asn Tyr Ile His Gly Ile Cys Tyr Tyr Met Thr Ser Tyr Asp Arg Ser
        130                 135                 140

Leu Val Pro Leu Asn Ile Ser Ile Met Leu Asn Ser Arg Thr Ile Ser
145                 150                 155                 160

Ser Asn Val Ala Tyr Ala Ile Gln Phe Glu Trp Asn Leu Asn Ala Lys
                165                 170                 175

Glu Ser Pro Glu Ser Asn Ile Ala Thr Leu Thr Thr Ser Pro Phe Phe
        180                 185                 190

Phe Ser Tyr Ile Arg Glu Asp Asp Asn
        195                 200

<210> SEQ ID NO 34
<211> LENGTH: 201
<212> TYPE: PRT
<213> ORGANISM: Adenovirus serotype 50

<400> SEQUENCE: 34

Gly Asp Ile Cys Ile Lys Asp Ser Ile Asn Thr Leu Trp Thr Gly Ile
1               5                   10                  15

Lys Pro Pro Asn Cys Gln Ile Val Glu Asn Thr Asp Thr Asn Asp
            20                  25                  30

Gly Lys Leu Thr Leu Val Leu Val Lys Asn Gly Gly Leu Val Asn Gly
        35                  40                  45

Tyr Val Ser Leu Val Gly Val Ser Asp Thr Val Asn Gln Met Phe Thr
50                  55                  60

Gln Lys Ser Ala Thr Ile Gln Leu Arg Leu Tyr Phe Asp Ser Ser Gly
65                  70                  75                  80

Asn Leu Leu Thr Asp Glu Ser Asn Leu Lys Ile Pro Leu Lys Asn Lys
                85                  90                  95

Ser Ser Thr Ala Thr Ser Glu Ala Ala Thr Ser Ser Lys Ala Phe Met
            100                 105                 110

Pro Ser Thr Thr Ala Tyr Pro Phe Asn Thr Thr Thr Arg Asp Ser Glu
        115                 120                 125

Asn Tyr Ile His Gly Ile Cys Tyr Tyr Met Thr Ser Tyr Asp Arg Ser
        130                 135                 140

Leu Val Pro Leu Asn Ile Ser Ile Met Leu Asn Ser Arg Thr Ile Ser
145                 150                 155                 160

Ser Asn Val Ala Tyr Ala Ile Gln Phe Glu Trp Asn Leu Asn Ala Lys
                165                 170                 175

Glu Ser Pro Glu Ser Asn Ile Ala Thr Leu Thr Thr Ser Pro Phe Phe
        180                 185                 190

Phe Ser Tyr Ile Arg Glu Asp Asp Asn
        195                 200

<210> SEQ ID NO 35
<211> LENGTH: 203
<212> TYPE: PRT
<213> ORGANISM: Adenovirus serotype 11

<400> SEQUENCE: 35

Asn Asn Ile Cys Ile Asp Asp Asn Ile Asn Thr Leu Trp Thr Gly Val
1               5                   10                  15

Asn Pro Thr Glu Ala Asn Cys Gln Ile Met Asn Ser Ser Glu Ser Asn
            20                  25                  30
```

```
Asp Cys Lys Leu Ile Leu Thr Leu Val Lys Thr Gly Ala Leu Val Thr
        35                  40                  45

Ala Phe Val Tyr Val Ile Gly Val Ser Asn Asn Phe Asn Met Leu Thr
 50                  55                  60

Thr His Arg Asn Ile Asn Phe Thr Ala Glu Leu Phe Phe Asp Ser Thr
 65                  70                  75                  80

Gly Asn Leu Leu Thr Arg Leu Ser Ser Leu Lys Thr Pro Leu Asn His
                 85                  90                  95

Lys Ser Gly Gln Asn Met Ala Thr Gly Ala Ile Thr Asn Ala Lys Gly
            100                 105                 110

Phe Met Pro Ser Thr Thr Ala Tyr Pro Phe Asn Asp Asn Ser Arg Glu
        115                 120                 125

Lys Glu Asn Tyr Ile Tyr Gly Thr Cys Tyr Tyr Thr Ala Ser Asp Arg
130                 135                 140

Thr Ala Phe Pro Ile Asp Ile Ser Val Met Leu Asn Arg Arg Ala Ile
145                 150                 155                 160

Asn Asp Glu Thr Ser Tyr Cys Ile Arg Ile Thr Trp Ser Trp Asn Thr
                165                 170                 175

Gly Asp Ala Pro Glu Val Gln Thr Ser Ala Thr Thr Leu Val Thr Ser
            180                 185                 190

Pro Phe Thr Phe Tyr Tyr Ile Arg Glu Asp Asp
        195                 200

<210> SEQ ID NO 36
<211> LENGTH: 202
<212> TYPE: PRT
<213> ORGANISM: Adenovirus serotype 16

<400> SEQUENCE: 36

Ser Ser Asn Ala Ile Thr Ile Glu Asn Asn Thr Leu Trp Thr Gly Ala
 1               5                  10                  15

Lys Pro Ser Ala Asn Cys Val Ile Lys Glu Gly Glu Asp Ser Pro Asp
             20                  25                  30

Cys Lys Leu Thr Leu Val Leu Val Lys Asn Gly Gly Leu Ile Asn Gly
        35                  40                  45

Tyr Ile Thr Leu Met Gly Ala Ser Glu Tyr Thr Asn Thr Leu Phe Lys
 50                  55                  60

Asn Asn Gln Val Thr Ile Asp Val Asn Leu Ala Phe Asp Asn Thr Gly
 65                  70                  75                  80

Gln Ile Ile Thr Tyr Leu Ser Ser Leu Lys Ser Asn Leu Asn Phe Lys
                 85                  90                  95

Asp Asn Gln Asn Met Ala Thr Gly Thr Ile Thr Ser Ala Lys Gly Phe
            100                 105                 110

Met Pro Ser Thr Thr Ala Tyr Pro Phe Ile Thr Tyr Ala Thr Glu Thr
        115                 120                 125

Leu Asn Glu Asp Tyr Ile Tyr Gly Glu Cys Tyr Tyr Lys Ser Thr Asn
130                 135                 140

Gly Thr Leu Phe Pro Leu Lys Val Thr Val Thr Leu Asn Arg Arg Met
145                 150                 155                 160

Leu Ala Ser Gly Met Ala Tyr Ala Met Asn Phe Ser Trp Ser Leu Asn
                165                 170                 175

Ala Glu Glu Ala Pro Glu Thr Thr Glu Val Thr Leu Ile Thr Ser Pro
            180                 185                 190

Phe Phe Phe Ser Tyr Ile Arg Glu Asp Asp
        195                 200
```

<210> SEQ ID NO 37
<211> LENGTH: 618
<212> TYPE: DNA
<213> ORGANISM: Artificial Sequence
<220> FEATURE:
<223> OTHER INFORMATION: Synthetic

<400> SEQUENCE: 37

```
catatgggcg acatctgcat caaagacagc attaacacgt tatggacggg catcaacccg     60
cctccgaatt gccagattgt ggagaatacc aataccaatg atggtaagct gaccctggtt    120
ctggtgaaaa acggtggcct ggtgaatggt tatgttagcc tggtcggcgt cagcgatacg    180
gttaaccaaa tgttcaccca aaagacggcg aatatccagc tgcgtctttwithdrawn ctttgactct    240
tcgggtaatc tgttgaccgg tgaatctgat ctgaaaatcc cgttgaaaaa caagagcagc    300
accgcaacct ccgaaacggt tgctagcagc aaggccttta tgccgagcac caccgcgtac    360
ccgtttaaca cggcgacccg tgatagcgaa aactacattc acggtatttg ttactatatg    420
accagctatg atcgctctct gtttccactg aacatttcga tcatgctgaa ttcccgtatg    480
atcagctcca acgtagcgta cgccattcag ttcgagtgga atctgaatgc aagcgagagc    540
ccggaaagca acattgcgac gttgaccact agcccgttct tcttcagcta tatcaccgag    600
gacgacaatt gagcttaa                                                   618
```

<210> SEQ ID NO 38
<211> LENGTH: 202
<212> TYPE: PRT
<213> ORGANISM: Artificial Sequence
<220> FEATURE:
<223> OTHER INFORMATION: Synthetic

<400> SEQUENCE: 38

Met Gly Asp Ile Cys Ile Lys Asp Ser Ile Asn Thr Leu Trp Thr Gly
1               5                   10                  15

Ile Asn Pro Pro Asn Cys Gln Ile Val Glu Asn Thr Asn Thr Asn
            20                  25                  30

Asp Gly Lys Leu Thr Leu Val Leu Val Lys Asn Gly Gly Leu Val Asn
        35                  40                  45

Gly Tyr Val Ser Leu Val Gly Val Ser Asp Thr Val Asn Gln Met Phe
    50                  55                  60

Thr Gln Lys Thr Ala Asn Ile Gln Leu Arg Leu Tyr Phe Asp Ser Ser
65                  70                  75                  80

Gly Asn Leu Leu Thr Gly Glu Ser Asp Leu Lys Ile Pro Leu Lys Asn
                85                  90                  95

Lys Ser Ser Thr Ala Thr Ser Glu Thr Val Ala Ser Ser Lys Ala Phe
            100                 105                 110

Met Pro Ser Thr Thr Ala Tyr Pro Phe Asn Thr Ala Thr Arg Asp Ser
        115                 120                 125

Glu Asn Tyr Ile His Gly Ile Cys Tyr Tyr Met Thr Ser Tyr Asp Arg
    130                 135                 140

Ser Leu Phe Pro Leu Asn Ile Ser Ile Met Leu Asn Ser Arg Met Ile
145                 150                 155                 160

Ser Ser Asn Val Ala Tyr Ala Ile Gln Phe Glu Trp Asn Leu Asn Ala
                165                 170                 175

Ser Glu Ser Pro Glu Ser Asn Ile Ala Thr Leu Thr Thr Ser Pro Phe
            180                 185                 190

Phe Phe Ser Tyr Ile Thr Glu Asp Asp Asn

```
<210> SEQ ID NO 39
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: Wherein N at any position is A, C, G or T; and
      wherein D at any position is A, G or T

<400> SEQUENCE: 39
nnnnndtgag gaggtndtg                                                  19
```

COMPOSITIONS AND METHODS FOR MODULATING THE ACTIVITY OF COMPLEMENT REGULATORY PROTEINS ON TARGET CELLS

CROSS-REFERENCES TO RELATED APPLICATIONS

This application claims the benefit of U.S. Provisional Application No. 61/165,434, filed Mar. 31, 2009, and U.S. Provisional Application No. 61/255,450, filed Oct. 27, 2009, which applications are incorporated herein by reference in their entirety.

STATEMENT OF GOVERNMENT LICENSE RIGHTS

This invention was made with U.S. Government support under grant number HL078836 awarded by the National Institutes of Health. The U.S. Government has certain rights in this invention.

BACKGROUND

The complement system is the major effector of the humoral aspect of the immune system. The classical pathway of complement activation involves the binding of soluble components, such as certain classes and subclasses of antibodies, to antigen targets within the body. Conformational changes in the Fc regions of these bound antibodies expose binding sites for C1, a soluble component of the complement system in its inactive state. Upon stable binding, C1 undergoes conformational changes resulting in active protease activity of one of the C1 subcomponents. The protease activity initiates a cascade of highly regulated interactions between complement components. A result of the cascade is the assembly of a membrane attack complex (MAC) on target cells.

An important step in the cascade of interactions of complement activation is the step of converting the component C3 into active C3b because there is tremendous amplification of the activation signal during this step. Particularly, an individual C3 convertase is able to convert hundreds of molecules of C3 into C3b. Each C3b component, in turn, forms part of a C5 convertase, producing C5b. Each activated C5b molecule initiates the formation of the MAC. The MAC is a macromolecular structure that penetrates through the cell membrane to create a transmembrane pore. The pore disrupts the integrity of the membrane and allows ions and small molecules to freely diffuse through, leading to complement-dependent-cytolysis (CDC).

Monoclonal antibodies (mAbs) have emerged as a potentially powerful class of novel therapeutics for a number of diseases. For example, in the field of oncology, there are several marketed therapeutic mAbs for treatment of cancer, and there are hundreds of mAbs currently in clinical development (see J. Castillo, et al., *Experimental Hematology* 36:755-768 (2008)). Many of these therapeutic mAbs operate by activating the complement cascade leading to the assembly of MACs on transformed tumor cells, causing CDC. This therapeutic approach can be advantageous because the antibodies can be specifically targeted towards antigens that are specific to transformed tumor cells, thus avoiding many side effects resulting from existing treatments.

However, the therapeutic potential of therapeutic mAbs can be limited due to the ability of diseased cells to block killing by CDC through the expression of membrane complement regulatory proteins (CRPs), such as CD35, CD46, CD55, and CD59 (D. Gancz and Z. Fishelson, *Molecular Immunology* 46:2794-2800 (2009); J. Golay, et al., *Blood* 98:3383-3389 (2001); K. A. Gelderman et al., *Laboratory Investigation: A Journal of Technical Methods and Pathology* 82:483-493 (2002); and N. Donin et al., *Clinical and Experimental Immunology* 131:254-263 (2003)). CD46 and CD55 block the complement cascade at the C3 activation stage and CD59 prevents assembly of the MAC of complement (Z. Fishelson et al., *Molecular Immunology* 40:109-123 (2003)).

Therefore, there is a need for compositions and methods to reduce the presence of CD35, CD46, CD55, and CD59 on the surface of target cells in order to reduce CRP-mediated inhibition of the MAC of complement.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The invention described herein provides compositions and agents capable of reducing the activity, amount, or density of complement regulatory proteins (CRPs) on target cells. The invention also provides methods of identification of such compositions and agents, methods of making, and uses thereof. Further, the invention also provides methods of increasing the susceptibility of a target cell or tissue to a therapeutic agent-mediated complement dependent cytolysis (CDC) and the therapeutic agent-mediated assembly of a membrane attack complex (MAC) on the target cell or tissue.

In one aspect, the invention described herein provides a composition comprising a modified polypeptide capable of reducing the activity, amount, or density of a complement regulatory protein (CRP) on a target cell surface, wherein the polypeptide comprises a non-naturally occurring amino acid sequence. In one embodiment, the polypeptide causes internalization or sequestration of the CRP. In another embodiment, the polypeptide binds to the CRP. In certain embodiments, the polypeptide binds to the CRP with a dissociation constant ($K_d$) of 1 nM or less or the polypeptide binds to the CRP with a dissociation constant ($K_d$) of 65 nM or less. In one specific embodiment, the polypeptide is an isolated viral protein. In such an embodiment, the polypeptide is derived from an adenoviral fiber knob protein—for example, an Ad35 fiber knob protein. In a related embodiment, the polypeptide is derived from the Ad35 fiber knob protein comprising at least one amino acid substitution at the residues selected from Asp207, Thr245, Ile256, and a combination thereof. In a specific embodiment, the amino acid substitution is Asp207Gly, Thr245Ala, Ile256Leu, or a combination thereof. In another embodiment, the polypeptide is less than 25,000 Daltons. In yet another embodiment, the composition comprises a dimeric form of the polypeptide, a trimeric form of the polypeptide, or a homotrimeric form of the polypeptide. In these embodiments, the CRP is a transmembrane protein and/or is a GPI-linked protein. In specific embodiments, the CRP is CD46, CD55, CD59, or CD35. In a very specific embodiment, the CRP is CD46. In another specific embodiment, the polypeptide binds CD46. The compositions provided in these embodiments are further capable of sensitizing the target cell to antibody-mediated complement-dependent cytolysis and/or assembly of a membrane attack complex. In the embodiments described herein, the target cell can be a tumor cell. The tumor cell can be selected from the group consisting of a cell obtained from a carcinoma, a cell obtained from a sarcoma, a cell obtained from a blastoma, a cell obtained from a germ cell cancer, and a cell obtained from a hematological tumor. The tumor cell can also be selected from the group consisting of primary lymphoma cells, Raji-Burkitt's lymphoma cells, BJAB cells, Farage cells, BT474 cells, HT1854 cells, LoVo cells, HT29 cells, Mino cells, Jurkat cells, K562 cells, HeLa cells, A549 cells, SKOV3 cells, HT29 cells, and MDA235MB cells. In one specific embodiment, the target cell comprises a cell surface marker for a solid tumor. The solid tumor can be a tumor of the breast, lung, colorectal system, stomach, prostate, ovary, uterus, cervix, kidney, pancreas, liver, brain, head and neck, nasopharyngeal system, or esophagus. In another specific embodiment, the target cell comprises a cell surface marker for a sarcoma. The sarcoma can be leiomyosarcoma, fibrosarcoma, rhabdomyosarcomas, or Ewing's sarcoma. In another specific embodiment, the target cell comprises a cell surface marker for a hematological tumor. A hematological tumor can be a leukemia, lymphoma, or myeloma. In a more specific embodiment, the target cell is a B-cell, either a normal B-cell or a malignant B-cell. The target cells can express one or cellular markers selected from the group consisting of CD3, CD10, CD19, CD20, CD22, CD23, CD25, CD30, CD33, CD35, CD37, CD38, CD40, CD44, CD52, CD70, CD80, CD133, CD200, epidermal growth factor receptor 1 (EGFR), epidermal growth factor receptor 2 (Her2/neu), human milk fat globule 1 (HMFG1), interleukin 2 receptor (IL2R), mucin 1, and vascular endothelial growth factors. In a specific embodiment, the target cell expresses CD20. In related embodiments, the polypeptide is further capable of increasing complement activation on the target cell surface and/or the polypeptide is capable of increasing the assembly of a membrane attack complex (MAC) on the target cell surface. In other related embodiments, the polypeptide is capable of reducing the activity, amount, or density of the complement regulatory protein (CRP) by at least 25% when compared to baseline or the unmodified polypeptide; the polypeptide is capable of reducing the activity, amount, or density of the complement regulatory protein (CRP) for at least 24 hours; and/or the polypeptide is active at concentrations of about 25 ng/ml or less. In other related embodiments, the polypeptide is not an antibody or an antibody fragment; the polypeptide is not a growth factor or a cytokine; the polypeptide does not bind a transcriptional regulatory region of a gene; the polypeptide does not bind a promoter region, enhancer region, silencer region or insulator region of a gene; and/or the polypeptide does not bind a transcription factor. In other related embodiments, the polypeptide is at least 120 amino acids in length; the polypeptide comprises at least one mutation of a naturally occurring protein or protein domain; the polypeptide comprises at least 90% amino acid sequence homology to a naturally occurring protein or protein domain; and/or the polypeptide is not a naturally occurring protein or protein fragment. In yet other related embodiments, the polypeptide is further modified to reduce immunogenicity. The immunogenicity of the polypeptide can be reduced by coupling the polypeptide to an alkyl-PEG, by epitope de-immunization, by co-administering an immunosuppressive agent, by adding a tolerizing regimen, by glycosylating the polypeptide, or by co-administering an agent that enhances complement activation. In another embodiment, the composition provided in this aspect comprises a modified virus or a modified CRP-interacting microorganism—for example, a *Neisseria* or *Streptococcal* bacterial strain. In one such embodiment, the virus is capable of interacting with the CRP and is selected from the group consisting of an adenovirus, an adeno-associated virus, a retrovirus, a herpes virus, a measles virus (Edmonston strain), human herpes virus 6, a bovine viral diarrhea virus, and a human coxsackie virus. In a specific related embodiment, the composition provided in this aspect does not comprise an adenovirus. In another specific related embodiment, the composition provided in this aspect does comprise an adenovirus—for example, an adenovirus serotype selected from the group consisting of Ad11, Ad16, Ad21, Ad34, Ad35, and Ad50. In a very specific embodiment, the adenovirus is Ad35, and the Ad35 adenovirus optionally comprises a mutated fiber knob protein.

In another aspect, the invention described herein provides an isolated polypeptide having a first domain and a second domain, wherein the first and second domains bind a CRP, wherein the first domain comprises the amino acid sequence set forth in SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, or SEQ ID NO:31, and wherein $X_1$ is not Aspartate, $X_2$ is not Threonine, or $X_3$ is not Isoleucine. In a specific embodiment, $X_1$ is Glycine or $X_1$ is Glutamate. In another specific embodiment, $X_2$ is Alanine, or $X_2$ is any non-polar amino acid. In yet another specific embodiment, $X_3$ is Leucine or any non-polar amino acid. In a related embodiment, the first domain comprises the amino acid sequence set forth in SEQ ID NO:19, wherein $X_1$ is not Aspartate; SEQ ID NO:26, wherein $X_2$ is not Threonine; or SEQ ID NO:31, wherein $X_3$ is not Isoleucine. In another related embodiment, the second domain comprises the amino acid sequence set forth in SEQ ID NO:19, wherein $X_1$ is not Aspartate; SEQ ID NO:26, wherein $X_2$ is not Threonine; or SEQ ID NO:31, wherein $X_3$ is not Isoleucine. In yet another related embodiment, the first and second domains bind the same CRP or, alternatively, the first and second domains bind different CRPs. In the embodiments provided in this aspect of the invention, the CRP is CD35, CD46, CD55, or CD59. In a specific embodiment, the CRP is CD46. In related embodiments, the polypeptide causes internalization or sequestration of the CRP into a cell; and/or the polypeptide binds to the CRP with a dissociation constant ($K_d$) of about 1 nM or less, or even about 0.65 nM or less. In some embodiments, the polypeptide is not an antibody or an antibody fragment. The polypeptide can be an isolated, modified viral protein—for example, a polypeptide derived from an adenoviral fiber knob protein. Such polypeptide derived from a fiber knob domain of an adenovirus can be, for example, selected from the group consisting of Ad11, Ad16, Ad21, Ad34, Ad35, and Ad50. In a very specific embodiment, the polypeptide is derived from the Ad35 fiber knob domain comprising at least one amino acid substitution at the residues selected from Asp207, Thr245, Ile256, and a combination thereof; or, more specifically, the amino acid substitution is Asp207Gly, Thr245Ala, Ile256Leu, or a combination thereof. In another embodiment, the polypeptide is less than 25,000 Daltons. In other related embodiments, the polypeptide provided dimerizes, trimerizes, or even homotrimerizes. In a related embodiment, the polypeptide homotrimerizes spontaneously. Such a polypeptide that trimerizes can further have a trimerization domain—for example, a trimerization domain derived from a viral protein. In a specific embodiment, the trimerization domain is a bacteriophage T4 fibritin domain or a reovirus fiber protein σ1 domain. In a very specific embodiment, the trimerization domain comprises the amino acid sequence set forth in SEQ ID NO:32. In some of the embodiments provided herein, the trimer has a three-dimensional structure, and each polypeptide of the homotrimer comprises two loops, wherein each loop binds a CRP. Specifically, the amino acid sequence between the loops is substitutable and does not substantially alter the binding to the CRP.

In yet another aspect, the invention described herein provides a polypeptide complex comprising any one of the polypeptides described herein. In one embodiment, the complex binds two or more CRP molecules. In a related embodiment, the CRP is CD35, CD46, CD55, or CD59. In a specific embodiment, the CRP is CD46.

In another aspect, the invention described herein provides a pharmaceutical composition comprising a therapeutically effective amount of any of the polypeptides described herein. In a specific embodiment, the pharmaceutical composition further comprises a second therapeutic agent. In such an embodiment, the second therapeutic agent can be selected from the group consisting of a protein, a polypeptide, a small molecule, a drug, an antibody, an antibody fragment, a hybrid antibody, an antibody drug-conjugate, a siRNA, an antisense RNA, a miRNA, a virus, and an aptamer; or the second therapeutic agent can be selected from the group consisting of a cytotoxic agent, a cytostatic agent, a chemotherapy agent, a complement-activating agent, a modulator of CRP expression, radiation, an immunomodulatory agent, a pro-apoptotic agent, an inhibitor of heat shock protein, a protease inhibitor, a desialyating agent, a MMP inhibitor, and a PKC inhibitor. In a specific embodiment, the second therapeutic agent is an antibody—for example, an antibody is selected from the group consisting of those antibodies listed in Table 1 or, even more specifically, an antibody selected from the group consisting of Rituxan, Arzerra, Eribitux, Mylotarg, Campath, Herceptin, and Avastin. In a further embodiment, the antibody or antibody fragment is modified to further enhance complement activation—for example, by way of an Fc modification. In another embodiment, the second therapeutic agent is a modulator of CRP expression selected from LI1b, IL4, and TGFb1. In yet another embodiment, the second therapeutic agent is an inhibitor of heat shock proteins selected from deoxyspergualine and geldanamyctanespimycin 17-AAG. In another related embodiment, the second therapeutic agent is a protease inhibitor, desialyating agent or a MMP inhibitor. In yet another related embodiment, the second therapeutic agent is a PKC inhibitor selected from tamoxifen, enzastaurin, and UBN-01. In a specific embodiment, the second therapeutic agent is a chemotherapy agent. In another specific embodiment, the second therapeutic agent is an immunomodulatory agent—for example, an immunomodulatory agent selected from the group consisting of interferon-α, interferon-γ, GM-CSF, a TLR agonist, a NOD receptor agonist, IL2, IL7, IL17, IL21, IL23, TNF, IMiDs, a RIG-1 receptor agonist, a natural killer cell ligand, a natural killer cell activating agent, an NKG2P ligand, and a natural antibody. In a very specific embodiment, the natural killer cell activating agent is an anti-CD137 antibody. In another very specific embodiment, the NKG2P ligand is selected from MICa, MICb, RAE1, and ULBP1.

In another aspect, the invention described herein provides a method comprising contacting a target cell expressing a CRP on its surface with any one polypeptide described herein. In one embodiment, the peptide is in direct contact with the target cell. In another embodiment, the polypeptide is not a part of a viral vector. In a related embodiment, contacting of a target cell with a polypeptide increases the susceptibility of target cell to a treatment with an antibody and/or increases antibody-mediated complement-dependent cytolysis. In a specific embodiment, the antibody is a monoclonal antibody—for example, the antibody is selected from the group consisting of those listed in Table 1 or, more specifically, the antibody is selected from the group consisting of Rituxan, Arzerra, Erbitux, Mylotarg, Campath, Herceptin, and Avastin. In the embodiments described this aspect of the invention, the contacting of the target cell with a polypeptide of the invention can be in vitro, in vivo, and/or ex vivo. In these embodiments, the CRP can be CD46, CD55, CD59, or CD35 and, in a specific embodiment, the CRP is CD46. The target cell can be a tumor cell—for example, a tumor cell selected from the group consisting of a cell obtained from a carcinoma, a cell obtained from a sarcoma, a cell obtained from a blastoma, a cell obtained from a germ cell cancer, and a cell obtained from hematological tumor. In the methods described in this aspect of the invention, the methods can further comprise contacting the target cell with a second therapeutic agent. The contacting with the second therapeutic agent can take place simultaneously, prior to, or following the contacting with any one of the polypeptides provided herein. In exemplary embodiments, the second therapeutic agent can be selected from the group consisting of a cytotoxic agent, a cytostatic agent, a chemotherapy agent, a complement-activating agent, radiation, an immunomodulatory agent, a pro-apoptotic agent, a protein, a polypeptide, a small molecule, a drug, an antibody, an antibody fragment, a hybrid antibody, an antibody drug-conjugate, a siRNA, an antisense RNA, a miRNA, a virus, and an aptamer. In a specific embodiment, the second therapeutic agent is an antibody—for example, an antibody selected from the group consisting of those listed in Table 1 or, more specifically, an antibody selected from the group consisting of Rituxan, Arzerra, Erbitux, Mylotarg, Campath, Herceptin, and Avastin. In a related specific embodiment, the antibody or antibody fragment is modified to further enhance complement activation—for example, an Fc modification. In alternative embodiments, the second therapeutic agent is a chemotherapy agent or an immunomodulatory agent. The immunomodulatory agent in such embodiments can be selected from the group consisting of interferon-α, interferon-γ, GM-CSF, a TLR agonist, a NOD receptor agonist, IL2, IL7, IL17, IL21, IL23, TNF, IMiDs, a RIG-1 receptor agonist, a natural-killer cell ligand, a natural-killer cell activating agent, and a natural antibody. In the contacting methods provided in this aspect, an activity, amount, or density of the CRP on the cell surface is reduced by at least 25% in some embodiments.

In another aspect, the invention described herein provides a method of treating a subject in need of treatment for a condition involving the immune system comprising administering to the subject any one of the pharmaceutical compositions described herein. In specific embodiments, the condition is related to a dysregulation of natural-killer cells, T cells, or B cells, the condition is cancer, an autoimmune condition, an infectious disease, or a condition following a transplant. In specific embodiments, the condition is selected from the group consisting of a carcinoma, a sarcoma, a lymphoma, leukemia, a blastoma, or a germ cell cancer.

In another aspect, the invention described herein provides a vector comprising a nucleic acid encoding a polypeptide operatively linked to a regulatory sequence, wherein the encoded polypeptide is capable of reducing activity, amount, or density of a CRP on a target cell surface wherein the encoded polypeptide comprises a non-naturally occurring amino acid sequence. In specific embodiments, the encoded polypeptide comprises at least one mutation of a naturally occurring protein or protein domain; the encoded polypeptide comprises at least 90% amino acid sequence homology to a naturally occurring protein or protein domain; the encoded polypeptide is not a naturally occurring protein or protein fragment; the encoded polypeptide is not an antibody, antibody fragment, growth factor, cytokine, or a transcriptional regulatory region; and/or the encoded polypeptide is at least 120 amino acids in length. In a related embodiment, the CRP is CD46, CD55, CD59, or CD35 or, more specifically, the CRP is CD46. In a related aspect, the invention described herein also provides a method of delivering a vector comprising a nucleic acid encoding a polypeptide capable of reducing activity of a CRP on a target cell surface comprising contacting the target cell with any of the vectors described herein.

In another aspect, the invention described herein provides a method for screening for a molecule capable of modifying a CRP activity, the method comprising: generating a library of candidate molecules; selecting for candidate molecules capable of binding the CRP; and determining if the molecule modifies the activity of the CRP. In one embodiment, the CRP is CD46, CD55, CD59, or CD35. In a specific embodiment, the CRP is CD46. In a related embodiment, the molecule binds the CRP with a binding affinity of 1 nM or less. In related embodiments, the molecule is selected from the group consisting of a protein, a polypeptide, a small molecule, a drug, an antibody, an antibody fragment, a hybrid antibody, an antibody drug-conjugate, a siRNA, an antisense RNA, a miRNA, a virus, and an aptamer. In a specific embodiment, the molecule is a small molecule. In another specific embodiment, the molecule is a polypeptide. In yet another embodiment, the molecule modifies the activity of the CRP by internalization or sequestration of the CRP into a cell. In a related embodiment, the molecule modifies the activity of the CRP by reducing the amount or density of the CRP on a cell surface.

In another aspect, the present invention provides a polypeptide comprising at least 12 contiguous amino acids of the amino acid sequence set forth as SEQ ID NO:3, wherein the polypeptide includes at least one amino acid substitution selected from the group consisting of Asp207Gly, Thr245Ala, and Ile256Leu or a combination thereof, and wherein the polypeptide can form homotrimers capable of binding to CD46.

In another aspect, the present invention provides a nucleic acid molecule comprising a nucleotide sequence encoding a polypeptide comprising at least 40 contiguous amino acids of the amino acid sequence set forth as SEQ ID NO:3, wherein the polypeptide includes at least one amino acid substitution selected from the group consisting of Asp207Gly, Thr245Ala, and Ile256Leu or a combination thereof, and wherein the polypeptide can form homotrimers capable of binding to CD46.

In another aspect, the present invention provides a composition for reducing cell surface levels of CD46. The composition according to this aspect of the invention comprises (a) an amount of an agent effective to reduce cell surface levels of CD46, the agent comprising a plurality of modified adenovirus fiber knob domain polypeptides, wherein the modified adenovirus fiber knob domain polypeptides are capable of forming homotrimers having enhanced affinity for CD46 binding as compared to homotrimers formed from a plurality of polypeptides consisting of SEQ ID NO:3; and (b) a pharmaceutically acceptable carrier.

In another aspect, the present invention provides a method for reducing the amount of CD46 on a target cell surface. The method according to this aspect of the invention comprises contacting a target cell expressing CD46 on its surface with an amount of a composition comprising a plurality of modified adenovirus fiber knob domain polypeptides, wherein the modified adenovirus fiber knob domain polypeptides are capable of forming homotrimers having enhanced affinity for CD46 binding as compared to homotrimers formed from polypeptides consisting of SEQ ID NO:3.

In another aspect, the present invention provides a method for inducing cytolysis in a target cell expressing CD46. The method in accordance with this aspect of the invention comprises (a) contacting the target cell expressing CD46 on its surface with an amount of an agent comprising a plurality of modified adenovirus fiber knob domain polypeptides effective to decrease the amount of CD46 present on the surface of the target cell; and (b) contacting the target cell treated in accordance with step (a) with an antibody or fragment thereof that binds to an antigen on the surface of the target cell and induces cytolysis.

In another aspect, the present invention provides a method of enhancing the anti-tumor effect of an anti-cancer monoclonal antibody in a mammalian subject in need thereof. The methods in accordance with this aspect of the invention comprise (a) administering at least once to the mammalian subject an amount of a composition comprising a plurality of modified adenovirus fiber knob domain polypeptides effective to decrease the amount of CD46 present on the surface of a target tumor cell; and (b) administering at least once a therapeutically effective amount of an anti-cancer antibody to the subject, wherein the anti-cancer antibody binds to a non-CD46 cell surface antigen expressed on the target tumor cell.

In another aspect, the present invention provides a kit comprising (a) a modified fiber knob domain polypeptide comprising at least 12 contiguous amino acids of the amino acid sequence set forth as SEQ ID NO:3, wherein the polypeptide includes at least one amino acid substitution selected from the group consisting of Asp207Gly, Thr245Ala, and Ile256Leu or a combination thereof, and wherein the polypeptide can form homotrimers capable of binding to CD46; and (b) an antibody or fragment thereof that binds to an antigen on the surface of a mammalian cell and induces cytolysis.

In another aspect, the present invention provides a method of enhancing the effect of an antibody therapeutic agent in the treatment of an autoimmune disease in a mammalian subject. The methods in accordance with this aspect of the invention comprise (a) administering at least once to the mammalian subject an amount of an agent comprising a plurality of modified adenovirus fiber knob domain polypeptides effective to decrease the amount of CD46 present on the surface of a target cell; and (b) administering at least once a therapeutically effective amount of an antibody therapeutic agent to the subject, wherein the antibody therapeutic agent binds to a non-CD46 cell surface antigen expressed on the target cell.

The polypeptides, nucleic acids, and compositions of the invention are useful for practicing the methods of the present invention.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1C is an amino acid alignment of the adenovirus knob domains for wild-type Ad35 (SEQ ID NO:3), mutant Ad35K++ (Asp207Gly and Thr245Ala) (SEQ ID NO:5), and other CD46 binding adenoviruses, i.e. Ad11p (SEQ ID NO:35), Ad16 (SEQ ID NO:36), Ad21 (SEQ ID NO:33), and Ad50 (SEQ ID NO:34);

FIG. 14 graphically illustrates the enhancement of mAb, killing by Ad35K++ with normal human serum (NHS) from different donors (blood group A and B)

FIG. 14A graphically illustrates the timeline of the experiment with BT474 cells;

FIG. 14B graphically illustrates the percentage of viable cells compared to PBS treated cells;

FIG. 15B graphically illustrates the amino acid sequence of Ad35K++ before ("Original"; SEQ ID NO:5) and after optimization ("Optimized"; SEQ ID NO:38) using DNA2.0 software and the "Consensus" sequence, which is identical to the "Original" sequence (SEQ ID NO:5);

FIG. 15C illustrates that the Ad35K++ DNA sequence was checked for the indicated unwanted motifs, including the Shine Dalgarno sequence (SEQ ID NO:39);

FIG. 16 graphically illustrates data from a non-human primate model;

FIG. 16A illustrates Ad35K++ enhanced B cell depletion in vitro by rituximab;

FIG. 16B illustrates an Ad35K++ hemagglutination assay with erythrocytes from macaques (*M. fascilcularis* and *M. nemestrina*), baboons (*P. Anubis*), and humans; and FIGS. 17A-17D graphically illustrate efficacy studies with Ad35K++ and rituximab in transgenic C57B1/6 mice that were double transgenic for human CD46 and CD20.

DETAILED DESCRIPTION

Figure 1A:
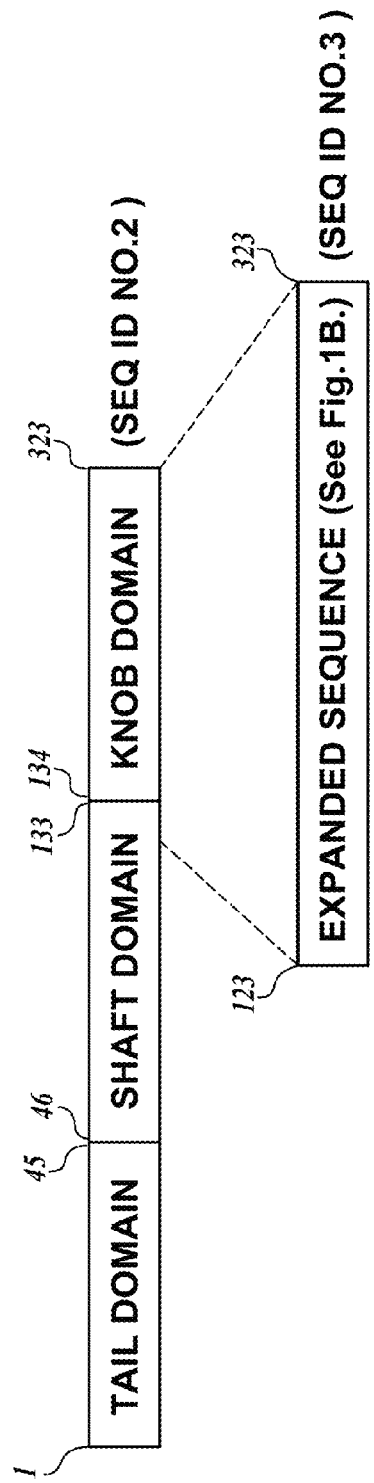
FIG. 1A is a schematic illustration of the full length wild type Adenovirus serotype 35 (Ad35) fiber polypeptide (SEQ ID NO:2) indicating the relative positions of the N-terminal tail domain (aa 1-45), the shaft domain (aa 46-133), and the C-terminal fiber knob (K) domain (aa 134-323)

Unless specifically defined herein, all terms used herein have the same meaning as they would to one skilled in the art of the present invention. Practitioners are particularly directed to Sambrook et al., *Molecular Cloning: A Laboratory Manual*, 3d ed., Cold Spring Harbor Press, Plainsview, N.Y. (2001); and Ausubel et al., *Current Protocols in Molecular Biology*, John Wiley & Sons, New York (2002) for definitions and terms of art.

The following definitions are provided to provide clarity with respect to the terms as they are used in the specification and claims to describe the present invention.

As used herein, the term "sequence identity" or "percent identical," as applied to nucleic acid molecules, is the percentage of nucleic acid residues in a candidate nucleic acid molecule sequence that are identical with a subject nucleic acid molecule sequence (such as the nucleic acid molecule sequence set forth in SEQ ID NO:4), after aligning the sequences to achieve the maximum percent identity, and not considering any nucleic acid residue substitutions as part of the sequence identity. No gaps are introduced into the candidate nucleic acid sequence in order to achieve the best alignment. Nucleic acid sequence identity can be determined in the following manner. The subject polynucleotide molecule sequence is used to search a nucleic acid sequence database, such as the Genbank database, using the program BLASTN version 2.1 (based on Altschul et al., *Nucleic Acids Research* 25:3389-3402 (1997)). The program is used in the ungapped mode. Default filtering is used to remove sequence homologies due to regions of low complexity as defined in J. C. Wootton and S. Federhen, *Methods in Enzymology* 266:554-571 (1996). The default parameters of BLASTN are utilized.

As used herein, the term "percent identity" or "percent identical," when used in connection with a polypeptide used in the practice of the present invention, is defined as the percentage of amino acid residues in a polypeptide sequence that are identical with the amino acid sequence of a specified polypeptide (such as the amino acid sequence of SEQ ID NO:3), after aligning the sequences to achieve the maximum percent identity. When making the comparison, no gaps are introduced into the biomarker sequences in order to achieve the best alignment. Amino acid sequence identity can be determined, for example, in the following manner. The amino acid sequence of a polypeptide (e.g., the amino acid sequence set forth in SEQ ID NO:3) is used to search a protein sequence database, such as the GenBank database using the BLASTP program. The program is used in the ungapped mode. Default filtering is used to remove sequence homologies due to regions of low complexity. The default parameters of BLASTP are utilized.

As used herein, the amino acid residues are abbreviated as follows: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

As used herein, the term "affinity," in the context of protein binding, refers to the strength of the interaction between the binding proteins. The strength of the binding generally results from greater intermolecular force between the two proteins and results in a stronger association between them.

As used herein, the abbreviation "Ad" refers to an adenovirus and is typically followed by a number indicating the serotype of the adenovirus. For example, "Ad35" refers to adenovirus serotype 35.

As used herein, the term "fiber polypeptide" refers the full length fiber polypeptide expressed by adenoviruses (e.g., SEQ ID NO:2) that comprises an N-terminal tail domain, a shaft domain, and a C-terminal knob domain. The fiber polypeptides spontaneously assemble into homotrimers, referred to as "fibers," which are located on the outside of the adenovirus virion at the base of each of the twelve vertices of the capsid.

As used herein, the term "fiber" refers to the homotrimeric protein structure composed of three individual fiber polypeptides. The adenovirus fiber mediates contact with, and internalization into, the target host cell.

Figure 1B:
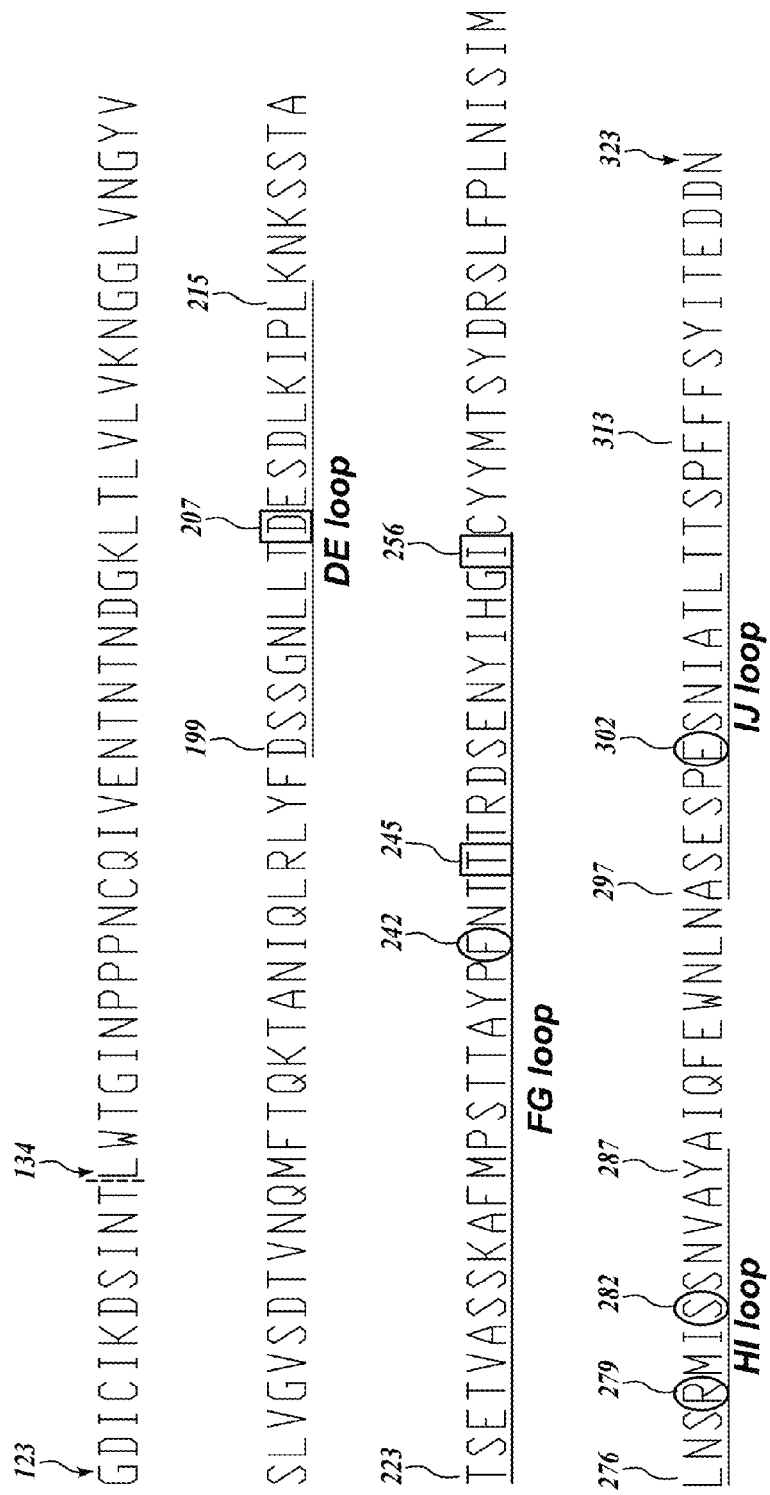
FIG. 1B illustrates the amino acid sequence of the knob domain (K) (SEQ ID NO:3) of the wild type Ad35 fiber polypeptide, wherein the loop regions designated as "DE" (SEQ ID NO:6), "FG" (SEQ ID NO:7), "HI" (SEQ ID NO:8), and "IJ" (SEQ ID NO:9) are underlined. The amino acid positions wherein substitutions have been shown to ablate CD46 binding are indicated by circles and the amino acid positions wherein substitutions have been shown to enhance CD46 binding are indicated by squares.
Figure 1C:
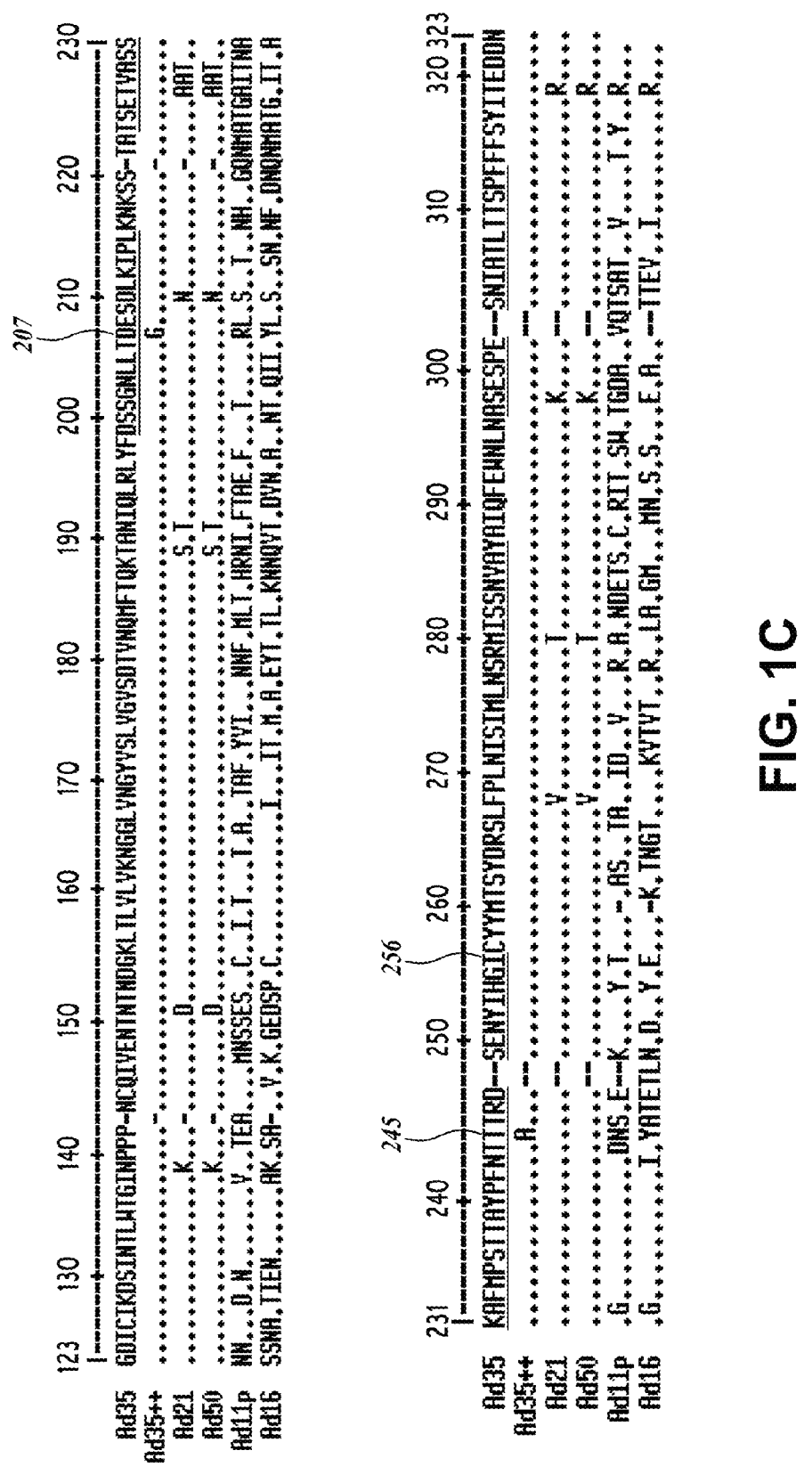

As used herein, the term "fiber knob domain polypeptide" refers to the C-terminal domain of the fiber polypeptide that is able to form into a homotrimer that binds to CD46. An example is the wild-type adenovirus serotype 35 knob domain set forth as SEQ ID NO:3, which is also referred to by the abbreviation "Ad35K polypeptide." As illustrated in FIG. 1B, the C-terminal portion of the fiber protein can trimerize and form a fiber structure that binds to CD46.

As used herein, the term "modified adenovirus fiber knob domain polypeptide" refers to a polypeptide comprising a variant of a wild-type adenovirus knob domain, wherein the modified polypeptide comprises at least one amino acid addition, deletion, or substitution or a combination thereof, wherein the modified polypeptide can form homotrimers capable of binding to CD46. Preferably, any substitution mutation is conservative in that it minimally disrupts the biochemical properties. Thus, where mutations are introduced to substitute amino acid residues, positively-charged residues (H, K, and R) preferably are substituted with positively-charged residues; negatively-charged residues (D and E) are preferably substituted with negatively-charged residues; neutral polar residues (C, G, N, Q, S, T, and Y) preferably are substituted with neutral polar residues; and neutral non-polar residues (A, F, I, L, M, P, V, and W) preferably are substituted with neutral non-polar residues.

In the broadest sense, the naturally occurring amino acids can be divided into groups based upon the chemical characteristic of the side chain of the respective amino acids. By "hydrophobic" amino acid is meant either Ile, Leu, Met, Phe, Trp, Tyr, Val, Ala, Cys, or Pro. By "hydrophilic" amino acid is meant either Gly, Asn, Gln, Ser, Thr, Asp, Glu, Lys, Arg, or His. This grouping of amino acids can be further subclassed as follows. By "uncharged hydrophilic" amino acid is meant either Ser, Thr, Asn, or Gln. By "acidic" amino acid is meant either Glu or Asp. By "basic" amino acid is meant either Lys, Arg, or His.

An example of a modified adenovirus fiber knob domain polypeptide is set forth as SEQ ID NO:5, which is the wild-type Adenovirus 35 knob domain sequence (SEQ ID NO:3), with the substitutions Asp207Gly and Thr245Ala. The specific modified adenovirus fiber knob domain polypeptide set forth in SEQ ID NO:5 is also referred to by the abbreviation "Ad35K++ polypeptide." Unless otherwise indicated, the location of specific amino acid substitutions, or replacement mutations, are herein described with reference to the full-length wild-type adenovirus 35 fiber polypeptide sequence (SEQ ID NO:2) by first designating the amino acid residue found in the wild-type sequence, followed by the designated amino acid position within the wild-type sequence, and designating the amino acid residue found in the mutated polypeptide. For example, the term "Asp207Gly" describes a substitution at amino acid position 207 in the wild-type sequence (SEQ ID NO:2), wherein the Asp is replaced with Gly. However, in some instances, the locations of specific amino acid positions within fiber polypeptide fragments are designated by the position in the specific fragment sequence. For example, amino acid position 207 of the full-length wild-type adenovirus 35 fiber polypeptide sequence, as set forth in SEQ ID NO:2, can also be described as position 85 in the knob fragment sequence, as set forth in SEQ ID NO:3.

As used herein, the term "contiguous," in the context of the amino acid sequence of a polypeptide, refers to the sequential ordering of amino acid residues as they appear in a reference sequence. A contiguous sequence of amino acids generally does not contain additions, deletions or substitutions in the reference sequence. However, when specified herein, a contiguous sequence of amino acids may contain substitutions without destroying the contiguity of the sequence. For example, the phrase "contiguous amino acids of SEQ ID NO:3" refers to a sequential ordering of amino acid residues as they appear in SEQ ID NO:3 without insertions, deletions, or most substitutions. This phrase, however, permits the incorporation of the further described amino acid substitutions (i.e., Asp207Gly, Thr245Ala, and Ile256Leu) without destruction of the contiguity of the sequence.

As used herein, the term "source of complement" refers to a mixture that includes some or all of the individual components of the complement system necessary to cause cytolysis and cell death upon induction, such as human serum.

As used herein, the "membrane attack complex" ("MAC") refers to a complex of the terminal 5 complement components (C5-C9) that inserts into and disrupts cell membranes.

As used herein, the term "antibody" encompasses antibodies and antibody fragments thereof, derived from any antibody-producing mammal (e.g., mouse, rat, rabbit, camelid, and primate, including human) or synthetically or recombinantly produced, that specifically binds to a target of interest or portions thereof. Exemplary antibodies include polyclonal, monoclonal, and recombinant antibodies; multispecific antibodies (e.g., bispecific antibodies); humanized antibodies; murine antibodies; chimeric, mouse-human, mouse-primate, primate-human monoclonal antibodies; and anti-idiotype antibodies, and may be any intact molecule or fragment thereof.

As used herein, the term "antigen binding fragment" refers to the antigen binding or variable region from or related to a full-length antibody. Illustrative examples of antibody fragments include Fab, Fab', F(ab)$_2$, F(ab')$_2$, and Fv fragments, scFv fragments, diabodies, nanobodies, linear antibodies, single-chain antibody molecules, and multispecific antibodies formed from antibody fragments.

As used herein, a "single-chain Fv" or "scFv" antibody fragment comprises the $V_H$ and $V_L$ domains of an antibody, wherein these domains are present in a single polypeptide chain. Generally, the Fv polypeptide further comprises a polypeptide linker between the $V_H$ and $V_L$ domains, which enables the scFv to form the desired structure for antigen binding.

As used herein, a "chimeric antibody" is a recombinant protein that contains the variable domains and complementarity-determining regions derived from a non-human species (e.g., rodent) antibody, while the remainder of the antibody molecule is derived from a human antibody.

As used herein, a "humanized antibody" is a chimeric antibody that comprises a minimal sequence that conforms to specific complementarity-determining regions derived from non-human immunoglobulin that is transplanted into a human antibody framework. Humanized antibodies are typically recombinant proteins in which only the antibody complementarity-determining regions are of non-human origin.

As used herein, the terms "systemic delivery" and "systemic administration" are intended to include, but are not limited to, oral and parenteral routes including intramuscular (IM), subcutaneous, intravenous (IV), intra-arterial, inhalational, sublingual, buccal, topical, transdermal, nasal, rectal, vaginal, and other routes of administration that effectively result in dispersement of the delivered agent to a single or multiple sites of intended therapeutic action.

Complement Regulatory Proteins

CD46 (also known as membrane cofactor protein MCP), CD55 (also known as decay-accelerating factor DAF), and CD59 (also known as Protectin) are interchangeably referred to as complement regulatory proteins (CRPs), membrane-bound complementary inhibitory proteins, complement regulators, and the like. Most cells are protected from complement by one or more of these CRPs. CD46 and CD55 target the initiation pathways at the C3/C5 convertase stage. CD59 blocks the terminal complement pathway and prevents MAC formation by binding to C8 and C9 during MAC assembly (Meri et al., 1990). Over-expression of CRPs has been noted, for example, in many primary tumors and tumor cell lines (Fishelson et al., Mol Immunol 40 (2-4):109-23 (2003); Gelderman et al., Lab Invest 82(4):483-93 (2002); Yan et al., (2008)); auto-immune diseases, and infections diseases.

CD46:

CD46 (MCP) is a type 1 transmembrane glycoprotein protein expressed on the membranes of nucleated cells. The human CD46 protein sequence is provided herein as SEQ ID NO:14, which corresponds to Genbank Accession Number ABK81636. From its extracellular amino terminus, human CD46 protein has four tandem complement control protein (CCP) modules: CCP1 (aa 35-88); CCP2 (aa 99-158), CCP3 (aa 162-224) and CCP4 (aa 228-283) followed by one or two heavily O-glycosylated serine/threonine/proline-rich (STP) domains, a transmembrane domain, and the cytoplasmic tail. The four CCP modules form the major part of the extracellular domain of CD46. CCPs contain three N-linked glycosylation sites. The STP domains and the cytoplasmic tail domain can each undergo alternative splicing, resulting in four major human isoforms of CD46 (BC1, BC2, C1, and C2) ranging in molecular mass from 55 to 65 kDa (A. Gaggar et al., *Journal of Virology* 79:7503-7513 (2005)).

CD46 was first described for its complement binding and regulatory properties (reviewed in M. K. Liszewski et al., *Advances in Immunology* 61:201-283 (1996)). In this regard, CD46 protects the cell against the formation of membrane attack complexes (MACs) on the cellular membrane. In particular, CD46 binds to complement factors C4b and C3b that are bound to the cell membrane and acts a cofactor to their proteolytic inactivation by plasma serine protease Factor I. This interaction is mediated by the CD46 CCP2, CCP3, and CCP4 domains. The proteolytic inactivation prevents the formation MAC formation on the cell by virtue of preventing C3 (C3a, C3b) and C5 (C5a, C5b) convertase activity of the bound complement factors (A. Gaggar et al., *Journal of Virology* 79:7503-7513 (2005)). Additionally, two human isoforms exist of the CD46 cytoplasmic domains that have opposing roles in regulating T cell-induced inflammatory reactions (J. C. Marie et al., *Nature Immunology* 3:659-666 (2002)).

Beyond its roles in the regulation of immunological responses, CD46 also serves as a receptor for various pathogens, including measles virus, human herpes virus 6 and two types of bacteria—*Streptococcus pygogenes* and pathogenic *Neisseria gonorrhoeae*. The measles virus hemaglutinin protein interacts with CD46 CCP1 and CCP2. CCP2 and CCP3 serve as the binding target for human herpes virus 6 and *Streptococcus*, whereas CCP3 and an STP domain are required for *Neisseria* attachment (A. Gaggar et al., *Journal of Virology* 79:7503-7513 (2005)). Additionally, it has been demonstrated that CD46 is a high-affinity receptor of a series of human adenovirus serotypes (S. Tuve et al., *Journal of Virology* 80:12109-12120 (2006); A. Gaggar et al., *Nature Medicine* 9:1408-1412 (2003); and D. Sirena et al., *Journal of Virology* 78:4454-4462 (2004)).

Additionally, it has been demonstrated that CD46 is a high-affinity receptor of a series of human adenovirus serotypes (S. Tuve et al., *Journal of Virology* 80:12109-12120 (2006); A. Gaggar et al., *Nature Medicine* 9:1408-1412 (2003); and D. Sirena et al., *Journal of Virology* 78:4454-4462 (2004)).

The CD46 CCP2 domain has been shown to mediate binding for two serotypes of adenovirus—Ad11 and Ad35. In particular, the native conformation of the CCP2 domain is crucial for Ad35 attachment, and substitutions at amino acid positions 130 to 135 or 152 to 156 on the domain completely abolish Ad35 binding. It has been suggested that the various pathogens that utilize CD46 for cellular attachment do so because it affords the pathogens the opportunity to modulate the immune response (R. Cattaneo, *Journal of Virology* 78:4385-4388 (2004)). For example, it has been reported that cross linking of CD46 at the cell surface, by either multivalent antibodies or by measles virus, induces pseudopodia that engulf the ligand in a process similar to macropinocytosis, thus leading to the degradation of cell surface CD46, which in turn protects cells from complement lysis (B. Crimeen-Irwin, et al., *Journal of Biological Chemistry* 278:46927-46937 (2003); J. Schneider-Schaulies, et al., *Journal of Virology* 70:255-263 (1996)).

Adenoviruses are non-enveloped double stranded DNA viruses. Human adenoviruses have been classified into six sub-groups (A to F) containing as many as 51 serotypes. Group B adenoviruses form two genetic clusters—B1 (including serotypes Ad3, Ad7, Ad16, Ad21, and Ad50), and B2 (including serotypes Ad11, Ad14, Ad34, and Ad35) (G.

Wadell et al., *Annals of the New York Academy of Sciences* 354:16-42 (1980)). Most B1 adenoviruses are mainly associated with acute respiratory disease and, unlike the Group C adenoviruses (e.g., Ad5), do not establish persistence (G. Wadell, *Current Topics in Microbiology and Immunology* 110:191-220 (1984)). The B2 serotypes Ad11p, Ad34, and Ad35 have mainly been associated with infections of the kidneys and urinary tract. Group B serotypes are unique among the adenoviruses in that they do not use coxsackievirus and adenovirus receptor (CAR) as their primary attachment receptor. In particular, B2 Group I serotypes, including Ad16, Ad21, Ad35, and Ad50 nearly exclusively use CD46 as the receptor; B2 Group II serotypes, including Ad3, Ad7p, and Ad14 use a yet unidentified receptor and not CD46; and finally, B2 Group III, serotype Ad11p, uses both CD46 and the yet unidentified receptor (S. Tuve et al., *Journal of Virology* 80:12109-12120 (2006)).

The adenovirus virion is an icosahedron characterized by a fiber located at the base of each of the 12 vertices of the capsid. The fiber on the virion is a homotrimeric structure consisting of 3 individual fiber polypeptides. Each adenovirus fiber polypeptide is an asymmetrical structure consisting of: an N-terminal tail, which interacts with the penton base protein of the capsid and contains the signals necessary for transport of the protein to the cell nucleus; a shaft, which contains a number of 15-residue repeating units; and a C-terminal knob domain that contains the determinants for receptor binding (J. S. Hong and J. A. Engler, *Journal of Virology* 70:7071-7078 (1996)). Adenoviruses from all groups, whether CAR-interacting or Group B adenoviruses, attach to their receptors through the knob structure on the end of the fiber (A. Gaggar et al., "CD46 Is a Cellular Receptor for Group B Adenoviruses," *Journal of Natatrual Medicines* 9:1408-1412 (2003)). Trimerization of the fiber polypeptides is required for binding of adenoviruses to their receptors (J. S. Hong and J. A. Engler, *Journal of Virology* 70:7071-7078 (1996); H. Wang et al., *Journal of Virology* 81:12785-12792 (2007)). Studies of mutant Ad2 fibers demonstrate that trimerization of the fiber polypeptides requires only portions of the C-terminal knob domain and a short portion of the C-terminal end of the shaft region. It appears that at least the N-terminal half of the fiber may be deleted without affecting trimerization (J. S. Hong and J. A. Engler, *Journal of Virology* 70:7071-7078 (1996)).

The specific structure of adenovirus knob domain has been determined for Group C serotype Ad5 (binds to the CAR receptor) (D. Xia et al., *Structure* 2:1259-1270 (1994)), Group B serotype Ad11 (binds to the CD46 receptor) (B. D. Persson et al., *Nature Structural & Molecular Biology* 14:164-166 (2007)), and Group B serotype Ad35 (binds to the CD46 receptor) (H. Wang et al., *Journal of Virology* 81:12785-12792 (2007)). The homotrimeric knob domain appears to form a structure like a three-bladed propeller, whereby each blade (i.e., individual knob domain) contains multiple, tightly-packed beta-sheets (labeled A to J). The crystallization of recombinant Ad11 fiber knob bound to CD46 domains CCP1 and CCP2 revealed three critical contact regions within the F-G, H-I, and I-J loops of the fiber knob domain (B. D. Persson et al., *Nature Structural & Molecular Biology* 14:164-166 (2007)). This model is supported by studies demonstrating that binding of Ad11 virus to CD46 can be abolished by introduction of a single amino acid substitution (Arg279Gln) within the Ad11 H-I loop (D. J. Gustafsson et al., *Journal of Virology* 80:1897-1905 (2006) [author's correction, 80:5101.]).

Crystallization and mutation studies have illuminated critical regions of the Ad35 fiber knob for binding CD46, leading to a model of Ad35 fiber knob domain CD46 interaction wherein one CD46 unit binds between each pair of fiber knob domains within the knob homotrimeric structure (H. Wang et al., *Journal of Virology* 81:12785-12792 (2007), incorporated herein by reference in its entirety). Thus, a single fiber knob homotrimer is capable of crosslinking three CD46 receptors. It has been established that trimerization is required for binding of the Ad35 fiber knob to soluble CD46 using an antibody specific for the trimeric form of the knob proteins (ab1187-100, lot No. 134173; Abcam), H. Wang et al., *Journal of Virology* 81:12785-12792 (2007). As described in H. Wang et al., an Ad35 fiber knob mutant polypeptide library was generated using mutagenic PCR to generate an average of one or two amino acid mutations per fiber knob domain polypeptide. The library was doubly selected for trimerization and binding to soluble CD46. None of the mutations that destroyed trimerization was able to bind to CD46. Four residues were identified wherein mutations abolished Ad35 fiber knob binding to CD46 without affecting trimerization: Phe at amino acid position 242, Arg at position 279, Ser at position 282, and Glu at position 302. These residues were located in areas corresponding to the three contact regions reported for the Ad11 fiber knob domain. Further rounds of screening did not uncover additional regions, indicating that all the detectable CD46 critical interacting areas had been found. Superimposition of crystallographic images indicated that the core structure between Ad35 and Ad11 are highly similar. Moreover, all of the Ad35 mutations were in exposed loop regions within the globular Ad35 fiber knob structure, underscoring their role in receptor binding. Particularly, the contact residues in the F-G and H-I loops were situated on opposite sides of the Ad35 monomer to the contact area in the I-J loop, indicating that one CD46 unit binds between two Ad35 fiber knob monomers. This was supported by stoichiometry data indicating a 1:1 interaction between the CD46 molecules and Ad35 fiber knob monomers (H. Wang et al., *Journal of Virology* 81:12785-12792 (2007)). Thus, the Ad35 fiber knob domain CD46 interaction leads not only to a tight association, but the crosslinking of several CD46 molecules as well.

CD55:

CD55 (DAF) is a 70 kDa protein that in humans is encoded by the CD55 gene (Medof M E, et al. (April 1987). "Cloning and characterization of cDNAs encoding the complete sequence of decay-accelerating factor of human complement". Proc. Natl. Acad. Sci. U.S.A. 84 (7): 2007-11). The human CD55 protein sequence corresponds to Genbank Accession Number AAC60633. CD55 is a 70 kDa membrane protein that regulates the complement system on the cell surface. It prevents the assembly of the C3bBb complex (the C3-convertase of the alternative pathway) or accelerates the disassembly of preformed convertase, whereby blocking the formation of the membrane attack complex. CD55 glycoprotein is broadly distributed among hematopoietic and non-hematopoietic cells. The protein shares some amino acid repeat motifs and functional similarities with some complement proteins. Osuka et al., "Molecular Cloning and Characterization of Novel Splicing Variants of Human Decay-Accelerating Factor," *Genomics* 88(3):316-322, September 2006; have reported a variety of splice variants that are expressed in almost all tissues tested but vary in their expression patterns. Some variants are soluble forms of CD55 secreted after glycosylation (M. A. Davitz et al., "Release of Decay-Accelerating Factor (DAF) From the Cell Membrane by Phosphatidylinositol-Specific Phospholipase C (PIPLC)," *Journal of Experimental Medicine* 163(5):1150-1161, May 1986).

CD55 is a complement regulator that functions intrinsically in the membranes of self cells to circumvent the deposition of autologous C3b on their surfaces (V. Nussenzweig et al., "Inhibition of Complement Activation on the Surface of Cells After Incorporation of Decay-Accelerating Factor (DAF) Into Their Membranes," *Journal of Experimental Medicine* 160(5):1558-1578, November 1984). It acts to accelerate decay-dissociation of the bimolecular C3 convertases, the central amplification enzymes of the cascade. (A. Nicholson-Weller et al., "Isolation of a Human Erythrocyte Membrane Glycoprotein With Decay-Accelerating Activity for C3 Convertases of the Complement System," *The Journal of Immunology* 129(1):184-189, July 1982; M. K. Pangburn et al., "Breakdown of C3 After Complement Activation: Identification of a New Fragment C3g, Using Monoclonal Antibodies," *Journal of Experimental Medicine* 156(1):205-216, July 1982; T. Fujita et al., "The Mechanism of Action of Decay-Accelerating Factor (DAF): DAF Inhibits the Assembly of C3 Convertases by Dissociating C2a and Bb," *Journal of Experimental Medicine* 166(5):1221-1228, November 1987).

CD55 is the cellular ligand for CD97 (J. Hamann et al., "The Seven-Span Transmembrane Receptor CD97 Has a Cellular Ligand (CD55, DAF)," *Journal of Experimental Medicine* 184(3):1185-1189, September 1996). CD55 is deficient in red blood cells from patients with paroxysmal nocturnal hemoglobinuria. Cells from these patients fail to adhere to cells expressing the counterreceptor. A deficiency of CD55 does not appear to have any associated hematologic or other abnormalities (D. M. Lublin et al., "Molecular Basis of Reduced or Absent Expression of Decay-Accelerating Factor in Cromer Blood Group Phenotypes," *Blood* 84(4):1276-1282, August 1994). The absence of CD55 in paroxysmal nocturnal hemoglobinuria leads to increased C3b uptake on affected cells (M. E. Medof et al., "Amelioration of Lytic Abnormalities of Paroxysmal Nocturnal Hemoglobinuria With Decay-Accelerating Factor," *Proceedings of the National Academy of Sciences USA (PNAS)* 82(9):2980-2984, May 1985).

CD55 is used as a receptor by some coxsackieviruses and other enteroviruses, for example echoviruses and coxsackie B viruses (Karnauchow T M, Tolson D L, Harrison B A, Altman E, Lublin D M, Dimock K (August 1996). "The HeLa cell receptor for enterovirus 70 is decay-accelerating factor (CD55)". J. Virol. 70 (8): 5143-52; Goodfellow et al., J Gen Virol 81(5):1393-401 (2000)). Recombinant soluble CD55-Fc has been tested in mice as an anti-enterovirus therapy for heart damage (Yanagawa B, Spiller O B, Choy J, Luo H, Cheung P, Zhang H M, Goodfellow I G, Evans D J, Suarez A, Yang D, McManus B M (January 2003). "Coxsackievirus B3-associated myocardial pathology and viral load reduced by recombinant soluble human decay-accelerating factor in mice". Lab. Invest. 83 (1): 75-85).

CD59:

CD59 is a glycosylphosphatidylinositol-anchored 18-20 kDa glycoprotein (GPi-anchored). The human CD59 protein sequence corresponds to Genbank Accession Number CAG46523. CD59 is expressed on human peripheral blood leukocytes, erythrocytes, and several human cell lines. The protein is expressed also on endothelial cells, on the Schwann cell sheath of peripheral nerve fibers, neurons, microglia, oligodendrocytes, astrocytes, ependymal cells and certain epithelial cells such as acinar cells of the salivary gland, bronchial epithelium, renal tubules and squamous epithelium (Nose et al., "Tissue distribution of HRF20, a novel factor preventing the membrane attack of homologous complement, and its predominant expression on endothelial cells in vivo," *Immunology* 70(2):145-9, June 1990; Vedeler et al., "The expression of CD59 in normal human nervous tissue," *Immunology* 82(4):542-7, August 1994; Hideshima et al., "Expression of HRF20, a regulatory molecule of complement activation, on peripheral blood mononuclear cells," *Immunology* 69(3):396-401, March 1990).

CD59 is known also as protectin or human leukocyte cell surface antigen MIC11, MIN1, MIN2, MIN3, MSK21. The protein has been identified as HRF20 [homologous restriction factor-20 kDa] and MACIF [membrane attack complex inhibitory factor](MAC-IP, MAC-inhibitory protein). It is closely related to mouse Ly6 antigen (Petranka et al., "Structure of the CD59-encoding gene: further evidence of a relationship to murine lymphocyte antigen Ly-6 protein," *Proc Natl Acad Sci USA.* 89(17):7876-9, September 1992). The human gene gives rise to more than 4 different mRNA molecules, which are generated by alternative polyadenylation (Tone et al., "Gene structure of human CD59 and demonstration that discrete mRNAs are generated by alternative polyadenylation," *J Mol Biol* 227(3):971-6, October 1992). Other designations are H19, MIRL [membrane inhibitor of reactive lysis], P18, 1F5, 16.3A5, BRIC 229, YTH 53.1.

The function of CD59 is to prevent the formation of a membrane attack complex, formed by activated terminal complement proteins C5b to C9, on the cell surface and to protect the cell from complement mediated cell lysis (for a factor with similar activities see also: CD55). Acosta et al. ("Molecular basis for a link between complement and the vascular complications of diabetes," *Proc Natl Acad Sci USA.* 97(10):5450-5, May 2000) have reported that human CD59 is glycated in vivo and that glycated human CD59 loses its inhibitory function on the formation of the membrane attack complex. Inactivation of CD59 increases membrane attack complex induced release of growth factors from endothelial cells.

Expression of CD59 on cell membranes restricts lysis of cells by homologous complement. The protein may not prevent cell killing by performs (Meri et al., "Human protectin (CD59), an 18-20-kD homologous complement restriction factor, does not restrict perforin-mediated lysis," *J Exp Med.* 172(1):367-70, July 1990). Cells remain sensitive to cytotoxic attack by IL2 activated lymphocytes (LAK cells), which release perforin (Okada et al., "HRF20, a membrane inhibitor of complement attack, does not protect cells from the cytotoxic reaction by lymphokine activated killer cells," *Biochem Biophys Res Commun.* 171(2):717-21, September 1990).

Hahn et al. ("Overlapping but nonidentical binding sites on CD2 for CD58 and a second ligand CD59," *Science* 256 (5065):1805-7, June 1992) have identified CD59 as a physiological ligand for CD2. Binding sites on CD2 for CD59 and the other CD2 ligand, CD58, overlap but are not identical. CD58 is the principal ligand for human CD2 and thus plays a costimulatory role in the cell activation of T-cells. This effect involves the costimulatory antigen CD58 (Menu et al., "CD59 costimulation of T cell activation. CD58 dependence and requirement for glycosylation," *J. Immunol.* 153(6):2444-56, September 1994). CD2 mediated CD59 stimulation in human keratinocytes results in secretion of IL1-alpha, IL6, and GM-CSF, which may have implications for the interaction of keratinocytes with intraepidermal T-lymphocytes (Naderi et al., "CD2-mediated CD59 stimulation in keratinocytes results in secretion of IL-1 alpha, IL-6, and GM-CSF: implications for the interaction of keratinocytes with intraepidermal T lymphocytes," *Int J Mol. Med.* 3(6):609-14, June 1999).

CD59 has been shown to be overexpressed in a number of malignant melanoma cell lines (Simon et al., "Identification of differentially expressed messenger RNAs in human melanocytes and melanoma cells," Cancer Res. 1996 Jul. 1; 56(13):3112-7 1996). These cells also constitutively release a soluble bioactive form of CD59 that reverses its effects on complement mediated lysis (Brasoveanu et al., "Melanoma cells constitutively release an anchor-positive soluble form of protectin (sCD59) that retains functional activities in homologous complement-mediated cytotoxicity," *J Clin Invest.* 100(5):1248-55, September 1997). This down-modulates the susceptibility of human melanoma cells to homologous complement (Coral et al., "Overexpression of protectin (CD59) down-modulates the susceptibility of human melanoma cells to homologous complement," *J Cell Physiol.* 185 (3):317-23, December 2000).

A number of echoviruses use CD59 as a cellular receptor or attachment protein for cell infection (Goodfellow et al., "Echovirus infection of rhabdomyosarcoma cells is inhibited by antiserum to the complement control protein CD59," *J Gen Virol.* 81(Pt 5):1393-401, May 2000).

CD35:

CD35 is interchangeably known as Erythrocyte complement receptor 1 (CR1), C3b/C4b receptor and immune adherence receptor) is a human gene. The human CD35 protein sequence corresponds to Genbank Accession Number NM_000651.4; GI:86793108. The protein encoded by this gene is a member of the regulators of complement activation (RCA) family and is located in the 'cluster RCA' region of chromosome 1. The gene encodes a monomeric single-pass type I membrane glycoprotein found on erythrocytes, leukocytes, glomerular podocytes, and splenic follicular dendritic cells. The Knops blood group system is a system of antigens located on this protein. The protein mediates cellular binding to particles and immune complexes that have activated complement. Decreases in expression of this protein and/or mutations in its gene have been associated with gallbladder carcinomas, mesangiocapillary glomerulonephritis, systemic lupus erythematosus and sarcoidosis. Mutations in this gene have also been associated with a reduction in *Plasmodium falciparum* rosetting, conferring protection against severe malaria. Alternate allele-specific splice variants, encoding different isoforms, have been characterized. Additional allele specific isoforms, including a secreted form, have been described but have not been fully characterized.

In primates, CD35 serves as the main system for processing and clearance of complement opsonized immune complexes. It has been shown that CD35 can act as a negative regulator of the complement cascade, mediate immune adherence and phagocytosis and inhibit both the classic and alternative pathways. The number of CR1 molecules decreases with aging of erythrocytes in normal individuals and is also decreased in pathological conditions such as systemic lupus erythematosus (SLE), HIV infection, some hemolytic anemias and other conditions featuring immune complexes.

Compositions, Polypeptides, and Methods of the of the Invention

Provided herein are compositions and methods to reduce the activity of CRPs on a target cell. Such reduction can be by way of reducing the number of active CD46, CD55, CD59, or CD35 receptors on a target cell; reducing the density of active CD46, CD55, CD59, or CD35 receptors on a target cell; causing the sequestration of CD46, CD55, CD59, or CD35 receptors on a target cell; causing internalization of CD46, CD55, CD59, or CD35 receptors on a target cell; binding CD46, CD55, CD59, or CD35 receptors on a target cell; blocking CD46, CD55, CD59, or CD35 receptors on a target cell; and/or otherwise reducing the signal transduction and signal effected through CD46, CD55, CD59, or CD35 receptors on a target cell. Such modulation and reduction of the activity of CRPs on a target cell can be useful in a variety of therapeutics for treatment of including, but not limited to, cancers, auto-immune diseases, infectious diseases, and transplant-related conditions. Provided herein are modified polypeptides or compositions comprising modified polypeptides capable of reducing the activity, amount, density, sequestration, or internalization of a complement regulatory protein (CRP) on a target cell surface, wherein the modified polypeptides comprise non naturally occurring sequences.

In one embodiment the polypeptides of the present disclosure are at least 5, 10, 15, 20, 25, 30, 35, 40, 45, 50, 55, 60, 65, 70, 75, 80, 85, 90, 95, 100, 110, 120, 125, 130, 140, 150, 160, 170, 175, 180, 200, 250, 300, 350, 400, 450, or even at least 500 amino acids in length. In one specific embodiment, the polypeptide is at least 125 amino acids in length. In a related embodiment, the polypeptide of the present disclosure is not a peptide. In another related embodiment, the polypeptide of the present disclosure can adopt a three dimensional structure.

In one embodiment, the polypeptides of the present disclosure are at least 1000, 2500, 5000, 7500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, or even 100,000 Daltons in weight.

In one embodiment, the polypeptide of the present disclosure is not a growth factor or a cytokine.

In one embodiment, the polypeptide of the present disclosure does not bind a transcriptional regulatory region. In a specific embodiment, the polypeptide does not bind a promoter region, enhancer region, silencer region or insulator region of a gene. In another specific embodiment, the polypeptide does not bind a transcription factor.

In one embodiment the polypeptide of the present disclosure comprises at least one mutation of a naturally occurring protein or protein domain. In another embodiment, the polypeptide comprises at least 30%, 40%, 50%, 60%, 70%, 75%, 80%, 85%, 90%, 95%, 99% or 100% amino acid sequence homology to a naturally occurring protein or protein domain. In another embodiment the polypeptide is not a naturally occurring protein or protein fragment.

In another embodiment, the polypeptide of present disclosure has a first domain and a second domain, wherein the first and second domains bind a CRP, wherein the first domain comprises the amino acid sequence set forth in SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, or SEQ ID NO:31, and wherein $X_1$ is not Aspartate, $X_2$ is not Threonine or $X_3$ is not Isoleucine. In a specific embodiment, $X_1$ is any amino acid except Aspartate, $X_1$ is Glycine, or $X_1$ is Glutamate. In another specific embodiment, $X_2$ is any amino acid except Threonine, $X_2$ is Alanine or $X_2$ is any non-polar amino acid. In yet another specific embodiment, $X_3$ is any amino acid except Isoleucine, $X_3$ is Leucine or $X_3$ is any non-polar amino acid. In a related embodiment, the first domain comprises the amino acid sequence set forth in SEQ ID NO:19, wherein $X_1$ is not Aspartate; SEQ ID NO:26, wherein $X_2$ is not Threonine; or SEQ ID NO:31, wherein $X_3$ is not Isoleucine. In another related embodiment, the second domain comprises the amino acid sequence set forth in SEQ ID NO:19, wherein $X_1$ is not Aspartate; SEQ ID NO:26, wherein $X_2$ is not Threonine; or SEQ ID NO:31, wherein $X_3$ is not Isoleucine.

Description of SEQ ID NO:15 to SEQ ID NO:31

SEQ ID NO: 15
(AA SEQUENCE OF THE DE LOOP OF THE AD35 FIBER KNOB DOMAIN)
DSSGNLLTX$_1$ESDLKIPL.

wherein X$_1$ is any amino acid;
wherein X$_1$ is D (wild type);
wherein X$_1$ is G (mutant); or
wherein X$_1$ is E (conservative substitution)

SEQ ID NO: 16
(PARTIAL AA SEQUENCE OF THE DE LOOP OF THE AD35 FIBER KNOB DOMAIN)
GNLLTX$_1$ESDLK.

wherein X$_1$ is any amino acid;
wherein X$_1$ is D (wild type);
wherein X$_1$ is G (mutant); or
wherein X$_1$ is E (conservative substitution)

SEQ ID NO: 17
(PARTIAL AA SEQUENCE OF THE DE LOOP OF THE AD35 FIBER KNOB DOMAIN)
NLLTX$_1$ESDL.

wherein X$_1$ is any amino acid;
wherein X$_1$ is D (wild type);
wherein X$_1$ is G (mutant); or
wherein X$_1$ is E (conservative substitution)

SEQ ID NO: 18
(PARTIAL AA SEQUENCE OF THE DE LOOP OF THE AD35 FIBER KNOB DOMAIN)
LLTX$_1$ESD.

wherein X$_1$ is any amino acid;
wherein X$_1$ is D (wild type);
wherein X$_1$ is G (mutant); or
wherein X$_1$ is E (conservative substitution)

SEQ ID NO: 19
(PARTIAL AA SEQUENCE OF THE DE LOOP OF THE AD35 FIBER KNOB DOMAIN)
LTX$_1$ES.

wherein X$_1$ is any amino acid;
wherein X$_1$ is D (wild type);
wherein X$_1$ is G (mutant); or
wherein X$_1$ is E (conservative substitution)

SEQ ID NO: 20
(PARTIAL AA SEQUENCE OF THE DE LOOP OF THE AD35 FIBER KNOB DOMAIN)
TX$_1$E.

wherein X$_1$ is any amino acid;
wherein X$_1$ is D (wild type);
wherein X$_1$ is G (mutant); or
wherein X$_1$ is E (conservative substitution)

SEQ ID NO: 21
(PARTIAL AA SEQUENCE OF THE DE LOOP OF THE AD35 FIBER KNOB DOMAIN)
GNLLTX$_1$ES.

wherein X$_1$ is any amino acid;
wherein X$_1$ is D (wild type);
wherein X$_1$ is G (mutant); or
wherein X$_1$ is E (conservative substitution)

SEQ ID NO: 22
(PARTIAL AA SEQUENCE OF THE DE LOOP OF THE AD35 FIBER KNOB DOMAIN)
GNLLTX$_1$.

wherein X$_1$ is any amino acid;
wherein X$_1$ is D (wild type);
wherein X$_1$ is G (mutant); or
wherein X$_1$ is E (conservative substitution)

SEQ ID NO: 23
(AA SEQUENCE OF THE FG LOOP OF THE AD35 FIBER KNOB DOMAIN)
TSETVASSKAFMPSTTAYPFNTX$_2$TRDSENYIHGX$_3$.

wherein X$_2$ is any amino acid;
wherein X$_2$ is T (wild type);
wherein X$_2$ is A (mutant);
wherein X$_2$ is C, G, N, Q, S, or Y; or
wherein X$_2$ is F, I, L, M, P, V, or W
wherein X$_3$ is any amino acid;
wherein X$_3$ is I (wild type)
wherein X$_3$ is L (mutant)
wherein X$_3$ is A, F, M, P, V, or W SEQ ID NO: 24
(PARTIAL AA SEQUENCE OF THE FG LOOP OF THE AD35 FIBER KNOB DOMAIN)
FNTX$_2$TRDSENYIHGX$_3$.

wherein X$_2$ is any amino acid;
wherein X$_2$ is T (wild type);
wherein X$_2$ is A (mutant);
wherein X$_2$ is C, G, N, Q, S, or Y; or
wherein X$_2$ is F, I, L, M, P, V, or W
wherein X$_3$ is any amino acid;
wherein X$_3$ is I (wild type)
wherein X$_3$ is L (mutant)
wherein X$_3$ is A, F, M, P, V, or W SEQ ID NO: 25
(PARTIAL AA SEQUENCE OF THE FG LOOP OF THE AD35 FIBER KNOB DOMAIN)
FNTX$_2$TRD.

wherein X$_2$ is any amino acid;
wherein X$_2$ is T (wild type);
wherein X$_2$ is A (mutant);
wherein X$_2$ is C, G, N, Q, S, or Y; or
wherein X$_2$ is F, I, L, M, P, V, or W SEQ ID NO: 26
(PARTIAL AA SEQUENCE OF THE FG LOOP OF THE AD35 FIBER KNOB DOMAIN)
NTX$_2$TR.

wherein X$_2$ is any amino acid;
wherein X$_2$ is T (wild type);
wherein X$_2$ is A (mutant);
wherein X$_2$ is C, G, N, Q, S, or Y; or
wherein X$_2$ is F, I, L, M, P, V, or W SEQ ID NO: 27
(PARTIAL AA SEQUENCE OF THE FG LOOP OF THE AD35
FIBER KNOB DOMAIN)
TX$_2$T.

wherein X$_2$ is any amino acid;
wherein X$_2$ is T (wild type);
wherein X$_2$ is A (mutant);
wherein X$_2$ is C, G, N, Q, S, or Y; or
wherein X$_2$ is F, I, L, M, P, V, or W SEQ ID NO: 28
(PARTIAL AA SEQUENCE OF THE FG LOOP OF THE AD35
FIBER KNOB DOMAIN)
X$_2$TRDSENYIHGX3.

wherein X$_2$ is any amino acid;
wherein X$_2$ is T (wild type);
wherein X$_2$ is A (mutant);
wherein X$_2$ is C, G, N, Q, S, or Y; or
wherein X$_2$ is F, I, L, M, P, V, or W
wherein X$_3$ is any amino acid;
wherein X$_3$ is I (wild type);
wherein X$_3$ is L (mutant); or
wherein X$_3$ is A, F, M, P, V, or W SEQ ID NO: 29
(PARTIAL AA SEQUENCE OF THE FG LOOP OF THE AD35
FIBER KNOB DOMAIN)
TRDSENYIHGX$_3$.

wherein X$_3$ is any amino acid;
wherein X$_3$ is I (wild type);
wherein X$_3$ is L (mutant); or
wherein X$_3$ is A, F, M, P, V, or W SEQ ID NO: 30
(PARTIAL AA SEQUENCE OF THE FG LOOP OF THE AD35
FIBER KNOB DOMAIN)
YIHGX$_3$.

wherein X$_3$ is any amino acid;
wherein X$_3$ is I (wild type);
wherein X$_3$ is L (mutant); or
wherein X$_3$ is A, F, M, P, V, or W SEQ ID NO: 31
(PARTIAL AA SEQUENCE OF THE FG LOOP OF THE AD35
FIBER KNOB DOMAIN)
HGX$_3$.

wherein X$_3$ is any amino acid;
wherein X$_3$ is I (wild type);
wherein X$_3$ is L (mutant); or
wherein X$_3$ is A, F, M, P, V, or W In yet another related embodiment, the first and second domains bind the same CRP or alternatively the first and second domains bind different CRPs. In the embodiments provided in this aspect of the invention, the CRP is CD35, CD46, CD55, or CD59. In a specific embodiment, the CRP is CD46. In related embodiments, the polypeptide causes internalization or sequestration of the CRP into a cell; and/or the polypeptide binds to the CRP with a dissociation constant (K$_d$) of about 1 nM or less or even about 0.65 nM or less. In some embodiments, the polypeptide is not an antibody or an antibody fragment. The polypeptide can be an isolated, modified viral protein, for example a polypeptide derived from an adenoviral fiber knob protein. Such polypeptide derived from a fiber knob domain of an adenovirus can be for example, selected from the group consisting of Ad11, Ad16, Ad21, Ad34, Ad35 and Ad50. In a very specific embodiment, the polypeptide is derived from the Ad35 fiber knob domain comprising at least one amino acid substitution at the residues selected from Asp207, Thr245, Ile256, and a combination thereof; or more specifically the amino acid substitution is Asp207Gly, Thr245Ala, Ile256Leu, or a combination thereof. In another embodiment, the polypeptide is less than 25,000 Daltons.

The polypeptides provided herein can dimerize, trimerize, homodimerize, or homotrimerize. In one embodiment, the polypeptide dimerizes, homodimerizes, trimerizes or homotrimerizes spontaneously. The dimer, trimer, homodimer, or homotrimer can have a three dimensional structure, wherein each monomer comprises two loops with affinity for binding a CRP. The sequence between the loops can be substitutable and without reducing the binding to the CRP.

In a related embodiment, provided herein is a monomeric polypeptide comprising a non-naturally occurring sequence that upon dimerization or trimerization is capable of binding to a complement regulatory protein (CRP). Dimer, trimer, homodimer, and homotrimer formations can be determined according to methods known to the practitioners in the art. For example, trimerization of polypeptides can be assessed by criteria including sedimentation in sucrose gradients, resistance to trypsin proteolysis, and electrophoretic mobility in polyacrylamide gels (Hong and Engler, *Journal of Virology* 70:7071-7078 (1996)).

The polypeptides of the present invention can further comprise a trimerization domain. In one embodiment, the trimerization domain is derived from a viral protein. By way of example, the trimerization domain is a bacteriophage T4 fibritin domain or a reovirus fiber protein σ1 domain. In one embodiment, the trimerization domain comprises the amino acid sequence: GYIPEAPRDGQAYVRKDGEWVLLSTFL (SEQ ID NO:32).

Also provided herein is a polypeptide complex comprising at least one, two, three, or more of any of the polypeptides described herein. In one embodiment, the polypeptide complex can bind two or more CRP molecules. The CRP can be CD35, CD46, CD55, or CD59. In one specific embodiment, the CRP is CD46.

In one embodiment, the polypeptide complex of the present disclosure is at least 1000, 2500, 5000, 7500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, or even 100,000 Daltons in weight.

In one specific embodiment, as described in Example 1, the specific amino acid substitutions within the Ad35 fiber knob domain (i.e., mutant or modified Ad35 fiber knob domain polypeptides) enhance binding affinity of the homotrimeric fiber knob domain polypeptides to CD46 as compared to the wild-type Ad35 fiber knob domain polypeptides. As demonstrated in Example 2, contacting the cells with the mutant Ad35 fiber knob domain polypeptides induces the internalization of the CD46-Ad35 fiber knob complexes, thereby reducing the prevalence of CD46 on the cell surface. Moreover, the mutant Ad35 fiber knob domain polypeptide (Asp207Gly and Thr245Ala) with enhanced binding affinity to CD46 caused a greater reduction of cell surface CD46, and the reduction lasted for a longer period of time, than that observed with the wild type Ad35 fiber knob domain polypeptide. As demonstrated in Examples 2 and 3, the transient reduction of surface CD46 levels resulted in the sensitization of tumor cells to CDC by anti-cancer mAbs. The sensitizing effect was greatest for the mutant Ad35 fiber knob domain polypeptides with enhanced binding to CD46, followed by wild type Ad35 fiber knob domain polypeptide, both of which had a greater effect than the sensitizing effect of anti-CD46 mAbs. As demonstrated in Example 3, the therapeutic effects of this sensitization were observed in vivo wherein mice receiving lymphoma xenografts had lower levels of lymphoma cells in their bone marrow and enhanced survival periods after receiving a sensitizing treatment of mutant Ad35 fiber knob domain polypeptides prior to a mAb treatment. As further demonstrated in Example 2, the reduction of surface levels of CD46 induced by mutant Ad35 fiber knob domain polypeptides reduced cellular infectivity by an Ad35-GFP vector. Thus, the high affinity of mutant Ad35 fiber knob domain polypeptides (e.g., Ad35K++) together with their ability to crosslink several CD46 molecules resulted in transient CD46 internalization, which in turn sensitized lymphoma cells to rituximab-medicated CDC in vitro, and in an in vivo animal model of lymphoma.

Reduction of Activity of a CRP on a Target Cell Surface

The binding of the polypeptides, dimers, or trimers to a CRP can be determined according to methods well known to practitioners in the art. For example, binding to CD46, CD55, CD59, or CD35 can be determined by simple western blotting or surface plasmon resonance assays as described in Wang, H., et al., *Journal of Virology* 81:12785-12792 (2007) and in Example 1 (for CD46). For example, the binding affinity of homotrimers for CD46 can be quantified according to methods well known to practitioners in the art, such as the surface plasmon resonance assay described in Example 1.

Accordingly, in one embodiment, a modified polypeptide comprising non-naturally occurring amino acid sequences and at least two domains capable of binding a CRP is provided. The polypeptide itself can bind a CRP, or can dimerize, trimerize, homodimerize, or homotrimerize to bind a CRP. The polypeptide can be further part of a protein complex which can bind a CRP. Provided herein are modified polypeptides comprising non-naturally occurring amino acid sequences, dimers or trimers comprising these modified polypeptides, or polypeptide complexes comprising two or more of these modified polypeptides wherein the modified polypeptides, dimers, trimers, or complexes can bind to a CRP with a greater affinity (such as at least 1, 1.5, 2, 3, 4, 5, 6, 7, 8, 9, 10, 15, 20, 23, 25, 30, 35, 40, 45, 50, 75, 100, 150, 200, 500, or at least about 1000 fold higher) as compared to an otherwise unmodified, wild-type or parental polypeptide. Accordingly the dissociation constant ($K_d$) of the CRP to the modified polypeptide, dimer, trimer, or complex is no more than 10 nM, 5 nM, 4 nM, 3 nM, 2 nM, 1.5 nM, 1 nM, 0.9 nM, 0.8 nM, 0.7 nM, 0.65 nM, 0.63 nM, 0.6 nM, 0.5 nM, 0.4 nM, 0.3 nM, 0.25 nM, 0.2 nM, 0.15 nM, 0.1 nM, 0.05 nM, 0.01 nM, 0.005 nM, 0.001 nM, 0.0005 nM, or 0.0001 nM. In a specific embodiment, as described in Example 1, the Kd of a modified fiber knob domain polypeptide and CD46 is 0.63 nM.

Accordingly, in one embodiment, the modified polypeptides provided herein are capable of forming trimers, or homotrimers that bind to a CRP (CD46, CD55, CD59, or CD35) expressed on a target cell surface and induces internalization of the CRP into the cell. In another embodiment, the modified polypeptides provided herein are capable of forming trimers, or homotrimers that bind to a CRP (CD46, CD55, CD59, or CD35) expressed on a target cell surface and induces sequestration of the CRP. In yet another embodiment, the modified polypeptides provided herein are capable of forming trimers or homotrimers that bind to a CRP (CD46, CD55, CD59, or CD35) expressed on a target cell surface and reduces the density of CRP receptors on the target cell. In another related embodiment, the modified polypeptides provided herein are capable of forming trimers or homotrimers that bind to a CRP (CD46, CD55, CD59, or CD35) expressed on a target cell surface and reduce the activity of the CRP on the target cell.

In one embodiment, incubation with or contacting of a modified polypeptide causes at least a 5% reduction of cell surface CRP levels, and preferably at least a 10%, 20%, 30%, 40%, 50%, 60%, or 70% reduction in the cell surface CRP levels.

In another embodiment, incubation with or contacting of a modified polypeptide causes at least a 5% reduction of CRP density at the cell surface, and preferably at least a 10%, 20%, 30%, 40%, 50%, 60%, or 70% reduction in CRP density at the cell surface.

In another embodiment, incubation with or contacting of a modified polypeptide causes at least a 5% reduction of CRP activity at the cell surface, and preferably at least a 10%, 20%, 30%, 40%, 50%, 60%, or 70% reduction in CRP activity at the cell surface.

In yet another embodiment, incubation with or contacting of a modified polypeptide causes at least a 5% increase in sequestration or internalization of the CRP at the cell surface, and preferably at least a 10%, 20%, 30%, 40%, 50%, 60%, or 70% increase in sequestration or internalization at the cell surface.

In some embodiments, the reduction in cell surface CRP levels, reduction in the density of the CRP on the cell surface, reduction of activity of the CRP on the target cell surface, increase in CRP internalization, increase in CRP sequestration by an incubation with a modified polypeptide lasts for at least 2 hours, 4 hours, 6 hours, 8 hours, 10 hours, and preferably lasts for at least 12 hours, 24 hours, 36 hours, 48 hours, 72 hours, or 96 hours, before the cell surface CRP levels return to the pre-incubation levels.

In an exemplary embodiment, a modified fiber knob domain polypeptide comprising at least 12 contiguous amino acid residues of the amino acid sequence set forth as SEQ ID NO:3, comprises scaffold motifs to facilitate CD46 binding.

Modified Adenovirus Fiber Knob Domain Polypeptides

In an exemplary embodiment, modified Adenovirus fiber knob domain polypeptides are used to reduce the activity of CD46 on a cell surface. FIG. 1A is a schematic illustration of the full length wild type Adenovirus serotype 35 (Ad35) fiber polypeptide, provided as SEQ ID NO:2 (which is encoded by the cDNA provided as SEQ ID NO:1), indicating the relative positions of the N-terminal tail domain (aa 1-45), the shaft domain (aa 46-133), and the C-terminal fiber knob (K) domain (aa 134-323). It was previously determined that in addition to the knob domain (aa 134-323), the C-terminal-most section of the shaft domain (aa 123-133) is required for fiber trimerization. Hong and Engler, *J. Virology* 70:7071-7078 (1996). Accordingly, as shown in FIG. 1B, the wild-type Ad35 polypeptide encompassing an 11 amino acid portion (aa 123-133) of the shaft domain, and the entire knob domain (aa 134-323) is provided as SEQ ID NO:3. Disclosed herein are amino acid substitutions numbered sequentially with respect to the first amino acid residue of SEQ ID NO:2 (shown in FIG. 1A). Accordingly, the first amino acid residue in SEQ ID NO:3 corresponds to amino acid 123 of the full length fiber polypeptide (SEQ ID NO:2). Unless otherwise indicated, this numbering scheme is also used for the corresponding amino acid positions in polypeptide sequences that comprise only a subpart or a variation of SEQ ID NO:2 to communicate the relative position of the sequence to the full length sequence. However, in some instances, the locations of specific amino acid positions within fiber polypeptide fragments are designated by the position in the specific fragment sequence.

As described herein, the following amino acid substitutions in the knob domain (SEQ ID NO:3) of the fiber polypeptide (SEQ ID NO:2): amino acid residue 207, wherein the Asp is replaced by Gly, amino acid residue 245, wherein the Thr is replaced by Ala, and amino acid residue 256, wherein the Ile is replaced by Leu, individually or in combination, result in enhanced binding affinity of the modified Ad35 fiber knob domain polypeptides to CD46. See Table 2 and Example 1.

Accordingly, in some embodiments, the invention provides a modified fiber knob domain polypeptide comprising at least 12 contiguous amino acids of the amino acid sequence set forth as SEQ ID NO:3, wherein the polypeptide includes at least one amino acid substitution selected from the group consisting of Asp207Gly, Thr245Ala, and Ile256Leu, or a combination thereof, and wherein the polypeptide can form homotrimers capable of binding to CD46.

As used herein, the phrase “contiguous amino acids of SEQ ID NO:3” refers to a sequential ordering of amino acids residues as they appear in SEQ ID NO:3 without insertions, deletions, or most substitutions. This phrase, however, permits the incorporation of the amino acid substitutions described (i.e., Asp207Gly, Thr245Ala, Ile256Leu). Thus, in one exemplary embodiment, the polypeptide may comprise at least residues 1-12 of SEQ ID NO:3 (corresponding to SEQ ID NO:2, amino acid residues 123-135), and one or more of a Gly substitution at position 85 (corresponding to Asp at position 207 of SEQ ID NO:2); an Ala substitution at position 123 (corresponding to Thr at position 245 of SEQ ID NO:2); and/or a Leu substitution at position 134 (corresponding to Ile at position 134 of SEQ ID NO:2).

In some embodiments, the modified fiber knob domain polypeptide comprises at least 20, at least 30, at least 40, at least 50, at least 100, at least 200, or at least 300 contiguous amino acids of SEQ ID NO:3 and further comprises at least one of the amino acid substitutions selected from the group consisting of Asp207Gly, Thr245Ala, and Ile256Leu.

In some embodiments, the modified fiber knob domain polypeptide comprises between at least 12 and about 20 contiguous amino acids of SEQ ID NO:3, including at least one of the amino acid substitutions selected from the group consisting of Asp207Gly, Thr245Ala, and Ile256Leu.

In other embodiments, the modified fiber knob domain polypeptide comprises between at least 20 and about 50 contiguous amino acids of SEQ ID NO:3, including at least one of the amino acid substitutions selected from the group consisting of Asp207Gly, Thr245Ala, and Ile256Leu.

In other embodiments, the modified fiber knob domain polypeptide comprises between at least 50 and about 100 contiguous amino acids of SEQ ID NO:3, including at least one of the amino acid substitutions selected from the group consisting of Asp207Gly, Thr245Ala, and Ile256Leu.

In still other embodiments, the modified fiber knob domain polypeptide comprises between about 100 and all of the contiguous amino acids of SEQ ID NO:3, including at least one of the amino acid substitutions selected from the group consisting of Asp207Gly, Thr245Ala, and Ile256Leu.

In one embodiment, the modified fiber knob domain polypeptide comprises at least 40 contiguous amino acids of SEQ ID NO:3, wherein the polypeptide includes Asp207Gly and Thr245Ala. In one embodiment, the polypeptide comprises SEQ ID NO:3 with the substitutions Asp207Gly and Thr245Ala, as set forth in SEQ ID NO:5, which is encoded by the cDNA set forth as SEQ ID NO:4.

In another embodiment, the modified fiber knob domain polypeptide comprises at least one of SEQ ID NO:6, SEQ ID NO:7, SEQ ID NO:8, and SEQ ID NO:9. SEQ ID NO:6 is the amino acid sequence of the DE loop region in the Ad35 fiber knob domain that connects the D beta sheet to the E beta sheet, and corresponds to a contiguous amino acid sequence of SEQ ID NO:2 from amino acid position 199 to amino acid position 215. In some embodiments, the polypeptide comprises SEQ ID NO:6 (the DE loop) including the amino acid substitution Asp207Gly.

SEQ ID NO:7 is the amino acid sequence of the FG loop region in the Ad35 fiber knob domain that connects the F beta sheet to the G beta sheet, and corresponds to a contiguous amino acid sequence of SEQ ID NO:2 from amino acid position 223 to amino acid position 256. In some embodiments, the polypeptide comprises SEQ ID NO:7 (the FG loop) including one or both amino acid substitutions Thr245Ala and/or Ile256Leu.

SEQ ID NO:8 is the amino acid sequence of the HI loop region in the Ad35 fiber knob domain that connects the H beta sheet to the 1 beta sheet, corresponding to a contiguous amino acid sequence of SEQ ID NO:2 from amino acid position 276 to amino acid position 287. SEQ ID NO:9 is the amino acid sequence of the IJ loop region in the Ad35 fiber knob domain that connects the 1 beta sheet to the J beta sheet, corresponding to a contiguous amino acid sequence of SEQ ID NO:2 from amino acid position 297 to amino acid position 313. In some embodiments, the modified fiber knob domain polypeptide is a scaffold polypeptide comprising SEQ ID NOS:5, 6, 7, and 8 in order to form a binding domain that binds to CD46.

Crystallography analysis of the Ad35 fiber knob domain has helped to demonstrate that the FG loop (SEQ ID NO:7) and HI loop (SEQ ID NO:8) are on the opposite sides of the Ad35 fiber knob domain in comparison to the contact area in the IJ loop (SEQ ID NO:9) (Wang et al., *Journal of Virology* 81:12785-12792 (2007)). The fact that amino acid residues within these loops are important for CD46 binding implies that one CD46 unit binds between two Ad35 fiber knob domains (i.e., between the FG and HI loops of one fiber knob domain, and the IJ loop of the other fiber knob domain). Further, the results described in Wang et al., *Journal of Virology* 82:10567-10579 (2008), and Example 1 support the importance of the mutant sequences encompassed by SEQ ID NOS:6 and 7 for enhanced binding to CD46. Crystallography analysis suggests that a substitution in the DE loop (SEQ ID NO:6) of the Asp at position 207 by Gly allows the DE and HI loops to approach the CD46. This is because in binding, the closest CD46 R-group to amino acid position 207 is a hydrophobic Ile residue (Ile13). The substitution of a hydrophobic Gly for a polar Asp may allow the CD46 HI loop to move closer to the Ile13 residue. Similarly, the introduction of a hydrophobic Ala for Thr at amino acid position 245 within the FG loop (SEQ ID NO:7) likely permits the Thr at position 246 to move closer to CD46 Tyr at position 46. Consequently, the FG loop is able to move closer to CD46.

In one embodiment, the modified fiber knob domain polypeptide comprises an amino acid sequence that is at least 50%, at least 60%, at least 70%, at least 75%, at least 80%, at least 85%, at least 90%, at least 95%, or is absolutely identical to SEQ ID NO:3. In one embodiment, the modified fiber knob domain polypeptide comprises the amino acid sequence of a mutant Ad35 fiber knob domain polypeptide that contains amino acid substitutions at position 207, wherein the Asp is replaced by Gly, and at position 245, wherein the Thr is replaced by Ala, set forth as SEQ ID NO:5. The combination of these two substitutions in the knob domain results in a mutant Ad35 fiber knob domain polypeptide (also referred to herein by Ad35K++) that trimerizes to form a homotrimeric knob structure with an affinity for binding to CD46 that is 23.2-fold higher than that of the homotrimeric knob structure formed by wild type Ad35 fiber knob domain polypeptide (SEQ ID NO:3) (also referred to herein as Ad35K), as shown in Table 2 and Example 1.

In accordance with this aspect of the invention, the modified fiber knob domain polypeptide is able to form homotrimeric knob structures that can bind to CD46 expressed on the surface of a cell. The formation of homotrimers occurs spontaneously, and does not require the entirety of the individual fiber polypeptides. As shown by Hong and Engler, *Journal of Virology* 70:7071-7078 (1996), incorporated herein by reference, deletion of the entire N-terminal half of the Ad2 fiber protein did not affect homotrimerization. Therefore, at most, the C-terminal half of the fiber protein is sufficient for trimerization. In particular, the investigators found that the minor deletions at the C-terminus (SEQ ID NO:2 aa 123-134) destroyed trimerization, whereas selected additions or substitutions preserving the residue charge resulted in relatively stable homotrimers. Therefore, fiber trimerization may be achieved with the entire fiber knob domain and at least the very C-terminal amino acids (SEQ ID NO:2 aa 123-134) of the shaft.

Homotrimer formation can be determined according to methods well known to the practitioners in the art. For example, trimerization of the fiber knob proteins can be assessed by criteria including sedimentation in sucrose gradients, resistance to trypsin proteolysis, and electrophoretic mobility in polyacrylamide gels (Hong and Engler, *Journal of Virology* 70:7071-7078 (1996)). Regarding electrophoretic mobility, the fiber knob domain homotrimer is a very stable complex and will run at a molecular weight consistent with that of a trimer when the sample is not boiled prior to SDS-PAGE. Upon boiling, however, the trimeric structure is disrupted and the protein subsequently runs at a size consistent with the protein monomer. Trimerization of the fiber knob proteins can also be determined using the rabbit polyclonal anti-His6-HRP antibody as described in Wang, H., et al., *Journal of Virology* 81:12785-12792 (2007) and in Example 1.

The binding of the homotrimers to CD46 can be determined according to methods well known to practitioners in the art. For example, binding to CD46 can be determined by simple western blotting or surface plasmon resonance assays as described in Wang, H., et al., *Journal of Virology* 81:12785-12792 (2007) and in Example 1. Furthermore, the binding affinity of the homotrimers for CD46 can be quantified according to methods well known to practitioners in the art, such as the surface plasmon resonance assay described in Example 1.

Homotrimer formation in general can be determined according to methods well known to the practitioners in the art. For example, trimerization of polypeptides can be assessed by criteria including sedimentation in sucrose gradients, resistance to trypsin proteolysis, and electrophoretic mobility in polyacrylamide gels (Hong and Engler, *Journal of Virology* 70:7071-7078 (1996)). Regarding electrophoretic mobility, the fiber knob protein homotrimer is a very stable complex and will run at a molecular weight consistent with that of a trimer when the sample is not boiled prior to SDS-PAGE. Upon boiling, however, the trimeric structure is disrupted and the protein subsequently runs at a size consistent with the protein monomer. Trimerization of the fiber knob proteins can also be determined using the rabbit polyclonal anti-His6-HRP antibody as described in Wang, H., et al., *Journal of Virology* 81:12785-12792 (2007) and in Example 1.

Figure 2A:
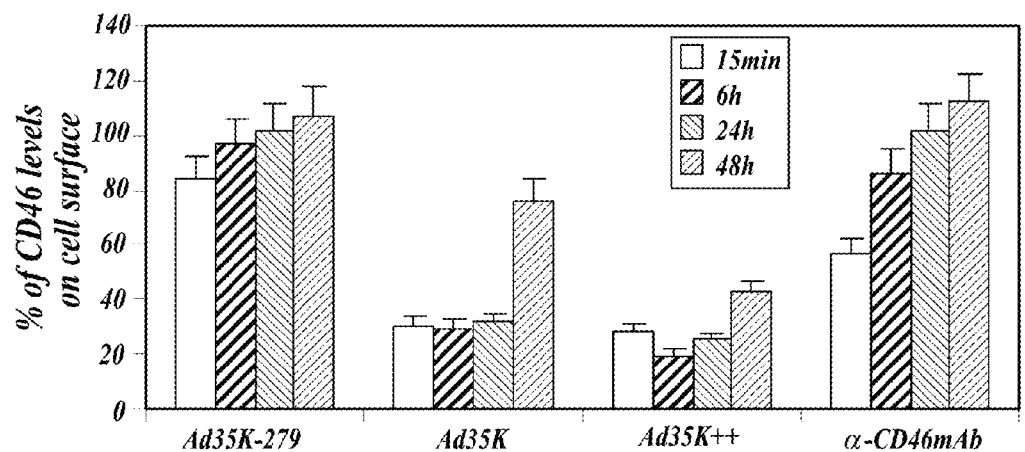
FIG. 2A graphically illustrates the relative levels of CD46 on the surface of HeLa cells at different time points after incubation with Ad35K-279 (ablated for binding to CD46), Ad35K (wild type), Ad45K++ (double mutant containing Asp207Gly and Thr245Ala), or with anti-CD46 mAb, wherein the levels of CD46 were analyzed by flow cytometry and are expressed as a percentage of CD46 mean fluorescence intensity of untreated cells (N>6), as described in Example 2.

In a specific embodiment, as described in Example 2, the binding of modified Ad35 fiber knob domain polypeptides (e.g., Ad35K++) to CD46 expressed on a cell membrane induces the internalization of the fiber knob domain polypeptide/CD46 complex into the interior of the cell, as described in Example 2. FIG. 2A illustrates the cell surface levels of CD46 on HeLa cells at different time points after the addition of 20 µg/ml of PBS (control), wild type Ad35K (wild type), Ad35K++ (SEQ ID NO:5), or anti-CD46 mAb. After 15 minutes, cells contacted with Ad35K++ had about a 70% reduction in CD46 levels on their surface compared to cells treated with PBS. Ad35K++ caused the greatest decline in CD46 levels and the slowest return toward pre-incubation levels. In contrast, cells treated with anti-CD46 mAbs showed only about a 30% decline in cell surface CD46 levels with a faster return to preincubation levels.

Figure 2B:
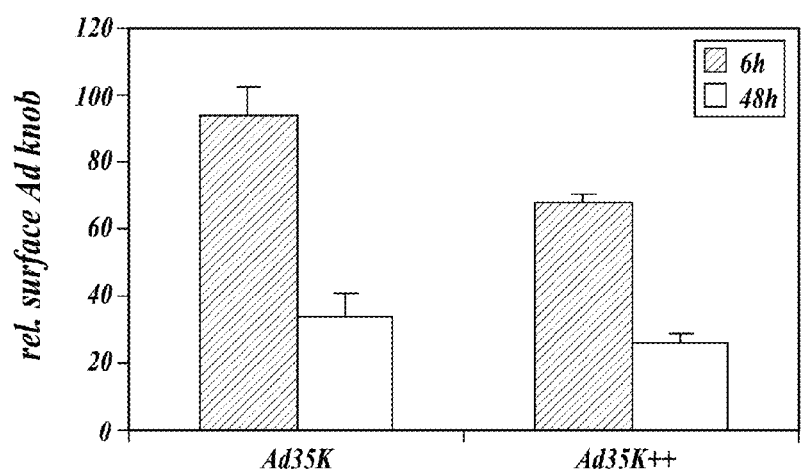
FIG. 2B graphically illustrates the relative levels of recombinant Ad35 fiber knob protein on the surface of HeLa cells at 6 or 48 hours after incubation with recombinant Ad35K (wild-type) or Ad35K++ (double mutant containing Asp207Gly and Thr245Ala), wherein levels were analyzed by flow cytometry using an anti-His$_6$ tag antibody followed by an anti-mouse antibody-Alexa Fluor 488, and are expressed as a percentage of mean fluorescence intensity of untreated cells (N>6), as described in Example 2.
Figure 2C:
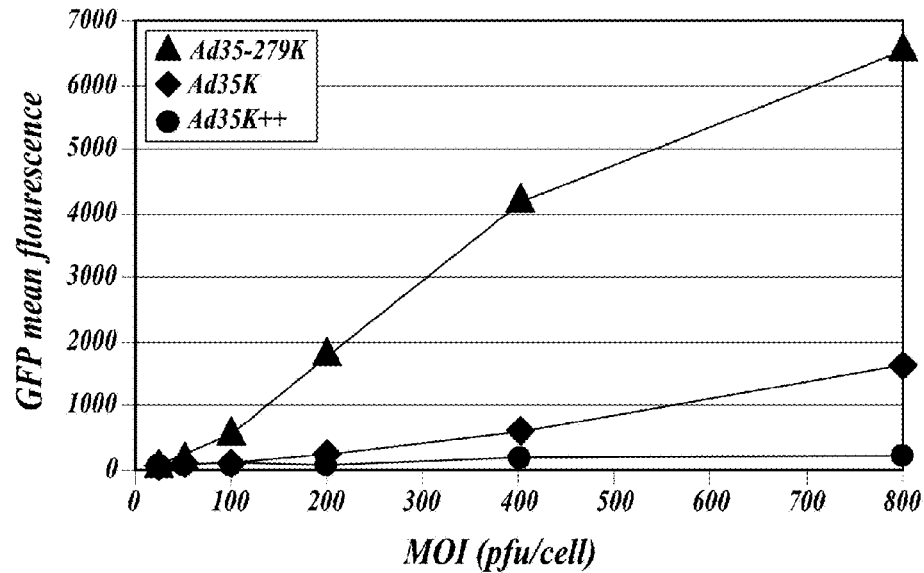
FIG. 2C graphically illustrates transduction levels of HeLa cells after Ad35-GFP infection, as measured by GFP mean fluorescence of HeLa cells 24 hours after exposure to increasing MOIs of Ad35-GFP infectious viral particles, wherein HeLa cells were pre-incubated with either recombinant fiber knob protein Ad35K-279 (ablated for binding to CD46), Ad45K (wild-type), or Ad45K++ (double mutant containing Asp207Gly and Thr245Ala) 72 hours prior to infection with Ad35-GFP viral particles, as described in Example 2.

FIG. 2B illustrates the results of flow cytometry studies showing a decrease of cell-bound Ad35K and Ad35K++, indicating that the fiber knob domain polypeptides are internalized along with the CD46. Immunofluorescence studies indicated that at 30 minutes after contacting cells with Ad35K and Ad35K++, the fiber knob domain polypeptides and CD46 were detected in the late endosome/lysosomes. Moreover, at 12 hours after contacting the cells with the fiber knob domain polypeptides, cells treated with Ad35K++ demonstrated predominantly cytoplasmic CD46 staining with an intensity indicating degradation of CD46 in the lysosomes. Similar to the results in Example 2, Ad35K++ mediated reduction in surface CD46 levels was observed for the following lymphoma/leukemia cells: Raji, Jurkat, K562, Mole, Mino, and Farage; and for the following solid tumor cells: A549 (lung), SKOV3 (ovarian), HT29 (colon), and MDA235MB cells (breast). Consistent with these results, as shown in FIG. 2C, attempts to infect cells with Ad35-GFP (requiring surface CD46 for infection) 72 hours after contacting cells with Ad35 fiber knob or Ad35K++ resulted in relatively resistant cells, indicating a lack of surface CD46. Similar CD46 flow cytometry and Ad35-GFP assay performed on other tumor cell lines, such as erythroleukemia Mole cells and B-lymphoma Raji cells gave similar results.

Identification of Molecules Capable of Reducing the Activity, Amount, or Density of a CRP on a Target Cell Surface In one embodiment, a method for screening for a molecule or compound capable of modifying a CRP activity is provided. The method includes generating a library of candidate molecules, selecting for candidate molecules capable of binding the CRP and determining if the molecule modifies the activity of the CRP. The CRP can be CD46, CD55, CD59, or CD35. In a specific embodiment, the CRP is CD46. In one embodiment, the molecule binds the CRP, for example with a binding affinity of 1 nM or less. The molecule being screened for can be selected from the group consisting of a protein, a polypeptide, a small molecule, a drug, an antibody, an antibody fragment, a hybrid antibody, an antibody drug-conjugate, a siRNA, an antisense RNA, a miRNA, a virus, and an aptamer. In an exemplary embodiment, the molecule is a small molecule. In another exemplary embodiment, the molecule is a polypeptide. In related embodiments, the molecule modifies the activity of the CRP by internalization or sequestration of the CRP into a cell, or by reducing the amount or density of the CRP on a cell surface.

A molecule capable of modifying the activity of a CRP or binding a CRP may identified by screening either a cell population or fractionated cells expressing a CRP against test molecules. Novel molecules may be isolated or identified using different test compounds of known composition bound to a substrate, such as an array or a plurality of particles, which can allow a large amount of chemical/structural space to be adequately sampled using only a small fraction of the space. Since the composition of each test compound on the substrate surface is known, this constitutes a screen for affinity elements. For example, a test compound array comprises test compounds at specific locations on the substrate addressable locations, and can be used to identify one or more binding agents for a CRP. The test compounds can be unrelated or related based on minor variations of a core sequence or structure. The different test compounds may include variants of a given test compound (such as polypeptide isoforms), test compounds that are structurally or compositionally unrelated, or a combination thereof.

Test compounds can be small molecules, drugs, peptoids, polysaccharides, organic compounds, inorganic compounds, polymers, lipids, nucleic acids, polypeptides, antibodies, antibody fragments, hybrid antibodies, antibody-drug conjugates, siRNAs, antisense RNAs, miRNAs, viruses, aptamers, proteins, polysaccharides, or other compounds. The test compounds can be natural or synthetic. The test compounds can comprise or consist of linear or branched heteropolymeric compounds based on any of a number of linkages or combinations of linkages (e.g., amide, ester, ether, thiol, radical additions, metal coordination, etc.), dendritic structures, circular structures, cavity structures or other structures with multiple nearby sites of attachment that serve as scaffolds upon which specific additions are made. These test compounds can be spotted on the substrate or synthesized in situ, using standard methods in the art. In addition, the test compounds can be spotted or synthesized in situ in combinations in order to detect useful interactions, such as cooperative binding.

In one embodiment, the test compounds can be polypeptides with known amino acid sequences. For example, soluble CRPs can be applied to a spotted array on a slide containing between a few and 1,000,000 test polypeptides having a length of variable amino acids. The polypeptides can be attached to the surface through the C-terminus. The sequence of the polypeptides can be generated randomly from 19 amino acids, excluding cysteine. The binding reaction can include a non-specific competitor, such as excess bacterial proteins labeled with another dye such that the specificity ratio for each polypeptide binding target can be determined. The polypeptides with the highest specificity and binding can be selected. The identity of the polypeptide on each spot is known, and thus can be readily identified.

An antibody or synthetic antibody to be used as a modulator of CRP activity can be identified through a peptide array. Another method is the use of synthetic antibody generation through antibody phage display. M13 bacteriophage libraries of antibodies (e.g., Fabs) are displayed on the surfaces of phage particles as fusions to a coat protein. Each phage particle displays a unique antibody and also encapsulates a vector that contains the encoding DNA. Highly diverse libraries can be constructed and represented as phage pools, which can be used in antibody selection for binding to immobilized antigens. Antigen-binding phages are retained by the immobilized antigen, and the nonbinding phages are removed by washing. The retained phage pool can be amplified by infection of an Escherichia coli host and the amplified pool can be used for additional rounds of selection to eventually obtain a population that is dominated by antigen-binding clones. At this stage, individual phase clones can be isolated and subjected to DNA sequencing to decode the sequences of the displayed antibodies. Through the use of phage display and other methods known in the art, high affinity designer antibodies for CRPs can be generated.

Bead-based assays can also be used to identify novel agents capable of binding or otherwise modulating the activity of CRPs.

The CRP binder or modulator agent can also be a novel aptamer. An aptamer for a target can be identified using systematic evolution of ligands by exponential enrichment (SELEX) (Tuerk & Gold, Science 249:505-510, 1990; Ellington & Szostak, Nature 346:818-822, 1990), such as described in U.S. Pat. No. 5,270,163. A library of nucleic acids can be contacted with a target CRP, and those nucleic acids specifically bound to the target are partitioned from the remainder of nucleic acids in the library which do not specifically bind the target. The partitioned nucleic acids are amplified to yield a ligand-enriched pool. Multiple cycles of binding, partitioning, and amplifying (i.e., selection) result in identification of one or more aptamers with the desired activity. Modified methods, such as Laser SELEX or deSELEX as described in U.S. Patent Publication No. 20090264508 can also be used.

Identification of Modified Polypeptides for Reducing the Activity, Amount or Density of a CRP on a Target Cell Surface Advances in protein engineering and the availability of powerful library selection technologies have allowed the exploration of numerous alternative protein scaffolds designed for binding virtually any protein target of choice. Scaffold libraries are based on protein conformational motifs that exhibit various binding characteristics. Categories include â-Sandwich, â-Barrel, Three-helix bundle, Repeat proteins, Peptide binders, small scaffolds, Scaffolds presenting constrained peptides, Scaffolds with intrinsic fluorescence, Scaffolds with intrinsic enzymatic activity, Protease inhibitors, and Disulfide-bonded scaffolds (Binz, H. K., and Pluckthun, A., "Engineered Proteins as Specific Binding Reagents," *Current Opinion in Biotechnology* 16:459-469 (2005)). Generally, a phage-display selection, as described above, can be generated to create numerous variants of known protein binding motifs. The particular variations that bind a particular target can be selected and sequenced. In this regard, one or more domains of a candidate polypeptide, for example the adenovirus knob domain sequence, can be incorporated into a selected scaffold motif, a library of variants can be created with techniques such as phage-display selection, and the effectiveness of alternative scaffolds may be assessed for CRP (CD46, CD655 or CD59) binding and therapeutic effect using the exemplary assays described in the examples herein.

Modified polypeptides may be produced using recombinant expression methods that are routine for those of skill in the art. For example, the recombinant Ad35 fiber knob domain polypeptide comprising SEQ ID NO:5 (Ad35K++) may be produced by cloning the cDNA sequence encoding Ad35K++ (SEQ ID NO:4), with or without a His tag into an expression vector such as pQE-30Xa expression vector (Qiagen). After transformation into *E. coli*, protein expression is induced by the addition of isopropyl-â-D-thio-galactoside (IPTG), the protein is then purified and digested with factor Xa protease, as suggested by the manufacturer. After digestion, factor Xa protease is removed using Xa Removal Resin. Cleaved $His_6$ tagged peptides and undigested $His_6$ tagged protein are then captured and removed using Ni-NTA affinity chromatography, as described in the manufacturer's instructions.

In one embodiment, provided herein is a method of identifying polypeptides that can bind to a CRP comprising the steps of: applying a 3-dimensional molecular modeling algorithm to the atomic coordinates of the CRP to determine the spatial coordinates for the binding domain/s of the CRP; and electronically screening the stored spatial coordinates of a set of candidate polypeptides against the spatial coordinates of the CRP binding domain/s to identify polypeptides that can bind to the CRP.

In another embodiment provided herein is a method of identifying polypeptides that can bind to a CRP comprising the steps of providing a crystal structure of the CRP and the candidate polypeptides; superimposing the crystal structure of the CRP and a candidate polypeptide; and determining whether there is a structural basis affinity between the candidate polypeptide and the CRP.

In yet another embodiment provided herein is a method for screening for a high affinity polypeptide capable of binding to a CRP, said method comprising: generating a library of candidate polypeptides; selecting for candidate polypeptides capable of homotrimerization; selecting for candidate polypeptides capable of binding the soluble form of the CRP; and identifying those polypeptides capable of binding to the CRP with a binding affinity of 0.65 nM or less.

In another aspect, the present invention provides isolated nucleic acid molecules encoding a modified polypeptide comprising a mutation. For the Ad35 fiber knob protein, the mutation is selected from the group consisting of Asp207Gly, Thr245Ala, and Ild245Leu. The mutations in the Ad35 fiber knob domain (SEQ ID NO:3) are numbered sequentially according to the first amino acid residue of the full length fiber polypeptide (SEQ ID NO:2).

In some embodiments, a nucleic acid is provided. In an exemplary embodiment, the nucleic acid further comprises nucleotide sequences encoding the peptide regions SEQ ID NO:6, SEQ ID NO:7, SEQ ID NO:8, and SEQ ID NO:9. As described above, these peptide fragments correspond to the DE loop, FG loop, HI loop, and IJ loop, respectively, of a Ad35 fiber knob domain polypeptide. In one embodiment, a nucleic acid molecule is provided that encodes a scaffold protein that binds to CD46 and comprises the nucleic acid sequences encoding the peptide regions SEQ ID NO:5, SEQ ID NO:6, SEQ ID NO:7, and SEQ ID NO:8 separated by intervening nucleic acid residues.

In one embodiment, the isolated nucleic acid encodes the mutant Ad35 fiber knob domain (Ad35K++ Asp207Gly and Thr245Ala), set forth as SEQ ID NO:5. A skilled artisan will understand that because of the degeneracy of the genetic code, each amino acid in a polypeptide sequence can be encoded by a multiplicity of known tri-nucleotide codon units. The variety codons that encode each amino acid are well known. As such, a polypeptide, such as SEQ ID NO:5, can be predictably encoded by numerous nucleic acids, each with unique variations in their sequences. Consequently, the variety of nucleic acids are contemplated that, through the degeneracy of the genetic code, all encode the polypeptide of SEQ ID NO:5. In another embodiment, the nucleic acid comprises SEQ ID NO:4.

In another aspect, an expression vector is provided that comprises a nucleic acid encoding the polypeptides described herein. An expression vector is a construct used to introduce a gene into a target cell, enabling the cell to produce quantities of stable messenger RNA (mRNA) from the gene. A non-limiting example of a commercially available expression vectors includes pQE100 (Qiagen, Valencia, Calif.) as was used in Example 1. The expression vector comprises a nucleic acid encoding a polypeptide that comprises at least 12 contiguous amino acids of SEQ ID NO:3 and includes at least one of the amino acid substitutions selected from the group consisting of Asp207Gly, Thr245Ala, and Ild245Leu.

Regardless of the source of vector, a person of ordinary skill in the art will appreciate that an expression vector comprising the nucleic acid described will also have an expression control sequence operably linked to the described nucleic acid sequence. Such expression control sequence can include promoter or enhancer sequences to enable or facilitate host cell transcription machinery to create mRNA copies of the nucleic acid. Specifically, the promoter sequences provide a site for the cell's RNA polymerase enzyme to attach to the DNA sequence near the gene targeted to be transcribed into mRNA. Preferred embodiments comprise such promoter or enhancer regions that permit production of large quantities of mRNA that, in turn, enable the cellular translation machinery to produce large amounts of polypeptides encoded by the nucleic acid. Non-limiting examples of such an expression control sequence is the lac operon, which contains promoter and repressor sequences. The repressor sequence can be blocked by lactose analogs, such as isopropyl-â-D-thio-galactoside (IPTG), thus permitting the promoter elements of the operon to facilitate gene transcription.

It will also be appreciated by persons of ordinary skill in the art that the expression vector may contain a selection marker, such a gene that confers resistance to an antibiotic agent to the cell that contains the vector and expresses the resistance marker gene. By virtue of this resistance marker gene, cells that successfully receive the vector and express genes encoded therein can be isolated from cells that do not. Non-limiting examples of such selection markers are genes that confer resistance to antibiotics, such as kanamycin and ampicillin.

In another aspect, a cultured cell is provided that is transfected with a vector comprising a nucleic acid encoding the polypeptide described above. In this regard, a cell is successfully transfected with a vector when the transcription machinery of the intact cell has access to the nucleic acid template for the production of mRNA. Protocols to facilitate transfection of vectors into cells are well known in the art.

In a further embodiment, the invention encompasses the progeny of a cultured cell that was stably transfected with the vector as described above. Such progeny will contain copies of the vector without having undergone the transfection protocol and are capable of transcribing the nucleic acids contained in vector under the control of an expression control sequence.

Techniques utilizing cultured cells transfected with expression vectors to produce quantities of polypeptides are well known in the art. Wang, H., et al., *Journal of Virology* 81:12785-12792 (2007), which is incorporated herein by reference, provides a non-limiting example of such a technique. Briefly, an expression vector is used that includes a lac operon adjacent to the target gene cloning site. The vector sequence also encodes a six His residue repeat motif at the N-terminus of the gene of interest. After transfection into *Escherichia coli* bacteria cells, expression of the gene can be induced by incubation with IPTG at a concentration of 1 mM. After a sufficient length of time, such as 5 hours, the cells are harvested and lysed using a buffer (50 mM $NaH_2PO_4$, 300 mM NaCl, 10 mM imidazole), followed by incubation with 1 mg/ml lysozyme for 30 minutes on ice and sonication. Cellular debris is removed by centrifugation and the supernatant is incubated with Ni-nitrilotriacetic acid (NTA) agarose beads at 4° C. for 3 hours. The NTA agarose binds to the His tags, facilitating protein purification. The beads are collected and washed with 50 mM $NaH_2PO_4$, 300 mM NaCl, 60 mM imidazole, and 20% glycerol. The recombinant protein is eluted from the NTA beads with 50 mM $NaH_2PO_4$, 300 mM NaCl, 250 mM imidazole, and 20% glycerol.

Methods of Reducing the Amount of CD46 on a Target Cell Surface

In another aspect, the present invention provides a method for reducing the amount of CD46 on a target cell surface. The method comprises contacting a target cell expressing CD46 on its surface with an amount of a composition comprising a plurality of modified adenovirus fiber knob domain polypeptides, wherein the modified adenovirus fiber knob domain polypeptides are capable of forming homotrimers having enhanced affinity for CD46 binding as compared to homotrimers formed from polypeptides consisting of SEQ ID NO:3 (wild-type Ad35 fiber knob). Modified adenovirus 35 fiber knob domain polypeptides for use in the methods of the invention are described herein. Additional modified adenovirus fiber knob domain polypeptides for use in the methods of this aspect of the invention can be derived from any adenovirus serotype that is able to bind to CD46 through its fiber knob domain using routine mutagenesis and screening methods, such as the methods described in Example 1. For example, Group B serotypes 11, 16, 21, 34, 35, and 50, produce fiber knob domain polypeptides that can bind CD46. Moreover, it is contemplated that knob domains from adenoviruses fiber polypeptides recognizing the CAR receptor can be sufficiently modified to enable binding of the trimeric knob structure to CD46.

CRP binding can be performed by various well-known methods. An exemplary method is described in detail in Example 1 for CRP binding, wherein a fiber knob domain mutant library is created and selected for strong CD46 binding. Briefly, random mutagenic PCR is performed using DNA encoding a wild-type adenovirus fiber knob domain polypeptide sequence as template. The amplification products are cloned into expression vectors, and transformed into cells that are then plated on agar plates. After protein expression is induced, bacterial colonies are transferred to filters, on which CD46 binding is visualized by incubating in sequence with soluble CD46, antiCD46 mAb, and labeled anti-Ig antibodies. DNA from the colonies exhibiting the strongest binding signals can then be easily sequenced, and favorable mutations identified. Other high throughput selection strategies for identifying enhancing mutations are known in the art. For example, phage display and peptide display selections can be efficiently performed on vast numbers of variants (approaching $10^8$). Polypeptide variants exhibiting enhanced binding capacity are physically linked to the gene encoding them, thus enabling easy determination of the sequence of the favorable mutations (discussed in Clackson, T., and Wells, J. A., "In Vitro Selection From Protein and Peptide Libraries," TIbTech, 12:173-184 (1994)). Other methods of producing modified adenovirus fiber knob domain polypeptides include utilization of standard techniques to manipulate the wild type fiber knob encoding DNA, such as restriction digestion, and rational design-based mutation. Artificial synthesis of preferred polypeptides is also contemplated.

In embodiments wherein the modified adenovirus fiber knob domain polypeptide is derived from adenovirus serotype 35, the modified Ad35K polypeptides described herein are useful in the practice of the method according to this aspect of the invention. In some embodiments of this method, the modified adenovirus polypeptide comprises at least 12 contiguous amino acid residues of the amino acid sequence set forth as SEQ ID NO:3, wherein the polypeptide includes at least one amino acid substitution selected from the group consisting of Asp207Gly, Thr245Ala, and Ile256Leu, or a combination thereof.

To facilitate the capacity of the homotrimers formed from individual polypeptides to bind to CD46, the homotrimers preferably form knob structures with tightly packed beta sheets. In a preferred embodiment, the polypeptide contains sequences corresponding to beta sheets (I-J) and that retain the beta sheet secondary structure. In another embodiment, the polypeptide contains sequences corresponding to the F-G, H-I, and I-J loops, which connect the beta sheets and present contact points with CD46. FIG. 1B illustrates exemplary beta sheet loop domains within the sequence of a fiber knob domain sequence.

In some embodiments, the modified fiber knob domain polypeptide comprises sequences at least 50%, 55%, 60%, 65%, 70%, 75%, or even at least 80% identical (such as at least 85%, at least 90%, at least 95% or 100% identical) to SEQ ID NO:6, SEQ ID NO:7, SEQ ID NO:8, and SEQ ID NO:9, and further includes an amino acid corresponding to SEQ ID NO:2 amino acid 207, wherein the Asp is replaced by Gly, and SEQ ID NO:2 amino acid 245, wherein the Thr is replaced by Ala. These sequences incorporated into the modified fiber knob domain polypeptide may be situated in any order. In preferred embodiments, these sequences are separated by polypeptide domains that exhibit beta sheet secondary structures.

In accordance with the methods of this aspect of the invention, binding by the homotrimer formed from the modified fiber knob domain polypeptide to CD46 induces internalization of CD46 into the cell. Exemplary methods of detecting internalization of CD46 are described in Example 2. In accordance with the method provided, target cells are contacted with compositions comprising a modified fiber knob domain polypeptide in an amount and time sufficient to cause at least a 40% reduction of CD46 levels on the cell surface compared to contacting target cells with a control, such as PBS. In preferred embodiments, the reduction of CD46 levels on the cell surface is at least 50%, preferably 60%, more preferably 70%, and more preferably 80%. In further embodiments, contacting the target cells with sufficient composition comprising the modified fiber knob domain polypeptide causes a greater reduction of cell surface CD46 compared to the reduction caused by wild-type fiber knob domain polypeptide or anti-CD46 mAb under the same conditions.

Contacting Cells with a Polypeptide Capable of Reducing the Activity of a CRP

The method may be practiced using any target cells that express a CD46, CD55, CD59, or CD35 (a CRP) on the cell surface, including target cells that reside in the body of a mammalian subject or in tissue culture. In some embodiments, as described in more detail herein, the target cells are cancer or tumor cells. In some embodiments, the target cells are vulnerable to infection by pathogens that attach to CD46, CD55, CD59, or CD35, such as, for example, adenoviruses, herpes virus, measles virus, pestivirus, echoviruses and coxsackie B viruses, *Streptococcus pyogenes*, and *Neisseria gonorrhoeae*. The methods provided herein reduce infection by pathogens that require the CD46, CD55, CD59, or CD35 to bind and attach to the cells. By virtue of the reduced cell surface levels of CD46, CD55, CD59, or CD35 on target cells, the pathogens have reduced opportunity to attach and invade the cells because the target cell experiences fewer attachments and contacts with the pathogen.

In an exemplary embodiment, as described in Example 2, the down regulation of CD46 in cells pre-treated with recombinant Ad35K++ (SEQ ID NO:5) reduced the GFP transduction level of infection by Ad35-GFP virions in comparison to untreated control cells.

With regard to contacting target cells in a mammalian subject, methods of administration of the agent are described below. With regard to contacting cells cultured in vitro, methods of presenting agents to cultured cells are routine and known to persons of ordinary skill in the art.

The specific amount of a composition comprising modified polypeptides will vary according to a number of factors that will be appreciated by those of skill in the art. Such factors include the origin of the target cells, the expression profile of CD46, CD55, CD59, or CD35 on the surface of the target cells, the growth environment and accessibility of the cells, the potency and stability of the agent, and the binding affinity of the homotrimeric polypeptides for CD46, CD55, CD59, or CD35.

Cells in culture, in vivo, or ex vivo can be contacted with any modified polypeptide in concentrations ranging from at least 0.001, 0.0025, 0.005, 0.0075, 0.01, 0.025, 0.05, 0.075, 0.1, 0.25, 0.5, 0.75, 1, 2, 5, 5, 7, 5, 10, 12.5, 15, 17.5, 20 and 25 µg/ml of culture medium.

As a non-limiting example, as described in Example 2, cells in culture can be contacted with modified fiber knob domain polypeptide in concentrations ranging from 0.025 and 25 µg/ml of culture medium.

In some embodiments, the internalization of CD46, CD55, CD59, or CD35 from the target cell surface is detectable within about 1, 2, 3, 4, 5, 6, 7, 8, 9, 10, 15, 20, 30, 45, 60, 75, or up to 120 minutes of contacting the target cell with the agent comprising a modified polypeptide. In some embodiments the cell surface levels of CD46, CD55, CD59, or CD35 return to pre-contact, or pre-incubation levels, only after 24 hours, preferably after 36 hours, more preferably after 48 hours, and more preferably after 72 or even 96 hours. Methods for detecting cell surface markers, such as CD46, CD55, CD59, or CD35 are well known in the art, such as flow cytometry and fluorescence staining. Exemplary methods for detecting cell surface levels of CD46 are described in Example 3.

Methods for Inducing Cytolysis in a Target Cell Expressing a CRP

In another aspect, the invention provides methods for inducing cytolysis in a target cell expressing CD46, CD55, CD59, or CD35 on its surface. The method in accordance with this aspect of the invention comprises (a) contacting the target cell expressing CD46, CD55, CD59, or CD35 on its surface with an amount of an agent comprising a plurality of modified polypeptides effective to decrease the amount of CD46, CD55, CD59, or CD35 present on the surface of the target cell; and (b) contacting the target cell treated in accordance with step (a) with an antibody or fragment thereof that binds to an antigen on the surface of the target cell and induces cytolysis.

It has been shown that cell surface expression of CD46, CD55, CD59, or CD35 protects the cell against complement dependent cytolysis. In accordance with the methods of this aspect of the invention, the reduction of cell surface CD46, CD55, CD59, or CD35 levels on the target cell sensitizes the cell to cytolysis by an agent that induces complement-dependent cytolysis (CDC), such as an antibody or fragment thereof. In an exemplary embodiment, as described in Example 2 and illustrated in FIG. 2, cells contacted with an composition comprising the modified adenovirus fiber knob domain polypeptide Ad35K++ (SEQ ID NO:5) experienced a reduction in the surface CD46 levels up to 70%, lasting at least 48 hours.

As a result of the reduction of the complement inhibitor functions of CD46, CD55, CD59, or CD35, the target cell becomes sensitized to an agent that binds to an antigen on the surface of the target cell or otherwise induces cytolysis. The agent that binds to the target cell or otherwise induces cell lysis may be considered a second therapeutic agent (the modified polypeptide capable of reducing the activity of a CRP being the first therapeutic agent) and may be any agent known in the art to have such an effect.

In some embodiments, the second therapeutic agent is selected from the group consisting of a protein, a polypeptide, a small molecule, a drug, an antibody, an antibody fragment, a hybrid antibody, an antibody drug-conjugate, a siRNA, an antisense RNA, a miRNA, a virus, and an aptamer. In other embodiments, the second therapeutic agent is selected from the group consisting of a cytotoxic agent, a cytostatic agent, a chemotherapy agent, a complement-activating agent, a modulator of CRP expression, radiation, an immunomodulatory agent, a pro-apoptotic agent, an inhibitor of heat shock protein, a protease inhibitor, a desialyating agent, a MMP inhibitor, and a PKC inhibitor.

In another embodiment, the second therapeutic agent is: a modulator of CRP expression selected from LI1b, IL4, and TGFb1; an inhibitor of heat shock protein selected from deoxyspergualine and geldanamyctanespimycin17-AAG; a protease inhibitor, desialyating agent or a MMP inhibitor; a PKC inhibitor selected from tamoxifen, enzastaurin, and UBN-01; a chemotherapy agent; or an immunomodulatory agent. Examples of immunomodulatory agents include for example interferon-α, interferon-γ, GM-CSF, a TLR agonist, a NOD receptor agonist, IL2, IL7, IL17, IL21, IL23, TNF, IMiDs, a RIG-1 receptor agonist natural killer cell ligands/activating agents, NKG2P ligands (for example MICa, MICb, RAE1, and ULBP1) and natural antibodies. A natural-cell activating agent can be an antiCD137 antibody. In some embodiments, the agent may be a lectin, or soluble components of the complement system, such as C4b and C3b.

As described above, in some embodiments, the second therapeutic agent that induces CDC is an antibody, or fragment thereof. The antibody can be selected from the group consisting of those listed in Table 1, or more specifically can be Rituxan, Arzerra, Mylotarg, Campath, Herceptin, or Avastin. The antibody or antibody fragment can be further modified to further enhance complement activation, for example with an Fc modification.

The antibody, or fragment thereof, that induces CDC is capable of (i) binding to a cell surface antigen, such as a cancer marker, and (ii) recruiting complement. Accordingly, antibody fragments for use in the methods of the invention generally retain the antigen binding domain and regions responsible for interacting with complement, which are known in the art. For example, it has been shown that regions of antibodies important for the induction of CDC include specific portions of the Fc region, specifically the hinge domain (Dall'Acqua, W., et al., *The Journal of Immunology* 177:1129-1138 (2006)) and/or the $C_H2$ domain (Idusogie, E. E., et al., *The Journal of Immunology* 166:2571-2575 (2001)). As a further example, antibody engineering studies have identified residues in the CH2 domain of the Fc region that enhance the ability of rituximab to bind C1q and mediate CDC (Wang, S. Y., et al., *Expert Opin. Biol. Ther.* 8:759-768 (2008)).

In one embodiment, the target cell may be in continuous contact with the agent that can bind to the cell and induce complement-dependent cytolysis, such as an antibody, including before and after the cell is contacted with the composition comprising modified polypeptides. In another embodiment, the method can be performed in one simultaneous step. In this regard, the composition comprising modified polypeptides and the agent that binds to the target cell and induces complement-dependent cytolysis (e.g., an antibody) can be contacted with the target cell at substantially the same time. In yet another embodiment, the target cell is contacted with the agent that binds to the target cell and induces complement-dependent cytolysis (step b) between about 10 minutes and 72 hours after the target cell is contacted with the composition comprising modified polypeptides (step a). For example, step b may be performed between about 15 minutes and 48 hours after step a is performed, and preferably between about 15 minutes and 12 hours after step a. In a preferred embodiment, step b is performed about 8 hours after step a.

Cytolysis may occur by induction of an antibody-dependent complement pathway, which is described above. In preferred embodiments, the agent is a monoclonal antibody (mAb), for example those exemplary antibodies of Table 1, known to specifically bind to a cell surface marker on the target cell, such as a cell's surface disease marker. In accordance with the methods provided herein, tumor cell cytolysis activated by antibody dependent complement signaling may also involve the participation of effector cells. In addition to initiating formation of MACs on a cell surface, the induction of the complement signaling cascade also produces chemotactic agents useful in recruiting effector cells capable of inducing cellular-mediate cytolysis of the cancer cell. Specifically, the release of complement components C3a and C5a results in a gradient that draws cells such as NK cells into a tumor. Further, molecules of iC3b deposited on the surface of a tumor cell activate complement receptor 3 (CR3) on the surface of effector cells and induce CR3-dependent cellular cytotoxicity in the presence of the yeast cell-wall â-glucan, providing a potential means of activating a cytotoxic mechanism against tumor cells that is typically reserved for yeast and fungi (Adams, G. P. and Weiner, L. M., *Nature Biotechnology* 23:1147-1157 (2005)).

In accordance with the methods of this aspect of the invention, the immediate environment of the target cell comprises all of the necessary components of the complement effector system sufficient to cause cytolysis upon induction. The term "source of complement" as used herein refers to a mixture that includes some or all of the individual components of the complement system necessary to cause cytolysis and cell death upon induction. Components of the complement system are known in the art, some of which are described herein. Moreover, it is well known that serum harvested from a vertebrate animal, such as a human or other mammal, is a source of all of the component's complement. In some embodiments, the method comprises providing the target cells with a source of complement, such as previously harvested serum. The components of the complement system may be administered according to methods known in the art, such as through the injection or infusion of complement components. In yet further embodiments, plasma may be optionally contacted to target cells residing in a tissue culture medium, as illustrated in Example 3. In other embodiments, complement components are provided by the organism in which the cell resides.

In the embodiments wherein the source of complement is provided to the target cells by the user of the method, the timing of providing the source of complement can be variable based on the circumstances. In some embodiments, the target cells can be contacted with a source of complement prior to the performance of step b. In other embodiments, the target cells can be contacted with a source of complement simultaneous with the performance of step b. In yet other embodiments, the target cells can be contacted with a source of complement subsequent to the performance of step b. In preferred embodiments, the target cells are provided with a source of complement within 30 minutes of the performance of step b.

In some embodiments, the method sensitizes target cells to CDC induced by a mAb that specifically binds to cell surface markers for abnormally proliferative cells, such as cancer cells. In this context, the use of the term cancer cells refers to cells that exhibit unregulated or uncontrolled cell division, and are well characterized in the art. Cancer cells can be cells residing in the body of an animal subject, or alternatively, be transformed cells in an artificial culture that exhibit unlimited capacity for cell division under the appropriate culturing conditions. Potential cancer types include carcinomas (derived from epithelial cells), sarcomas (derived from connective tissue, or mesenchymal cells), lymphoma and leukemias (derived from hemopoietic cells), blastomas (which are derived from immature or embryonic cells), or germ cell cancers. In other embodiments, the target cells are in vitro models for cancer, which are readily known to those skilled in the art. Non-limiting examples include: Raji-Burkitt's Lymphoma cells (Lapalombella, R., et al., "A Novel Raji-Burkitt's Lymphoma Model for Preclinical and Mechanistic Evaluation of CD52-Targeted Immunotherapeutic Agents," *Clinical Cancer Research* 14:569-578 (2008)), BJAB cells (EBV-negative Burkitt's lymphoma), Farage cells (non-Hodgkin's B-cell lymphoma), Mino cells (mantel cell lymphoma), Jurkat cells, K562, HeLa (cervix), A549 (lung), SKOV3 (ovarian), HT29 (colon), MDA265 MB (breast).

Methods of Enhancing the Anti-Tumor Effect of an Anti-Cancer mAb in a Mammalian Subject Among the FDA-approved mAbs for hematological malignancies is rituximab (also known as Mabthera and Rituxan), which is currently used for the treatment of B-cell non-Hodgkin lymphoma, mantle cell lymphoma, hairy cell leukemia, and chronic lymphocytic leukemia. Rituximab is a humanized unconjugated IgG1 mAb against CD20. CD20 is expressed on the surface of normal B-lymphocytes and B-cell lymphoma but not on hematopoietic stem cells, pro-B cells and plasma cells. In vitro and in vivo studies have shown that rituximab is effective in inducing CDC on B-cell lymphoma cells (Di Gaetano, N., et al., *J. Immunol.* 171:1581-1587 (2003); Golay, J., et al., *Haematologica* 91:176-183 (2006); Reff, M. E., et al., *Blood* 83:435-445 (1994); Bellosillo, B., et al., *Blood* 98:2771-2777 (2001); and, van der Kolk, L. E., et al., *British Journal of Haematology* 115:807-811 (2001)). Binding of rituximab to lymphoma cells via CD20 leads to activation of the classical complement pathway, culminating in the formation of the MAC (Di Gaetano, N., et al., *J. Immunol.* 171:1581-1587 (2003)). A similar role of CDC in tumor cell killing has been reported for ofatumumab (also known as HuMax CD20; Arzerra) (an anti-CD20 mAb) (Castillo, J., Winer, E., & Quesenberry, P., *Experimental Hematology* 36:755-768 (2008)), alemtuzumab (an anti-CD52 mAb), which is used for treatment of chronic lymphocytic leukemia (Zent, C. S., et al., *Leukemia Research* (2008)), and for gemtuzumab (an anti-CD33 mAb) used for treatment of acute myeloid leukemia (AML) (Castillo, J., Winer, E., & Quesenberry, P., *Experimental Hematology* 36:755-768 (2008)).

Rituxan can also be administered for the treatment of autoimmune diseases, for example including but not limited to autoimmune hemolytic anemia, rheumatoid arthritis and autoimmune neurological disorders (Devic's disease, myasthenia gravis, autoimmune neuropathies, and inflammatory myopathies).

In another aspect, the invention provides a method of enhancing the anti-tumor effect of an anti-cancer monoclonal antibody in a mammalian subject in need thereof. The method in accordance with this aspect of the invention comprises (a) administering at least once to the mammalian subject an amount of a composition comprising a plurality of modified polypeptides effective to decrease the amount of CD46, CD55, CD59, or CD35 present on the surface of a target tumor cell; and (b) administering at least once a therapeutically effective amount of an anti-cancer antibody to the subject, wherein the anti-cancer antibody binds to a non-CD46, CD55, CD59, or CD35 cell surface antigen expressed on the target tumor cell.

As described herein, an agent comprising a plurality of modified polypeptides sensitizes target cells to CDC induced by a mAb that specifically binds to cell surface markers of target cells, such as cancer cells residing in the body of a mammalian subject, such as a human. Potential cancer types include carcinomas (derived from epithelial cells), sarcomas (derived from connective tissue, or mesenchymal cells), lymphoma and leukemias (derived from hemopoietic cells), blastomas (which are derived from immature or embryonic cells), or germ cell cancers.

In some embodiments, the mAb specifically binds to cell surface markers for hematological malignancies, such as leukemias, including but not limited to acute lymphoblastic leukemia (ALL), chronic lymphocytic leukemia (CLL), acute myelogenous leukemia (AML), chronic myelogenous leukemia (CML), and hairy cell leukemia. CLL subtypes include precursor B acute lymphoblastic leukemia, precursor T acute lymphoblastic leukemia, Burkitt's leukemia, and acute biphenotypic leukemia. CLL subtypes include B-cell prolymphocytic leukemia. AML subtypes include acute promyelocytic leukemia, acute myeloblastic leukemia, acute myelomonocytic leukemia and acute megakaryoblastic leukemia. CML subtypes include chronic monocytic leukemia. Other hematological malignancies include multiple myeloma, Waldenstrom's macroglobulinemia, Hodgkin's lymphoma in addition to non-Hodgkin's lymphoma, which includes mantle cell lymphoma, large cell lymphoma, follicular lymphoma, T cell lymphoma, NK/T lymphoma, Burkitt's lymphoma, mucosa-associated lymphoid tissue (MALT) lymphoma, and mantle cell lymphoma.

In some embodiments, the mAb specifically binds to cell surface markers for solid tumors, such as breast cancer, lung cancer, colorectal cancer, stomach cancer, prostate cancer, ovarian cancer, uterine cancer, cervical cancer, kidney cancer, pancreatic cancer, liver cancer, brain cancer, head and neck cancer, nasopharyngeal carcinoma and esophageal cancer. In some embodiments, the mAb specifically binds to cell surface markers for sarcomas such as leiomyosarcoma, fibrosarcoma, rhabdomyosarcoma and Ewing's sarcoma. In some embodiments, the mAb specifically binds to cell surface markers for hematological tumors such as leukemias, lymphomas or myelomas.

Cancer cells are usually highly abnormal compared to the cells from which they originate. Often, cancer cells display a range of unusual cell surface antigens that are either inappropriate for the cell type, the cell's environment, or are normally present during other stages in the organism's development. Alternatively, the levels of cell surface protein expression may be altered in cancer cells. Consequently, various cell surface markers exist that can uniquely identify cancer cells from normal cells. In accordance with the methods provided, markers for cell disease include markers for cancer cells. Cancer cell markers can include viral associated proteins, altered self tumor antigens that are expressed at increased levels on cancer cells, tumor-specific antigens that are expressed exclusively on cancer cells (including mutated versions of self molecules). In preferred embodiments, the level of expression of the marker is greater on the cancer cells than in normal cells, and more preferably, the marker is expressed nearly exclusively on cancer cells. Non-limiting examples of useful cell surface markers for cancer target cells include: CD3, CD10, CD19, CD20, CD22, CD23, CD25, CD30, CD33, CD35, CD37, CD38, CD40, CD44, CD52, CD70, CD80, CD133, CD200, epidermal growth factor receptor 1 (EGFR), epidermal growth factor receptor 2 (Her2/neu), human milk fat globule 1 (HMFG1), interleukin 2 receptor (IL2R), mucin 1, and vascular endothelial growth factors.

Monoclonal antibodies have emerged as a promising class of anti-cancer therapeutics. Owing to their ability to specifically bind markers characteristic of cancer cells, mAbs enable the targeting of the patient's own immune systems to the destruction of the cancer cells. Monoclonal antibodies useful in the methods provided herein are often modified to contain human Fc domains to reduce the immunogenicity of the antibody and to enhance the ability to recruit human immune effector systems. It is contemplated that as these methods are applied to non-human subjects, the Fc domains of the antibodies may be modified to match the subject. Different isotypes of human antibodies can be used as the backbone of anti-cancer therapeutic mAbs. Typically, IgM is the most effective isotype for complement activation, however it is not widely used in clinical oncology because it does not readily extravasate from vascular structures (Adams, G. P., and Weiner, L. M., "Monoclonal Antibody Therapy of Cancer," *Nature Biotechnology* 23:1147-1157 (2005)). Therefore, the applicability of the IgM isotype may be more limited to hematological malignancies. IgG1 and IgG3 isotypes are both very effective at directing CDC. Non-limiting examples of useful anti-cancer mAb antibodies are listed in Table 1, and as further described in Campoli, M., et al., *Principles & Practice of Oncology* 23(1&2):1-19 (2009), incorporated herein by reference.

TABLE 1

Tumor-Antigen Specific mAbs for Cancer Treatment

| Antibody | Isotype | Target | Disease Indication |
| --- | --- | --- | --- |
| OKT3 (Muromonab) | murine IgG2a | CD3 | T cell acute lymphoblastic leukemia; transplant rejection* |
| Zanolimumab (Hu-Max-CD4) | humanized IgG1 | CD4 | cutaneous T-Cell lymphoma (CTCL), peripheral T-cell lymphoma (PTCL), mycosis fungocides (MF) |
| SGN-19A | humanized IgG1 | CD19 | non-Hodgkin lymphoma, chronic lymphocytic leukemia, acute lymphoblastic leukemia |

TABLE 1-continued

Tumor-Antigen Specific mAbs for Cancer Treatment

| Antibody | Isotype | Target | Disease Indication |
|---|---|---|---|
| Rituximab (Rituxan) | chimeric IgG1 | CD20 | low-grade lymphoma*, diffuse large B-Cell lymphoma*, follicular lymphoma*, B-Cell non-Hodgkin lymphoma*, mantel cell lymphoma*, hairy cell leukemia*, chronic lymphocytic leukemia*, autoimmune diseases*, acute antibody mediated rejection of transplants* |
| Ofatumumab (Arzerra) | humanized IgG1 | CD20 | chronic lymphocytic leukemia (CLL), relapsed follicular non-Hodgkin's lymphoma (FL), diffuse large B cell lymphoma |
| 90Y ibritumomab + tiuxetan | radiolabeled murine IgG1 | CD20 | CD20(+) low-grade lymphoma* |
| 131-I tositumomab | radiolabeled murine IgG1 | CD20 | CD20(+) low-grade lymphoma* |
| Epratuzumab | Humanized IgG1 | CD22 | B-Cell non-Hodgkin's lymphoma, Diffuse Large B-Cell lymphoma (DCLBCL), follicular non-Hodgkin's lymphoma (FL) |
| Lumiliximab (IDEC-152) | Chimeric prim-humanized IgG1 | CD23 | Chronic lymphoid leukemia (CLL) |
| Daclizumab (Zenapax) | humanized IgG1 | CD25 | graft versus host disease; acute rejection of transplants*, adult T-cell leukemia/lymphoma, renal allograft rejection, |
| Basiliximab (Simulect) | chimeric | CD25 | graft versus host disease; acute rejection of transplants |
| HeFi-1 | Mouse IgG1 | CD30 | Anaplastic large-cell lymphoma (ALCL); Hodgkin's disease (HD), CD30(+) lymphoma |
| MDX-060 | Humanized IgG1 | CD30 | Anaplastic large-cell lymphoma (ALCL); Hodgkin's disease (HD), CD30(+) lymphoma |
| SGN-30 | Chimeric IgG1 | CD30 | Anaplastic large-cell lymphoma (ALCL); Hodgkin's disease (HD), CD30(+) lymphoma |
| Lintuzumab | humanized IgG1 | CD33 | acute myeloid leukemia (AML), myelodysplastic syndromes (MDS), advanced MDS |
| Bi213-Hum195 | Humanized IgG1 | CD33 | acute myeloid leukemia (AML), chronic myelogenous leukemia (CML), acute promyelocytic leukemia (APML), myelodysplastic syndromes (MDS) |
| Gemtuzumab + oxogamacin (Mylotarg) | recombinant humanized IgG4-conjugated to calicheamicin | CD33 | acute myelogenous leukemia* |
| TRU-016 | humanized IgG1 | CD37 | chronic lymphocytic leukemia |
| Dacetuzumab (SGN-40) | humanized IgG1 | CD40 | non-Hodgkin lymphoma, multiple myeloma, Diffuse Large B-Cell lymphoma (DCLBCL), follicular non-Hodgkin's lymphoma (FL) |
| Lucatumumab CHIR-12.12 | Humanized IgG1 | CD40 | Chronic lymphoid leukemia (CLL); multiple myeloma, |
| Alemtuzumab (Campath) | humanized IgG1 | CD52 | chronic lymphocytic leukemia* |
| SGN-75 | humanized IgG1 | CD70 | solid tumors, including renal cell cancer, CD70 + hematologic malignancies |
| Galiximab | chimeric prim-humanized IgG1 | CD80 | follicular lymphoma, B-cell non-Hodgkin lymphoma |
| Tastuzumab | humanized IgG1 | HER2/neu | HER2/neu(+) breast cancer* |
| Cetuximab | Chimeric IgG1 | EGFR | EGFR(+) colon cancer* |
| Panitumumab | Fully human IgG2 | EGFR | EGFR(+) colon cancer* |

TABLE 1-continued

Tumor-Antigen Specific mAbs for Cancer Treatment

| Antibody | Isotype | Target | Disease Indication |
| --- | --- | --- | --- |
| Matuzumab | Humanized IgG1 | EGFR | non-squamous non-small cell lung cancer (NSCLC), head and neck squamous cell carcinoma (HNSCC), breast and pancreatic cancer, colon cancer (CC) |
| Pertuzumab | Humanized IgG1 | EGFR | NSCLC, HNSCC, CC, breast and ovarian cancer |
| Ipilimumab (MDX-010) | Humanized IgG1 | CTLA-4 | NSCLC, RCC, metastatic melanoma |
| Tremelimumab (CP-675, 206) | Humanized IgG1 | CTLA-4 | NSCLC, RCC, metastatic melanoma |
| Sibrotuzumab | Humanized IgG1 | FAP** | NSCLC, CC |
| DR-4-specific mapatumumab (TRM-1, HGS-ETR1) | Humanized IgG1 | TRAIL | NSCLC, CC, ovarian cancer, multiple myeloma, |
| DR-5-specific lexatumumab (HGS-ETR2, TRA-8) | Humanized IgG1 | TRAIL | solid tumors |
| Cantuzumab mertansine | Humanized IgG1-maytansinoid | CanAg*** | CC, pancreatic cancer |
| Bevacizumab (Avastatin) | humanized IgG1 | vascular endothelial growth factor (VEGF) | colon cancer*, non-squamous non-small cell lung cancer (NSCLC)*, metastatic breast cancer* |
| Apolizumab (Hu1D10) | humanized IgG1 | HLA-DR | B-Cell non-Hodgkin's lymphoma, Chronic lymphoid leukemia (CLL); acute lymphoblastic leukemia (ALL); acute myeloid leukemia (AML); Waldenstrom's, Hodgkin's disease, |
| Milatuzumab | humanized IgG1 | HLA-DR | B-Cell non-Hodgkin's lymphoma, Chronic lymphoid leukemia (CLL); multiple myeloma, |

*Current FDA approval exists for the indicated disease
**FAP is a Type II membrane-bound glycoprotein belonging to the serine protease gene family which is found on sarcoma cell lines.
***CanAg is a glycoform of cell-associated mucin (MUC1) found on most pancreatic, biliary and colorectal cancers.

The capacity of any antibody to induce CDC on a cell rests on its ability to recruit C1q, a constituent of the first component of complement. C1q binds to the $C_H2$ domain of Ig molecules. Modifications can be incorporated into the mAbs that enhance their effectiveness to recruit complement and induce CDC on the target cell. For instance, two residues have been identified within the $C_H2$ domain that enhance the CDC induction by rituximab (Idusogie, E. E., et al., *The Journal of Immunology* 166:2571-2575 (2001)). Specifically, Idusogie et al., show that substitutions at amino acid positions K326 and E333 enhanced C1q binding to the antibody, resulting in increased CDC activity. In DAll'Acqua, W., et al., *The Journal of Immunology* 177:1129-1138 (2006), the investigators engaged in a systematic analysis of the functional characteristics of a human IgG1 hinge region in the context of interactions with complement activation. The targeted mutations were designed to increase or decrease flexibility of the hinge, or increase or decrease the length of the hinge. The investigators found that the loss of rigidity of the middle hinge is detrimental to C1q binding, whereas loss of rigidity in the upper hinge had minimal or no effect. Moreover, several substitutions were identified in the upper hinge that enhanced complement fixation, indicating an influential role of this hinge.

In some embodiments, the agent comprising a plurality of modified polypeptides further comprises additional molecules or domains that enhance the efficacy of an anti-cancer monoclonal antibody. For example additional molecules or domains may decrease immunogenicity. In one embodiment, the agent further comprises one or more polyethylene glycol (PEG) chains. PEG chains conjugated to therapeutic polypeptides can provide various advantages, such as increased size to reduce agent filtration in the kidney, to mask antigenic epitopes, increase solubility of the agent due to PEG hydrophobicity, and decreased accessibility of the agent for proteolytic enzymes and antibodies. Thus, therapy can be enhanced through PEGylation by increased retention of the agent in the body, a reduction of the immunogenicity of the agent, and increased stability of the agent. PEGylation chemistry is maturing and a variety of PEG chains with varying attributes are known. Also known are strategies to carry out PEGylation while preserving the activity of the agent. For a review, see Veronese, F. M., and Pasut, G., *Drug Discovery Today* 10:1451-1458 (2005).

Dosages and Routes of Administration

The agent comprising a plurality of modified polypeptides may be administered to the subject before, simultaneously, or after administration of the therapeutic antibody, for example the anti-cancer antibody.

The timing of administrations of the anti-cancer antibody relative to the agent comprising a plurality of modified polypeptides can be varied to achieve the greatest anti-tumor effect. This can be determined, for example, by administering the composition comprising modified polypeptides, periodically harvesting the target cells, and determining the cell surface level of the CRP. An example of this approach is described in Example 3 for CD46. Ideally, the anti-cancer mAb is administered at a time to ensure its contact with the target cell corresponds with the lowest levels of surface CD46. For example, the anti-cancer mAb can be administered prior to, simultaneously with, after each administration of the composition comprising modified polypeptides. In some embodiments, the anti-cancer mAb can be administered prior to the administration of the agent, for example up to 5 minutes, 10 minutes, 15 minutes, 30 minutes, 45 minutes, 1 hour, 2 hours, 3 hours, 4 hours, 5 hours, 6 hours, 8 hours, 10 hours, 12 hours, 18 hours, 24 hours, 30 hours, 36 hours, 40 hours, 42 hours, 48 hours, 54 hours, 60 hours, 66 hours, 72 hours, 78 hours, 84 hours, 90 hours, or even up to 96 hours prior to the administration of the agent. In this regard, the timing of administration could account for the half-life of the anti-cancer mAb. For example, rituximab is known to have a half-life of about 40 hours. Therefore, the agent comprising a modified polypeptide may not be administered more than 40 hours after the administration of rituximab.

In other embodiments, the anti-cancer mAb can be administered simultaneously with or up to 96 hours after an administration of the agent, such as between about 10 minutes and 72 after administration of the agent, or up to 5 minutes, 10 minutes, 15 minutes, 30 minutes, 45 minutes, 1 hour, 2 hours, 3 hours, 4 hours, 5 hours, 6 hours, 8 hours, 10 hours, 12 hours, 18 hours, 24 hours, 30 hours, 36 hours, 40 hours, 42 hours, 48 hours, 54 hours, 60 hours, 66 hours, 72 hours, 78 hours, 84 hours, 90 hours, or even up to 96 hours after to the administration of the agent. For example, the anti-cancer mAb can be administered between about five hours and 48 hours after each administration of the composition comprising modified polypeptides.

A non-limiting example of timing is illustrated in Example 2, where rituximab is administered to cells eight hours after administration of an composition comprising modified fiber knob domain polypeptides (Ad35K++, SEQ ID NO:5). Another non-limiting example is illustrated in Example 3, where rituximab is administered to mice ten hours after administration of an composition comprising modified fiber knob domain polypeptides (Ad35K++).

The routes and methods of administration of the agent and antibody are variable and can be tailored appropriately to the condition being treated. Administration can be systemic or local. Systemic routes of administration include intramuscular, subcutaneous, intravenous, intra-arterial, inhalational, sublingual, buccal, topical, transdermal, nasal, rectal, and vaginal.

The effective dosage of the composition comprising modified polypeptides varies depending on such factors as the subject's age, weight, height, sex, general medical condition, and medical history. Exemplary dosages stated herein are provided in mg of agent per kilogram of the subject receiving the dosage. As an illustration, compositions comprising modified polypeptides can be administered in dosage ranges between 0.01 and 250 mg/kg, preferably between 0.1 and 10 mg/kg, and more preferably between 0.10 to 0.5 mg/kg. Dosages of approved anti-cancer mAb are readily identifiable by medical practitioners. For example, dosages of many anti-cancer mAbs can range from 2-250 mg/kg of the subject in need. However, experimental treatments with rituximab, an anti-CD20 mAb, for the treatment of CLL have included up to 2250 mg/kg (O'Brien, S. M., et al., *Journal of Clinical Oncology* 19:2165-2170 (2001)).

Administrations of the composition comprising modified polypeptides can be repeated to enhance the therapeutic outcome. The timing of the subsequent administration may be variable. In one embodiment, the subsequent administration of an composition comprising modified polypeptides is performed after sufficient time to allow the CD46, CD55, CD59, or CD35 levels to return to previous levels on surviving cells. In an exemplary embodiment, based on in vitro data involving Ad35++, this time period may be more than 48 hours after the prior administration of the composition comprising modified adenovirus fiber knob domain polypeptides. In another embodiment, the time period may be 72 hours after the prior administration of the composition comprising modified polypeptides, or even more. In other embodiments, the timing of any subsequent administration is determined by the established dosage protocols of the mAb used in the method.

In some embodiments of the method, multiple administrations of the composition comprising modified polypeptides are carried out without inducing in the subject an adverse immunological reaction that interferes with the anti-tumor effect of the method. In accordance with such embodiments, the composition comprising modified adenovirus fiber knob domain polypeptides lacks T- or B-cell epitopes recognized by the subject's immune system, and thus fails to stimulate any immune response upon a second or subsequent administration, or antibodies produced against the modified adenovirus fiber knob domain polypeptides do not reduce the effectiveness of the therapy. As described in Example 4, intravenous administration of recombinant modified adenovirus fiber knob domain polypeptides (Ad35K++) did not result in any detectable antibodies against the recombinant polypeptides in a mammalian subject.

As described in Example 6, potential epitopes of modified recombinant fiber knob proteins can be predicted. The amino acid residues of these potential epitopes may be subjected to site directed mutagenesis according to methods well known in the art in an effort to reduce the immunogenicity of the polypeptides. For example, variants can be administered to immunocompetent animals and resulting antibody titers can be easily determined. In another approach, variants produced in a mutagenesis library, as described herein, can be selected for lack of immunogenicity.

The design of anti-cancer and other therapeutic mAbs is quite advanced for purposes of reducing immunogenicity. Most available mAbs incorporate human Fc domains that do not stimulate immune responses. Chimeric mAbs are usually composed of murine variable regions, which recognize the targets, fused onto human constant regions, which helps avoid human immune responses against the mAb. These antibodies are typically about 65% human. Humanized mAbs are produced by using only the murine hypervariable region, resulting in an antibody that is approximately 95% human. Finally, human monoclonal antibodies can be produced in transgenic mice or phage display libraries.

Pharmaceutical Compositions

In another aspect, the invention provides compositions for reducing the activity, the cell surface levels, or the density of CD46, CD55, CD59, or CD35. In accordance with this aspect of the invention, the compositions comprise (a) an amount of an agent effective to reduce cell surface levels of CD46, CD55, CD59, or CD35, the composition comprising a plurality of modified polypeptides, wherein the modified polypeptides are capable of forming homotrimers having enhanced affinity for CD46, CD55, CD59, or CD35 binding as compared to homotrimers formed from otherwise unmodified polypeptides, for example those unmodified polypeptides consisting of SEQ ID NO:3 (wild-type Ad35 fiber knob domain); and (b) a pharmaceutically acceptable carrier. The compositions comprising modified polypeptides can be administered to a subject in need thereof, at therapeutically effective doses to treat or ameliorate conditions associated with cell surface expression of CD46, CD55, CD59, or CD35.

A therapeutically effective dose refers to the amount of the compositions comprising modified polypeptide sufficient to result in amelioration of symptoms of the condition. Exemplary compositions comprising a modified polypeptide are described herein. In some embodiments, the composition further comprises at least one agent that induces complement dependent cytolysis, such as an anti-cancer antibody or fragment thereof, as described herein.

Toxicity and therapeutic efficacy of compositions comprising modified polypeptides can be determined by standard pharmaceutical procedures employing experimental animal models, such as the murine xenograft lymphoma model described in Example 3, wherein $3 \times 10^6$ Raji cells are injected into the tail vein of immunodeficient CB17 SCID mice. Using such animal models, the NOAEL (no observed adverse effect level) and the MED (the minimally effective dose) can be determined using standard methods. The dose ratio between NOAEL and MED effects is the therapeutic ratio, which is expressed as the ratio NOAEL/MED. Compositions comprising modified polypeptides that exhibit large therapeutic ratios or indices are most preferred. The data obtained from the cell culture assays and animal studies can be used in formulating a range of dosages for use in humans. The dosage of the compositions comprising modified polypeptides preferably lies within a range of circulating concentrations that include the MED with little or no toxicity. The dosage may vary within this range depending upon the dosage form employed and the route of administration utilized.

For any compound formulation, the therapeutically effective dose can be estimated using animal models. For example, a dose may be formulated in an animal model to achieve a circulating plasma concentration range that includes the MED. Quantitative levels of the compositions comprising modified polypeptides in plasma may also be measured, for example, by high performance liquid chromatography.

Generally, the dosage of administered compositions comprising the described compositions varies depending on such factors as the subject's age, weight, height, sex, general medical condition, and previous medical history. As an illustration, compositions comprising modified adenovirus fiber knob domain polypeptide, such as Ad35K++ (SEQ ID NO:5) can be administered in dosage ranges from about 0.01 to 250.0 mg/kg, preferably 0.1 to 10.0 mg/kg, more preferably 0.10 to 0.5 mg/kg of the subject body weight.

Therapeutic efficacy of compositions comprising modified polypeptide and related methods in a given subject, and appropriate dosages, can be determined in accordance with assays well known to those of skill in the art. For example, survival studies and quantification of target cancer cells by flow cytometry can be performed using animal models after administration of compositions comprising modified polypeptide, as described in Example 3. The therapeutic efficacy of compositions comprising modified polypeptide in human subjects can be determined by assays well known in oncology. For instance, the size of tumor lesions may be monitored quantitatively by physical examination and radiological studies, including but not limited to the use of CT scans, X-rays, MRIs and ultrasound. Tumor cells in the blood and bone marrow may be quantified by routine microscopic and/or immunological methods. Serum may be monitored for the presence and/or levels of cancer markers. Examples of serum markers indicative of cancer include monoclonal antibody spikes in multiple myeloma, CA-125 in ovarian cancer, alpha fetal protein levels in testicular cancer and liver cancer, and human chorionic gonadotropin in choriocarinoma. Urine may also be monitored for indicators of disease, such as the presence and/or level of light chains in urine may be indicative of multiple myeloma.

Similarly, the agents described herein can be assessed for potential of repeated administrations employing experimental lab animal models, such as CD46 transgenic C57B1/6 mice line MCP8B, as described in Example 4. Immunocompetent animals can be assessed for generation of immune responses against the agents described herein after receiving agents according to a standard vaccination schedule known in the art. Furthermore, agents can be assayed against human serum to ascertain the presence of anti-agent antibodies. Preferably, compositions comprising modified polypeptides elicit minimal or no immune response from the patient. However, regardless of antibody generation, preferred compositions comprising modified polypeptides will retain the capacity to reduce cell surface levels of CD46, CD55, CD59, or CD35 upon repeated administrations.

Pharmaceutical Carriers

In general, the provided compositions comprising modified polypeptides, combined with any other selected therapeutic agents, are suitably contained in a pharmaceutically acceptable carrier. The carrier is non-toxic, biocompatible and is selected so as not to detrimentally affect the biological activity of the compositions comprising modified polypeptides (and any other therapeutic agents combined therewith). Exemplary pharmaceutically acceptable carriers for peptides are described in U.S. Pat. No. 5,211,657 to Yamada. The compositions comprising modified polypeptides useful in the invention may be formulated into preparations in solid, semi-solid, gel, liquid or gaseous forms such as tablets, capsules, powders, granules, ointments, solutions, suppositories, inhalants, and injections, allowing for oral, parenteral, or surgical administration.

Suitable carriers for parenteral delivery via injectable, infusion, or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids, such as oleic acid, find use in the preparation of injectables. The carrier and agent may be compounded as a liquid, suspension, polymerizable or non-polymerizable gel, paste or salve.

The carrier may also comprise a delivery vehicle to sustain (i.e., extend, delay, or regulate) the delivery of the agent(s) or to enhance the delivery, uptake, stability, or pharmacokinetics of the therapeutic agent(s). Such a delivery vehicle may include, by way of non-limiting example, microparticles, microspheres, nanospheres, or nanoparticles composed of proteins, liposomes, carbohydrates, synthetic organic compounds, inorganic compounds, polymeric or copolymeric hydrogels, and polymeric micelles. Suitable hydrogel and micelle delivery systems include the PEO:PHB:PEO copolymers and copolymer/cyclodextrin complexes disclosed in International Publication No. WO 2004/009664 A2, and the PEO and PEO/cyclodextrin complexes disclosed in U.S. Publication No. 2002/0019369 A1. Such hydrogels may be injected locally at the site of intended action, or subcutaneously or intramuscularly to form a sustained release depot.

For intrathecal (IT) or intracerebroventricular (ICV) delivery, appropriately sterile delivery systems (e.g., liquids; gels, suspensions, etc.) can be used to administer the provided agents and compositions. For oral administration of non-peptidergic agents, the compositions comprising modified polypeptide may be carried in an inert filler or diluent such as sucrose, cornstarch, or cellulose.

The compositions of the present invention may also include biocompatible excipients, such as dispersing or wetting agents, suspending agents, diluents, buffers, penetration enhancers, emulsifiers, binders, thickeners, flavoring agents (for oral administration).

More specifically with respect to compositions comprising modified polypeptides, exemplary formulations can be parenterally administered as injectable dosages of a solution or suspension of the compound in a physiologically acceptable diluent with a pharmaceutical carrier that can be a sterile liquid such as water, oils, saline, glycerol, or ethanol. Additionally, auxiliary substances such as wetting or emulsifying agents, surfactants, pH buffering substances and the like can be present in compositions comprising modified polypeptides. Additional components of pharmaceutical compositions include petroleum (such as of animal, vegetable, or synthetic origin), for example, soybean oil and mineral oil. In general, glycols such as propylene glycol or polyethylene glycol are preferred liquid carriers for injectable solutions.

The compositions comprising modified polypeptides can also be administered in the form of a depot injection or implant preparation that can be formulated in such a manner as to permit a sustained or pulsatile release of the active agents.

Delivery

The pharmaceutical compositions comprising modified polypeptides may be administered in a number of ways depending on whether a local or systemic mode of administration is most appropriate for the condition being treated.

As used herein, the terms "systemic delivery" and "systemic administration" are intended to include, but are not limited to, oral and parenteral routes including intramuscular (IM), subcutaneous, intravenous (IV), intra-arterial, inhalational, sublingual, buccal, topical, transdermal, nasal, rectal, vaginal, and other routes of administration that effectively result in dispersement of the delivered agent to a single or multiple sites of intended therapeutic action. Preferred routes of systemic delivery for the present compositions include intravenous, intramuscular, subcutaneous, and inhalational. It will be appreciated that the exact systemic administration route for selected agents utilized in particular compositions of the present invention will be determined in part to account for the agent's susceptibility to metabolic transformation pathways associated with a given route of administration. For example, peptidergic agents may be most suitably administered by routes other than oral.

Compositions comprising modified polypeptides can be delivered into a subject in need thereof by any suitable means. Methods of delivery of such agents include administration by oral, pulmonary, parenteral (e.g., intramuscular, intraperitoneal, intravenous (IV), or subcutaneous injection), inhalation (such as via a fine powder formulation), transdermal, nasal, vaginal, rectal, or sublingual routes of administration, and can be formulated in dosage forms appropriate for each route of administration.

By way of representative example, compositions comprising modified polypeptides can be introduced into a living body by application to a bodily membrane capable of absorbing the polypeptides, for example the nasal, gastrointestinal, and rectal membranes. The polypeptides are typically applied to the absorptive membrane in conjunction with a permeation enhancer. (See, e.g., Lee, V. H. L., *Crit. Rev. Ther. Drug Carrier Sys.* 5:69, 1988; Lee, V. H. L., *J. Controlled Release* 13:213, 1990; Lee, V. H. L., Ed., *Peptide and Protein Drug Delivery*, Marcel Dekker, New York (1991); DeBoer, A. G., et al., *J. Controlled Release* 13:241, 1990.) For example, STDHF is a synthetic derivative of fusidic acid, a steroidal surfactant that is similar in structure to the bile salts, and has been used as a permeation enhancer for nasal delivery. (Lee, W. A., *Biopharm.* 22, November/December 1990.)

The compositions comprising modified polypeptides may be introduced in association with another molecule, such as a lipid, to protect the polypeptides from enzymatic degradation. For example, the covalent attachment of polymers, especially polyethylene glycol (PEG), has been used to protect certain proteins from enzymatic hydrolysis in the body and thus prolong half-life (Veronese, F. M., and G. Pasut, "PEGylation, successful approach to drug delivery," *Drug Discovery Today* 10:1451-1458, (2005)). Many polymer systems have been reported for protein delivery (Bae, Y. H., et al., *J. Controlled Release* 9:271, 1989; Hori, R., et al., *Pharm. Res.* 6:813, 1989; Yamakawa, I., et al., *J. Pharm. Sci.* 79:505, 1990; Yoshihiro, I., et al., *J. Controlled Release* 10:195, 1989; Asano, M., et al., *J. Controlled Release* 9:111, 1989; Rosenblatt, J., et al., *J. Controlled Release* 9:195, 1989; Makino, K., *J. Controlled Release* 12:235, 1990; Takakura, Y., et al., *J. Pharm. Sci.* 78:117, 1989; Takakura, Y., et al., *J. Pharm. Sci.* 78:219, 1989).

Recently, liposomes have been developed with improved serum stability and circulation half-times (see, e.g., U.S. Pat. No. 5,741,516, to Webb). Furthermore, various methods of liposome and liposome-like preparations as potential drug carriers have been reviewed (see, e.g., U.S. Pat. No. 5,567,434, to Szoka; U.S. Pat. No. 5,552,157, to Yagi; U.S. Pat. No. 5,565,213, to Nakamori; U.S. Pat. No. 5,738,868, to Shinkarenko; and U.S. Pat. No. 5,795,587, to Gao).

The compositions provided herein may be systemically administered on a periodic basis at intervals determined to maintain a desired level of therapeutic effect. For example, compositions may be administered, such as by intravenous injection, every two to four weeks or at less frequent intervals. The dosage regimen will be determined by the physician considering various factors that may influence the action of the combination of agents. These factors will include the extent of progress of the condition being treated, the patient's age, sex and weight, and other clinical factors. The dosage for each individual agent will vary as a function of the composition comprising modified polypeptides that is included in the composition, as well as the presence and nature of any drug delivery vehicle (e.g., a sustained release delivery vehicle). In addition, the dosage quantity may be adjusted to account for variation in the frequency of administration and the pharmacokinetic behavior of the delivered agent(s).

In another aspect, the present invention provides a kit comprising (a) a modified polypeptide comprising a non naturally occurring amino acid sequence and wherein the polypeptide can optionally form dimers, or trimers capable of binding to CD46, CD55, CD59, or CD35; and (b) an antibody or fragment thereof that binds to an antigen on the surface of a mammalian cell and induces cytolysis. Modified polypeptides for use in the kits are described herein, such as, for example, a modified fiber knob domain polypeptide comprising SEQ ID NO:5. Exemplary Antibodies or fragments thereof for use in the kits are also described herein, for example, as provided in Table 1.

In a specific embodiment, the present invention provides a kit comprising (a) a modified fiber knob domain polypeptide comprising at least 12 contiguous amino acids of the amino acid sequence set forth as SEQ ID NO:3, wherein the polypeptide includes at least one amino acid substitution selected from the group consisting of Asp207Gly, Thr245Ala, and Ile 256Leu, or a combination thereof, and wherein the polypeptide can form homotrimers capable of binding to CD46; and (b) an antibody or fragment thereof that binds to an antigen on the surface of a mammalian cell and induces cytolysis. Modified fiber knob domain polypeptides for use in the kits are described herein, such as, for example, a modified fiber knob domain polypeptide comprising SEQ ID NO:5. Exemplary Antibodies or fragments thereof for use in the kits are also described herein, for example, as provided in Table 1.

In another aspect, the present invention provides methods of enhancing the effect of an antibody therapeutic agent in the treatment of an autoimmune disease in a mammalian subject. The methods in accordance with this aspect of the invention comprise: (a) administering at least once to the mammalian subject an amount of an agent comprising a plurality of modified polypeptides effective to decrease the amount or density of CD46, CD55, CD59, or CD35 present on the surface of a target cell; and (b) administering at least once a therapeutically effective amount of an antibody therapeutic agent to the subject, wherein the antibody therapeutic agent binds to a non-CD46, CD55, CD59, or CD35 cell surface antigen expressed on the target cell. Modified polypeptides for use in this aspect of the methods of the invention are described herein. Additional modified polypeptides for use in this aspect of the invention can be derived using routine mutagenesis and screening methods, such as the methods described in Example 1.

In accordance with the methods of this aspect of the invention, the reduction of cell surface CD46, CD55, CD59, or CD35 levels on the target cell sensitizes the target cell, such as a B cell or T cell to cytolysis by an antibody therapeutic agent that induces complement-dependent cytolysis (CDC), such as an antibody or fragment thereof. As described in Example 8, Ad35K++ was shown to enhance the cytolysis of primary B cells by rituximab. As further demonstrated in Example 8, Ad35K++ (SEQ ID NO:5) treatment of peripheral blood mononuclear cells (PBMCs) triggered the removal of CD46 from the cell surface.

As described herein, a composition comprising a plurality of modified polypeptides, for example a plurality of modified fiber knob domain polypeptides sensitizes target cells to CDC induced by a mAb that specifically binds to cell surface markers of target cells, such as T cells or B cells residing in the body of a mammalian subject, such as a human. The methods in accordance with this aspect of the invention may be used to enhance the therapeutic effect of an antibody therapeutic agent used to treat an autoimmune disease such as those named herein with agent that binds to a cell surface antigen on a B cell (e.g., CD20) or an agent that binds to a cell surface antigen on a T cell (e.g., CD25 or CD4).

The methods of this aspect of the invention may be used to treat an autoimmune disease by depleting target B and/or T cells, such as, for example, rheumatoid arthritis, diabetes, disorders of the thyroid, multiple sclerosis, antibody-mediated rejection of a transplanted organ, idiopathic membranous nephropathy, psoriasis, dysimmune neuropathy (i.e., chronic inflammatory demyelinating polyneuropathy, polymyositis, dermatomyositis, multifocal motor neuropathy or monoclonal gammopathy), myasthenia gravis, aseptic pachymeningitis, inflammatory bowel disease, and autoimmune hemolytic anemia (AIHA).

For example, rituximab (anti-CD20 mAb) has been utilized to treat the following autoimmune diseases: rheumatoid arthritis (Owczarczyk, K., et al., *Ann Rheum Dis* 67:1648-1649 (2008); multiple sclerosis (Petereit, H., et al., *Mult Scler* 15:189-192 (2009); antibody-mediated rejection of a transplanted organ (Yang, Y. W., et al., *Exp Clin Transplant* 6:211-214 (2008); idiopathic membranous nephropathy (Kuppachi, S., et al., *J. Nephrol* 22(4):561-4 (2009); dysimmune neuropathies (Argyriou, A. A., *Mol Med* 15(7-8):283-7 (2009); myasthenia gravis (Nelson, P. P., et al., *J Clin Neuromuscul Dis* 10(4): 170-7 (2009); polymyositis, dermatomyositis, aseptic pachymeningitis (Schmid, L., et al. *Arthritis Rheum* 60(6):1632-4 (2009); and autoimmune hemolytic anemia (AIHA) (Annicchiarico, B. E., et al., *Transplant Proc.* 41(4): 1380-2 (2009).

It is known that lymphoproliferative and autoimmune disorders share monoclonal dysregulation and survival advantage of B-lymphocytes (see Castillo, J., et al., *Expert Opin Investig Drugs* 18(4):491-500 (2009). It is known that CD20 is expressed in B-lymphocytes and modulation of B cells with monoclonal antibodies that bind to CD20 such as rituximab have been used to treat both lymphoproliferative diseases and autoimmune disorders. It will be appreciated by those of skill in the art that the methods described herein to administer a composition comprising a plurality of modified polypeptides to sensitize target B cells to CDC induced by a mAb that specifically binds to B cell surface markers (e.g., CD20) of target cells are not limited to rituximab (anti-CD20) treatments, and may be applied to sensitize cells to CDC in the context of other anti-CD20 mAbs, such as ofatumumab (anti-CD20 mAb, otherwise known as Arzerra, GlaxoSmithKline), as shown in TABLE 1.

It will also be appreciated by those of skill in the art that the methods described herein may be used to sensitize target T cells to CDC induced by a mAb that specifically binds to T cell surface markers (e.g., CD25 or CD4) of target T cells may be accomplished by, but are not limited to, the use of daclizimab (anti-CD25 mAb) or zanolimumab (anti-CD4 mAb), as further shown in Table 1.

The following examples merely illustrate the best mode now contemplated for practicing the invention, but should not be construed to limit the invention. All literature citations are expressly incorporated by reference.

EXAMPLE 1

This example describes the production of mutant Ad35 fiber knob proteins with increased affinity for binding to CD46.

Creation of Ad35 Fiber Knob Mutant Library

Random mutagenic PCR was performed on the DNA encoding the adenovirus 35 fiber knob domain (SEQ ID NO:1) according to a protocol previously described by Wang, H., et al. *Journal of Virology* 81:12785-12792 (2007). Specifically, the nucleic acid sequence encoding the Ad35 fiber knob protein domain, corresponding to amino acids 123 to 320 of the full length sequence was obtained by PCR amplification of Ad35 wild-type DNA (SEQ ID NO:1) using the primers P1 (5'-TTTAAGGATCCGGTGACATTTG-TATAAAGGATAG-3') (SEQ ID NO:10) and P2 (5'-TATATAAGCTTAGTTGTCGTCTTCTGTAAT-3') (SEQ ID NO:11).

The PCR products were cloned into pQE30 (Qiagen, Valencia, Calif.) for expression in *Escherichia coli* with an N-Terminal His$_6$ tag.

Random mutagenic PCR was performed, optimized to achieve on average one or two amino acid mutations per fiber knob domain polypeptide. The PCR was performed using following reagents: 20 fmoles of pQE-Ad35knob DNA template, 30 pmol of PCR primer Pmut1 (5'-CGTCAGCACG-GATCCGGTGACATTTGTATAAAGGATAG-TATTAACACCTT ATGGACTGGA-3') (SEQ ID NO 12), 30 pmol of PCR primer Pmut2 (5'-CCAAGCTCAGCTAAT- TAAGCTTAGTTGTCGTC-3') (Seq ID No 13), 10× mutagenic buffer (2.5 µl, 3.5 µl, 5 µl, or 10 µl; 70 mM MgCl$_2$, 500 mM KCl, 100 mM Tris [pH 8.3 at 25° C.], and 0.1% [wt/vol] gelatin), 10 µl of 5 mM MnCl$_2$, 10 µl of deoxynucleoside triphosphate mix (2 mM dGTP, 2 mM dATP, 10 mM dCTP, and 10 mM dTTP), and 5 units of Taq polymerase (Promega, Madison, Wis.). The reagents were mixed into a final volume of 100 µl. The cycling conditions were 94° C. for one minute, 45° C. for one minute, and 72° C. for one minute for 30 cycles. The mutant PCR products (645 bp) were purified, digested with appropriate restriction enzymes, and cloned into the pQE100 vector (Qiagen).

Screening of Ad35 Fiber Knob Mutant Library for Mutants with Increased Binding Affinity for CD46

The Ad35 fiber knob mutant plasmid library was transformed into *E. Coli* cells, host strain M15, and plated on Luria-Bertani agar plates (master plate) with kanamycin and ampicillin. About 800 to about 1,000 colonies per 15 cm Petri dish were grown. After growth overnight, a 0.45 µm pore size Durapore filter membrane (Millipore, Billerica, Mass.) was placed on top of the colonies. The membrane was peeled off and placed carefully, with the colonies facing upwards, on two sheets of Whatman 3MM paper soaked in Luria-Bertani medium supplemented with antibiotics and 1 mM IPTG (isopropyl-â-D-thiogalactopyranoside) to induce transgenic protein expression in the colonies. After incubation for 20 minutes at room temperature (RT), the filter with the colonies was placed on top of a nitrocellulose filter and a Whatman 3MM paper soaked in native lysis buffer (20 mM Tris-C1, pH 8, 300 mM NaCl, 50 mM MgCl$_2$, 0.1 mg/ml lysozyme, 0.75 mg/ml DNase 1, and one-half of a complete EDTA-free protease inhibitor cocktail tablet/10 ml [Roche, Palo Alto, Calif.]). The "filter sandwich" was freeze-thawed four times for 10 minutes at −80° C. and 10 minutes at 30° C. The nitrocellulose membrane was removed from the sandwich and blocked with 3% bovine serum albumin in TBS (10 mM Tris-C1, pH 7.5, 150 mM NaCl) at 4° C. overnight. The membranes were then incubated with soluble recombinant CD46 (sCD46), produced as described previously in Wang, H., et al., *Journal of Virology* 81:12785-12792 (2007), in TBS and 3% milk for one hour at RT and then washed three times for ten minutes in TBS-0.05% Tween 20 (TBS-T) buffer. The blot was then incubated with anti-CD46 antibody (clone J4.48; Fitzgerald, Concord, Mass.) (1:50 dilution) in TBS and 3% milk for one hour at RT and then washed three times for ten minutes in TBS-T buffer. To visualize binding, the blot was incubated with goat anti-mouse immunoglobulin (Ig)-horseradish peroxidase (BD Pharmingen, San Jose, Calif.) (1:1,000 dilution) in TBS and 3% milk for one hour at RT, washed, and subjected to ECL substrate (Pierce, Rockford, Ill.). Out of 10,000 colonies plated, 20 colonies with the most intense binding to CD46 were picked from the original master plates. Plasmid DNA from these colonies was sequenced. Of the 20 colonies picked and sequenced, 16 colonies contained seven distinct fiber knob sequences encoding single or combined amino acid substitutions at residues Asp270, Thr245, or Ile256, as show below in Table 2.

Surface Plasmon Resonance (SPR) Analysis

The recombinant Ad35 fiber knob mutant proteins encoded by each mutant DNA sequence were produced in *E. coli* and purified by Ni-nitrilotriacetic acid affinity chromatography. Binding of the purified recombinant fiber knob proteins to soluble CD46 was verified by Western Blot analysis as described in Wang, H., et al. *Journal of Virology* 81:12785-12792 (2007) (data not shown). Briefly described, recombinant fiber knob proteins were separated by polyacrylamide gel electrophoresis and then transferred onto nitrocellulose membranes. The protein samples were loaded in loading buffer (50 nM Tris-C1, pH 8.0, 100 mM dithiothreitol, 2% sodium dodecyl sulfate, 10% glycerol, 0.2% bromophenol blue) with and without boiling. The blot was incubated with sCD46 and subsequently anti-CD46 antibody, and binding was visualized as described above in the context of screening the Ad35 fiber knob mutant library. All recombinant mutant fiber knob proteins produced *E. coli* spontaneously formed trimers, as determined by analysis with polyacrylamide gel electrophoresis under nondenaturing conditions and confirmed via binding of rabbit polyclonal anti-His$_6$-HRP antibody (ab1187-100, lot 134173; Abcam, Cambridge, Mass.) (data not shown), which recognizes Ad35 fiber knob only as a trimer (see Wang, H., et al., *Journal of Virology* 81:12785-12792 (2007)).

The binding affinity of each recombinant mutant fiber knob protein to sCD46 was determined by comparing the surface plasmon resonance to those of a wild-type Ad35 fiber knob protein and an Ad35 fiber knob protein that contained an Arg279Cys substitution resulting in ablation of CD46 binding, as described previously in Wang, H., et al., *Journal of Virology* 81:12785-12792 (2007). Briefly described, the Ad35 fiber knob proteins were biotinylated using an EZ-Link Sulfo-NHS-LC-Biotin kit (Pierce) according to the manufacturer's instructions. The biotinylated products were coupled to streptavidin-coated sensor chips (Biacore, Piscataway, N.J.) by manual injection until the required values for resonance unites (RU) were obtained. Various concentrations of sCD46 were injected over the activated surface until the desired surface densities were achieved. Activated, coupled surfaces were then quenched of reactive sites with 1 M ethanolamine (pH 8) for 3 to 5 minutes. All data were collected at 1 Hz using two replicate injections for each concentration of analyte. All analyses were carried out on a Biacore T100 instrument at a flow rate of 30 µl/ml in HBS-EP (Biacore). To completely remove remaining amounts of sCD46 bound to the sensor chip surface, the sensor chip surface was regenerated after each cycle by injection of 10 mM glycine-HCl, pH 3. Data processing and kinetic analysis were performed using Biacore T100 evaluation software.

The $K_D$ (equilibrium dissociation constant) of the wild-type fiber knob protein (SEQ ID NO:3) was 14.64 nM, while the $K_D$s for fiber knob mutants with the single amino acid substitutions Asp207Gly, Thr245Ala, and Ile256Leu were 1.77, 7.64, and 10.96 nM, respectively, as shown below in Table 2. This translates into affinities 8.3-, 1.9-, and 1.3-fold higher than that of the wild-type fiber knob protein. The majority of identified fiber knob mutants contained two or three of the above-listed substitutions. The highest affinity ($K_D$ of 0.63; 23.2-fold higher than that of the wild-type Ad35) was that of a fiber knob mutant with a double Asp207Gly, Thr245Ala substitution (i.e., polypeptide SEQ ID NO:5). Two of the identified fiber knob mutants with multiple mutations had substitution Asn217Asp or Thr226Ala; however, when analyzed individually, these substitutions had no impact on fiber knob affinity (data not shown). The association rate constants and the dissociation rate constants of the wild-type and all fiber knob mutants are shown in Table 2. The association kinetics for all the fiber knob proteins tested are comparable. However, the dissociation rate constants are inversely correlated with the fiber knob affinities. This indicates that fiber knob protein mutants with higher affinity dissociate more slowly from CD46 than the wild-type Ad35 fiber knob protein.

TABLE 2

Surface Plasmon Resonance (SPR) Analysis of Ad35 fiber knob Mutants[a]

| Ad35 fiber knob mutant[b] | $K_a$ (1/Ms) | $K_d$ (1/s) | $K_D$ (nM) |
|---|---|---|---|
| Wild type Ad35 | $1.52 \times 10^6$ | 0.0234 | 14.64 |
| Asp207Gly | $3.51 \times 10^6$ | 0.0034 | 1.77 |
| Thr245Ala | $2.25 \times 10^6$ | 0.0173 | 7.64 |
| Ile256Leu | $2.13 \times 10^6$ | 0.0236 | 10.96 |
| Asp207Gly + Thr245Ala | $2.48 \times 10^6$ | 0.0017 | 0.63 |
| Asp207Gly + Thr226Ala | $1.97 \times 10^6$ | 0.0026 | 1.41 |
| Asn217Asp + Thr245Pro + Ile256Leu | $2.25 \times 10^6$ | 0.0097 | 4.82 |
| Asp207Gly + Thr245Ala + Ile256Leu | $1.96 \times 10^6$ | 0.0018 | 0.92 |

[a]$K_a$, association rate constant ($k_{on}$); $K_d$, dissociation rate constant ($K_{off}$); $K_D$, equilibrium dissociation rate constant.
[b]Ad35 fiber knob mutants other than the wild type are listed by reference to the mutations contained in each protein, wherein the first amino acid residue corresponds to the wildtype residue at the designated position and the second amino acid residue corresponds to the substituted residue in the mutated polypeptide.

Modeling the Interactions Between Mutant Ad35 Fiber Knob Domain Polypeptides and CD46

In an attempt to understand the structural basis for the increased affinity of the fiber knob mutants to CD46, the crystal structures of the Ad35 fiber knob proteins were superimposed with that of CD46. Crystal structure of wild-type Ad35 fiber knob protein was obtained previously (see Wang et al. *J. Virol.* 81:12785-12792 (2007)), and the crystal structures of the newly generated mutants were generated according to the same protocol. Particularly, N-terminal His$_6$ tagged mutant Ad35 fiber knob proteins were produced in *E. coli* and purified by Ni-nitrilotriacetic acid affinity and gel filtration chromatography and dialyzed against 20 mM Tris-HCl (pH 8.0), 200 mM NaCl, and 5 mM dithiothreitol. The protein was crystallized using NeXtal DWBlock crystallization screening suites. Crystals grew at 21° C. in 30% polyethylene glycol 1000 and 0.2 M MgBr$_2$ (pH 8.0). Native data sets were collected from National Synchrotron Radiation Research Center beam lines BL13B1 and BL13C1 in Taiwan, using an ADSC Quantum charged-coupled-device detector, and processed with HKL2000 software (Otwinowski, Z., and W. Minor, pp. 307-326). In Carter, C., and Sweet, R. (eds.) *Methods in Enzymology: Macromolecular Crystallography*, Academic Press, San Diego, Calif. (1997)). The structure was solved by molecular replacement with the Open-EPMR program (Kissinger, C., et al., *Acta Crystallographer* D57:1474-1479 (2001)) using Ad3 head (Protein Data Bank [PDB] entry 1h7z) as a search model. The model was rebuilt using the O program (Jones, T., et al., *Acta Crytallographer* A47:110-119 (1991)) and refined using the CNS program with the maximum-likelihood target and automatic weight optimization (Brunger, A., et al., *Acta Crytallographer* D54:905-921 (1998)). The crystal structure of CD46 was obtained from Persson, et al., *Nat. Struct. Mol. Biol.* 14:164-166 (2007).

With regard to the Asp207Gly mutant, the hydrophobic Ile13 residue of CD46 is the closest amino acid R group to Asp207, with its hydroxyl group being 5.93 and 4.4 angstroms from the nearest Ile methyl groups. While not wishing to be bound by any particular theory, an Asp207Gly substitution may enable the Ad35 DE loop (SEQ ID NO:6) to approach CD46 more closely to Ile13 because, unlike the polar Asp residue, glycine is hydrophobic (lacking a side chain). Subsequently, the HI loop (SEQ ID NO:8) would also get closer to CD46.

With regard to the Thr245Ala mutant, the original Ad35-CD46 binding model indicates that the Ad35 Thr246 residue interacts with the CD46 Tyr67 residue and is important for binding. In this conformation, the hydroxyl group of the Ad35 neighboring Thr245 residue is relatively close to the backbone carbonyl and R group hydroxyl group of CD46 residue Thr64 (4.35 and 5.21 angstroms) and to the R group carbonyl and hydroxyl group of CD46 residue Glu63 (4.46 and 5.76 angstroms). Although the hydroxyl group of residue Thr245 is not close enough to form a strong hydrogen bond with any of these groups, the proximity of the groups likely influences the loop conformation in this region. Again, while not wishing to be bound by any particular theory, the introduction of hydrophobic alanine at this position (Thr245Ala) may make the Thr246-to-Tyr67 interaction stronger since the FG loop (SEQ ID NO:7) can move closer to CD46.

With regard to the Ile256Leu mutant, Ad35 residue Ile256 is oriented toward the central core of the fiber trimer in the center of the G sheet and its hydrophobic R group is closest to the polar carboxyl group in the side chain of Asn271 within the H sheet. Again, while not wishing to be bound by any particular theory, the model suggests that the methyl groups of Leu256 would be closer to Asn271 than those of Ile256, even though the rotation of leucine in the Ile256Leu mutant is unknown. The increased repulsion would likely push the G and H sheets further apart. While not wishing to be bound by any particular theory, it is believed that the higher affinity of the Ad35 fiber knob protein containing the Ile256Leu mutation for CD46 may be due to increased stability of the fiber knob trimer.

In summary, recombinant fiber knob mutant proteins were identified with increased binding affinity for CD46.

EXAMPLE 2

This Example demonstrates that incubation of tumor cells with mutant Ad35K++ (Asp207Gly and Thr245Ala) removes CD46 from the tumor cell surface.

Rationale

Several preclinical studies have shown that tumor cells can be sensitized to rituximab-induced, complement-dependent-cytolysis (CDC) by CD55 and/or CD59 blocking antibodies (Ziller, F., et al., *European Journal of Immunology* 35:2175-2183 (2005); and Guo, B., et al., *Clinical Immunology* 128:155-163 (2008)). However, in addition to blocking complement activation, CD55 and CD59 are also involved in T-cell activation (Hamann, J., et al., *European Journal of Immunology* 28:1701-1707 (1998); Deckert, M., Kubar, J., and Bernard, A., *J. Immunol.* 148:672-677 (1992)). This may give tumor cells that lost these two proteins a selective advantage in escaping immune-mediated destruction and may explain why CD55 and CD59 are often absent on tumors (Hara, T., et al., *Br. J. Haematol.* 82:368-373 (1992)). It has been proposed that CD46 alone may protect tumor cells from complement lysis (Madjd, Z., et al., *Cancer Immunol. Immunother.* 54:149-156 (2005)). Consistent with this theory, the reduction of CD46 expression using anti-sense oligonucleotides was able to sensitize tumor cells to rituximab-induced CDC, demonstrating a predominant role of CD46 in protection of tumor cells against CDC (Zell, S., et al., *Clinical and Experimental Immunology* 150:576-584 (2007)). CD46 is uniformly expressed at high levels on many malignancies (Rushmere, N. K., et al., *International Journal of Cancer* 108:930-936 (2004); Varela, J. C., et al., *International Journal of Cancer* 123:1357-1363 (2008)), including hematological malignancies (Hara, T., et al., *Br. J. Haematol.* 82:368-373 (1992)).

An experiment was carried out to determine if the mutant Ad35 fiber knob protein (Ad35K++) with enhanced affinity for CD46 could downregulate CD46 on tumor cells and render the tumor cells susceptible to CDC.

Materials and Methods

Production of Fiber Knob Proteins:

Recombinant modified Ad35 fiber knob proteins with increased affinity to CD46 were selected from an *E. coli* expression library as described in Example 1. The recombinant mutant fiber knob proteins were produced in *E. coli* with N-terminal tags of six consecutive histidine residues (6-HIS) and purified by Ni-NTA agarose chromatography as described in Example 1. The fiber knob proteins were dialyzed against 20 mM Hepes, 200 mM NaCl, 17% glycerol. Endotoxin tests were performed using the *Limulus Amebocyte* Lysate test kit from Cape Cod Inc. (E. Falmouth, Mass.).

Cells:

Cell lines 293 (Microbix, Toronto, Ontario, Canada) and HeLa (American Type Culture Collection, ATCC) were cultured in Dulbecco modified Eagle medium (DMEM) supplemented with 10% fetal bovine serum (FBS) and with 2 mM L-glutamine, 100 units/ml penicillin, and 100 μg/ml streptomycin. Raji (human Burkitt's lymphoma) (ATCC CCL-86), Mino (Mantle cell lymphoma) (ATCC CRL-300), Farage (non-Hodgkin's B cell lymphoma) (ATCC CRL-2630), and BJAB cells (EBV-negative Burkitt's lymphoma) (obtained from Edward A. Clark, University of Washington) were cultured in RPMI supplemented with 10% FBS and with L-glutamine/(Pen-Strep).

Primary chronic lymphocytic leukemia (B-CLL) cells were obtained from peripheral blood of patients after informed consent. The diagnosis of CLL was based on immunophenotype, morphology of the lymphocytes, and the clinical manifestations of the disease. Mononuclear cells were isolated by centrifugation over Lymphoprep (Nycomed Pharm, Oslo, Norway). On average, 96% (range 91-98%) of the isolated cells from CLL patients belonged to the leukemic clone as determined by co-expression of CD5, CD19, and CD20 in flow cytometric analysis. Thawed B-CLL cells were cultured in RPMI 1640 medium containing 10% FCS, 2 mM sodium pyruvate, 2 mM Hepes, 100 μM 2-mercaptoethanol, 100 units/ml penicillin, 100 μg/ml streptomycin, 2 mM L-glutamine. Two days after thawing, CLL cells were used for the experiment.

Antibodies:

Rituximab was obtained from Genentech, Inc. (South San Francisco, Calif.). Daclizumab was obtained from Roche Pharmaceuticals (Nutley, N.J.). FITC-mouse anti-human CD20 (clone 2H7) and FITC-mouse anti-human CD46 (clone E4.3) were obtained from BD Pharmingen (San Jose, Calif.). PE conjugated CD46 antibody (clone E4.3) was obtained from Santa Cruz Biotechnology (Santa Cruz, Calif.). Unconjugated CD46 blocking antibody (clone MEM-258) was obtained from AbD Serotec (Raleigh, N.C.). Anti-His tag antibody (mouse monoclonal IgG1, #34660) was obtained from Qiagen (Valencia, Calif.).

Measurement of CD46 Cell Surface Levels:

The levels of CD46 on cell surfaces were measured as follows. Suspension cells (Mole, Raji, etc.) were chilled on ice for 45 minutes and then incubated with 20 μg/ml of recombinant wild type Ad35 fiber knob protein (referred to as wild-type Ad35K), mutant Ad35 fiber knob protein with Asp207Gly and Thr245Ala substitutions (referred to as Ad35K++) or mouse anti-human CD46 antibody (MEM-258, AbD Serotec) in 100 μl volume on ice for 1 hour. Then, cells were washed twice with cold PBS containing 2% FBS and incubated with fresh media at 37° C. At the indicated time points, cells were washed and incubated with phycoerythrin (PE)-conjugated anti-human CD46 antibody (clone E4.3, Santa Cruz Biotechnology Inc., Santa Cruz, Calif.) 1:20 in 100 μl volume for one hour on ice. After three times washing, PE mean fluorescence intensity was immediately analyzed by flow cytometry (described below). HeLa cells incubated with 20 μg/ml Ad35K, Ad35K++, or anti-CD46-antibody were washed and transferred to 37° C. for the indicated time periods. After incubation, HeLa cells were detached by versene and analyzed by flow cytometry as described below.

Immunofluorescence:

Recombinant fiber knob proteins Ad35K (wild-type) and Ad35K++ mutant protein were labeled with Cy3 fluorochrome (Amersham CyTM Bis-Reactive Dye, GE Healthcare, Little Chalfont, United Kingdom) according to the manufacturer's protocol. Tumor cells ($2 \times 10^4$ cells/well) were seeded into eight-chamber glass slides in standard growth media one day prior to the experiment. The following day, cells were washed with PBS and incubated with 20 μg/ml of Cy3-Ad35 fiber knob proteins in 200 μl medium for one hour at 37° C. Cells were washed twice with PBS and moved to a 37° C./5% CO2 incubator. At the indicated time points, cells were washed with PBS and fixed with cold fixative (Acetone and Methanol 1:1) for 15 minutes at 4° C. The fixed cells were first incubated with 2% non-fat milk for 20 minutes to block non-specific binding of antibodies. Monoclonal anti-CD46 antibody (1:100, Fitzgerald, Concord, Mass.) was added and incubated overnight at 4° C. After washing twice with PBS, cells were incubated with Alexa Fluor 488-conjugated, goat anti-mouse IgG (1:200, Molecular Probes, Eugene, Oreg.) for 30 minutes. After washing, the slides were mounted with Vectashield containing DAPI (Vector Laboratories, Inc., Burlingame, Calif.). Photographs were taken on a Zeiss META confocal microscope using a 40× oil lens.

Flow Cytometry:

HeLa cells were detached by treatment with versene and washed three times with ice-cold wash buffer (PBS containing 2% FBS). Lymphoma cells grown in suspension were washed three times with wash buffer. After washing, $2 \times 10^5$ cells were resuspended in 100 μl wash buffer incubated with specific antibodies on ice for one hour. Cells were then washed twice and analyzed in duplicate by flow cytometry.

Ad35 Infection Studies:

The Ad35-GFP vector has been described previously (Gao, W., and Gambotto, A., in press (2008)). Ad35-GFP was purified by ultracentrifugation in CsCl gradients. The ratio of viral particles to plaque-forming units was 15:1. For transduction studies, $2 \times 10^5$ HeLa cells were incubated with PBS or 20 μg/ml of Ad35K (wild-type), mutant Ad35K-279 (reduced CD46 binding) or mutant Ad35K++ (increased CD46 binding) fiber knob protein in 200 μl medium at room temperature for 1 hour. Cells were washed twice with PBS and incubated with fresh media at 37° C. After 72 hours incubation, cells were infected with Ad35-GFP at MOIs of 25, 50, 100, 200, 400, and 800 pfu/cell. Virus containing medium were washed two hours after infection. Twenty-four hours after infection, GFP expression was analyzed by flow cytometry.

In Vitro Viability Assays:

$5 \times 10^4$ Raji cells/well were plated in triplicate in 96 well plates with RPMI complemented with 10% heat inactivated FBS, and preincubated with (1) PBS, (2) 25 μg/ml CD46 antibody (MEM-258, Serotec), (3) 25 μg/ml mutant Ad35 fiber knob Arg279Cys, (4) 25 μg/ml wild-type Ad35K, or (5) 25 μg/ml mutant Ad35K++ with high affinity to CD46. Eight hours later, 15 μg/ml rituximab was added to the cells and incubated at room temperature for 30 minutes. Normal human serum (NHS) was added as a source of complement and the cells were incubated at 37° C. for another three hours for lysis (total volume were added up to 150 μl). The following NHS dilutions were used; for Raji (5% NHS), for BJAB (20% NHS), for Farage (10% NHS), and for primary B-CLL cells (25% NHS). Viable cells in each well were counted after trypan blue staining. Each sample was carried out in triplicate and each well was counted four times. Three independent studies were performed.

Western Blots:

Recombinant fiber knob proteins or hexon (0.5 ug/lane) were loaded in loading buffer (50 mM Tris-HCl, pH 6.8, 100 mM dithiothreitol, 2% sodium dodecyl sulfate, 10% glycerol, 0.2% bromophenol blue) without denaturation. Ad5 viral particles ($1 \times 10^9$ vp/lane) were boiled for five minutes in Laemmli buffer. Proteins were separated by polyacrylamide gel electrophoresis. Gels were either stained with Coomassie blue or transferred onto nitrocellulose membranes. Filters were incubated with human or mouse serum (1:100 diluted in PBS). Binding of human IgG was developed with goat anti-human IgG-horseradish peroxidase (HRP) (Millipore, Billerica, Mass.). Binding of mouse IgG was detected with goat anti-mouse IgG-HRP (BD Pharmingen) (1:1000) in PBS and 3% dry milk for 1 hour at RT. Filters were washed three times for 10 minutes in TBS-T buffer and subjected to enhanced chemiluminescence substrate (Pierce, Rockford, Ill.).

Results

Incubation of Tumor Cells with Mutant Ad35K++ (Asp207Gly and Thr245Ala) Removes CD46 from the Surface of the Tumor Cells The level of CD46 on the surface of HeLa cells was measured at different time points after adding 20 µg/ml of recombinant Ad35K (wild-type; SEQ ID NO:3) or Ad35K++ mutant (Asp207Gly+Thr245Ala; SEQ ID NO:5) fiber knob protein to the culture medium using flow cytometry with an anti-CD46 antibody that did not interfere with the interaction between Ad35 fiber knob protein and CD46. As shown in FIG. 2A, within 15 minutes after adding Ad35K or Ad35K++, CD46 levels decreased about 70% as compared to PBS treated control cells. No decrease in CD46 levels was seen with an Ad35 fiber knob protein that was ablated for CD46 binding (mutant Ad35K-279) (see Wang, H., et al., *Journal of Virology* 81:12785-12792 (2007)). In contrast, as further shown in FIG. 2A, incubation with an anti-CD46 mAb resulted in only a 30% decline of CD46 levels with a faster return to pre-incubation levels. Moreover, this observed 30% decline of CD46 levels may be partially caused by interference between the "effector" and "detector" anti-CD46 mAbs, even though they were directed against different epitopes. In addition to the decrease of surface CD46, less cell-bound Ad35K (wild-type) and Ad35K++ mutant fiber knob proteins were observed in flow cytometry studies, as show in FIG. 2B, indicating that CD46 and Ad35 fiber knobs are taken up together. No cell-associated signals were found for Ad35K-279 (data not shown).

Immunofluorescence studies for CD46 and recombinant Ad35 fiber knob proteins further corroborated the finding of less surface-CD46 in Ad35K (wild-type) and Ad35K++ mutant treated cells as compared to cells incubated with Ad35K-279. It was observed that 30 minutes after adding recombinant fiber knob proteins, more Ad35K++ than Ad35K was found inside the cells (data not shown). Ad35K (wild-type) and Ad35K++ mutant protein together with CD46 were detected in late endosomes/lysosomes with antibodies for the marker cathepsin B (data not shown). At 12 hours after adding recombinant fiber knob proteins, cells treated with Ad35K++ demonstrated predominantly cytoplasmic CD46 staining, whereas it appeared that the overall CD46 signal was less than before incubation with recombinant Ad35K++ mutant, indicating degradation of internalized CD46/Ad35K++ complexes in lysosomes (data not shown).

In addition to flow cytometry studies using anti-CD46 mAbs to assess the effect of recombinant Ad35 fiber knob proteins on surface CD46 levels, transduction studies were performed with a GFP-expressing Ad35 vector (Ad35-GFP) that uses CD46 as a binding receptor for infection. Previous studies have shown that transduction with Ad35-fiber containing vectors directly correlates with the density of CD46 on the cell surface (Anderson, et al., *Cancer Res.* 64:4919-4926 (2004)). HeLa cells were incubated with recombinant Ad35 fiber knob proteins and anti-CD46 mAb. 72 hours later, when CD46 ligands were no longer detectable on the cell surface, the cells were infected with increasing MOIs of Ad35-GFP. As shown in FIG. 2C, HeLa cells incubated with Ad35K++ became relatively resistant to infection by Ad35-GFP over a large range of MOIs (5 to 1,000 pfu/cell). GFP expression levels were >1000-fold lower in cells treated with mutant Ad35K++, compared to cells incubated with Ad35K-279.

In addition to HeLa cells, CD46 flow cytometry and Ad35-GFP transduction studies were also performed on other tumor cell lines, including erytholeukemia Mole cells and B-lymphoma Raji cells. In all cell lines analyzed, transient removal of CD46 from the cell surface upon incubation with Ad35K (wild type) or Ad35K++ mutant proteins was observed (data not shown).

Figure 3:
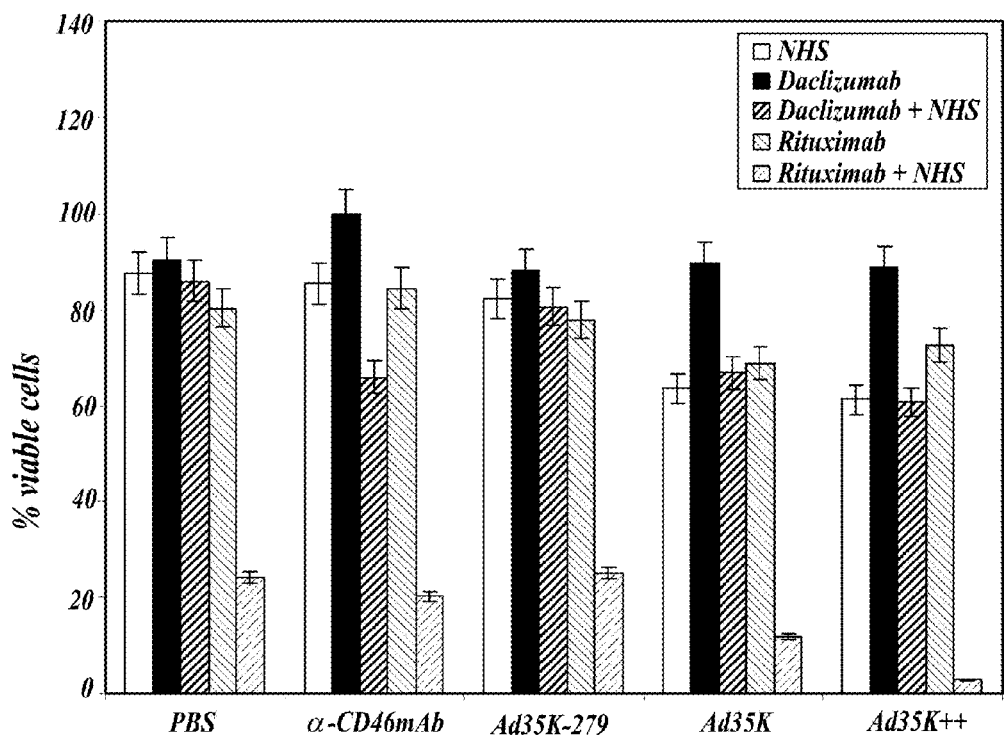
FIG. 3 graphically illustrates the relative levels of viable Raji cells (CD20 positive, CD25 negative) as a measure of complement-dependent cytolysis (CDC) after pre-incubation with phosphate buffered saline (PBS), anti-CD46 mAb, or recombinant fiber knob proteins Ad35K (wild-type), or Ad35K++ (double mutant containing Asp207Gly and Thr245Ala), followed by subsequent incubation with rituximab (anti-CD20 mAb) or daclizumab (anti-25 mAb), and followed by normal human serum (NHS) providing complement, wherein Raji cell viability levels are expressed as a percentage of the mean viability of untreated cells (N>6), as described in Example 2.

Incubation of Lymphoma Cells with Mutant Ad35k++ (Asp207gly and Thr245ala) Sensitizes them to Rituximab-Mediated Complement-Dependent Cytolysis A study was performed with established and primary B-cell lymphoma cultures to test whether incubation with Ad35K (wild-type) or Ad35K++ mutant protein would render them more susceptible to rituximab-mediated complement dependent cytolysis (CDC). Initial experiments were performed with Raji cells, a CD20-positive, human Burkitt's lymphoma cell line. Flow cytometry studies showed high and relatively uniform levels of CD46 on the cell surface of these cells, indicating a potential resistance to CDC. Notably, CD20 levels on Raji cells varied more (about two orders of magnitude). As shown in FIG. 3, incubation of Raji cells with rituximab followed by normal human serum (NHS), as a source of complement, resulted in killing of about 70% of Raji cells within three hours. It is noteworthy that the remaining viable Raji cells had CD20 levels that were about 50-fold lower than the mean CD20-fluorescence level of the control population (no rituximab or no NHS) (data not shown). To test the specificity of rituximab-mediated CDC to CD20-positive lymphoma cells, the humanized mAb daclizumab that binds to CD25 (which is not expressed on Raji cells) was used (data not shown). No significant cell killing mediated by this antibody when combined with NHS was observed (FIG. 3). Furthermore, it was observed that incubation of HeLa cells (which do not possess detectable CD20 surface levels) with rituximab/NHS did not lead to significant cell killing (data not shown).

To test whether the efficacy of rituximab-mediated CDC could be increased by Ad35K++ mediated internalization of CD46, Raji cells were incubated with Ad35K-279 mutant (decreased binding), Ad35K (wild-type), and Ad35K++ mutant (increased binding affinity) for eight hours. As shown in FIG. 3, pretreatment with wild-type Ad35K and mutant Ad35K++ increased cell killing with rituximab/NHS, by about 2- and 10-fold, respectively, compared to rituximab/NHS only. The sensitizing effect of Ad35K++ was seen at doses as low as 25 ng/ml and concentrations ranging from 25 ng/ml to 25 µg/ml resulted in similar levels of sensitization to CDC. Ad35K-279 had no effect on rituximab/NHS-mediated killing. Pre-incubation of Raji cells with anti-CD46 mAb followed by incubation with rituximab/NHS resulted in significantly less rituximab-mediated cell killing than pre-incubation with Ad35K (wild-type) or Ad35K++ mutant (anti-CD46 mAb vs Ad35K: p=0.024). The inability of anti-CD46 mAb to enhance rituximab-mediate CDC, as compared to Ad35K and Ad35K++, is likely a result of the mAbs' inability to cross-link several CD46 molecules. Incubation of Raji cells with CD46 ligands (anti-CD46 mAb, Ad35K, or Ad35K++) together with NHS (alone or in combination with daclizumab) caused a ~30% decline in cell viability, most likely as a result of CDC when CD46 is blocked (FIG. 3).

Figure 4A:
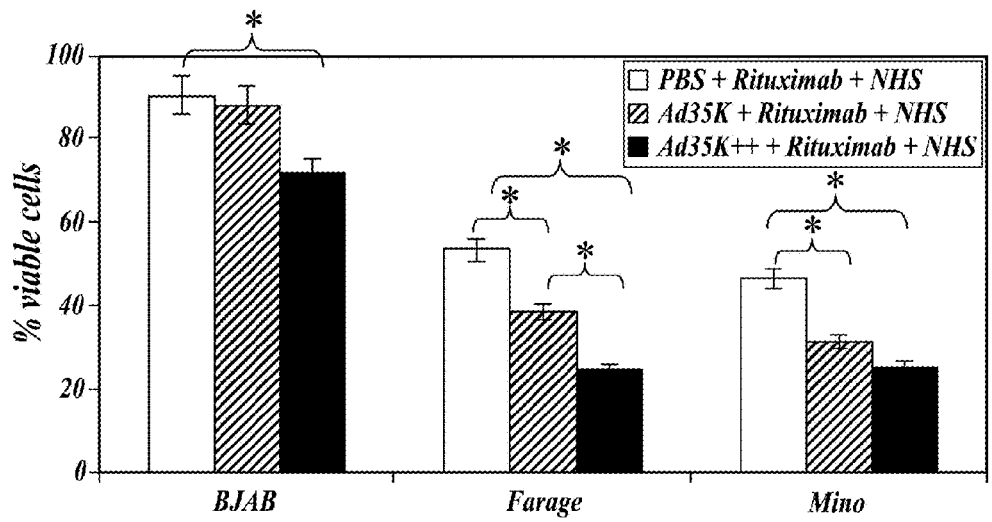
FIG. 4A graphically illustrates the enhanced rituximab-mediated CDC in CD20 positive cell lines BJAB, Farage and Mino resulting from pre-incubation with recombinant fiber knob proteins Ad35K (wild-type) or Ad35K++ (double mutant containing Asp207Gly and Thr245Ala), wherein cell viability levels are expressed as a percentage of the mean viability of untreated cells (N>6), as described in Example 2.

To extend these findings to other CD20-positive cell lines, additional experiments were performed on the following CD20-positive cells: BJAB (EBV-negative Burkitt's lymphoma), Farage (non-Hodgkin's B cell lymphoma), and Mino (Mantle cell lymphoma). As shown in FIG. 4A, all CD20-positive cell lines tested were found to have a significant increase in rituximab/NHS-mediated cell killing when the cells were pre-incubated with Ad35K++.

Figure 4B:
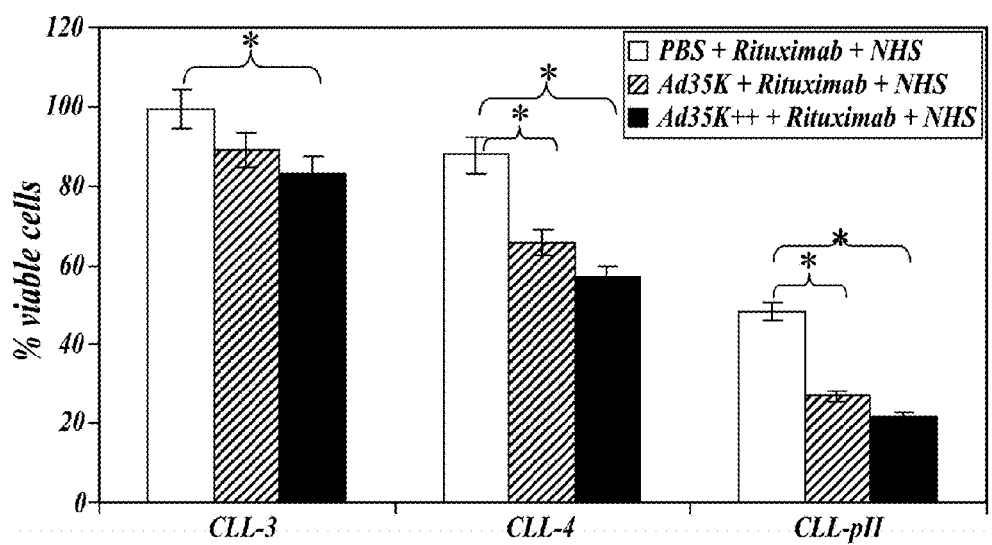
FIG. 4B graphically illustrates the enhanced rituximab-mediated CDC in primary lymphoma cells from patients with B cell chronic lymphocytic leukemia (CLL) after pre-incubation with recombinant fiber knob proteins Ad35K (wild-type) or Ad35K++ (double mutant containing Asp207Gly and Thr245Ala), wherein cell viability levels are expressed as a percentage of the mean viability of untreated cells (N>6), as described in Example 2.

Primary lymphoma cells from B-CLL patients were also tested. CD20 surface levels on primary lymphoma cells varied more than on established cell lines (data not shown). It appeared that CD20 levels determined the sensitivity of primary lymphoma cultures to killing by rituximab/NHS. For example, CCL-3 cells that expressed low levels of CD20 were relatively resistant to killing by rituximab/NHS, whereas CCL-pII cells that expressed higher levels of CD20 were more susceptible to killing by rituximab/NHS. Overall, as shown in FIG. 4B, pre-incubation of CCL cells with Ad35K++ mutant protein significantly increased the efficacy of rituximab-mediated killing in primary and established CD20-positive lymphoma cells. These results demonstrated that recombinant Ad35K++ mutant may be used to reduce CD46 levels on plasma membranes and thereby increase tumors cells susceptibility to CDC mediated anti-cancer mAb therapies, and also reduce the susceptibility of cells to challenge by pathogens that require CD46 for attachment.

Figure 4C:
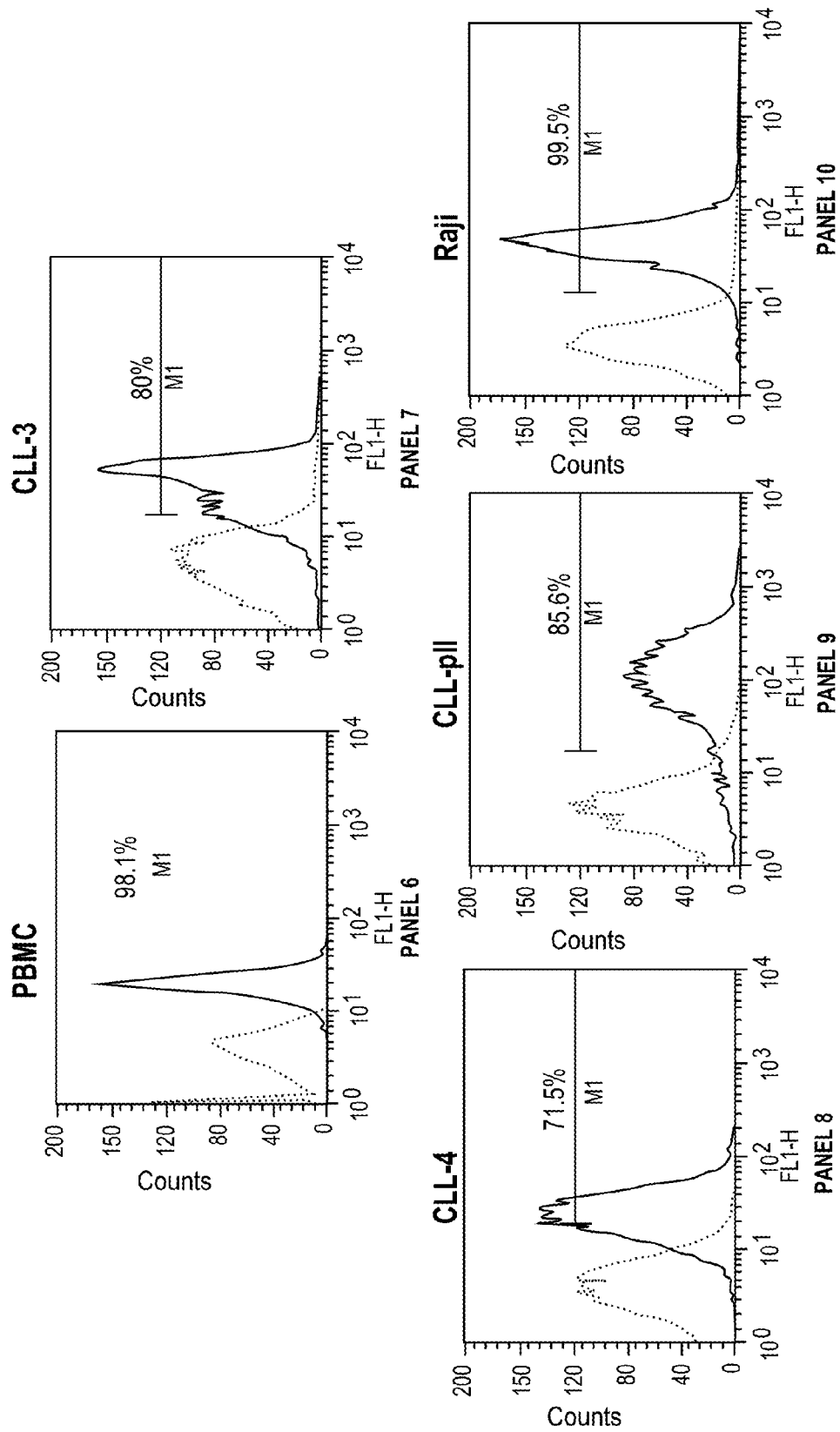
FIG. 4C graphically illustrates that the cell sample that was most resistant to Ad35K++/rituximab killing (CCL-3) had the lowest percentage of CD20+ cells and the lowest CD20 levels.

FIG. 4C shows CD20 and CD46 levels on normal PBMC, primary lymphoma cells from B-CLL patients, and Raji cells. Flow cytometry was performed using PE-conjugated mouse anti-human CD20 mAbs (clone 2H7) and FITC-conjugated mouse anti-human CD46 mAbs (clone E4.3). Shown are representative samples. The figure graphically illustrates that the cell sample that was most resistant to Ad35K++/rituximab killing (CCL-3) had the lowest percentage of CD20+ cells and the lowest CD20 levels.

Figure 4D:
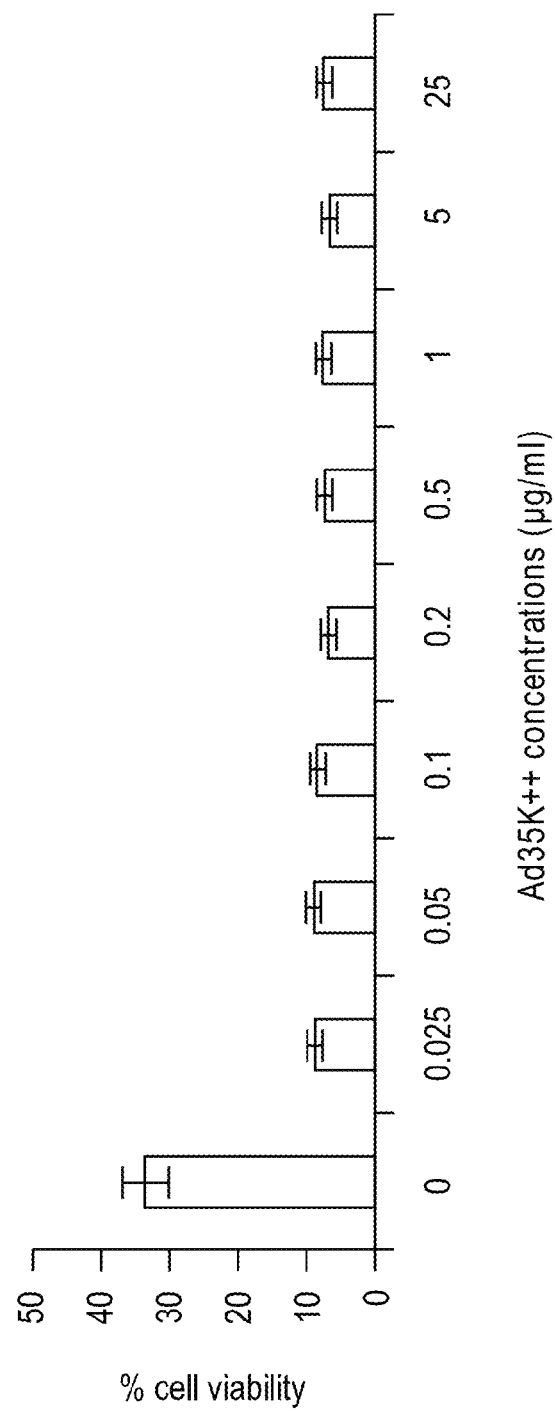
FIG. 4D graphically illustrates that the sensitizing effect of Ad35K++ on Raji cells was seen at a dose as low as 25 ng/ml.

FIG. 4D graphically illustrates the effect of Ad35K++ fiber knob concentration on rituximab-mediated CDC. The figure shows that the sensitizing effect of Ad35K++ was seen at doses as low as 25 ng/ml. The experimental conditions were as described above. Ad35K++ concentrations tested ranged from 0.025 mg/ml ($4.63 \times 10^5$ trimeric fiber knob molecules/cell or 9.3 trimeric fiber knob molecules per CD46 molecule) to 25 mg/ml.

EXAMPLE 3

This example demonstrates that pre-treatment with mutant Ad35K++ (Asp207Gly and Thr245Ala; SEQ ID NO:5) protein improves the anti-tumor efficacy of rituximab in a xenograft mouse lymphoma model.

Materials and Methods

Production of Recombinant Fiber Knob Protein:

Recombinant Ad35 mutant fiber knob proteins with increased affinity to CD46 were produced as described in Examples 1 and 2. For in vivo studies, preparations of recombinant Ad35K (wild-type; SEQ ID NO:3) and Ad35K++ (Asp207Gly and Thr245Ala; SEQ ID NO:5) mutant protein with less than 0.25 EU/ml of endotoxin were used.

Cells:

Raji cells were maintained as described in Example 2.

Animal Studies:

All experiments involving animals were conducted in accordance with the institutional guidelines set forth by the University of Washington. Mice were housed in specific-pathogen-free facilities. To establish a xenograft lymphoma model, $3.5 \times 10^6$ Raji cells in 200 μl of PBS were injected into the tail vein of Immunodeficient CB17 SCID-beige mice. After 14 days, 50 μg of recombinant Ad35K-279 mutant (decreased CD46 binding) or Ad35K++ mutant (increased CD46 binding) fiber knob proteins in 200 μl PBS was intravenously injected. Rituximab (50 μg in 200 μl PBS) or PBS was injected via the tail vein 10 hours thereafter. In the first experiment, mice were sacrificed seven hours after rituximab or PBS injection and bone marrow cells were flushed from femurs. For analysis of human CD20-positive cells in bone marrow by flow cytometry, $1 \times 10^6$ bone marrow cells were pretreated with Fc-block (anti-CD16/CD32, BD Biosciences) for 15 minutes and then incubated with 20 μl of FITC-conjugated-anti CD20 antibody (clone 3H7, BD Pharmingen) for one hour at 4° C. In the second experiment, mice were evaluated for onset of hind leg paralysis as the end point of Kaplan-Meiers survival studies. For the survival studies, mice were injected with Raji cells and treated with recombinant Ad35K-279 mutant or Ad35K++ mutant fiber knob proteins followed by rituximab or PBS as described above.

To establish a second lymphoma xenograft model, $5 \times 10^6$ human Farage cells (CD20+) were injected intravenously into CB17 SCID/beige mice. At 21 days after injection with Farage cells, 50 μg of recombinant Ad35K-279 mutant (decreased CD46 binding) or Ad35K++ mutant (increased CD46 binding) fiber knob proteins in 200 μl PBS was intravenously injected. Rituximab (50 μg in 200 μl PBS) or PBS was injected via the tail vein ten hours thereafter and mice were observed for the onset of hind leg paralysis.

Results

Intravenous Injection of Ad35K++ is Well Tolerated

Previous studies by others using hCD20-transgenic mice have shown that rituximab treatment is well tolerated. Here, recombinant mutant Ad35K++ protein was intravenously injected at a dose of 50 μg/mouse (2.5 mg/kg) into immunocompetent CD46-transgenic C57B1/6 mice (line MCP8B) (Marie, J. C., et al., *Nature Immunology* 3:659-666 (2002)), or immunodeficient CB17 SCID/beige mice. Ad35K++ injection did not cause changes in animal appearance or behavior (data not shown). Analyses of blood cell counts and key serum enzymes at six hours and six days after Ad35K++ injection did not show abnormalities (data not shown). At necropsy (day 14 post injection (p.i.)), no pathological or histological changes were found in any of the organs analyzed (brain, lung, heart, liver, kidney, intestines, bone marrow). These results demonstrate that intravenous injection of Ad35K++ is well tolerated in mice without any adverse effects observed at the dose administered. The lack of complement damage to normal cells after Ad35K++ injection is most likely due to the redundancy of the complement block system.

Pre-Treatment with Mutant Ad35K++ Protein Improves Anti-Tumor Efficacy of Rituximab In Vivo To establish a xenograft lymphoma model, human Raji cells (CD20+) were injected intravenously into CB17 SCID/ beige immuno-deficient mice. At different time points after injection of Raji cells, mice were sacrificed and samples of peripheral white blood cells, splenocytes, and bone marrow cells were analyzed for the presence of Raji cells by flow cytometry for human CD20. No significant amounts of hCD20-positive cells were found in splenocytes and white blood cells at all time points. However, in bone marrow, the percentage of hCD20-positive cells increased from 20% at day 10 p.i. to about 75% at day 14 p.i. At days 15/16 after Raji cell injection, mice developed hind leg paralysis, a symptom that was used as an endpoint in Kaplan-Meier survival studies.

Figure 5A:
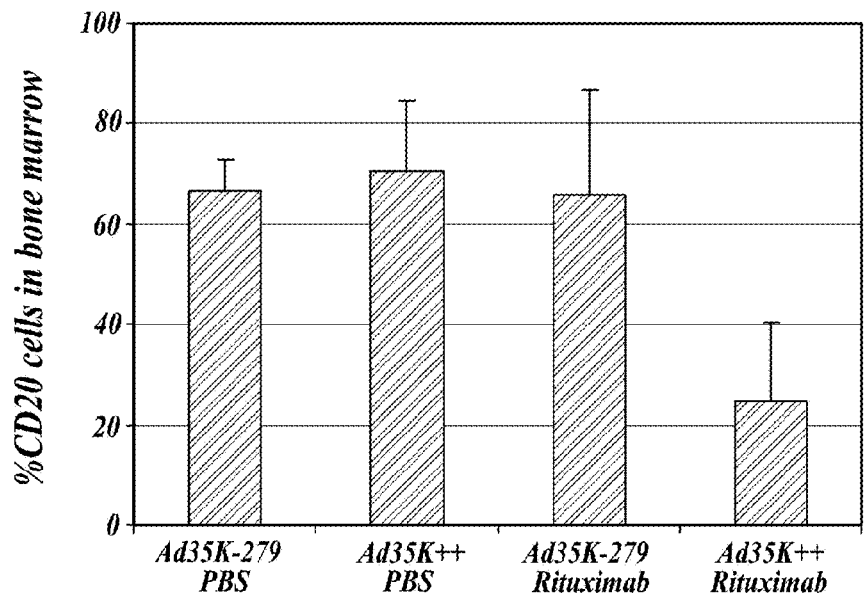
FIG. 5A graphically illustrates the relative levels of human CD20 positive cells in the bone marrow of xenograft lymphoma mice treated with a first injection of either Ad35K-279 (ablated for binding to CD46) or Ad35K++ (double mutant containing Asp207Gly and Thr245Ala with enhanced binding to CD46), followed by a second injection of either PBS or rituximab (anti-CD20 mAb), wherein the CD20 positive cell levels were measured 6 hours after the second injection and are expressed as a percentage of cells in the bone marrow positive for CD20, as described in Example 3.
Figure 5B:
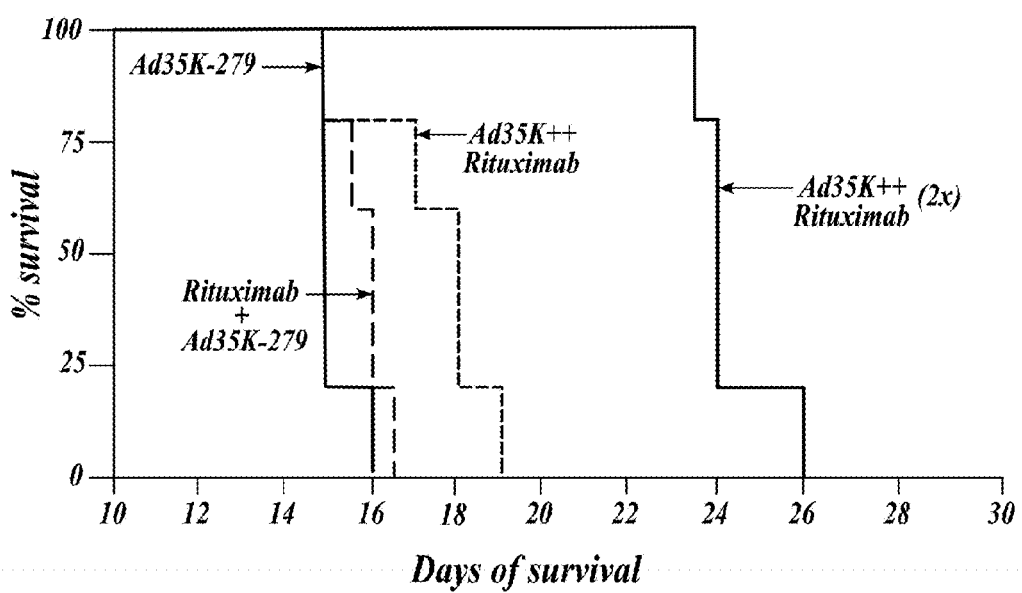
FIG. 5B graphically illustrates the results of a Kaplan-Meier survival study of xenograft lymphoma mice (receiving Raji cells) treated with a first injection of either Ad35K-279 (ablated for binding to CD46) or Ad35K++ (double mutant containing Asp207Gly and Thr245Ala with enhanced binding to CD46), followed by a second injection of either PBS or rituximab (anti-CD20 mAb), wherein one group of mice received a second treatment of Ad35K++/rituximab 48 hours after the first injection of rituximab, as described in Example 3.

In a study carried out to evaluate Ad35K++ as a therapeutic, 14 days after injection of Raji cells, mice received either 50 µg of Ad35K++ mutant protein (increased CD46 binding) or 50 µg of Ad35K-279 mutant (decreased CD46 binding). Ten hours later, treatment of either PBS or 50 µg of rituximab was injected via the tail vein. One group of mice was sacrificed six hours later and the effect of the various treatments on killing of Raji cells in vivo was measured based on the percentage of hCD20-positive cells in the bone marrow, as shown in FIG. 5A. Compared to Ad35K-279-treated control mice, no significant therapeutic effect was observed when mutant Ad35K++ protein or rituximab were injected alone. However, as shown in FIG. 5A, the combination of pre-treatment with mutant Ad35K++ protein followed by administration of rituximab resulted in a significant decrease in hCD20-positive cells in the bone marrow. These findings were confirmed in survival studies. As shown in FIG. 5B, there was a significant increase in survival when mice were pre-treated with Ad35K++/rituximab as compared to rituximab only or mock treatment (rituximab vs Ad35K++/rituximab: p=0.0050; Ad35K-279 vs Ad35K++/rituximab: p=0.0016). There was no difference in survival between the control (Ad35K-279) and Ad35K++ only groups (data not shown). Interestingly, rituximab alone did not exert a therapeutic effect in vivo (Ad35K-279 vs. rituximab: p=0.1289), which is in contrast to what was observed in vitro. It is likely that the effect of rituximab is dose dependent and may be stronger at higher doses.

Importantly, pre-injection of Ad35K++ greatly improved the anti-tumor efficacy of rituximab injected at a dose that was equivalent to a dose used in human patients (which ranges from 2 to 250 mg/kg). In an attempt to further increase the therapeutic efficacy of this approach, a second round of Ad35K++/rituximab was initiated 72 hours after the first injection of rituximab (FIG. 5B). As in the first round of therapy, Ad35K++ mutant fiber knob protein was intravenously injected into the mice, followed ten hours thereafter by rituximab injection via the tail vein. As shown in FIG. 5B, repeated injection of Ad35K++ mutant protein and rituximab increased the medium survival to 24 days, compared to 16.5 days with rituximab treatment alone.

Figure 5C:
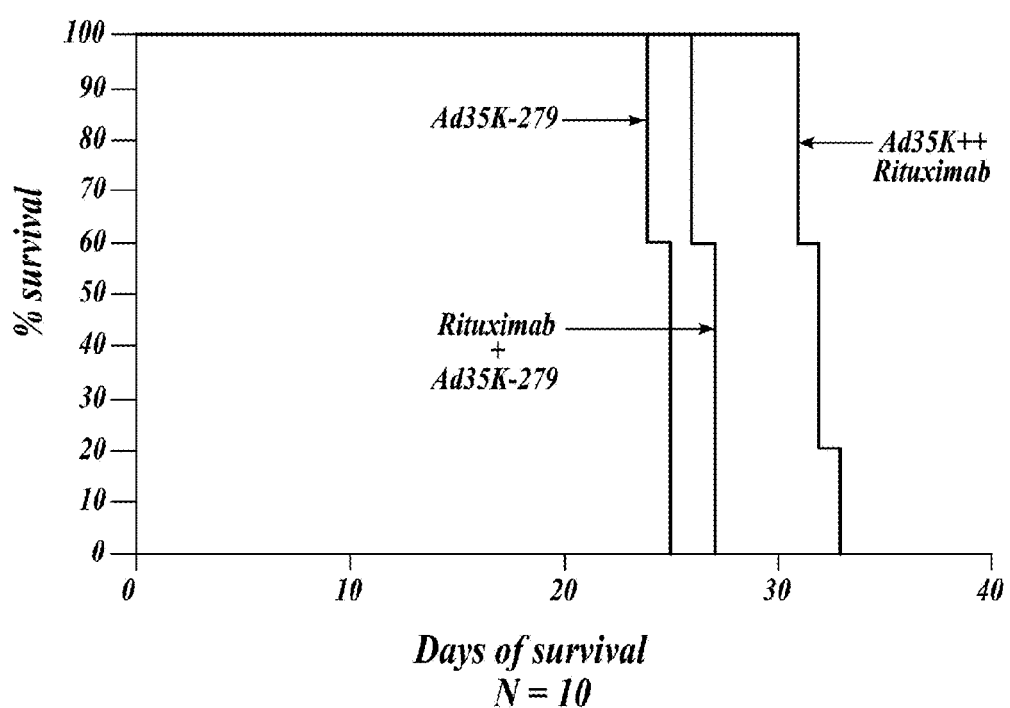
FIGS. 5C and 5D graphically illustrate the results of survival studies of xenograft lymphoma mice (receiving Farage cells) treated with a first injection of either Ad35K-279 (ablated for binding to CD46) or Ad35K++ (double mutant containing Asp207Gly and Thr245Ala with enhanced binding to CD46), followed by a second injection of either PBS or rituximab (anti-CD20 mAb), as described in Example 3.
Figure 5D:
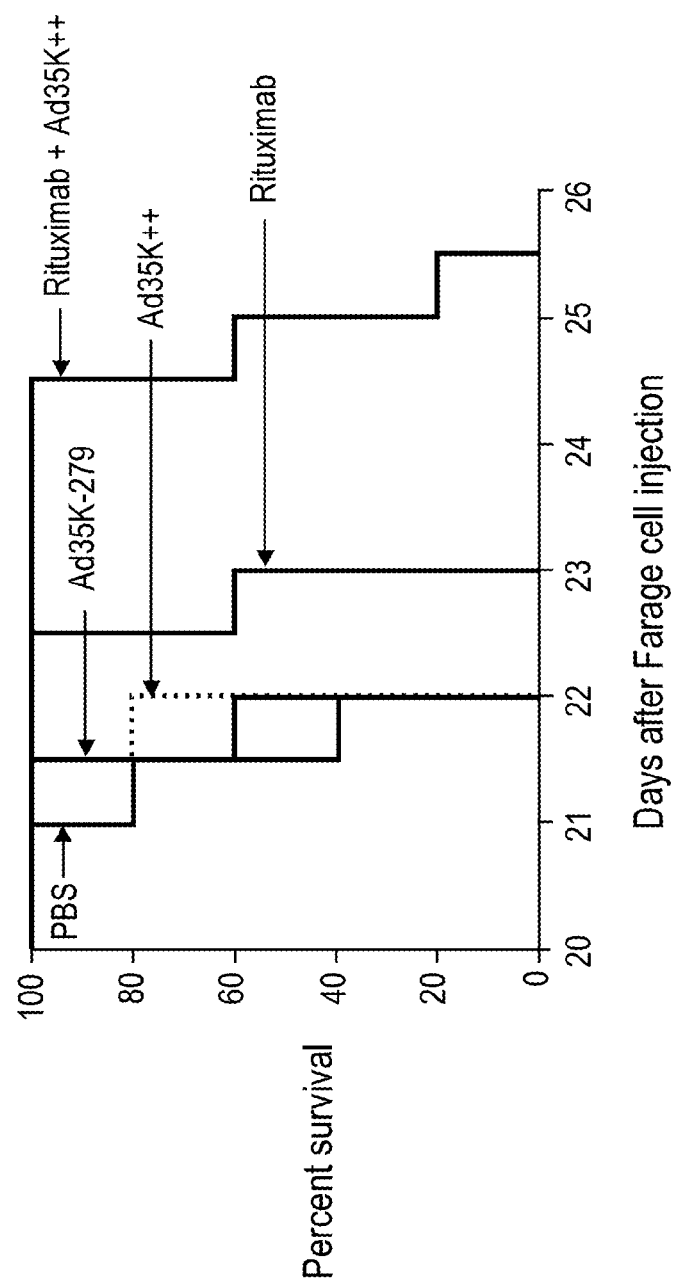

To establish a second lymphoma xenograft model, $5 \times 10^6$ human Farage cells (CD20+) were injected intravenously into CB17 SCID/beige immuno-deficient mice. Onset of morbidity was observed 23 days post injection with tumor lesions detected in the spleen and liver. To evaluate the efficacy of Ad35K++ as a therapeutic in this model, 21 days after injection of Farage cells, mice received either 50 µg of Ad35K++ mutant protein (increased CD46 binding) or 50 µg of Ad35K-279 mutant (ablated for CD46 binding). Ten hours later, treatment of either PBS or 50 µg of rituximab was injected via the tail vein. As shown in FIGS. 5C and 5D, there was a significant increase in survival when mice were pre-treated with Ad35K++ before rituximab treatment as compared to rituximab only or mock treatment (p<0.001). There was no difference in survival between the control (Ad35K-279) and Ad35K++ only groups (FIG. 5D). As in the context of the Raji cell xenograft model, treatment of rituximab alone did not exert a therapeutic effect in vivo. (p=0.145).

Figure 5E:
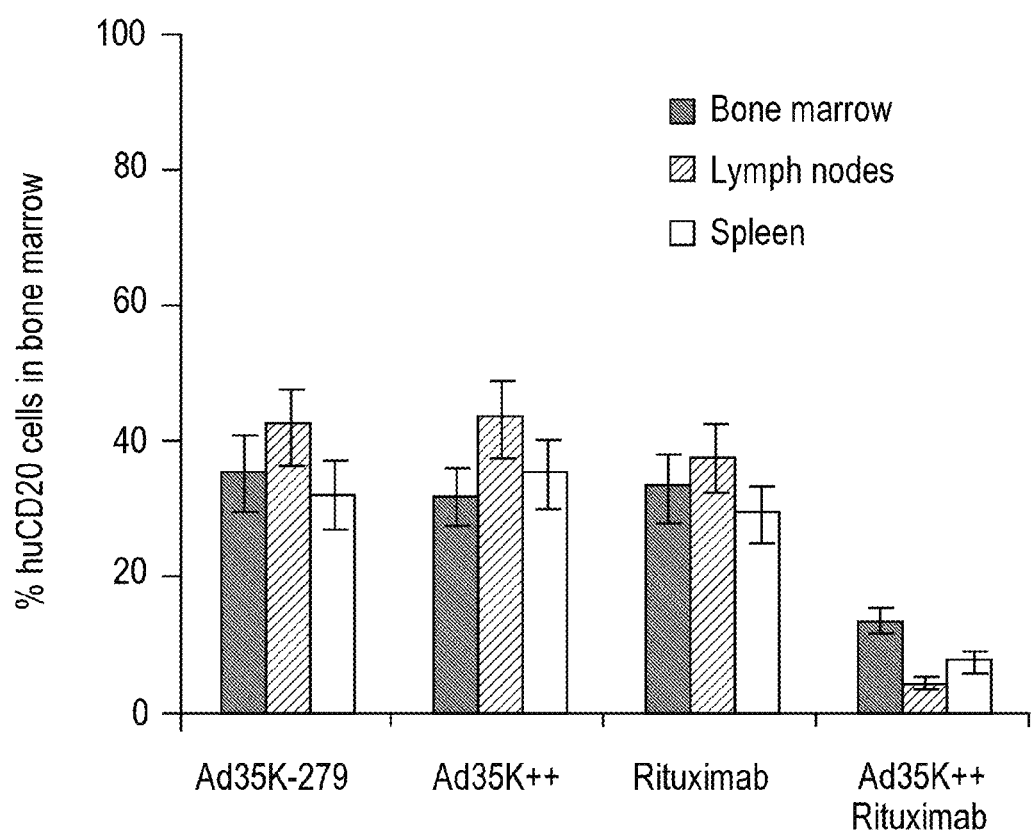
FIG. 5E graphically illustrates the percentage of human CD20 positive cells in bone marrow, lymph nodes, or spleen in a xenograft mouse model injected with human Farage cells, pre-treated with Ad35K-279 or Ad35K++, then sacrificed 12 hours after administration of either PBS or rituximab, as measured by flow cytometry, as described in Example 3.

FIG. 5E graphically illustrates the percentage of human CD20 positive cells in bone marrow, mesenteric lymph nodes, or spleen in treated mice sacrificed 12 hours after administration of either PBS or rituximab, as measured by flow cytometry. The combination of Ad35K++ and rituximab resulted in a significant decrease in human CD20 positive cells in the bone marrow, lymph nodes and spleen (P<0.03), n=7.

In summary, the results in this Example demonstrate that pre-treatment with Ad35K++ mutant protein followed by rituximab increases tumor cell killing as compared to treatments with rituximab alone.

The fact that Ad35K++ drastically increased the anti-tumor efficacy in immunodeficient mice indicates that immune cells are not involved in rituximab/complement mediated tumor killing. This result demonstrates that Ad35K++/rituximab treatment is effective in immuno-suppressed mice, which is predictive for the efficacy of an anti-tumor effect in immuno-suppressed patients, which avoids the potential issue regarding development of neutralizing antibodies against the viral Ad35K++ protein, allowing for repeated cycles of treatment. Further in this regard, it has been shown in animal models that repeated injection of oncolytic adenovirus vectors upon immuno-suppression is effective and increases the anti-tumor efficacy of virotherapy (Thomas, M. A., et al., *Mol. Ther.* 16:1665-1673 (2008)).

Dose responses will be generated in the in the Raji-cell xenograft lymphoma model using CB17 SCID-beige mice. The therapeutic effect of mutant Ad35K++/rituximab administration will be further analyzed by quantifying human lymphoma cells in the peripheral blood and lymph nodes of xenograft CB17 SCID-beige mice.

It will be appreciated by those of skill in the art that the methods described herein to administer Ad35K++ to sensitize cells to CDC are not limited to CD20/rituximab treatments, and may be applied to sensitize cells to CDC in the context of other anti-cancer mAbs. For example, Ad35K++ may be used to sensitize tumor cells expressing CD52 to Alemtuzumab (Campath), an anti-CD52 mAb, for treatment of chronic lymphocytic leukemia. In another example, Ad35K++ may be used to sensitize tumor cells expressing CD33 to Gemtuzumab, an anti-CD33 mAb, for treatment of acute myelocytic leukemia.

EXAMPLE 4

This example describes analysis of the immunogenicity of the recombinant wild-type Ad35 fiber knob protein (SEQ ID NO:3) and mutant Ad35K++ (Asp207Gly and Thr245Ala; SEQ ID NO:5) in human cancer patients.

Materials and Methods

The serum of 20 human cancer patients was analyzed for the presence of antibodies that reacted with either recombinant Ad35K (wild-type) protein or recombinant Ad35K++ (Asp207Gly and Thr245Ala) mutant protein.

Human Study

The serum of 20 cancer patients was tested for the presence of antibodies that reacted with either recombinant Ad35K (wild-type) protein or recombinant Ad35K++ mutant protein as follows. Recombinant (non-denatured) Ad5 hexon, Ad5 fiber knob, Ad35K, and Ad35K++ as well as denatured Ad5 virions were separated by PAG electrophoresis and the blotted proteins were incubated with human serum. The presence of Ad-specific antibodies in serum was then detected by anti-human IgG-HRP.

Results

Table 3 summarizes the results of Western blot analysis of the experiment carried out to measure the presence of Ad-specific antibodies in human serum.

TABLE 3

Immuno-Reactivity of Ad35 fiber knobs With Serum From Cancer Patients.

|  | Ad5 virus | Ad5 hexon | Ad5K | Ad35K | Ad35K++ |
|---|---|---|---|---|---|
| Coomassie Stain | ++ | ++ | +++ | +++ | +++ |
| Western (serum from human cancer patients) | ++ | ++ | + | − | − |

As shown above in Table 3, no antibodies were detected that reacted with either Ad35K or Ad35K++ in the serum of the 20 cancer patients tested. On the other hand, the majority of human serum samples tested did contain antibodies specific to Ad5 hexon, Ad5 fiber knob, and Ad5 penton. This result was not surprising. While the vast majority of humans have neutralizing antibodies against Ad5 (Sumida, S. M., et al., *Journal of Immunology* 174:7179-7185 (2005)), less than 10% of humans have neutralizing antibodies against Ad35 (Nwanegbo, E., et al., *Clin. Diagn. Lab. Immunol.* 11:351-357 (2004); Abbink, P., et al., *Journal of Virology* 81:4654-4663 (2007); Reddy, P. S., et al., *Virology* 311:384-393 (2003).

EXAMPLE 5

This example describes analysis of the immunogenicity of the wild type Ad35 fiber knob protein (SEQ ID NO:3) and recombinant mutant Ad35K++ (Asp207Gly and Thr245Ala; SEQ ID NO:5) in immunocompetent mice by repeated injections of the recombinant protein and analysis of the presence of anti-Ad35K++ antibodies after injection.

Mouse Studies:

For immunization studies with recombinant Ad35 fiber knob proteins, five immunocompetent CD46 transgenic C57B1/6 mice (line MCP8B) (Marie, J. C., et al., *Nature Immunology* 3:659-666 (2002)) received either a single intravenous injection of 50 μg of recombinant Ad35K++ protein or Ad35K protein at day 0 (therapeutic regimen) or a total of three subcutaneous injections of 5 μg recombinant Ad35K++ protein or Ad35K protein at day 0, 3, and 6 (vaccination regimen). Serum was collected from the mice four weeks later and analyzed for Ad-specific antibodies by Western blot, as described in Example 2. All experiments involving animals were conducted in accordance with the institutional guidelines set forth by the University of Washington.

Results

TABLE 4 summarizes the results of Western blot analysis of the experiment carried out to measure the presence of Ad35K or Ad35K++ specific antibodies in mouse serum after a single intravenous injection or after a series of three subcutaneous injections of Ad35K or Ad35K++.

TABLE 4

Immuno-Reactivity of Ad35 fiber knob Proteins after Injection Into Mice

|  | Ad35K | Ad35K++ | Ad35 virus |
|---|---|---|---|
| Coomassie Stain | ++ | ++ | + |
| Western (serum after vaccination regimen: series of three subcutaneous injections) | + | ++ | − |
| Western (serum after therapeutic regimen: single I.V. administration) | − | − | − |

As shown above in TABLE 4, antibodies were detected in serum that reacted with Ad35K++ and, to a lesser degree, with Ad35K in mice that received three subcutaneous injections of the recombinant proteins; however, no detectable antibodies were observed when recombinant Ad35K++ or Ad35K proteins were injected intravenously. This is likely due to inefficient uptake of the recombinant proteins (Ad35K++ or Ad35K) by antigen-presenting cells after intravenous injection.

TABLE 5 shows the Hematological parameters after Ad35K++ injection. Male and female CD46 transgenic mice (strain MCP8B) were intravenously injected with 50 mg Ad35K++ and blood samples were analyzed 16 and 48 hours later. Shown is the average of two measurements in comparison to mock-treated animals. In mice the homologue of CD46 is expressed only in the testis. So, transgenic mice that express huCD46 in a pattern and at levels similar to humans may be a better model for safety studies. The same dose of Ad35K++ that was used in the therapy studies was intravenously injected into huCD46 transgenic, immunocompetent C57B1/6 mice (strain MCP-8B). Analyses of blood cell counts and other hematological parameters at 6 and 48 hours after Ad35K++ injection did not show abnormalities (TABLE 5). At necropsy (day 14p.i.), no pathological or histological changes were found in all organs analyzed (brain, lung, heart, liver, kidney, intestines, bone marrow).

TABLE 5

Hematological parameters after Ad35K++ injection

|  | Mock | | Ad35K++ (16 h p.i.) | | Ad35K++ (48 h p.i.) | |
|---|---|---|---|---|---|---|
|  | Male | Female | Male | Female | Male | Female |
| White Blood Cells (K/ml) | 11.98 | 10.62 | 10.61 | 12.7 | 11.92 | 10.76 |
| Neutrophils (%) | 19.91 | 23.15 | 22.56 | 30.1 | 22.27 | 22.21 |
| Lymphocytes (%) | 75.93 | 69.88 | 68.46 | 62.28 | 68.69 | 72.12 |
| Monocytes (%) | 6.18 | 6.49 | 7.46 | 6.14 | 6.44 | 5.33 |
| Eosinophils (%) | 0.92 | 0.39 | 1.3 | 1.2 | 2.17 | 0.25 |
| Basophils (%) | 0.06 | 0.09 | 0.23 | 0.28 | 0.43 | 0.1 |

TABLE 5-continued

Hematological parameters after Ad35K++ injection

| | Mock | | Ad35K++ (16 h p.i.) | | Ad35K++ (48 h p.i.) | |
|---|---|---|---|---|---|---|
| | Male | Female | Male | Female | Male | Female |
| Red Blood Cells (M/ml) | 9.52 | 9.31 | 9.28 | 8.81 | 9.23 | 9.52 |
| Platelets (K/ml) | 721 | 781 | 605 | 586 | 539 | 843 |
| Hemoglobin (g/dL) | 16.2 | 16 | 15.1 | 14.7 | 15.3 | 15.2 |
| Sodium (mEq/L) | 156 | 152 | 152 | 154 | 152 | 154 |
| Potassium (mEq/L) | 8.2 | 6.8 | 7.2 | 7.6 | 8.2 | 8.2 |
| Chloride (mEq/L) | 120 | 120 | 118 | 120 | 116 | 120 |
| Carbon dioxide(mEq/L) | 18 | 20 | 18 | 22 | 20 | 16 |
| Ion Gap | 18 | 12 | 16 | 12 | 16 | 18 |
| Glucose (mg/dL) | 110 | 168 | 128 | 158 | 142 | 120 |
| Urea Nitrogen (mg/dL) | 18 | 18 | 20 | 18 | 14 | 16 |
| Creatinine (mg/dL) | 0.2 | <0.1 | <0.1 | <0.1 | 0.2 | 0.2 |
| Protein (Total) (g/dL) | 5 | 4.8 | 5 | 5 | 4.8 | 4.6 |
| Albumin (g/dL) | <1.0 | <1.0 | <1.0 | <1.0 | <1.0 | <1.0 |
| Bilirubin (Total) (mg/dL) | <0.1 | 0.2 | 0.4 | 0.6 | 0.4 | <0.1 |
| Calcium (mg/dL) | 10.8 | 10.8 | 10.8 | 10.8 | 10.6 | 10.4 |
| GOT (U/L) | 356 | 182 | 178 | 222 | 242 | 382 |
| Alk. phosphatase (U/L) | 172 | 196 | 160 | 198 | 148 | 184 |
| GPT (U/L | 74 | 52 | 52 | 58 | 50 | 48 |

Figure 6:
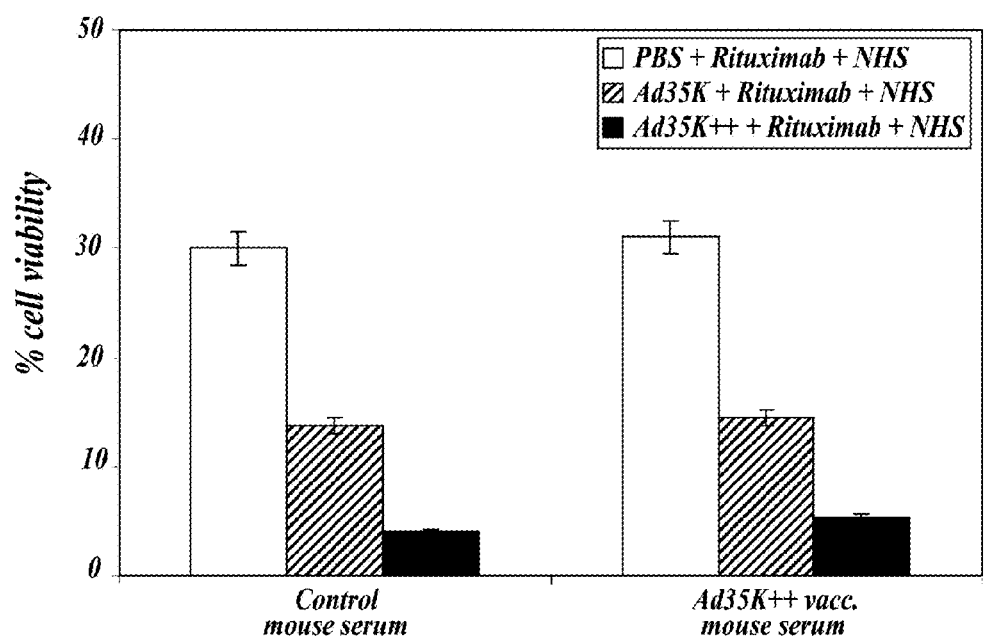
FIG. 6 graphically illustrates the enhanced CDC mediated cell killing effect observed after pre-incubation with recombinant fiber knob protein Ad35K (wild type) or Ad35K++ (double mutant containing Asp207Gly and Thr245Ala with enhanced binding to CD46), followed by rituximab treatment in the presence (Ad35K++ vaccinated mouse serum) or absence (control mouse serum) of antibodies reactive to Ad35K++, demonstrating the lack of inhibitory effect by the anti-Ad35K++ antibodies on CDC; wherein cell viability levels are expressed as a percentage of the mean viability of untreated cells (N>6), as described in Example 4.

Additionally, in order to determine the effect of the presence of anti-Ad35K++ antibodies on cell killing in the assay described in Example 2, the serum from vaccinated or naïve mice was used together with Ad35K++ in rituximab-mediated CDC assays. As shown in FIG. 6, regardless of the presence of anti-Ad35K++ antibodies, the same stimulating effect of Ad35K++ in sensitizing cells to CDC mediated cell killing was observed. While not wishing to be bound to any particular theory, it is believed that this may be due to the fact that the Ad35K++ interaction with CD46 is of very high affinity and cannot be disrupted by polyclonal anti-Ad35K++ antibodies that developed in the subcutaneously Ad35K++ injected mice.

EXAMPLE 6

This example describes methods for reducing the immunogenicity of the modified Ad35K fiber knob proteins to ensure the safety and efficacy of repeat administrations in a mammalian subject.

Rationale

As noted above in Example 5, a difference was observed between the levels of antibodies that were induced with Ad35K++ versus Ad35K, as shown in TABLE 4. While not wishing to be bound by any particular theory, it is believed that small changes within the Ad35K fiber knob protein lead to loss or decrease of immunogenicity. It has been reported previously that epitopes within the Ad5 fiber knob are conformational (Gahery-Segard, H., et al., *Journal of Virology* 72:2388-2397 (1998)). It has also been suggested that conformational changes caused by the variations of exposed surface loops in the Ad fiber knob might be an efficient way for the virus to escape antibody neutralization (Pache, L., et al., *Journal of Virology* 82:7923-7931 (2008)). Therefore, the immunogenicity of the recombinant Ad35 mutant proteins may be reduced using routine methods known in the art, as described in detail below.

Epitope Modeling

The antigenicity/hydrophilicity profile of Ad35K++ is modeled using the MacVector 6.5.3 software package, based on the Kyte-Doolittle and Hopp-Wood algorithms (Kyte and Doolittle, 1982; Hopp and Woods, 1981). The MHC Class I and II binding regions have been predicted using ProPred-I and -II (Singh, H., and Raghava, G. P. S., "ProPred1: Prediction of Promiscuous MHC Class-I Binding Sites," *Bioinformatics* 19:1009-1014 (2003); Singh, H., and Raghava, G. P. S., "ProPred: Prediction of HLA-DR Binding Sites," *Bioinformatics* 17:1236-37 (2001)).

Corresponding mutations are introduced into the protein using a commercially available site-directed mutagenesis PCR kit as described elsewhere (Wang et al., *Journal of Virology* 82:10567-10579 (2008)).

Generation of Low Immunogenic Mutants

Random mutations are introduced into the nucleic acid encoding AD35K++ (SEQ ID NO:3, encoded by SEQ ID NO:4) by creating a random mutant library as described in Example 1. Resulting blots are selected for preservation of CD46 binding sites and low reactivity to anti-Ad35K++ antibodies. Specifically, blots were incubated with serum from subjects known to have Ad35K neutralizing antibodies. Binding of neutralizing antibodies are visualized with anti-human FC HRP. Colonies not bound to neutralizing antibodies are selected. Purified fiber knob proteins from selected colonies are then analyzed for the ability to bind CD46. The recombinant Ad35K mutant proteins identified in the assay are then administered to lymphoma cells in conjunction with rituximab as described in Examples 2 and 3, and efficacy of the mutants will be assessed in the presence of patient serum. The reduced immunogenicity of the selected mutant Ad35K recombinants is confirmed by repeated subcutaneous injections of the mutant proteins in immunocompetent mice as described in Example 5.

EXAMPLE 7

This example describes methods for enhancing the therapeutic potential of recombinant mutant Ad35K by modification to include polyethylene glycol chains.

Methods

Polyethylene glycol chains are added to recombinant modified Ad35K proteins, such as Ad35K++, by mixing 100 μg of purified recombinant protein with 10 mg/ml of either methoxypolyethylene glycol-succinimidyl propionate (mPEG SPA, MW 5000; Nektar Therapeutics, Huntsville, Ala.) or Sunbright ME-050HC (MW 5000; NOF, Tokyo, Japan) in 0.1 mM potassium phosphate buffer (10 mM K2PO4, 150 mM NaCl, 1 mM MgCl$_2$, 5% [w/v] sucrose; pH 7.8). After incubation for one hour at room temperature, the reaction is quenched with lysine. Excess lysine and nonreactive PEG molecules are removed by gel-filtration chromatography (Sephadex G50; GE Healthcare Bio-Sciences, Piscataway, N.J.). Resulting PEGylated Ad35K++ are assessed for CD46 binding and the capacity to enhance CDC induced by rituximab, as described in Example 2. Furthermore, the in vivo efficacy of therapy involving PEGylated Ad35K++/rituximab is assessed by survival studies and by quantifying human lymphoma cells in the peripheral blood and lymph nodes of xenograft CB17 SCID-beige mice, as described in Example 3.

EXAMPLE 8

This Example describes the effect of Ad35K++ on peripheral blood mononuclear cells (PBMCs).

A. The Effect of Pre-Incubation of Ad35K++ on Normal Human PBMC, CD20 Positive Cells Sorted from Normal Human PBMC, and a Series of Primary Human Cell Cultures.

Methods

Human PBMCs pooled from three healthy donors were sorted for CD20 positive cells using FACS. The CD20 positive cells were cultured for three days. A total of 1×10$^5$ CD20 positive cells, or PBMCs (unsorted, cultured for three days) were treated with Ad35K++ (25 µg/ml), followed by rituximab (15 µg/ml) and NHS (25% final concentration) eight hours later. Four hours after adding NHS, viable cells were counted based on trypan blue exclusion. Cell viability of PBS-treated cells was taken as 100%.

In vitro studies were also carried out on a series of primary human cell cultures, including vascular endothelial cells, cornea epithelial cells, ovarian surface epithelial cells, and foreskin fibroblasts. A total of 1×10$^5$ cells were treated with Ad35K++ (25 µg/ml), followed by rituximab (15 µg/ml) and NHS (20% final concentration) eight hours later. Four hours after adding NHS, cells were washed and viability was measured by the WST-1 cell proliferation assay (commercially available from Roche, Cat No. 11 644 807 001) 30 minutes after adding the staining reagent. Cell viability of PBS-treated cells was taken as 100%.

Results

Figure 7A:
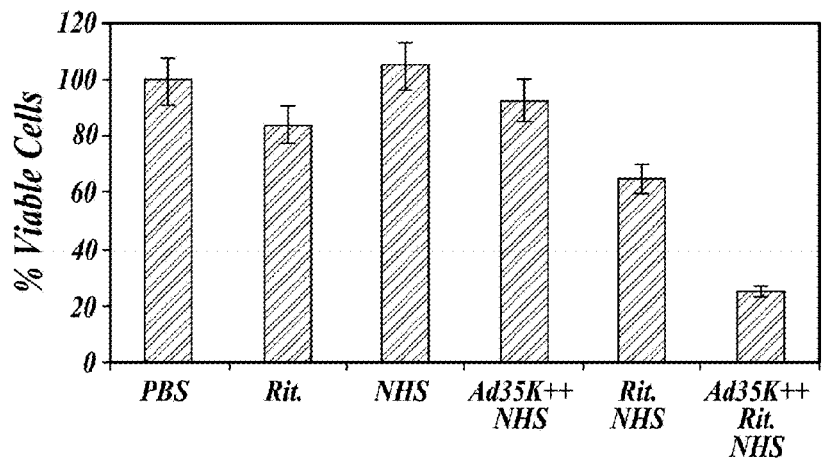
FIG. 7A graphically illustrates the percent viable CD20 positive cells cultured from human peripheral blood mononuclear cells (PBMCs) (from healthy donors) after incubation with phosphate buffered saline (PBS), rituximab only, normal human serum (NHS), Ad35K++ pretreatment plus NHS, Rituximab plus NHS, or Ad35K++ pretreatment plus Rituximab plus NHS, as described in Example 8.

FIG. 7A graphically illustrates the percent viable CD20 positive cells cultured from human PBMCs after incubation with phosphate buffered saline (PBS), Rituximab only, normal human serum (NHS), Ad35K++ pretreatment plus NHS, Rituximab plus NHS, or Ad35K++ pretreatment plus Rituximab plus NHS. As shown in FIG. 7A, rituximab killed 15% of the cells, and addition of NHS to rituximab increased the percentage of dead CD20+ cells to 35% when compared to PBS treated controls (p<0.05). As further shown in FIG. 7A, pre-incubation with Ad35K++ resulted in rituximab/NHS-mediated killing of approximately 75% of the primary human CD20+ cells. As further shown in FIG. 7A, there was no change in cell viability for cells incubated with NHS alone. Ad35K++ pretreatment alone did not kill CD20 positive PBMCs (data not shown). As shown in FIG. 7A, the combination of Ad35K++ pretreatment and NHS resulted in a non-significant decline in cell viability (p=0.12).

Figure 7B:
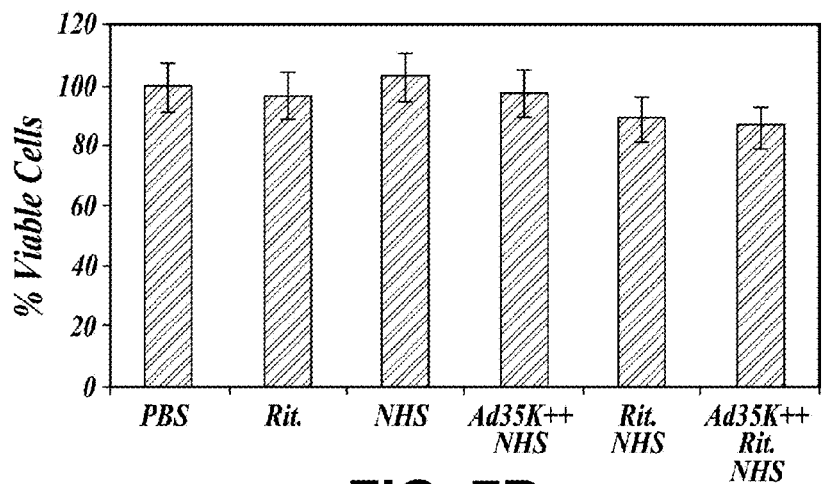
FIG. 7B graphically illustrates the percent viable human PBMCs cultured with phosphate buffered saline (PBS), rituximab only, normal human serum (NHS), Ad35K++ pretreatment plus NHS, rituximab plus NHS, or Ad35K++ pretreatment plus rituximab plus NHS, as described in Example 8.

FIG. 7B graphically illustrates the percent viable human PBMCs cultured with phosphate buffered saline (PBS), Rituximab only, normal human serum (NHS), Ad35K++ pretreatment plus NHS, Rituximab plus NHS, or Ad35K++ pretreatment plus Rituximab plus NHS. As shown in FIG. 7B, no significant decrease in cell viability was observed after incubation with rituximab/NHS and Ad35K++/rituximab/NHS.

Figure 7C:
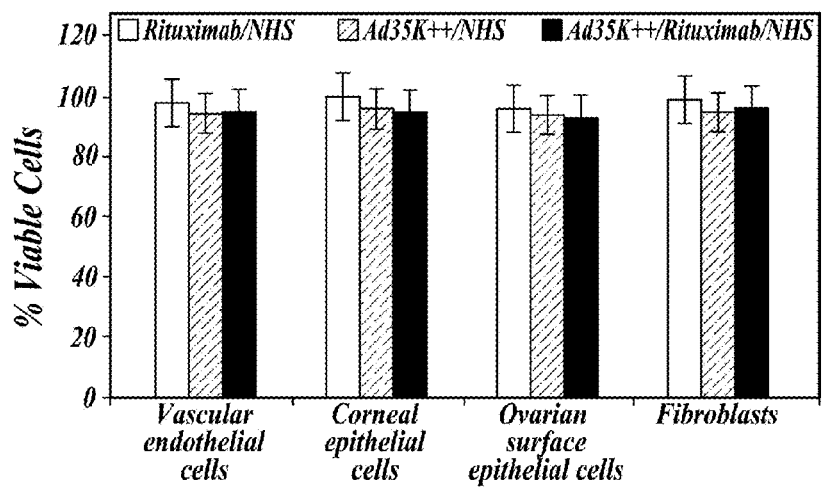
FIG. 7C graphically illustrates the percentage of cell viability for primary human vascular endothelial cells, corneal epithelial cells, ovarian epithelial cells or foreskin fibroblast cells incubated with Ad35K++, rituximab, or NHS alone as compared to PBS treated control cells (N=5), as described in Example 8.

As shown in FIG. 7C, there was no significant difference in cell viability for vascular endothelial cells, corneal epithelial cells, ovarian epithelial cells or foreskin fibroblast cells incubated with Ad35K++, rituximab, or NHS alone as compared to PBS treated control cells (N=5). Notably, Ad35K++/NHS and Ad35K++/rituximab/NHS resulted in an insignificant decline of cell viability, likely due to the fact that these cell types do not express CD20. Similar data was obtained after incubation of CD20 negative transformed cell lines such as HeLa (cervical cancer), Mole (erythroleukemia), BT474 (breast cancer), SK-BR-3 (breast cancer), A549 (lung cancer), and HT-29 (colon cancer) cells with rituximab, Ad35K++/NHS, or Ad35K/rituximab/NHS (data not shown).

In summary, the in vitro studies show that Ad35K++ pre-incubation of primary CD20 positive PBMC, primary B-CLL cells and lymphoma cell lines increase the cytotoxicity of rituximab (anti-Cd20 mAb). In contrast, no significant Ad35K++ mediated complement mediated killing of primary CD20 negative cells was observed.

B. CD20 and CD46 Levels of Normal PBMC, Primary Lymphoma Cells from B-CLL Patients and Raji Cells.

CD20 and CD46 levels of normal PBMC, primary lymphoma cells from B-CLL patients and Raji cells were determined using Flow cytometry. Flow cytometry was performed using PE-conjugated mouse anti-human CD20 mAbs (clone 2H7, BD Pharmingen Franklin Lakes, N.J.) and FITC-conjugated mouse anti-human CD46 mAbs (clone E4.3, Santa Cruz Biotechnology, Santa Cruz, Calif.). The results are shown below in TABLE 6.

TABLE 6

Results of Flow Cytometry Analysis

| Cell Type | % CD20+ Positive (mean fluorescence intensity) | % CD46+ Positive (mean fluorescence intensity) |
|---|---|---|
| PBMC | 9.1% | 98.1% |
| CLL-3 | 49.3% | 80% |
| CLL-4 | 53.1% | 71.5% |
| CLL-pII | 85% | 85.6% |
| Raji | 99.8% | 99.5% |

As shown above in TABLE 6, flow cytometry studies showed high and relatively uniform levels of CD46 on primary chronic lymphocytic leukemia (B-CLL) cells and test lymphoma cells. As described above in Example 2, pre-incubation of B-CLL cells with Ad35K++ significantly increased the efficacy of rituximab/NHS treatment. It is notable that the cell sample that was most resistant to Ad35K++/rituximab killing was CCL-3 (see FIG. 4B) which also had the lowest percentage of CD20-positive cells and the lowest CD20 levels as compared to other primary cells from other B-CLL patients.

C. Ad35K++ Mediated Removal of CD46 from the Surface of Normal Human PBMCs.

Methods: Human PBMCs pooled from three healthy donors, as described above, were incubated with either phosphate buffered saline (PBS), or Ad35K++ (10 ug/ml) for 12 hours. CD46 expression was then analyzed via FACS using PE-labelled anti-CD46 antibodies.

Results: It was determined that the mean fluorescence intensity values for PBMCs incubated in PBS were 563 (+/−23). The mean fluorescence intensity values for PBMCs incubated in Ad35K++ were significantly reduced at 286 (+/−16). Therefore, these results demonstrate that incubation of PBMCs with Ad35K++ causes a decrease in surface CD46 levels.

Discussion: As described above, CD20 is expressed on mature human B cells. This example shows that Rituximab/ NHS kills primary CD20 positive PBMC, and this cytolysis is enhanced by pre-incubation of the cells with Ad35K++. It is important to consider this side effect in clinical settings. On the other hand, the enhancing effect of Ad35K++ on rituximab killing of primary B cells has practical implications, as Rituximab is currently used in patients to treat autoimmune diseases (Owczarczyk, K., et al. *Ann Rheum Dis.* 67:1648- 1649 (2008); Petereit, H., et al. *Mult. Scler.* 15:189-192 (2009)), and is also used in patients to treat acute antibody- mediated rejection of transplants (Yang, Y. W., et al., *Exp Clin Transplant* 6:211-214 (2008).

However, studies on PBMCs and CD20 negative primary human cells demonstrated that incubation with Ad35K++/ NHS caused only minimal toxicity, even though it was shown that Ad35K++ treatment of PBMCs triggered the removal of CD46 from the cell surface. Notably, human PBMCs, in contrast to Raji cells, express high levels of two other membrane complement regulatory proteins, CD55 and CD59, which can protect them from CDC. Furthermore, the density of CD46 on primary cells is at least one order of magnitude lower than on lymphoma cells, as shown above in TABLE 6. As further described in this Example, subsequent to incubation with Ad35K++, the mean CD46 fluorescence intensity decreased only 1.97 (+/−0.21)-fold on PBMCs, while it declined by 7.54 (+/−0.35)-fold on Raji cells. It is also noteworthy that the in vitro assays described in this Example used an Ad35K++ concentration (25 ug/ml=5×108 Ad35K++ fiber knob molecules per cell), an amount that is unlikely to be achieved after intravenous Ad35K++ injection in vivo. [Note 0.025 ug/ml Ad35K++ equals $4.63 \times 10^5$ trimeric fiber knob molecules/cell or 9.3 trimeric fiber knob molecules per CD46 molecule.]

EXAMPLE 9

This Example demonstrates that Ad35K++ treatment improves the anti-tumor efficacy of rituximab in vivo in a xenograft lymphoma model.

Methods:

1. Experimental Scheme #1:

To establish a xenograft lymphoma model, $3 \times 10^6$ human lymphoma Raji cells (CD20 positive) were injected into immunodeficient CB17-SCID/beige mice via tail vein injection. Fourteen days later, when control mice developed the first clinical symptoms, animals were intravenously injected with 50 ug (2.5 mg/kg) of Ad35K-279 (mutant negative control) or 50 ug (2.5 mg/kg) Ad35K++. Rituximab (50 ug) or PBS was given intravenously 10 hours later via tail vein. In Experimental Scheme #1, mice were sacrificed 12 hours later and tissues were analyzed for human CD20 positive cells to determine the effect of Ad35K-279, Ad35K++, rituximab and Ad35K++/rituximab on killing of Raji cells in vivo based on the percentage of human CD20 positive cells in the bone marrow and lymph nodes.

Measurement of Raji (CD20 Positive Cells):

At 14 days after intravenous Raji cell injection, mice were sacrificed, femurs, spleens, and mesenteric lymph nodes were harvested and peripheral white blood cells, splenocytes, cells from mesenteric lymph nodes, and bone marrow cells were analyzed for the presence of Raji cells by flow cytometry for human CD20 and Immunofluorescence microscopy. Lymph nodes and spleen sections were analyzed by immunofluorescence microscopy with FITC labeled anti-CD20 antibodies. For bone sections, the "Klear Mouse DAB detection kit" (Golden Bridge International Inc., Mukilteo Wash.) was used. The specificity of staining was confirmed by staining with corresponding isotype matched antibodies (negative control), and antibodies specific to a human mitochondrial marker (positive control).

Results

At 14 days after intravenous Raji cell injection, it was determined that human CD20 positive Raji cells were predominantly found in the bone marrow and lymph nodes and were very sparse in the spleen (data not shown). The percentage of human CD20 positive cells increased from 20 (+/−4) % (bone marrow) and 5 (+/−1.2) % (lymph nodes) at day 10 after Raji cell injection to 75 (+/−6) % and 42 (+/−4) %, respectively, at day 14 post injection. At day 15 or 16 after Raji cell injection, mice developed hind leg paralysis, a symptom that was later used as an endpoint in Kaplan-Meier survival studies.

Figure 8A:
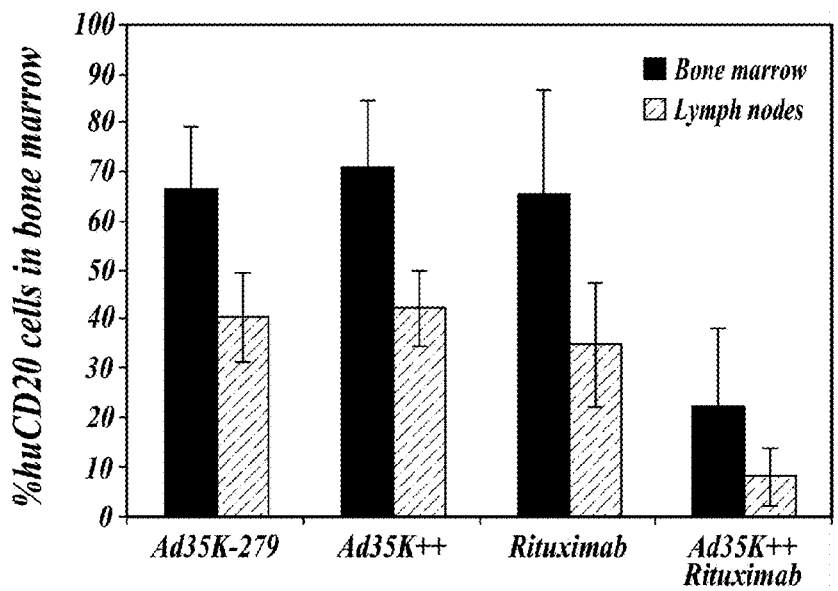
FIG. 8A graphically illustrates the percentage of human CD20 positive cells in bone marrow or mesenteric lymph nodes in a xenograft mouse model injected with human Raji cells, pre-treated with Ad35K-279 or Ad35K++, then sacrificed 12 hours after administration of either PBS or rituximab, as measured by flow cytometry (N=5), as described in Example 9.

FIG. 8A graphically illustrates the percentage of human CD20 positive cells in bone marrow or mesenteric lymph nodes in treated mice sacrificed 12 hours after administration of either PBS or rituximab, as measured by flow cytometry (N=5). As shown in FIG. 8A, compared to Ad35K-279- treated control mice, no significant decrease in human CD20 positive cell numbers was observed when Ad35K++ or rituximab were injected alone. In contrast, the combination of Ad35K++ and rituximab resulted in a significant decrease in human CD20 positive cells in both the bone marrow and lymph nodes (p<0.03).

Figure 8B:
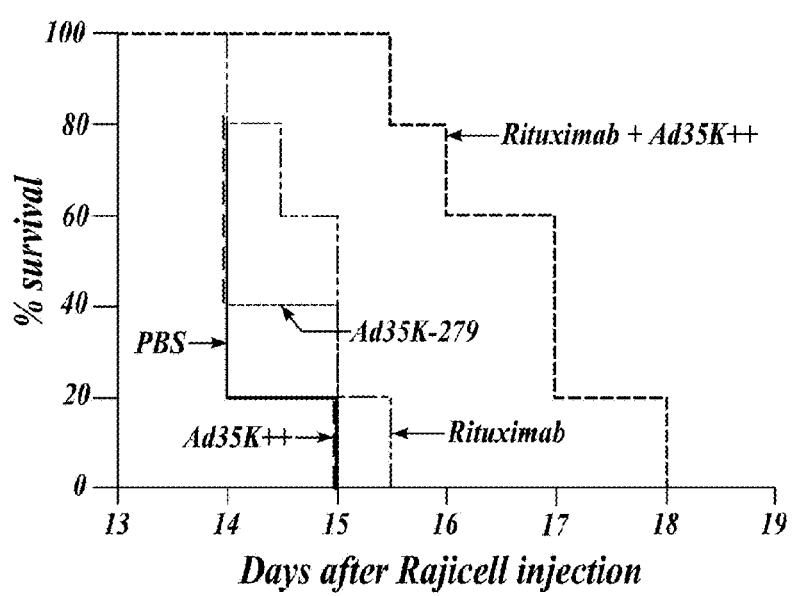
FIG. 8B is a Kaplan-Meier survival graph of the xenograft model mice treated in accordance with Experimental Treatment Scheme #1 (N=10), which involved injecting Raji cells into the mice, pretreating the mice with Ad35K-279 or Ad35K++, followed by administration of PBS or rituximab, demonstrating a remarkable increase in survival when the mice were treated with Ad35K++/Rituximab as compared to Rituximab only or Ad35K-279 control, as described in Example 9.

FIG. 8B illustrates a Kaplan-Meier survival of the mice treated in accordance with Experimental Scheme #1 (N=10). In accordance with the findings demonstrated in FIG. 8A, there was a remarkable increase in survival when the mice were treated with Ad35K++/Rituximab as compared to Rituximab only or Ad35K-279 control. The differences in survival were significant (rituximab versus Ad35K++/rituximab: p=0.0050); (Ad35K-279 versus Ad35K++/rituximab: p=0.0016). There was no significant difference in survival between the controls (PBS or Ad35K-279) and Ad35K++ only groups.

It is noted that Rituximab at a dose of 2.5 mg/kg alone did not exert a significant therapeutic effect in vivo (Ad35K-279 versus Rituximab: p=0.1289). A rituximab dose-response study was carried out as follows. Mice were injected with Raji cells as described for Experimental Scheme #1. Two weeks later, PBS or different doses of rituximab (50 ug, 100 ug and 250 ug per mouse, in a total volume of 200 ul) were intravenously administered. Survival (onset of hind leg paralysis) was monitored (N=7). It was determined that an increase of Rituximab to a dose of 12.5 mg/kg resulted in therapeutic efficacy (data not shown).

2. Experimental Scheme #2:

A second experimental scheme was tested and found to enable long-term survival of mice transplanted with Raji lymphoma cells. The second experimental scheme was carried out as follows:

To establish a xenograft lymphoma model, $3 \times 10^6$ human lymphoma Raji cells (CD20 positive) were injected into Immunodeficient CB17-SCID/beige mice via tail vein injection. Thirteen days later, the first treatment cycle was started with two intravenous injections of 50 µg (2.5 mg/kg) Ad35K++ 6 hours apart. Six hours after the second Ad35K++ injection, mice received an intravenous injection of Rituximab (50 µg). A second treatment cycle was started 36 hours later, which was the same as the first treatment cycle (i.e., two intravenous injections of 50 µg (2.5 mg/kg) Ad35K++ 6 hours apart. Six hours after the second Ad35K++ injection, mice received an intravenous injection of Rituximab (50 µg). Onset of hind leg paralysis served as an endpoint in survival studies.

Results

Figure 8C:
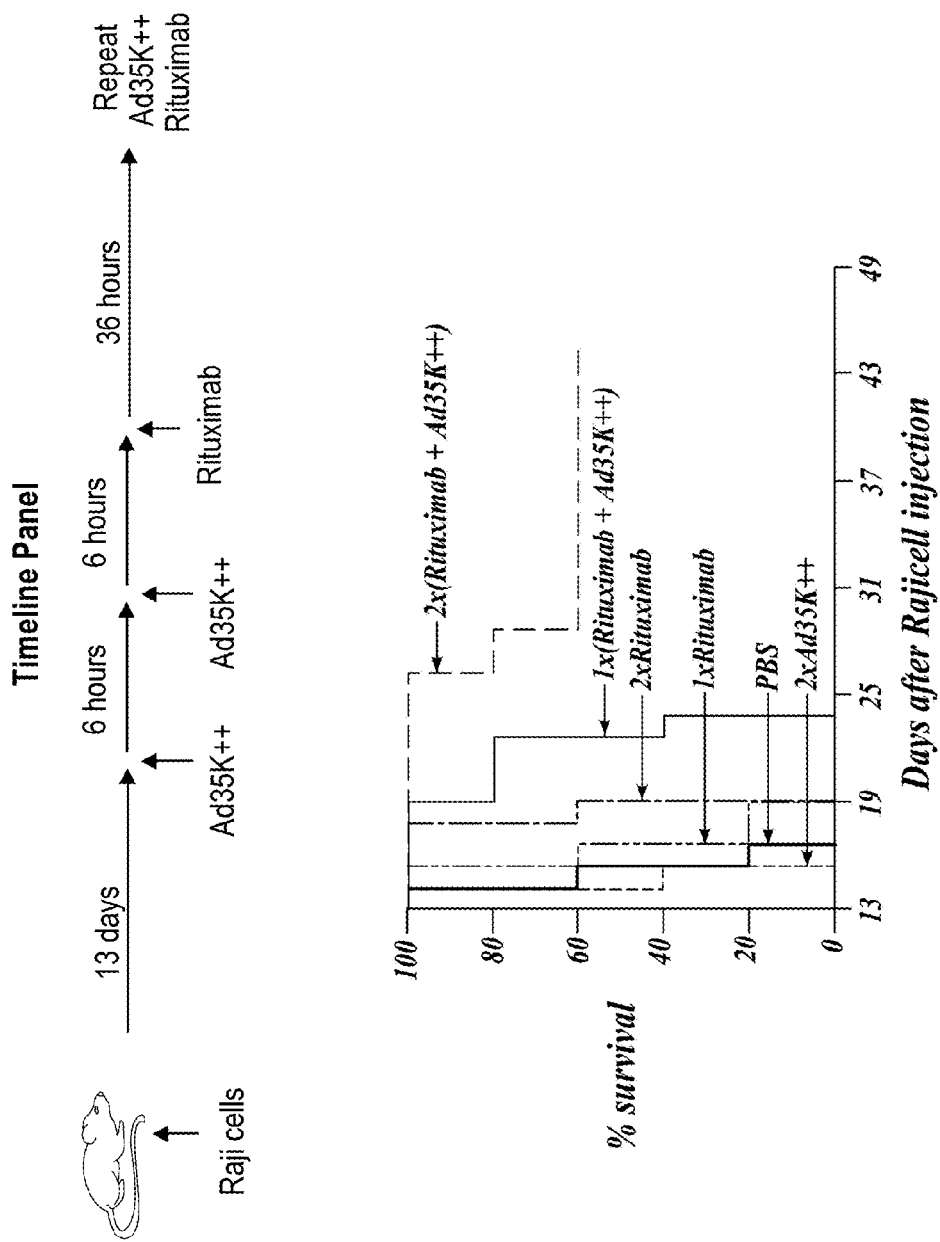
FIG. 8C is a Kaplan-Meier survival graph of the xenograft mice treated in accordance with Experimental Treatment Scheme #2, which involved two cycles of double Ad35K++ injection followed by rituximab, showing long-term survival in mice receiving 2× (rituximab plus Ad35K++ treatment), in comparison to PBS treated control mice, as described in Example 9.

FIG. 8C is a Kaplan-Meier survival study of the mice treated in accordance with treatment scheme #2, showing survival (measured by onset of hind leg paralysis) in mice that received either one treatment cycle (1x: rituximab plus Ad35K++), or mice that received two treatment cycles (2x: rituximab plus Ad35K++), or the control treatments: 1x rituximab, 2x rituximab, 2x Ad35K++ or PBS. As demonstrated in FIG. 8C, treatment scheme #2, which involved two cycles of double Ad35K++ injection followed by rituximab application enabled long-term survival of mice transplanted with Raji lymphoma cells. It is notable that treatment was started at a very advanced stage (i.e., 3 days) before the control mice would die. As shown in FIG. 8C, sixty percent of Raji lymphoma-bearing mice with treatment regiments of 2x(rituximab plus Ad35K++) survived longer than 44 days (the time of follow-up). In contrast, all PBS treated control mice died within 16 days after Raji cell transplantation.

Figure 8D:
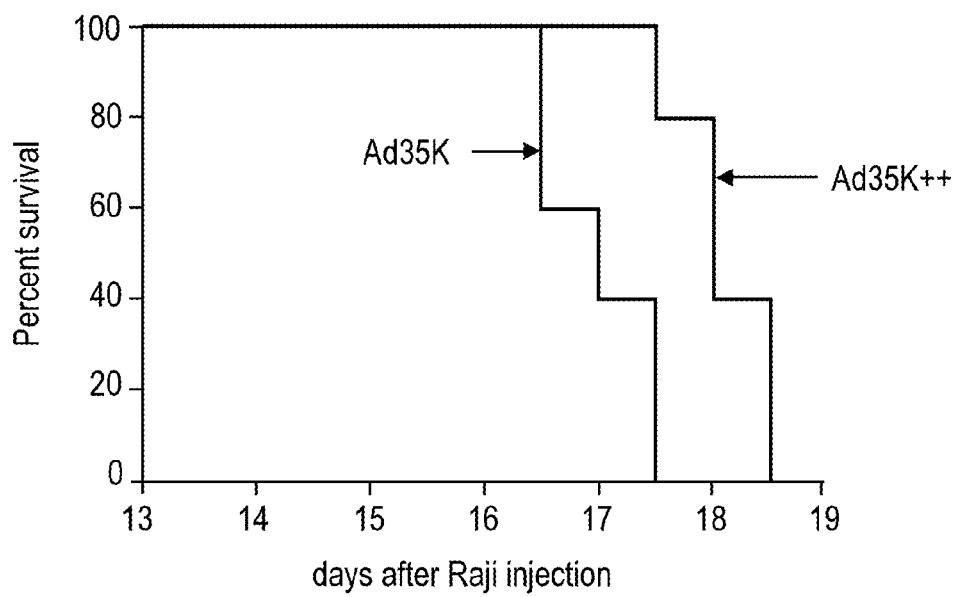
FIG. 8D graphically illustrates that compared with the wild-type Ad35K protein, Ad35K++ exerted a significantly stronger enhancing effect on rituximab therapy.

FIG. 8D is a comparison of wild-type Ad35K and Ad35K++ knob domains in enhancement of rituximab therapy, a Kaplan-Meier survival study. At day 14 after Raji cell implantation, mice received an intravenous injection of 50 mg of Ad35K or Ad35K++. Ten hours later 50 mg rituximab were injected and onset of hind leg paralysis was monitored. (N=5, p=0.0079). The figure shows that compared with the wild-type Ad35K protein, Ad35K++ exerted a significantly stronger enhancing effect on rituximab therapy.

Discussion

The results described in this Example demonstrate that rituximab plus Ad35K++ achieved superior anti-tumor effects and animal survival compared to animals treated with rituximab alone. The therapeutic efficacy of Ad35K++/rituximab treatment in Immunodeficient mice indicates that T and B cells are not involved in tumor cell killing. This suggests that the Ad35K++/rituximab approach will also be efficient in immuno-suppressed patients (i.e., patients that receive chemotherapy). Notably, the combination of rituximab with myeloreductive chemotherapy is often used clinically and has been shown to prolong progression-free survival in non-Hodgkin's lymphoma (NHL) patients (Wang, M., et al., *Cancer* 113:2734-2741 (2008)). However, chemotherapy is also associated with leukopenia and proneness to infections and therefore approaches to increase rituximab efficacy without the need for immune-suppression are desirable.

Preclinical studies showed that the anti-lymphoma effect of rituximab activity was completely abolished in C57Bl/6 mice lacking C1q, thus demonstrating the role of complement activation in rituximab therapy in mice (DiGaetano, N., et al., *J Immunol* 171:1581-1587 (2003)). It is well established that CDC plays a part in mediating the efficacy of rituximab through its ability to enhance antibody-dependent cell mediated cytotoxicity (ADCC), immune effector cell chemotaxis, and activation of anti-tumor T-cell responses (Wang, S. Y., et al., *Expert Opin Biol Ther* 8:759-768 (2008)). Further in this regard, it is noted that mAbs are currently being developed with increased ability to activate CDC (see Idusogie, E. E., et al., *J Immunol* 166:2571-2575 (2001), such as ofatumumab, another CD20-specific mAb (Arzerra) (Maloney, D. G., et al., *Hematology Am Soc Hematol Educ Program* 2007:226-232). Furthermore, a role of CDC in tumor cell killing has been reported for alemtuzumab (an anti-CD52 mAb), which is used for the treatment of chronic lymphocytic leukemia (Zent, C. S., et al., *Leuk Res* 2008); for gemtuzumab (an anti-CD33 mAb) which is used for the treatment of AML (Castillo, J., et al., *Exp Hematol* 36:755-768 (2008); as well as for panitumumab and cetuximab (anti-EGFR mAbs), used for the treatment of colon cancer (Dechant, M., et al., *Cancer Res* 68:4998-5003 (2008). Overall, this indicates that the Ad35K++ based adjuvants approach is useful for mAb therapy beyond the combination with rituximab, as further demonstrated in Example 10.

In summary, this preclinical study and the in vivo studies described in Example 3 demonstrate the efficacy and safety of the use of Ad35K++ to enhance rituximab and other monoclonal antibody based anti-cancer therapy.

EXAMPLE 10

This Example demonstrates that pre-incubation of tumor cells with mutant Ad35K++ (Asp207Gly and Thr245Ala) sensitizes the tumor cells to Campath/Alemtuzumab, Herceptin, Erbitux, Mylotarg, Arzerra, and Rituxan mediated complement dependent cytolysis.

Rationale: An experiment was carried out to determine if the mutant Ad35 fiber knob protein (Ad35K++) with enhanced affinity for CD46 could down regulate CD46 on the following cells: Raji (CD52 positive), BT-474 (Her2/Neu positive) LOVO (EGFR-positive), CD33+ cells, and CD20+, and render the cells susceptible to complement-dependent cytolysis mediated by Campath/Alemtuzumab (anti-CD52), Herceptin (anti-Her2/neu) Erbitux (anti-EGFR), Mylotarg (anti-CD33), Arzerra (anti-CD20), and Rituxan (anti-CD20).

Materials and Methods

Production of Fiber Knob Proteins:

Recombinant modified Ad35 fiber knob proteins with increased affinity to CD46 were selected from an *E. coli* expression library as described in Example 1. The recombinant mutant fiber knob proteins were produced in *E. coli* with N-terminal tags of six consecutive histidine residues (6-HIS) and purified by Ni-NTA agarose chromatography as described in Example 1. The fiber knob proteins were dialyzed against 20 mM Hepes, 200 mM NaCl, 17% glycerol. Endotoxin tests were performed using the *Limulus Amebocyte* Lysate test kit from Cape Cod Inc. (E. Falmouth, Mass.).

Cell Lines:

Raji (CD52 positive) (human Burkitt's lymphoma) (ATCC CCL-86) was cultured in RPMI supplemented with 10% FBS and with L-glutamine/(Pen-Strep).

Jurkat (CD52-negative) were cultured in RPMI supplemented with 10% FBS, Pen-strep.

BT-474 (Her2/Neu-positive) (human breast cancer) was cultured in ATCC hybrid Care Medium (Cat #46-X), 10% FCS, Pen-strep.

MDA-231 (Her2/neu-negative) (human breast cancer) was cultured in DMEM, 10% FCS, Pen-strep.

LOVO (EGFR-positive)(human colon cancer) was cultured in DMEM, 10% FCS, Pen-strep.

HeLa (EGFR-negative) (American Type Culture Collection, ATCC) were cultured in Dulbecco modified Eagle medium (DMEM) supplemented with 10% fetal bovine serum (FBS) and with 2 mM L-glutamine, 100 units/ml penicillin, and 100 µg/ml streptomycin.

Antibodies:

Campath/Alemtuzumab (anti-CD52), used for treatment of chronic lymphocytic leukemia, was obtained from Genzyme. Herceptin/trastuzumab (anti-Her2/neu), used for treatment of breast cancer, was obtained from Genentech. Erbitux/cetuximab (anti-EGFR), used for treatment of colon cancer, was obtained from Amgen. Mylotarg, Arzerra and Rituxan were also obtained from commercial sources.

In Vitro Viability Assays:

1. Campath/Alemtuzumab (Anti-CD52)

5×10⁴ cells/well of Raji (CD52 positive) or Jurkat cells (CD52 negative) were plated in triplicate in 96 well plates with RPMI complemented with 10% heat inactivated FBS, and preincubated with (1) PBS or (2) 25 µg/ml mutant Ad35K++ (Asp207Gly and Thr245Ala) with high affinity to CD46.

Eight hours later, 15 µg/ml Campath (anti-CD52) mAb was added to the cells and incubated at room temperature for 30 minutes. Normal human serum (NHS) (25% final concentration NHS) was added as a source of complement and the cells were incubated at 37° C. for another four hours for lysis Viable cells in each well were counted after trypan blue staining. Each sample was carried out in triplicate and each well was counted four times. Three independent studies were performed. Cell viability of untreated cells was taken as 100%.

2. Herceptin/Trastuzumab (Anti-Her2/neu)

5×10⁴ cells/well of BT-474 (Her2/neu positive) or MDA-231 (Ner2/neu negative) cells were plated in triplicate in 96 well plates with RPMI complemented with 10% heat inactivated FBS, and preincubated with (1) PBS or (2) 25 µg/ml mutant Ad35K++ (Asp207Gly and Thr245Ala) with high affinity to CD46.

Eight hours later, 15 µg/ml Herceptin (anti-Her2/neu) mAb was added to the cells and incubated at room temperature for 30 minutes. Normal human serum (NHS) (25% final concentration NHS) was added as a source of complement and the cells were incubated at 37° C. for another four hours for lysis. Viable cells in each well were counted after trypan blue staining. Each sample was carried out in triplicate and each well was counted four times. Three independent studies were performed. Cell viability of untreated cells was taken as 100%.

3. Erbitux/Cetuximab (Anti-EGFR)

5×10⁴ cells/well of LOVO (EGFR positive) or HeLa (EGFR negative) cells were plated in triplicate in 96 well plates with RPMI complemented with 10% heat inactivated FBS, and preincubated with (1) PBS or (2) 25 µg/ml mutant Ad35K++ (Asp207Gly and Thr245Ala) with high affinity to CD46.

Eight hours later, 15 µg/ml Erbitux (anti-EGFR) mAb was added to the cells and incubated at room temperature for 30 minutes. Normal human serum (NHS) (25% final concentration NHS) was added as a source of complement and the cells were incubated at 37° C. for another four hours for lysis Viable cells in each well were counted after trypan blue staining. Each sample was carried out in triplicate and each well was counted four times. Three independent studies were performed. Cell viability of untreated cells was taken as 100%.

Results

Figure 9A:
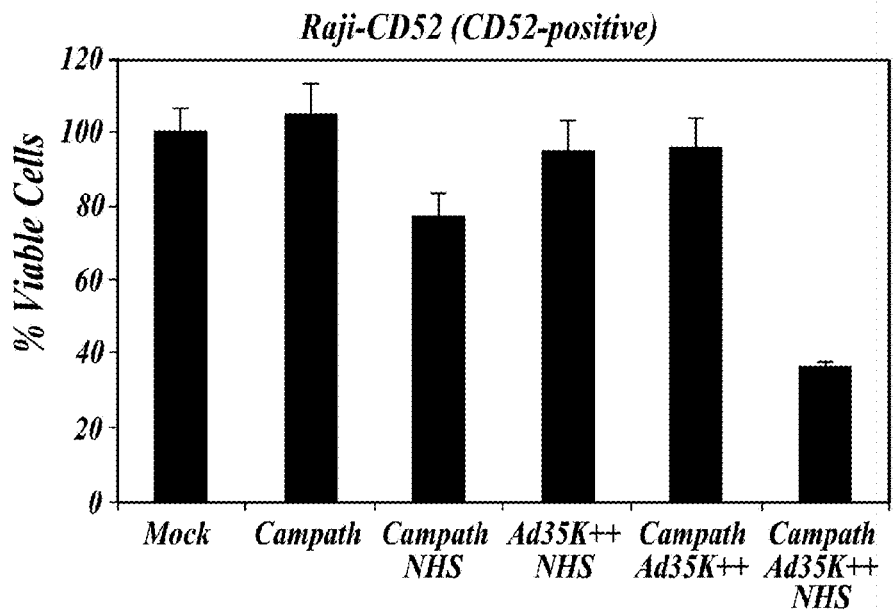
FIG. 9A graphically illustrates that pre-incubation with Ad35K++ enhanced CDC-mediated killing of Raji (CD52 positive) cells by Campath (anti-CD52 mAb), as described in Example 10.
Figure 9B:
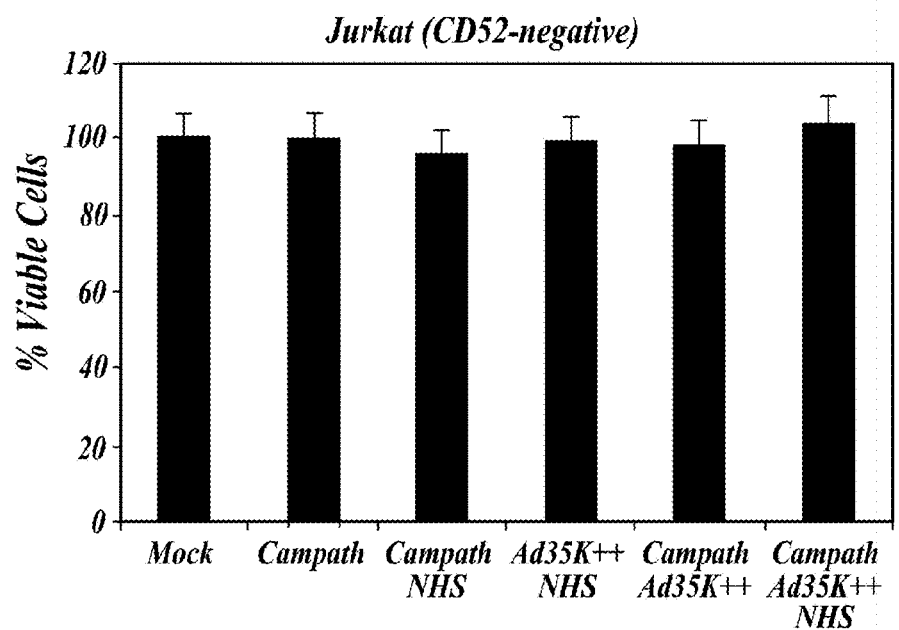
FIG. 9B graphically illustrates that preincubation with Ad35K++ did not have an effect on the viability of Jurkat cells (CD52 negative) in the presence of Campath (anti-CD52 mAb), as described in Example 10.

As shown in FIG. 9A, pre-incubation with Ad35K++ enhances CDC-mediated killing by Campath (anti-CD52 mAb) of Raji cells, which are CD52 positive. In contrast, as shown in FIG. 9B, pre-incubation with Ad35K++ did not have an effect on Jurkat cells (CD52 negative) in the presence of Campath.

Figure 10A:
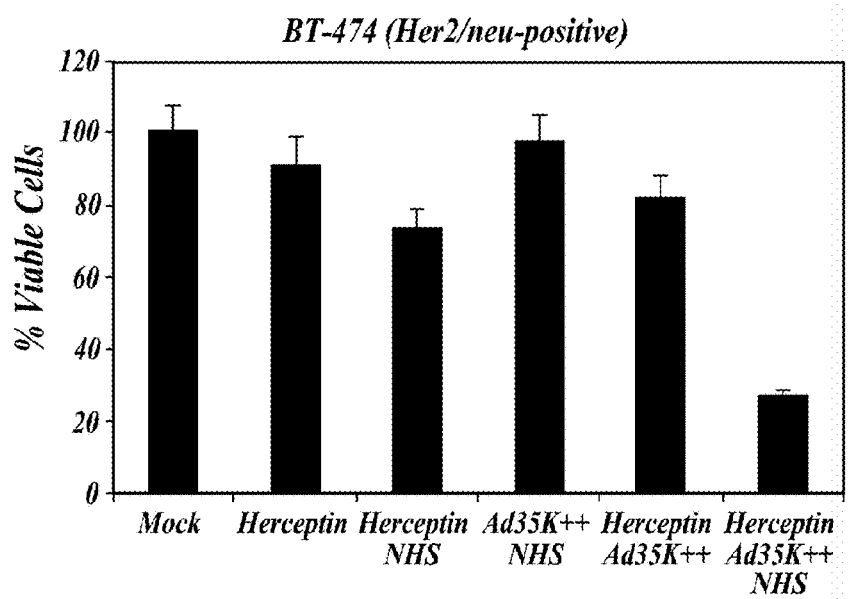
FIG. 10A graphically illustrates that preincubation with Ad35K++ enhanced CDC-mediated killing of BT-474 breast cancer (Her2/neu positive) cells by Herceptin (anti-Her2/neu mAb), as described in Example 10.
Figure 10B:
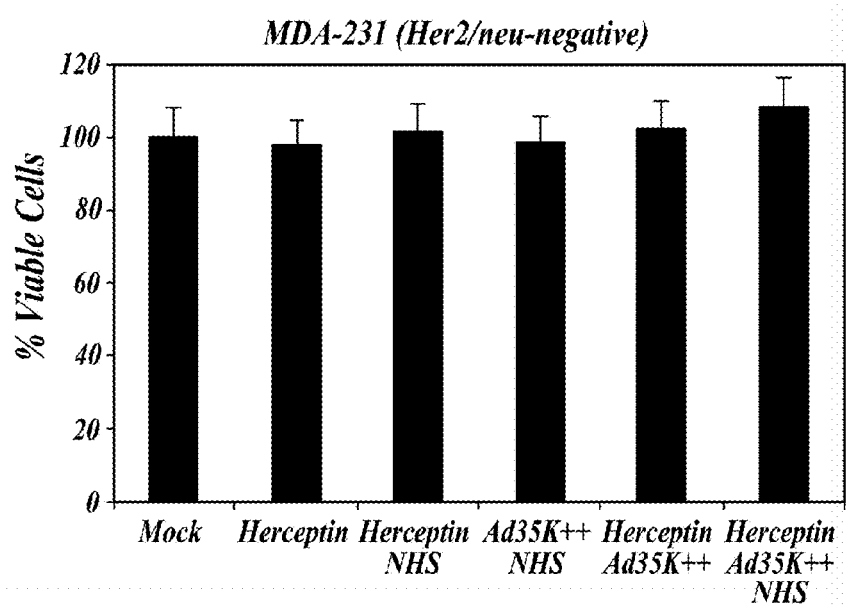
FIG. 10B graphically illustrates that preincubation with Ad35K++ did not have an effect on the viability of MDA-231 cells breast cancer (Her2/neu negative) in the presence of Herceptin (anti-Her2/neu mAb), as described in Example 10.

As shown in FIG. 10A, pre-incubation with Ad35K++ enhances both CDC-dependent and independent killing by Herceptin (anti-Her2/neu mAb) of BT-474 cells, which are Her2/neu positive. In contrast, as shown in FIG. 10B, pre-incubation with Ad35K++ did not have an effect on MDA-231 cells (Her2/neu negative) in the presence of Herceptin.

Figure 11A:
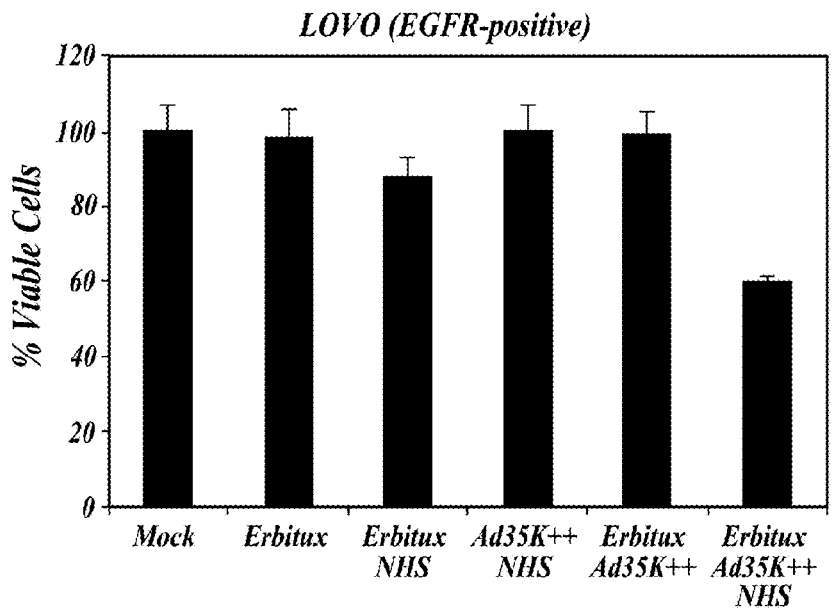
FIG. 11A graphically illustrates that preincubation with Ad35K++ enhanced CDC-mediated killing of LOVO colon cancer (EGFR positive) cells by Erbitux (anti-EGFR mAb), as described in Example 10.
Figure 11B:
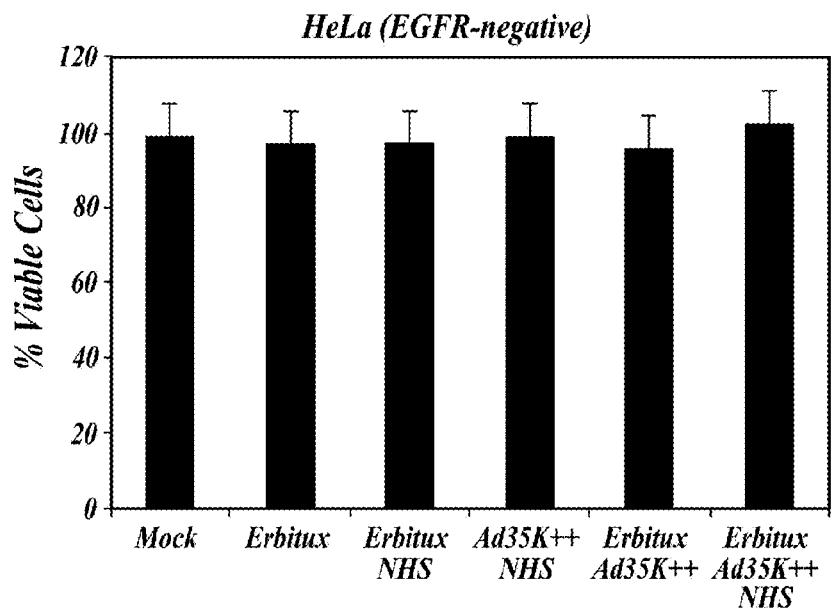
FIG. 11B graphically illustrates that preincubation with Ad35K++ did not have an effect on the viability of HeLa cells (EGFR negative) in the presence of Erbitux (anti-EGFR mAb), as described in Example 10.

As shown in FIG. 11A, pre-incubation with Ad35K++ enhances CDC-dependent killing by Erbitux (anti-EGFR mAb) of BT-474 cells, which are EGFR positive. In contrast, as shown in FIG. 11B, pre-incubation with Ad35K++ did not have an effect on HeLa cells (EGFR negative) in the presence of Erbitux.

Therefore, these results demonstrate that the methods described herein to administer Ad35K++ to sensitize cells to CDC are not limited to CD20/rituximab treatments, and may be applied to sensitize cells to CDC in the context of other anti-cancer mAbs, for example, anti-CD52 mAbs, anti-Her2/neu mAbs and anti-EGFR mAbs.

Figure 12:
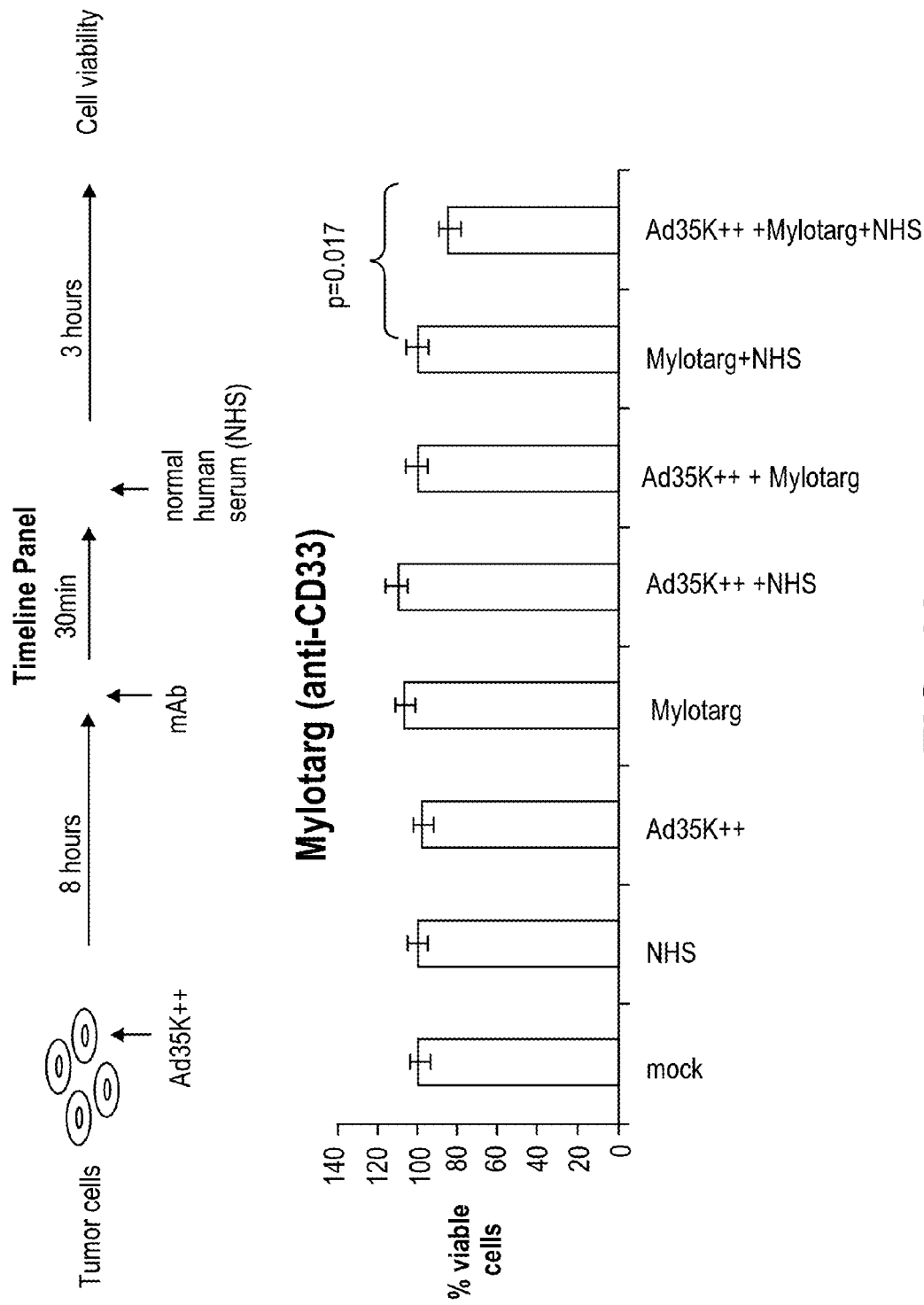
FIG. 12 graphically illustrates that pre-incubation with Ad35K++ enhances killing of AML HL60 (CD33-positive cells) by Mylotarg.
Figure 13:
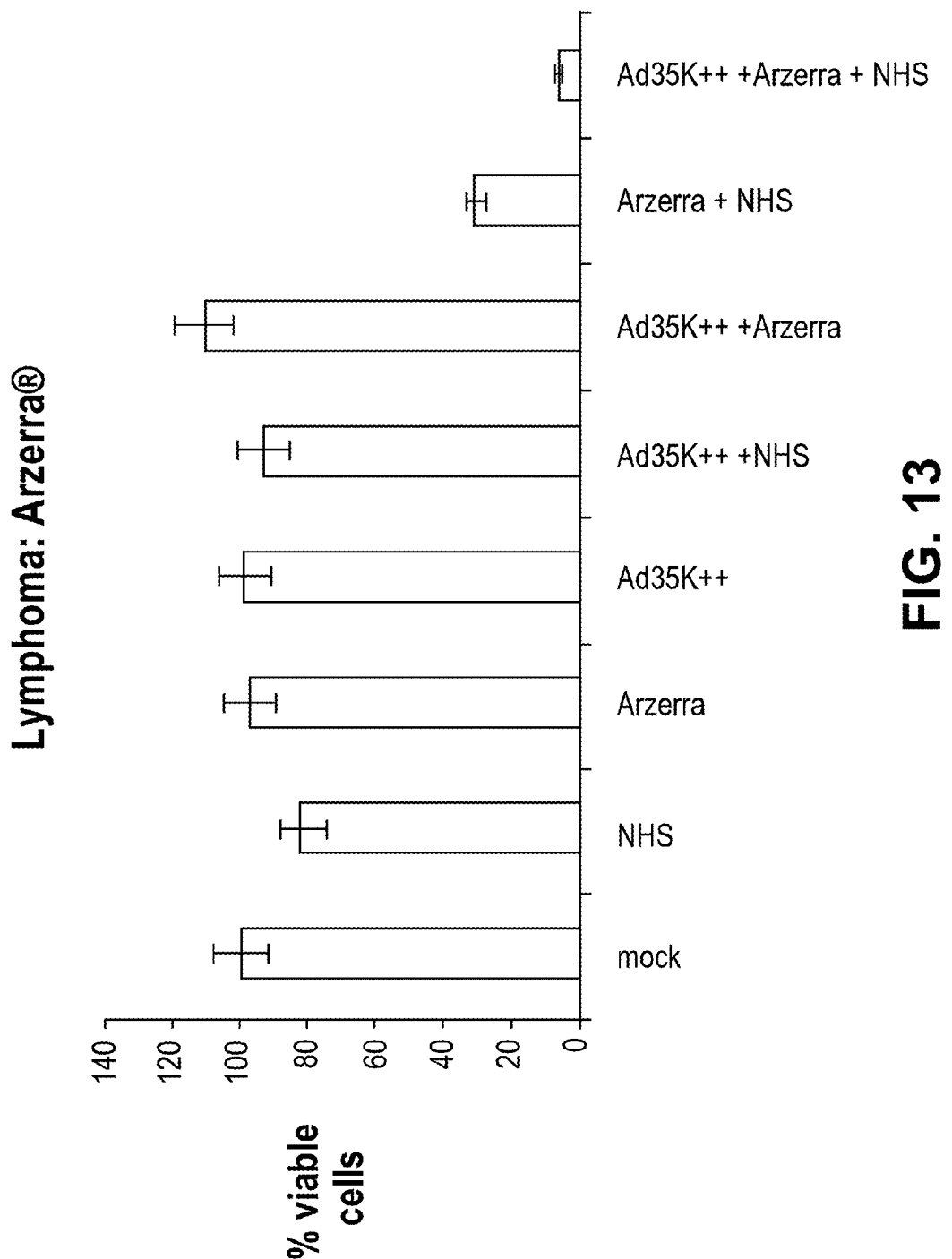
FIG. 13 graphically illustrates that pre-incubation with Ad35K++ enhances killing of Farage (CD20-positive) cells by Arzerra.

As shown in FIG. 12 and FIG. 13, pre-incubation with Ad35K++ enhances killing by Mylotarg and Arzerra, respectively.

As shown in the timeline in FIG. 14A, BT474 (breast cancer tumor cells) cells were incubated with Ad35K++ or control proteins. Eleven hours later, Herceptin mAbs were added to cells and incubated at room temperature. After 30 minutes, normal human serum (NHS) was added and viable cells were counted 3 hours later based on trypan blue exclusion. Shown in FIG. 14B is the killing of BT474 cells in the presence of two different serum samples (left panel is serum from Donor 1; right panel is serum from Donor 2). Shown is the % cell viability of cells by PBS (mock), herceptin/NHS, and Herceptin/Ad35K++/NHS in the presence of the two different serum samples.

Figure 14C:
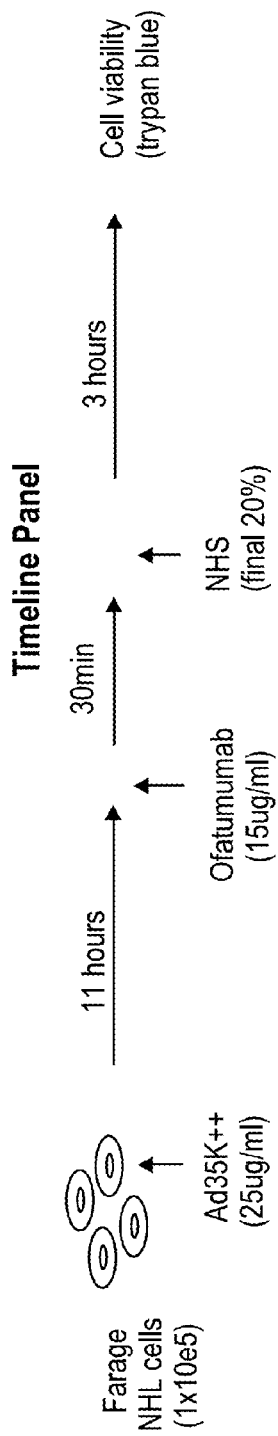
FIG. 14C graphically illustrates the timeline of the experiment with Farage cells and Arzerra.
Figure 14C:
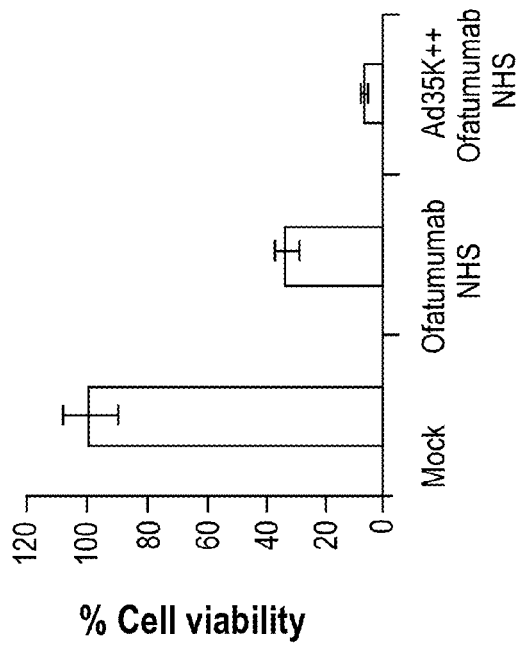
Figure 14D:
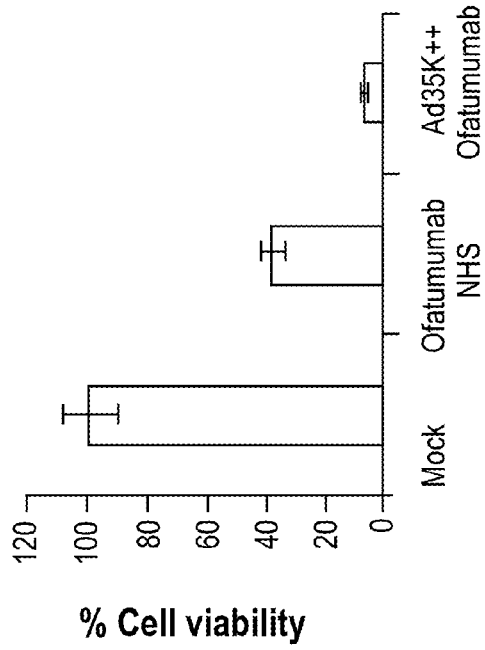
FIG. 14D, graphically illustrates the killing of Farage cells by Arzerra in the presence of different NHS sources.

As shown in the timeline in FIG. 14C, CD20 positive Farage Non-Hodgkins Lymphoma cells (NHL cells) were incubated with Ad35K++ or control proteins. Eleven hours later, Ofatumumab (Arzerra) mAbs were added to cells and incubated at room temperature. After 30 minutes, normal human serum (NHS) was added and viable cells were counted 3 hours later based on trypan blue exclusion. Shown in FIG. 14D is the killing of the CD20 positive Farage NHL cells in the presence of two different serum samples (left panel is serum from Donor 1 blood group A; right panel is serum from Donor 2 blood group AB). Shown is the % cell viability of cells by PBS (mock), Arzerra/NHS, and Arzerra/Ad35K++/NHS in the presence of the two different serum samples. Ad35K++ enhances mAb-triggered CDC with different NHS samples, including AB serum.

Both donors had neutralizing antibodies against Ad35 (titer 1:16), but the Ad35++ effect was still significant.

EXAMPLE 11

Figure 15A:
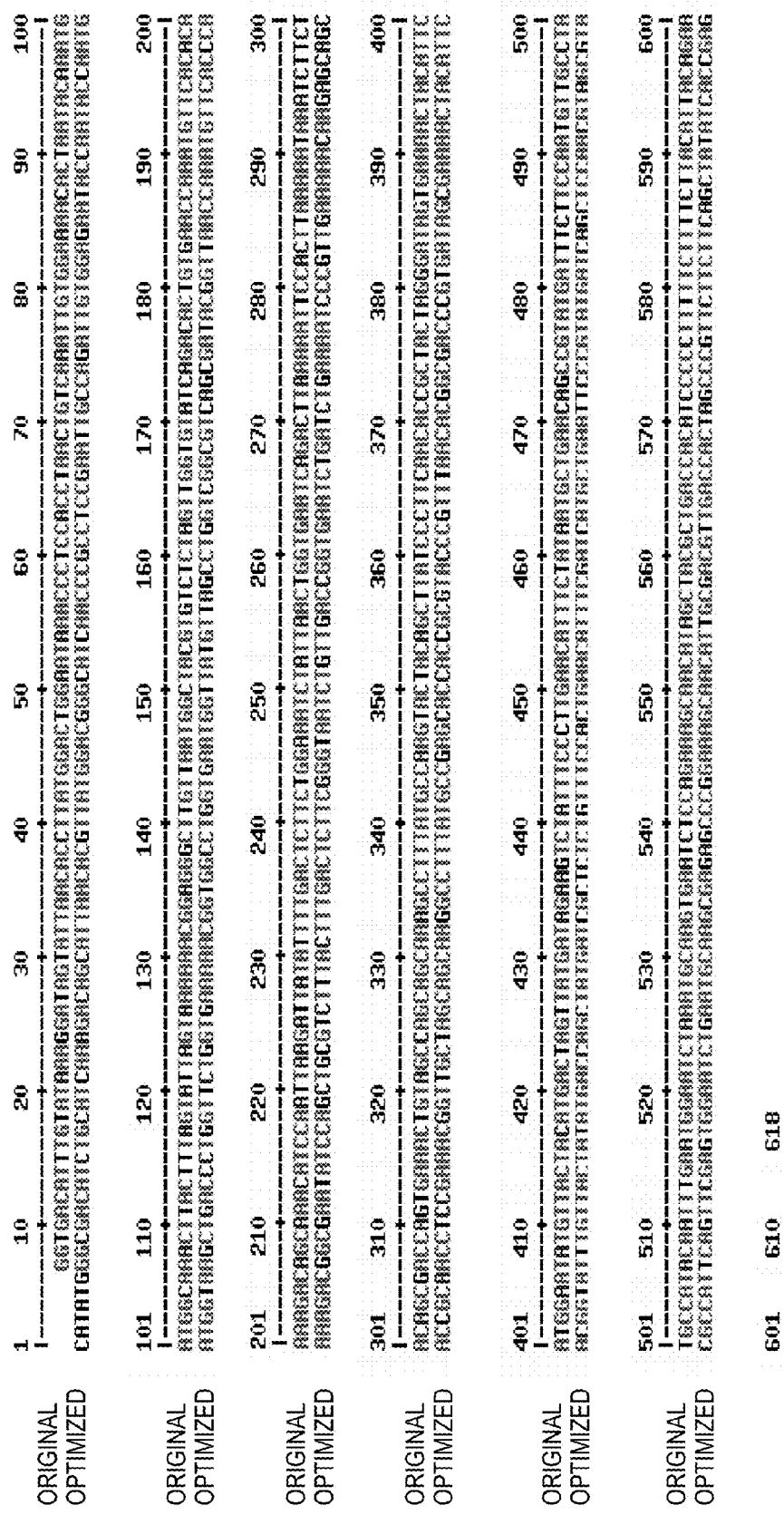
FIG. 15A graphically illustrates the DNA sequence of Ad35K++ before ("Original"; SEQ ID NO:4) and after optimization ("Optimized"; SEQ ID NO:37) using DNA2.0 software.

The sequence of AD35++ was optimized using DNA2.0 software, as show in FIG. 15A and FIG. 15B. In addition to optimization of codon usage and RNA structure, the Ad35K++ DNA sequence was checked for unwanted motifs (FIG. 15C). bacterial lysates were separated by PAGE and blotted. The filter was incubated with soluble recombinant CD46, followed by incubation with anti-CD46 antibody (clone J4.48; Fitzgerald, Concord, Mass.) and goat anti-mouse immunoglobulin G (IgG)-horseradish peroxidase (HRP) (BD Pharmingen, San Jose, Calif.). FIG. 15C shows that in addition to optimization of codon usage and RNA structure, the Ad35K++ DNA sequence was checked for unwanted motifs.

Figure 15D:
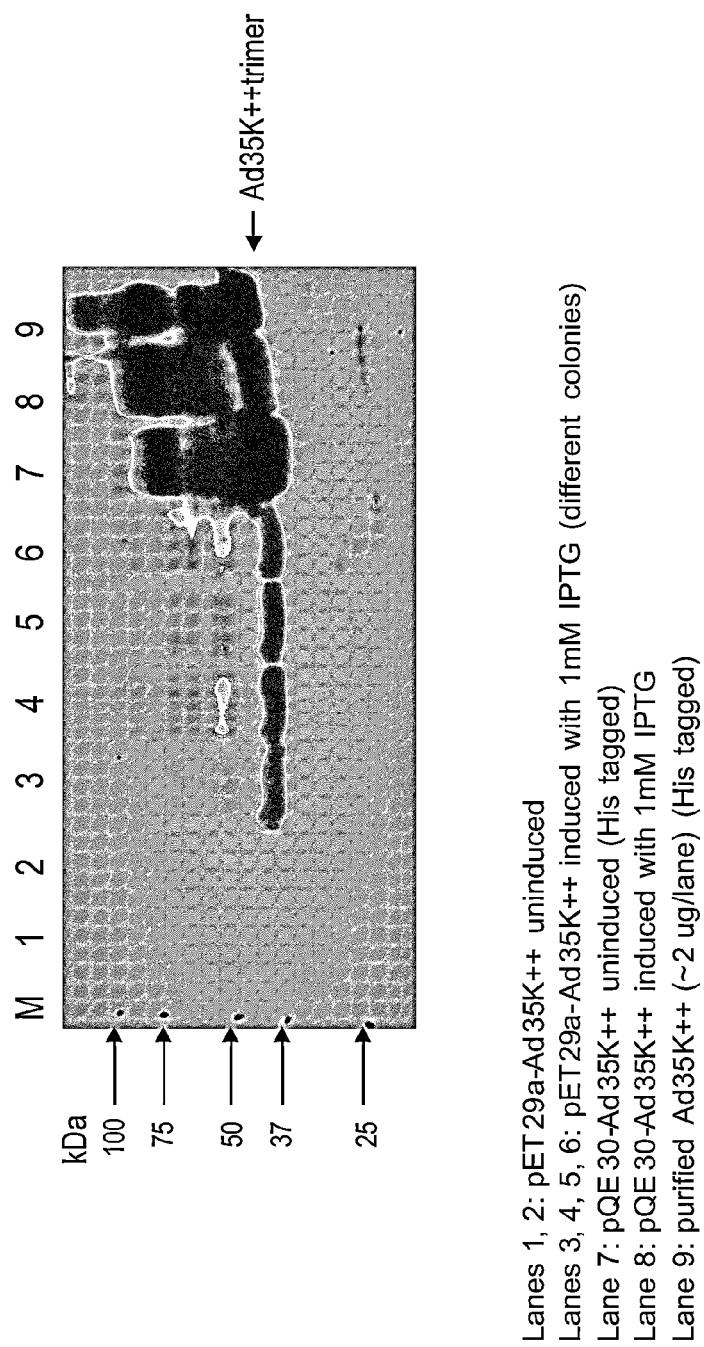
FIG. 15D illustrates the detection of Ad35K++ in HMS174 containing pET29-Ad35K++ after IPTG induction.

To detect whether the optimized protein binds to CD46, colonies of pET29a-Ad35K++ or pQE30-Ad35K++ were picked from freshly streaked plates and cultured in 4 ml LB medium at 30° C. for 14 hours. IPTG was added to a final concentration of 1 mM and the culture was incubated at 37° C. under vigorous shaking for another 8 hours. Bacteria were then pelleted by centrifugation, resuspended in 350 ul lysis buffer (50 mM NaH$_2$PO$_4$, 200 mM NaCl, 10 mM imidazole, pH8.0), and subjected to sonication. 20 ul of the protein supernatant was mixed with loading buffer (Tris, 50 mM DTT, 1% SDS (1:1) (without boiling) and loaded on a 5-15% PAA gel. After blotting, filters were successively incubated with soluble CD46, mouse anti-CD46 mAb (clone J4.48; Fitzgerald, Concord, Mass.), and goat anti-mouse IgG-HRP. FIG. 15D shows the detection of Ad35K++ in HMS174 containing pET29-Ad35K++ after IPTG induction.

EXAMPLE 12

Next, a non-human primate model was examined. FIG. 16A shows B cell depletion in vitro. Specifically PBMCs were purified from *Macaca fascicularis*, *Macaca nemestrina*, and *Papio anubis* and cultured for one day. CD20+ cells were sorted using a (cross-reacting) anti-human CD20-PE antibody. For CDC assays, CD20+ cells were incubated with 25 ug/ml Ad35K++ or PBS for 12 hours. Rituximab (15 ug/ml) or PBS was added, followed by NHS (20% final) 30 min later. Cell viability was counted after 3 hours of incubation based on trypan blue exclusion. N=8 FIG. 16B shows an Ad35K++ hemagglutination assay. Specifically, serial dilutions of Ad35K++ protein were incubated with 1% erythrocytes and hemagglutionation was assessed 1 hour later.

Of all mammals, only NHPs express CD46 expression in a pattern similar to humans. In contrast to humans, NHP have CD46 on erythrocytes.

In vitro, Rituxan® depletes CD20+ B-cells of all tested NHP species (*Macaca fascicularis*, *Macaca nemestrina*, and *Papio anubis*) and Ad35K++ significantly enhances this process.

Ad35K++ hemagglutinates erythrocytes from baboons (*P. Anubis*), but not erythrocytes from humans and from macaque species, including *M. fascilcularis* and *M. nemestina*.

Taken together, these results suggest that *M. fascicularis* and *M. nemestina* are models to study both the efficacy and safety of the Ad35K++/Rituxan® approach as well as other combinations of a polypeptide capable of modulation the activity or decreasing the presence of a CRP on a target cell surface in combination with a therapeutic antibody of choice.

EXAMPLE 13

Figure 17D:
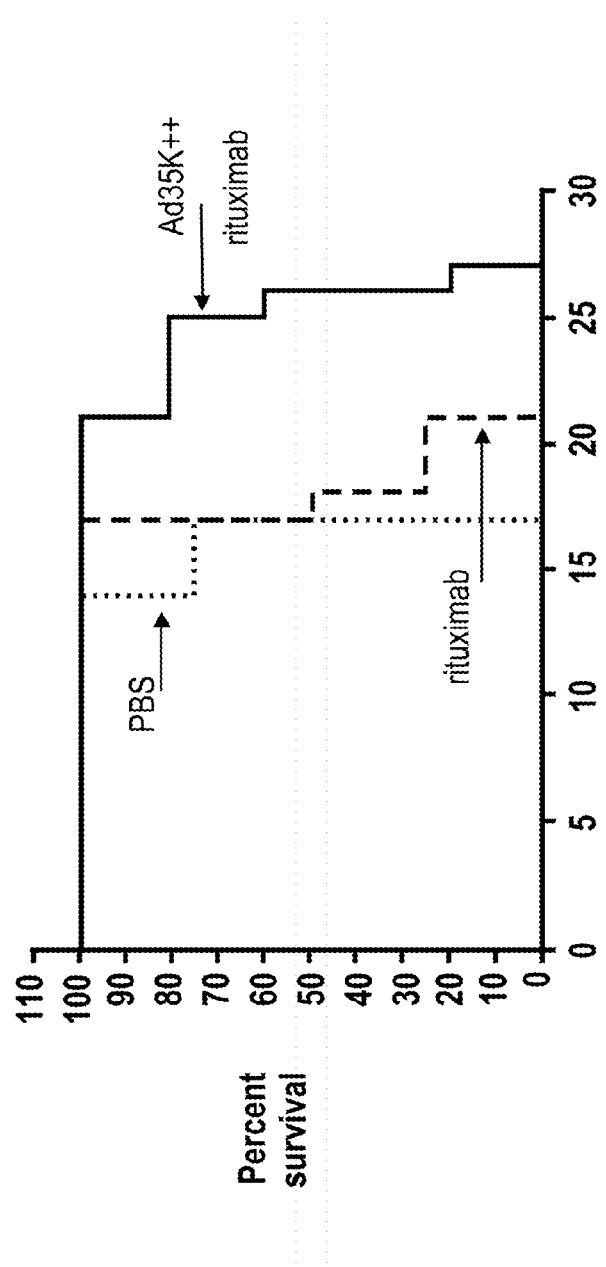

C57B1/6 mice that were double transgenic for human CD46 and CD20 were intravenously injected with syngeneic 38C13myeloma cells that ectopically expressed human CD46 and CD20 at levels found on human lymphoma cells (FIG. 17, lower panel). PBS-injected mice became moribund at day 17 after injection of 38C13 cells with tumor cells localized in the bone marrow, spleen, lymph nodes and liver. In a therapy experiment, tumor-bearing mice received 2 mg/kg Ad35K++ or PBS intravenously. Ten hours later mice were injected with rituximab (2 mg/kg) and survival was monitored (N=5) (FIG. 17, lower panel).

While embodiments of the invention have been illustrated and described, it will be appreciated that various changes can be made therein without departing from the spirit and scope of the invention.

The embodiments of the invention in which an exclusive property or privilege is claimed are defined as follows:

1. A modified polypeptide capable of reducing the activity, amount, or density of a complement regulatory protein (CRP) on a target cell surface, wherein the polypeptide comprises at least two loop domains with CRP binding affinity and has at least 90% sequence identity to the Ad35 fiber knob sequence of SEQ ID NO:3, wherein the first loop comprises amino acids 81-89 of SEQ ID NO:3 and the second loop comprises amino acids 120-126 of SEQ ID NO:3, wherein the polypeptide comprises at least one of a substitution of a glycine (Gly) for the aspartic acid (Asp) at position 85 of SEQ ID NO:3, a substitution of any amino acid for the threonine (Thr) at position 123 of SEQ ID NO:3, or both.

2. The polypeptide of claim 1 wherein the polypeptide causes internalization or sequestration of the CRP.

3. The polypeptide of claim 1 wherein, the polypeptide binds to the CRP with a dissociation constant ($K_d$) of 1 nM or less.

4. The polypeptide of claim 1 wherein the CRP is a transmembrane protein.

5. The polypeptide of claim 1 wherein the CRP is CD46, CD55, CD59, or CD35.

6. The polypeptide of claim 1 wherein the polypeptide is further capable of sensitizing the target cell to antibody-mediated complement-dependent cytolysis.

7. The polypeptide of claim 1 wherein the target cell is a tumor cell.

8. The polypeptide of claim 1 wherein the target cell is a B-cell that expresses CD20.

9. The polypeptide of claim 1 wherein the polypeptide is capable of reducing the activity, amount or density of the complement regulatory protein (CRP) for at least 24 hours.

10. The polypeptide of claim 1 wherein the polypeptide is active at concentrations of about 25 ng/ml or less.

11. The polypeptide of claim 1 wherein the first loop comprises amino acids 77-93, amino acids 77-90, amino acids 77-87, or amino acids 77-85 of SEQ ID NO:3, and wherein the polypeptide comprises at least one of a substitution of a glycine (Gly) for the aspartic acid (Asp) at position 85 of SEQ ID NO:3, a substitution of any amino acid for the threonine (Thr) at position 123 of SEQ ID NO:3, or both.

12. A pharmaceutical composition comprising a therapeutically effective amount of the polypeptide of claim 1.

13. The pharmaceutical composition of claim 12 further comprising a second therapeutic agent.

14. The pharmaceutical composition of claim 13 wherein the second therapeutic agent is selected from the group consisting of a protein, a polypeptide, a small molecule, a drug, an antibody, an antibody fragment, a hybrid antibody, an antibody drug-conjugate, a siRNA, an antisense RNA, a miRNA, a virus, and an aptamer.

15. The pharmaceutical composition of claim 13 wherein the second therapeutic agent is selected from the group consisting of a cytotoxic agent, a cytostatic agent, a chemotherapy agent, a complement-activating agent, a modulator of CRP expression, radiation, an immunomodulatory agent, a pro-apoptotic agent, an inhibitor of heat shock protein, a protease inhibitor, a desialyating agent, a MMP inhibitor, and a PKC inhibitor.

16. The polypeptide of claim 1, wherein the polypeptide comprises at least one amino acid substitution selected from the group consisting of Thr123Ala and Ile134Leu, or a combination thereof, and wherein the polypeptide can form homotrimers capable of binding to CD46.

17. A method for reducing the amount of CD46 on a target cell surface, the method comprising:

contacting the cell expressing CD46 on its surface with the polypeptide of claim 1.

18. A method for inducing cytolysis in a target cell expressing CD46 on its surface comprising:

(a) contacting the cell expressing CD46 on its surface with an amount of the polypeptide of claim 1, wherein said polypeptide comprises a modified adenovirus fiber knob domain polypeptide effective to decrease the amount of CD46 present on the surface of the target cell; and (b) contacting the cell treated in accordance with step (a) with an antibody or fragment thereof that binds to an antigen on the surface of the cell and induces cytolysis.

19. The polypeptide of claim 11 wherein the polypeptide comprises a substitution of any amino acid for the threonine (Thr) at position 123 of SEQ ID NO:3, and wherein the polypeptide further comprises a substitution of any amino acid for the aspartic acid (Asp) at position 85 of SEQ ID NO:3.

20. The polypeptide of claim 1, comprising a substitution of an alanine (Ala) for the threonine (Thr) at position 123 of SEQ ID NO:3.

21. The polypeptide of claim 1 wherein the second loop further comprises amino acids 127-134, amino acids 130-134, or amino acids 132-134 of SEQ ID NO:3.

22. The polypeptide of claim 21 further comprising a substitution of any amino acid for the isoleucine (Ile) at position 134 of SEQ ID NO:3.

23. The polypeptide of claim 22 wherein the amino acid substituted for the isoleucine (Ile) at position 134 of SEQ ID NO: 3 is leucine (Leu).

24. The polypeptide of claim 1 wherein the second loop comprises amino acids 101-134, amino acids 120-134, or amino acids 123-134 of SEQ ID NO:3, and wherein the polypeptide comprises at least one of a substitution of a glycine (Gly) for the aspartic acid (Asp) at position 85 of SEQ ID NO:3, a substitution of any amino acid for the threonine (Thr) at position 123 of SEQ ID NO:3, or both.

25. The polypeptide of claim 24 wherein the polypeptide comprises at least one of a substitution of any amino acid for the threonine (Thr) at position 123 of SEQ ID NO:3, a substitution of any amino acid for the isoleucine (Ile) at position of 134 of SEQ ID NO:3, or both.

26. The polypeptide of claim 25 wherein the polypeptide comprises at least one of a substitution of an alanine (Ala) for the threonine (Thr) at position 123 of SEQ ID NO:3, a substitution of a leucine (Leu) for the isoleucine (Ile) at position 134 of SEQ ID NO:3, or both.

27. The polypeptide of claim 1 wherein the polypeptide further comprises amino acids 154-165 of SEQ ID NO:3, amino acids 175-191 of SEQ ID NO:3, or amino acids 154-165 and amino acids 175-191 of SEQ ID NO:3.

28. The polypeptide of claim 1 wherein the polypeptide is capable of forming homotrimers.

29. The polypeptide of claim 28 wherein the polypeptide homotrimers binds to the CRP with at least 1.5 fold higher affinity as compared to a homotrimer formed by three polypeptides, each consisting of SEQ ID NO:3.

30. A polypeptide capable of reducing the activity, amount, or density of a complement regulatory protein (CRP) on a target cell surface, wherein the polypeptide comprises an amino acid sequence with at least 90% sequence identity to the Ad35 fiber knob sequence of SEQ ID NO:3, wherein the amino acid sequence further comprises:

a first CRP binding domain comprising amino acids 81-89 of SEQ ID NO:3; and a second CRP binding domain comprising amino acids 120-126 of SEQ ID NO:3 with a substitution of any amino acid for the threonine (Thr) at position 123 of SEQ ID NO:3.

* * * * *

UNITED STATES PATENT AND TRADEMARK OFFICE
CERTIFICATE OF CORRECTION

| | | |
|---|---|---|
| PATENT NO. | : 8,753,639 B2 | Page 1 of 1 |
| APPLICATION NO. | : 12/751943 | |
| DATED | : June 17, 2014 | |
| INVENTOR(S) | : Lieber et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 695 days.

Signed and Sealed this
Fourth Day of August, 2015

Michelle K. Lee
*Director of the United States Patent and Trademark Office*